United States Patent
Pinkerton et al.

(10) Patent No.: US 9,868,707 B2
(45) Date of Patent: Jan. 16, 2018

(54) SMALL MOLECULE AGONISTS OF NEUROTENSIN RECEPTOR 1

(71) Applicants: SANFORD-BURNHAM MEDICAL RESEARCH INSTITUTE, La Jolla, CA (US); DUKE UNIVERSITY, Durham, NC (US)

(72) Inventors: Anthony Pinkerton, La Jolla, CA (US); Patrick Maloney, La Jolla, CA (US); Paul Hershberger, La Jolla, CA (US); Satyamaheshwar Peddibhotla, La Jolla, CA (US); Michael Hedrick, La Jolla, CA (US); Lawrence Barak, La Jolla, CA (US); Marc Caron, La Jolla, CA (US)

(73) Assignees: SANFORD-BURNHAM MEDICAL RESEARCH INSTITUTE, La Jolla, CA (US); DUKE UNIVERSITY, Durham, NC (US)

( * ) Notice: Subject to any disclaimer, the term of this patent is extended or adjusted under 35 U.S.C. 154(b) by 0 days.

(21) Appl. No.: 14/652,705

(22) PCT Filed: Dec. 19, 2013

(86) PCT No.: PCT/US2013/076735
§ 371 (c)(1),
(2) Date: Jun. 16, 2015

(87) PCT Pub. No.: WO2014/100501
PCT Pub. Date: Jun. 26, 2014

(65) Prior Publication Data
US 2015/0329497 A1    Nov. 19, 2015

Related U.S. Application Data

(60) Provisional application No. 61/740,362, filed on Dec. 20, 2012.

(51) Int. Cl.
| | | |
|---|---|---|
| C07D 239/94 | (2006.01) |
| A61K 31/517 | (2006.01) |
| A61K 31/519 | (2006.01) |
| A61K 31/506 | (2006.01) |
| C07D 403/04 | (2006.01) |
| A61K 45/06 | (2006.01) |
| A61K 31/5377 | (2006.01) |
| A61K 9/00 | (2006.01) |
| A61K 47/26 | (2006.01) |
| A61K 47/38 | (2006.01) |
| A61K 9/48 | (2006.01) |
| C07D 403/12 | (2006.01) |
| C07D 401/14 | (2006.01) |
| C07D 215/42 | (2006.01) |
| C07D 217/22 | (2006.01) |
| C07D 401/04 | (2006.01) |
| C07D 401/12 | (2006.01) |
| C07D 405/04 | (2006.01) |
| C07D 471/04 | (2006.01) |

(52) U.S. Cl.
CPC .......... *C07D 239/94* (2013.01); *A61K 9/0019* (2013.01); *A61K 9/4866* (2013.01); *A61K 31/506* (2013.01); *A61K 31/517* (2013.01); *A61K 31/519* (2013.01); *A61K 31/5377* (2013.01); *A61K 45/06* (2013.01); *A61K 47/26* (2013.01); *A61K 47/38* (2013.01); *C07D 215/42* (2013.01); *C07D 217/22* (2013.01); *C07D 401/04* (2013.01); *C07D 401/12* (2013.01); *C07D 401/14* (2013.01); *C07D 403/04* (2013.01); *C07D 403/12* (2013.01); *C07D 405/04* (2013.01); *C07D 471/04* (2013.01)

(58) Field of Classification Search
CPC .................................................... C07D 403/04
See application file for complete search history.

(56) References Cited

U.S. PATENT DOCUMENTS

| | | | |
|---|---|---|---|
| 5,866,562 A | 2/1999 | Schohe-Loop et al. |
| 2005/0096327 A1* | 5/2005 | Caprathe ............. C07D 239/42 |
| | | | 514/252.17 |
| 2006/0217377 A1 | 9/2006 | Gonzalez, III |
| 2009/0163545 A1 | 6/2009 | Goldfarb |
| 2009/0259044 A1 | 10/2009 | Kazantsev |

FOREIGN PATENT DOCUMENTS

| | | |
|---|---|---|
| CN | 102786483 A | 11/2012 |
| EP | 0638567 A1 | 2/1995 |
| JP | S58172379 A | 10/1983 |
| WO | WO-0224667 A1 | 3/2002 |
| WO | WO-2006007864 A1 | 1/2006 |
| WO | WO-2007071055 A1 | 6/2007 |
| WO | WO-2011153553 A2 | 12/2011 |
| WO | WO-2014052699 A1 | 4/2014 |
| WO | WO-2014100501 A1 | 6/2014 |
| WO | WO-2015200534 A2 | 12/2015 |

OTHER PUBLICATIONS

Vippagunta et al. (2001).*
Peddibhotla et al., ACS Med. Chem Letters, 4(9) pp. 846-851 (2013).*
Allen et al. Discovery of β-arrestin-biased dopamine D2 ligands for probing signal transduction pathways essential for antipsychotic efficacy. PNAS USA 108:18488-18493 (2011).
Bridges et al. Tyrosine kinase inhibitors. 8. An unusually steep structure-activity relationship for analogues of 4-(3-bromoanilino)-6,7-dimethoxyquinazoline (PD 153035), a potent inhibitor of the epidermal growth factor receptor. J Med Chem 39(1):267-276 (1996).

(Continued)

*Primary Examiner* — Paul V Ward
(74) *Attorney, Agent, or Firm* — Wilson Sonsini Goodrich & Rosati

(57) ABSTRACT

Provided herein are small molecule neurotensin receptor agonists, compositions comprising the compounds, and methods of using the compounds and compositions comprising the compounds.

18 Claims, 1 Drawing Sheet

(56) References Cited

OTHER PUBLICATIONS

Fan et al. The identification of neurotensin NTS1 receptor partial agonists through a ligand-based virtual screening approach. Bioorg Med Chem Lett. 18(21):5789-5791 (2008).

Griebel et al. Neuropeptide receptor ligands as drugs for psychiatric diseases: the end of the beginning? Nat Rev Drug Discov 11(6):462-478 (2012).

Gully et al. Biochemical and pharmacological activities of SR 142948A, a new potent neurotensin receptor antagonist. J Pharmacol Exp Ther 280(2):802-812 (1997).

Gully et al. Biochemical and pharmacological profile of a potent and selective nonpeptide antagonist of the neurotensin receptor. PNAS USA 90(1):65-69 (1993).

PCT/US2013/076735 International Preliminary Report on Patentability dated Jul. 2, 2015.

PCT/US2013/076735 International Search Report and Written Opinion dated Apr. 30, 2014.

Peddibhotla et al. Discovery of ML314, a Brain Penetrant Non-Peptidic β-Arrestin Biased Agonist of the Neurotensin NTR1 Receptor. ACS Med Chem Lett 4(9):846-851 (2013).

Rajagopal et al. Teaching old receptors new tricks: biasing seven-transmembrane receptors. Nat Rev Drug Discovery 9:373-386 (2010).

Schaeffer et al. SR142948A is a potent antagonist of the cardiovascular effects of neurotensin. J Cardiovasc Pharmacol 31(4):545-550 (1998).

Sirisoma et al. Discovery of N-(4-methoxyphenyl)-N,2-dimethylquinazolin-4-amine, a potent apoptosis inducer and efficacious anticancer agent with high blood brain barrier penetration. J. Med. Chem. 42(8):2341-2351 (2009).

Thomas et al. The identification of nonpeptide neurotensin receptor partial agonists from the potent antagonist SR48692 using a calcium mobilization assay. Bioorg Med Chem Lett 19(5):1438-1441 (2009).

Whalen et al. Therapeutic potential of β-arrestin- and G protein-biased agonists. Trends Mol Med 17(3):126-139 (2011).

White et al. Structure of the agonist-bound neurotensin receptor. Nature 490(7421):508-513 (2012).

Chemical Abstracts—Retrieved from STN Database Accession No. 1002177-75-4 (2008).

Chemical Abstracts—Retrieved from STN Database Accession No. 1003477-61-9 (2008).

Chemical Abstracts—Retrieved from STN Database Accession No. 1328207-13-1 (2011).

Chemical Abstracts—Retrieved from STN Database Accession No. 1338120-56-1 (2011).

Chemical Abstracts—Retrieved from STN Database Accession No. 1338170-26-5 (2011).

Chemical Abstracts—Retrieved from STN Database Accession No. 1369053-41-7 (2012).

Chemical Abstracts—Retrieved from STN Database Accession No. 496873-57-5 *496873-57-5; 496873-55-3; 496873-18-8; 496872-42-5; 496872-41-4; 496872-40-3; 496872-36-7; 496872-35-6; 496872-24-3; 496872-17-4; 496872-04-9; 496867-91-5* (12 pgs) (2003).

Chemical Abstracts—Retrieved from STN Database Accession No. 667897-12-3; *667897-12-3; 667897-00-9; 667896-98-2;667896-24-4;667896-21-1;667896-14-2; 667896-13-1; 667896-12-0* (8 pgs) (2004).

Chemical Abstracts—Retrieved from STN Database Accession No. 677748-35-5 (2004).

Chemical Abstracts—Retrieved from STN Database Accession No. 929432-71-3 (2007).

Chemical Abstracts—Retrieved from STN Database Accession No. 929455-75-4 (2007).

Dilly et al. Identification of a pharmacophore of SKCa channel blockers. J Enzyme Inhib Med Chem 20(6):517-523 (2005).

Herschberger et al. Small Molecule Agonists for the Neurotensin 1 Receptor (NTR1 Agonists). Probe Reports from the NIH Molecular Libraries Program—NCBI Bookshelf. Available at http://www.ncbi.nlm.nih.gov/books/NBK184496 (12 pgs) (Retrieved May 13, 2016).

Marugan et al. Evaluation of quinazoline analogues as glucocerebrosidase inhibitors with chaperone activity. J Med Chem 54(4)1033-1058 (2011).

Di Fruscia et al. The discovery of indole full agonists of the neurotensin receptor 1 (NTSR1). Bioorg Med Chem Lett. 24(16):3974-3978 (2014 ).

PCT/US2015/037515 International Preliminary Report on Patentability dated Jan. 5, 2017.

PCT/US2015/037515 International Search Report and Written Opinion dated Feb. 29, 2016.

* cited by examiner

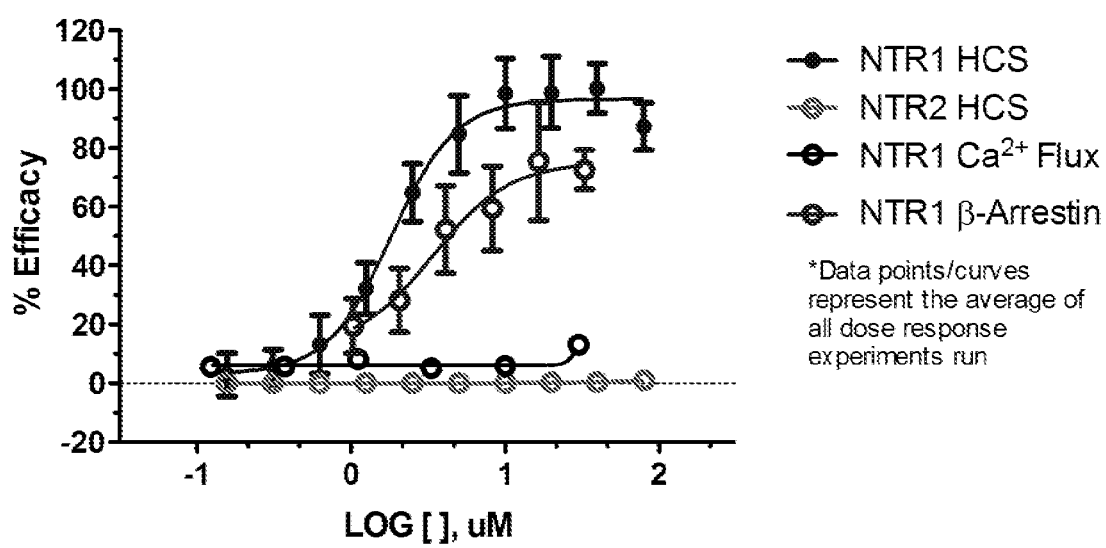

SMALL MOLECULE AGONISTS OF NEUROTENSIN RECEPTOR 1

RELATED APPLICATIONS

This application is filed pursuant to 35 U.S.C. §371 as a United States National Phase Application of International Application No. PCT/US2013/076735 entitled "SMALL MOLECULE AGONISTS OF NEUROTENSIN RECEPTOR 1", filed Dec. 19, 2013, which claims the benefit of U.S. provisional patent application No. 61/740,362 entitled "SMALL MOLECULE AGONISTS OF NEUROTENSIN RECEPTOR 1 FOR THE TREATMENT OF DISEASE" filed on Dec. 20, 2012, each of which is incorporated by reference in its entirety.

STATEMENT AS TO FEDERALLY SPONSORED RESEARCH

This invention was made with the support of the United States government under Grants number U54 HG005033-03, 1 R03 MH089653-01 and 5P30DA029925.

SUMMARY OF THE INVENTION

Described herein are compounds that modulate the activity of the neurotensin 1 receptor (NTR1). The neurotensin 1 receptor is a therapeutic target for the treatment of a variety of diseases or conditions. In some embodiments, the neurotensin 1 receptor is a therapeutic target for the treatment of diseases or conditions such as, but not limited to, neurological diseases or conditions, and cancer. In some embodiments, the compounds described herein are agonists of the neurotensin 1 receptor.

In one aspect, provided herein is a compound of Formula I, or a pharmaceutically acceptable salt, solvate, tautomer, or N-oxide thereof:

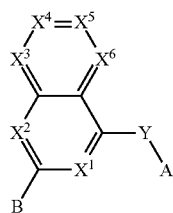

Formula I wherein:
A is $A^1$, —O-$A^1$, —NH-$A^1$, —C(=O)-$A^1$, or —S(=O)$_2$-$A^1$; $A^1$ is selected from the group consisting of optionally substituted phenyl, optionally substituted naphthyl, optionally substituted 5-membered heteroaryl, optionally substituted 6-membered heteroaryl, optionally substituted 9-membered heteroaryl and optionally substituted 10-membered heteroaryl; wherein optional substituents for A are selected from the group consisting of hydrogen, halogen, —CN, —OH, —NO$_2$, —N(R$^{13}$)—R$^{14}$, —C(=O)—N(R$^{13}$)—R$^{14}$, —NR$^{13}$C(=O)R$^{15}$, —C(=O)—O—R$^{13}$, —O—C(=O)—R$^{15}$, —SR$^{13}$, —S(=O)R$^{15}$, —S(=O)$_2$R$^{15}$, —N(R$^{13}$)S(=O)$_2$R$^{15}$, —S(=O)$_2$—N(R$^{13}$)—R$^{14}$, —C(=O)R$^{13}$, optionally substituted alkyl, optionally substituted cycloalkyl, optionally substituted heterocycloalkyl, optionally substituted alkoxy, optionally substituted haloalkyl, optionally substituted haloalkoxy, optionally substituted phenyl, and optionally substituted 5- or 6-membered heteroaryl;

B is selected from the group consisting of optionally substituted phenyl, optionally substituted 5-membered heteroaryl, optionally substituted 6-membered heteroaryl, optionally substituted alkyl, optionally substituted cycloalkyl and optionally substituted heterocycloalkyl;

Y is selected from optionally substituted heterocyloalkyl, optionally substituted spiroheterocyloalkyl, optionally substituted with alkyl, and —NR$^2$(CH$_2$)$_n$NR$^3$—;

n is 2, 3, 4, 5, or 6;

$R^2$ is H or alkyl;

$R^3$ is H or alkyl;

$X^1$ is N or C(R$^1$);

$X^2$ is N or C(R$^1$);

$X^3$ is N or C(R$^4$);

$X^4$ is N or C(R$^5$);

$X^5$ is N or C(R$^6$);

$X^6$ is N or C(R$^7$);

each $R^1$ is independently selected from the group consisting of hydrogen, halogen, —CN, —OH, —NO$_2$, optionally substituted alkyl, optionally substituted alkoxy, optionally substituted haloalkyl, and optionally substituted haloalkoxy;

each of $R^4$, $R^5$, $R^6$, and $R^7$ is independently selected from the group consisting of hydrogen, halogen, —CN, —OH, —NO$_2$, —N(R$^{13}$)—R$^{14}$, —C(=O)—N(R$^{13}$)—R$^{14}$, —NR$^{13}$C(=O)R$^{15}$, —C(=O)—O—R$^{13}$, —O—C(=O)—R$^{15}$, —SR$^{13}$, —S(=O)R$^{15}$, —S(=O)$_2$R$^{15}$, —N(R$^{13}$)S(=O)$_2$R$^{15}$, —S(=O)$_2$—N(R$^{13}$)—R$^{14}$, —C(=O)R$^{13}$, optionally substituted alkyl, optionally substituted cycloalkyl, optionally substituted heterocycloalkyl, optionally substituted alkoxy, optionally substituted haloalkyl, optionally substituted haloalkoxy, optionally substituted phenyl, and optionally substituted 5- or 6-membered heteroaryl;

or $R^5$ and $R^6$ are taken together with the atoms connecting $R^5$ and $R^6$ to form an optionally substituted heterocycloalkyl;

each of $R^{13}$ and $R^{14}$ is independently selected from the group consisting of hydrogen, optionally substituted alkyl, optionally substituted cycloalkyl, optionally substituted heterocycloalkyl, optionally substituted alkoxy, optionally substituted haloalkyl, optionally substituted haloalkoxy, optionally substituted phenyl, and optionally substituted 5- or 6-membered heteroaryl;

or $R^{13}$ and $R^{14}$, when on the same nitrogen atom, are taken together with the nitrogen atom to which they are attached to form an optionally substituted heterocycloalkyl;

$R^{15}$ is selected from the group consisting of optionally substituted alkyl, optionally substituted cycloalkyl, optionally substituted heterocycloalkyl, optionally substituted alkoxy, optionally substituted haloalkyl, optionally substituted haloalkoxy, optionally substituted phenyl, and optionally substituted 5- or 6-membered heteroaryl.

Any combination of the groups described above or below for the various variables is contemplated herein. For example, in some embodiments $X^1$ is N or C(R$^1$). In other embodiments $X^1$ is N. In some other embodiments, $X^1$ is C(R$^1$). In some embodiments, $X^2$ is N or C(R$^1$). In other embodiments $X^2$ is N. In some other embodiments, $X^2$ is C(R$^1$).

In some embodiments, $X^1$ is $C(R^1)$; and $X^2$ is $C(R^1)$.
In some embodiments, $X^1$ is N; and $X^2$ is $C(R^1)$.
In some embodiments, $X^1$ is $C(R^1)$; and $X^2$ is N.
In some embodiments, $X^1$ is N; and $X^2$ is N.
In some embodiments, $X^3$ is N; $X^4$ is $C(R^5)$; $X^5$ is $C(R^6)$; and $X^6$ is N or $C(R^7)$.
In some embodiments, $X^3$ is $C(R^4)$; $X^4$ is N; $X^5$ is $C(R^6)$; and $X^6$ is $C(R^7)$.
In some embodiments, $X^3$ is $C(R^4)$; $X^4$ is $C(R^5)$; $X^5$ is N; and $X^6$ is $C(R^7)$.
In some embodiments, $X^3$ is N or $C(R^4)$; $X^4$ is $C(R^5)$; $X^5$ is $C(R^6)$; and $X^6$ is N.
In some embodiments, $X^3$ is $C(R^4)$; $X^4$ is $C(R^5)$; $X^5$ is $C(R^6)$; and $X^6$ is $C(R^7)$.

In some embodiments, the compound of Formula I has the following structure of Formula II, or a pharmaceutically acceptable salt, solvate, tautomer, or N-oxide thereof:

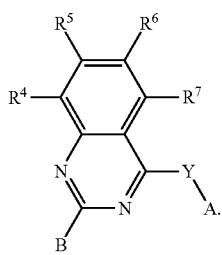

Formula II

In some embodiments, Y is selected from optionally substituted 5-, 6-, 7-, or 8-membered heterocyloalkyl, optionally substituted spiroheterocyloalkyl, and $-NR^2(CH_2)_nNR^3-$.

In some embodiments, Y is an optionally substituted 6-membered heterocyloalkyl.

In some embodiments, Y is an optionally substituted piperidinyl or optionally substituted piperazinyl.

In some embodiments, Y is

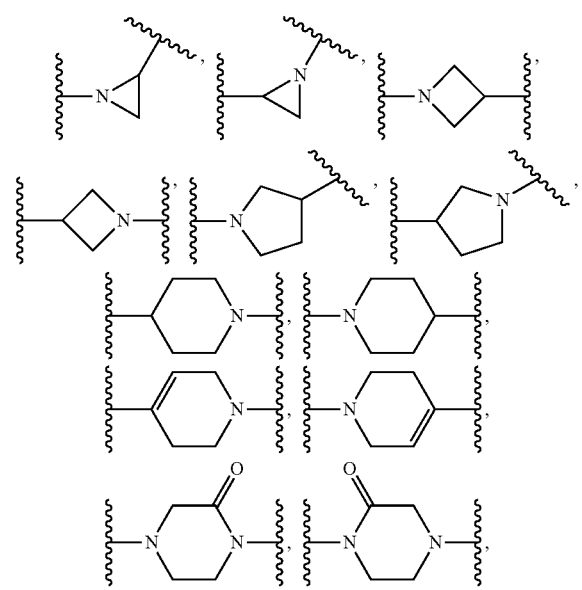

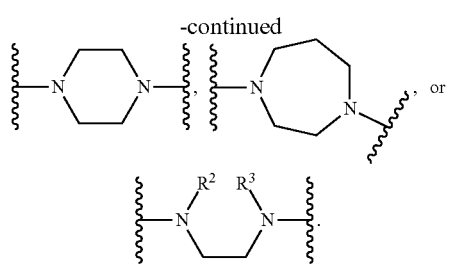

In some embodiments, the compound has the following structure of Formula III, or a pharmaceutically acceptable salt, solvate, tautomer, or N-oxide thereof:

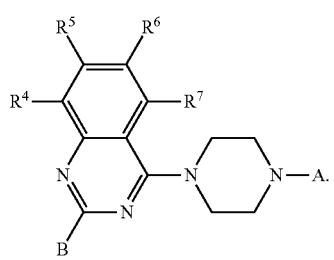

Formula III

In some embodiments, $R^4$ is hydrogen; and $R^7$ is hydrogen.

In some embodiments, the compound has the following structure of Formula IV, or a pharmaceutically acceptable salt, solvate, tautomer, or N-oxide thereof:

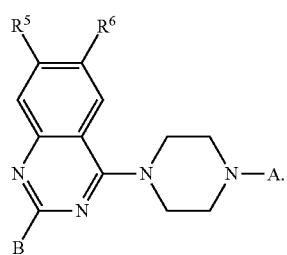

Formula IV

In some embodiments, the compound has the following structure of Formula V, or a pharmaceutically acceptable salt, solvate, tautomer, or N-oxide thereof:

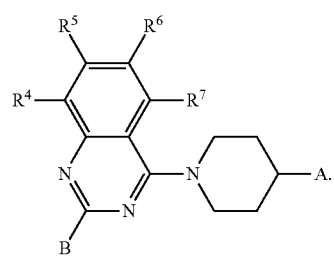

Formula V

In some embodiments, $R^4$ is hydrogen; and $R^7$ is hydrogen.

In some embodiments, the compound has the following structure of Formula VI, or a pharmaceutically acceptable salt, solvate, tautomer, or N-oxide thereof:

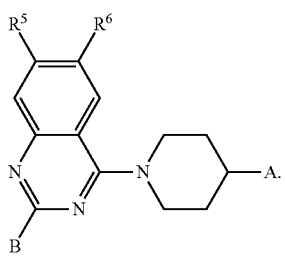

Formula VI

In some embodiments, A is selected from the group consisting of optionally substituted phenyl, optionally substituted naphthyl, optionally substituted furanyl, optionally substituted pyrrolyl, optionally substituted oxazolyl, optionally substituted thiazolyl, optionally substituted imidazolyl, optionally substituted pyrazolyl, optionally substituted triazolyl, optionally substituted tetrazolyl, optionally substituted isoxazolyl, optionally substituted isothiazolyl, optionally substituted oxadiazolyl, optionally substituted thiadiazolyl, optionally substituted pyridinyl, optionally substituted pyrimidinyl, optionally substituted pyrazinyl, optionally substituted pyridazinyl, optionally substituted triazinyl, optionally substituted quinolinyl, optionally substituted isoquinolinyl, optionally substituted quinazolinyl, optionally substituted quinoxalinyl, optionally substituted naphthyridinyl, optionally substituted indolyl, optionally substituted indazolyl, optionally substituted benzoxazolyl, optionally substituted benzisoxazolyl, optionally substituted benzofuranyl, benzothienyl, optionally substituted benzothiazolyl, optionally substituted benzimidazolyl, optionally substituted purinyl, optionally substituted cinnolinyl, optionally substituted phthalazinyl, and optionally substituted pteridinylene.

In some embodiments, A is selected from the group consisting of optionally substituted phenyl, optionally substituted pyridinyl, optionally substituted pyrimidinyl, optionally substituted pyrazinyl, optionally substituted pyridazinyl, and optionally substituted triazinyl.

In some embodiments, A is an optionally substituted phenyl.

In some embodiments, the compound has the following structure of Formula V, or a pharmaceutically acceptable salt, solvate, tautomer, or N-oxide thereof:

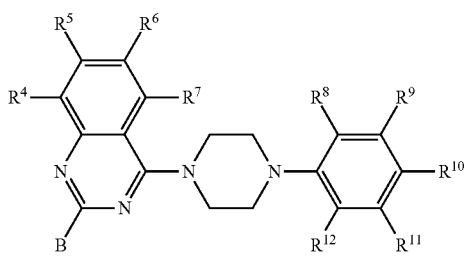

Formula VII wherein:
each of $R^8$, $R^9$, $R^{10}$, $R^{11}$ and $R^{12}$ is independently selected from the group consisting of hydrogen, halogen, —CN, —OH, —NO$_2$, —N($R^{13}$)—$R^{14}$, —C(=O)—N($R^{13}$)—$R^{14}$, —N$R^{13}$C(=O)$R^{15}$, —C(=O)—O—$R^{13}$, —O—C(=O)—$R^{15}$, —S$R^{13}$, —S(=O)$R^{15}$, —S(=O)$_2$$R^{15}$, —N($R^{13}$)S(=O)$_2$$R^{15}$, —S(=O)$_2$—N($R^{13}$)—$R^{14}$, —C(=O)$R^{13}$, optionally substituted alkyl, optionally substituted cycloalkyl, optionally substituted heterocycloalkyl, optionally substituted alkoxy, optionally substituted haloalkyl, optionally substituted haloalkoxy, optionally substituted phenyl, and optionally substituted 5- or 6-membered heteroaryl.

In some embodiments, at least two of $R^8$, $R^9$, $R^{10}$, $R^{11}$, and $R^{12}$ is hydrogen.

In some embodiments, $R^4$ is hydrogen; $R^7$ is hydrogen; and at least two of $R^8$, $R^9$, $R^{10}$, $R^{11}$, and $R^{12}$ is hydrogen.

In some embodiments, the compound has the following structure of Formula VI, or a pharmaceutically acceptable salt, solvate, tautomer, or N-oxide thereof:

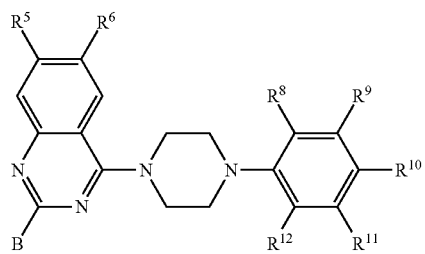

Formula VIII

In some embodiments, the compound has the following structure of Formula V, or a pharmaceutically acceptable salt, solvate, tautomer, or N-oxide thereof:

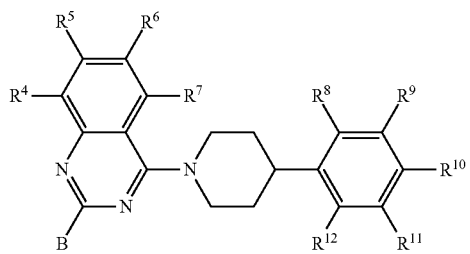

Formula IX wherein:
each of $R^8$, $R^9$, $R^{10}$, $R^{11}$, and $R^{12}$ is independently selected from the group consisting of hydrogen, halogen, —CN, —OH, —NO$_2$, —N($R^{13}$)—$R^{14}$, —C(=O)—N($R^{13}$)—$R^{14}$, —N$R^{13}$C(=O)$R^{15}$, —C(=O)—O—$R^{13}$, —O—C(=O)—$R^{15}$, —S$R^{13}$, —S(=O)$R^{15}$, —S(=O)$_2$$R^{15}$, —N($R^{13}$)S(=O)$_2$$R^{15}$, —S(=O)$_2$—N($R^{13}$)—$R^{14}$, —C(=O)$R^{13}$, optionally substituted alkyl, optionally substituted cycloalkyl, optionally substituted heterocycloalkyl, optionally substituted alkoxy, optionally substituted haloalkyl, optionally substituted haloalkoxy, optionally substituted phenyl, and optionally substituted 5- or 6-membered heteroaryl.

In some embodiments, at least two of $R^8$, $R^9$, $R^{10}$, $R^{11}$, and $R^{12}$ is hydrogen.

In some embodiments, $R^4$ is hydrogen; $R^7$ is hydrogen; and at least two of $R^8$, $R^9$, $R^{10}$, $R^{11}$, and $R^{12}$ is hydrogen.

In some embodiments, the compound has the following structure of Formula X, or a pharmaceutically acceptable salt, solvate, tautomer, or N-oxide thereof:

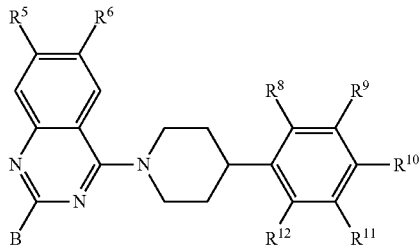

Formula X

In some embodiments, B is selected from the group consisting of optionally substituted phenyl, optionally substituted 5-membered heteroaryl, optionally substituted 6-membered heteroaryl, optionally substituted alkyl, optionally substituted cycloalkyl and optionally substituted heterocyloalkyl.

In some embodiments, B is an optionally substituted cycloalkyl.

In some embodiments, B is an optionally substituted cyclopropyl, an optionally substituted cyclobutyl, an optionally substituted cyclopentyl, or optionally substituted cyclohexyl.

In some embodiments, B is an optionally substituted cyclopropyl.

In some embodiments, B is an optionally cyclobutyl.

In some embodiments, B is methyl; ethyl; propyl; isopropyl; butyl; isobutyl; tert-butyl; vinyl; cyclopropylmethyl; benzyl; 2-(4-(2-methoxyphenyl)piperazin-1-yl)ethyl; N,N-dimethylaminoethyl; cyclopropyl; cyclobutyl; cyclopentyl; cyclohexyl; 2-methyl-cyclopropyl; 4-methyl-cyclohexyl; 4-methoxy-cyclohexyl; piperidin-4-yl; 1-methyl-piperidin-4-yl; tetrahydro-furan-3-yl, tetrahydro-pyran-4-yl; pyrrolidin-3-yl; 4-methyl-pyrrolidin-3-yl; 1,4-dimethyl-pyrrolidin-3-yl; 1-methyl-pyrrolidin-3-yl; 3-chloro-3-methylcyclobutyl; 3-methyl-cyclobutyl; 1-methyl-cyclopropyl; or 1-trifluoromethyl-cyclopropyl.

In some embodiments, the compound has the following structure of Formula XI, or a pharmaceutically acceptable salt, solvate, tautomer, or N-oxide thereof:

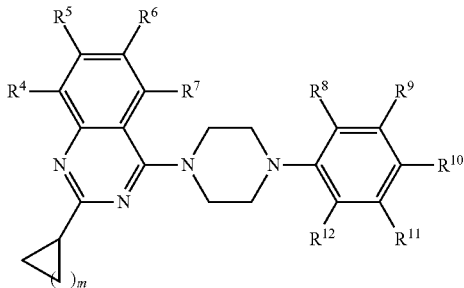

Formula XI wherein:
m is 1, 2, 3, 4, 5, 6, or 7.
In some embodiments, m is 1 or 2; at least two of $R^8$, $R^9$, $R^{10}$, $R^{11}$, and $R^{12}$ is hydrogen.
In some embodiments, $R^4$ is hydrogen; and $R^7$ is hydrogen.
In some embodiments, the compound has the following structure of Formula XII, or a pharmaceutically acceptable salt, solvate, tautomer, or N-oxide thereof:

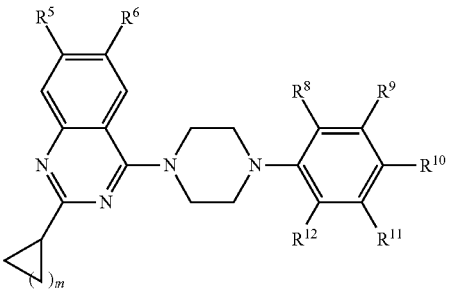

Formula XII

In some embodiments, the compound has the following structure of Formula XIII, or a pharmaceutically acceptable salt, solvate, tautomer, or N-oxide thereof:

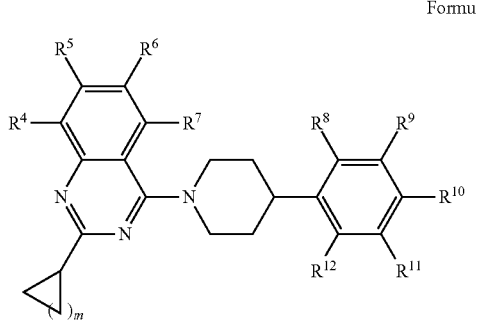

Formula XIII wherein:
m is 1, 2, 3, 4, 5, 6, or 7.
In some embodiments, m is 1 or 2; at least two of $R^8$, $R^9$, $R^{10}$, $R^{11}$, and $R^{12}$ is hydrogen.
In some embodiments, $R^4$ is hydrogen; and $R^7$ is hydrogen.
In some embodiments, the compound has the following structure of Formula XIV, or a pharmaceutically acceptable salt, solvate, tautomer, or N-oxide thereof:

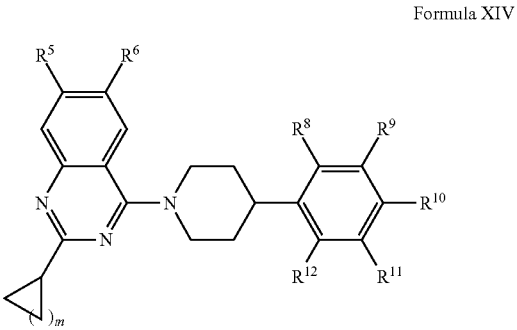

Formula XIV

In some embodiments, m is 1.
In some embodiments, m is 2.
In some embodiments, the compound is
2-cyclobutyl-6,7-dimethoxy-4-(4-(2-methoxyphenyl)piperazin-1-yl)quinazoline;
2-phenyl-6,7-dimethoxy-4-(4-(2-methoxyphenyl)piperazin-1-yl)quinazoline;

2-phenyl-6,7-dimethoxy-4-(4-(phenyl)piperazin-1-yl)quinazoline;
2-phenyl-6,7-dimethoxy-4-(4-(2-fluorophenyl)piperazin-1-yl)quinazoline;
2-phenyl-6,7-dimethoxy-4-(4-(4-fluorophenyl)piperazin-1-yl)quinazoline;
2-phenyl-6,7-dimethoxy-4-(4-(2-chlorophenyl)piperazin-1-yl)quinazoline;
2-phenyl-6-ethoxy-7-methoxy-4-(4-(2-methoxyphenyl)piperazin-1-yl)quinazoline;
2-phenyl-6-ethoxy-7-methoxy-4-(4-(phenyl)piperazin-1-yl)quinazoline;
2-phenyl-6-ethoxy-7-methoxy-4-(4-(2-fluorophenyl)piperazin-1-yl)quinazoline;
or a pharmaceutically acceptable salt, solvate, tautomer, or N-oxide thereof.

In some embodiments, the compound has the following structure, or a pharmaceutically acceptable salt, solvate, tautomer, or N-oxide thereof:

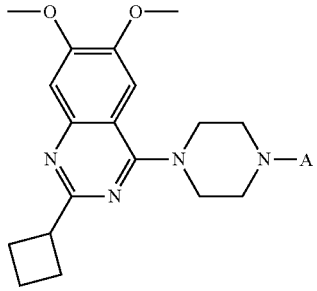

wherein,
A is phenyl, 2-methoxyphenyl, 3-methoxyphenyl, 4-methoxyphenyl, 2,4-dimethoxyphenyl, 2-methylphenyl, 2,6-dimethylphenyl, 2-fluorophenyl, 2-chlorophenyl, pyridin-2-yl, or 2-nitrophenyl.

In some embodiments, the compound has the following structure, or a pharmaceutically acceptable salt, solvate, tautomer, or N-oxide thereof:

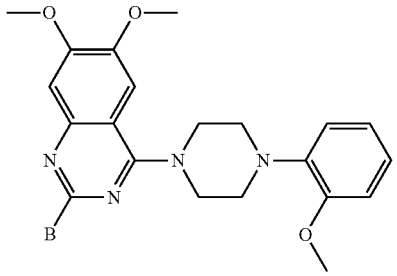

wherein:
B is hydrogen, methyl, ethyl, n-propyl, i-propyl, i-butyl, -vinyl, cyclopropyl, cyclobutyl, cyclopentyl, methylcyclopropyl, —CH$_2$Ph, —CH$_2$CH$_2$NMe$_2$, or

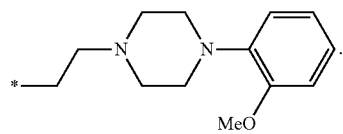 [SMILES: *CCN1CCC(c2ccccc2OC)CC1]

In some embodiments, the compound is
2-cyclobutyl-6,7-dimethoxy-4-(4-(2-methoxyphenyl)piperazin-1-yl)quinazoline;
2-cyclobutyl-6-methoxy-4-(4-(2-methoxyphenyl)piperazin-1-yl)quinazoline;
2-cyclobutyl-7-methoxy-4-(4-(2-methoxyphenyl)piperazin-1-yl)quinazoline;
2-cyclobutyl-4-(4-(2-methoxyphenyl)piperazin-1-yl)quinazoline;
6-cyclobutyl-8-(4-(2-methoxyphenyl)piperazin-1-yl)-[1,3]dioxolo[4,5-g]quinazoline;
2-cyclopropyl-6-methoxy-4-(4-(2-methoxyphenyl)piperazin-1-yl)quinazoline;
or a pharmaceutically acceptable salt, solvate, tautomer, or N-oxide thereof.

In some embodiments, the compound has the following structure, or a pharmaceutically acceptable salt, solvate, tautomer, or N-oxide thereof:

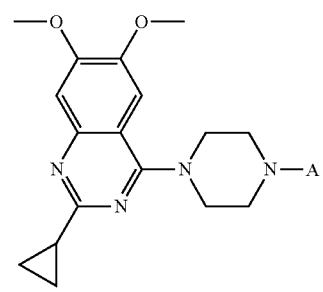

wherein,
A is hydrogen, 2-methoxyphenyl, 2-ethoxyphenyl, 2-chlorophenyl, —SO$_2$-phenyl, 4-methylbenzyl, 2-methoxybenzyl, benzoyl, and 2-methoxybenzoyl.

Any combination of the groups described above or below for the various variables is contemplated herein. Throughout the specification, groups and substituents thereof are chosen by one skilled in the field to provide stable moieties and compounds.

In one aspect, provided herein is a pharmaceutical composition comprising a compound of Formula I, or a pharmaceutically acceptable salt thereof, and a pharmaceutically acceptable excipient.

In some embodiments, the compound of Formula I, or a pharmaceutically acceptable salt thereof, is formulated for intravenous injection, subcutaneous injection, oral administration, inhalation, nasal administration, topical administration, ophthalmic administration or otic administration. In some embodiments, the compound of Formula I, or a pharmaceutically acceptable salt thereof, is formulated as (i.e. incorporated into) a tablet, a pill, a capsule, a liquid, an inhalant, a nasal spray solution, a suppository, a suspension, a gel, a solution, an ointment, a lotion, an eye drop or an ear drop In another aspect, described herein is a method of treating a disease, disorder or condition mediated by neurotensin and/or neurotensin receptor 1 in a subject in need thereof, which method comprises administering to the subject a therapeutically effective amount of a compound of Formula I, or a pharmaceutically acceptable salt thereof. In another aspect, described herein is a method of treating a disease in a subject mediated by neurotensin and/or neurotensin receptor 1, which method comprises administering to the subject a pharmaceutical composition comprising a compound of Formula I, or a pharmaceutically acceptable salt thereof. In some embodiments, the disease, disorder, condition is drug abuse. In some embodiments, the disease, disorder or condition is Parkinson's disease. In some embodiments, the disease is schizophrenia. In some embodiments, the disease, disorder or condition is pain.

In any of the aforementioned aspects are further embodiments in which: (a) the effective amount of the compound of Formula I, is systemically administered to the mammal; and/or (b) the effective amount of the compound is administered orally to the mammal; and/or (c) the effective amount of the compound is intravenously administered to the mammal; and/or (d) the effective amount of the compound is administered by inhalation; and/or (e) the effective amount of the compound is administered by nasal administration; or and/or (f) the effective amount of the compound is administered by injection to the mammal; and/or (g) the effective amount of the compound is administered topically to the mammal; and/or (h) the effective amount of the compound is administered by ophthalmic administration; and/or (i) the effective amount of the compound is administered rectally to the mammal; and/or (j) the effective amount is adminstered non-systemically or locally to the mammal.

In any of the aforementioned aspects are further embodiments comprising single administrations of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In any of the aforementioned aspects involving the administration of a compound of Formula I, or a pharmaceutically acceptable salt thereof, to a subject are further embodiments comprising administering at least one additional agent in addition to the administration of a compound having the structure of Formula I, or a pharmaceutically acceptable salt thereof. In various embodiments, the compound of Formula I and the additional agent are administered in any order, including simultaneously. In some embodiments, the compound of Formula I and the additional agent are administered to the subject in the same pharmaceutical composition or in separate pharmaceutical compositions.

In any of the embodiments disclosed herein, the subject is a human.

In some embodiments, compounds and compositions provided herein are administered to a human.

In some embodiments, compounds and compositions provided herein are orally administered.

In other embodiments, compounds provided herein are used for the formulation of a medicament for the modulation of the activity of the neurotensin 1 receptor in a subject.

Articles of manufacture, which include packaging material, a compound of Formula I, or a pharmaceutically acceptable salt thereof, within the packaging material, and a label that indicates that the compound or composition, or pharmaceutically acceptable salt, tautomers, pharmaceutically acceptable N-oxide, pharmaceutically active metabolite, pharmaceutically acceptable prodrug, or pharmaceutically acceptable solvate thereof, is used for the treatment of diseases or conditions that would benefit from modulation of the neurotensin 1 receptor, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description

BRIEF DESCRIPTION OF THE DRAWINGS

FIG. 1 illustrates the dose response of compound 315 in the NTR1 and NTR2 HCS, NTR1 β-Arrestin, and NTR1 $Ca^{2+}$ Flux Assays

DETAILED DESCRIPTION OF THE INVENTION

Neurotensin is a 13 amino acid neuropeptide that is implicated in the regulation of luteinizing hormone and prolactin release and has significant interaction with the dopaminergic system. Neurotensin was first isolated from extracts of bovine hypothalamus based on its ability to cause a visible vasodilation in the exposed cutaneous regions of anesthetized rats. Neurotensin is distributed throughout the central nervous system, with highest levels in the hypothalamus, amygdala and nucleus accumbens. It induces a variety of effects, including: analgesia, hypothermia and increased locomotor activity. It is also involved in regulation of dopamine pathways. In the periphery, neurotensin is found in endocrine cells of the small intestine, where it leads to secretion and smooth muscle contraction Neurotensin has been implicated in the modulation of dopamine signaling, and produces a spectrum of pharmacological effects resembling those of antipsychotic drugs, leading to the suggestion that neurotensin may be an endogenous neuroleptic. Neurotensin-deficient mice display defects in responses to several antipsychotic drugs consistent with the idea that neurotensin signaling is a key component underlying at least some antipsychotic drug actions. These mice exhibit modest defects in prepulse inhibition (PPI) of the startle reflex, a model that has been widely used to investigate antipsychotic drug action in animals. Antipsychotic drug administration augments PPI under certain conditions. Comparisons between normal and neurotensin-deficient mice revealed striking differences in the ability of different antipsychotic drugs to augment PPI. While the atypical antipsychotic drug clozapine augmented PPI normally in neurotensin-deficient mice, the antipsychotic haloperidol and the antipsychotic quetiapine were ineffective in these mice, in contrast to normal mice where these drugs significantly augmented PPI. These results suggest that certain antipsychotic drugs require neurotensin for at least some of their effects. Neurotensin-deficient mice also display defects in striatal activation following haloperidol, but not clozapine administration in comparison to normal wild type mice, indicating that striatal neurotensin is required for the full spectrum of neuronal responses to a subset of antipsychotic drugs.

Neurotensin is an endogenous neuropeptide involved in thermoregulation that can induce hypothermia and neuroprotection in experimental models of cerebral ischemia.

The neurotensin receptors are transmembrane receptors that bind the neurotransmitter neurotensin. Two of the receptors encoded by the NTSR1 and NTSR2 genes contain seven transmembrane helices and are G protein coupled. The third receptor has a single transmembrane domain and is encoded by the SORT1gene.

Addiction is the continued repetition of a behavior despite adverse consequences, or a neurological impairment leading to such behaviors. Addictions can include, but are not limited to, drug abuse, exercise addiction, food addiction, sexual addiction, computer addiction and gambling. Classic hallmarks of addiction include impaired control over substances or behavior, preoccupation with substance or behavior, continued use despite consequences, and denial. Habits and patterns associated with addiction are typically characterized by immediate gratification (short-term reward), coupled with delayed deleterious effects (long-term costs). Some drugs associated with addiction include alcohol, substituted amphetamines (e.g. methamphetamine), barbiturates, benzodiazepines (particularly alprazolam, temazepam, diazepam and clonazepam), cocaine, methaqualone, and opioids.

Neurotensin (NT) receptors are expressed on dopaminergic neurological pathways associated with reward, and the neurotensin receptor 1 (NTR1) is a therapeutic target for the treatment of methamphetamine abuse. In particular, peptide-based NTR1 agonists produce behaviors that are opposite to the psychostimulant effects observed with psychoactive drugs, such as but not limited to methamphetamine, such as hyperactivity, neurotoxicity, psychotic episodes, and cognitive deficits.

NTR1 is a G protein coupled receptor (GPCR). Two distinct, interdependent paradigms are associated with GPCR signaling. In addition to the well-defined signaling cascades involving heterotrimeric G proteins, recent advances in receptor pharmacology have identified the importance of β-arrestins in regulating alternative biochemical cascades that produce their own unique biological effects. For example, in a mouse model, Allen et al developed a series of β-arrestin-2 biased agonists for the D(2)R with antipsychotic properties, and most importantly, a reduced propensity to induce catalepsy like standard neuroleptic antagonists (Allen et al. Discovery of β-Arrestin-Biased Dopamine D2 Ligands for Probing Signal Transduction Pathways Essential for Antipsychotic Efficacy. *Proc. Natl. Acad. Sci. USA.* 2011, 108, 18488-18493; Rajagopal et al. Teaching old receptors new tricks: biasing seven-transmembrane receptors. *Nat. Rev. Drug Discovery* 2010, 9, 373-386.). Studies with those biased compounds illustrate how ligand directed signaling bias, in this case favoring β-arrestin, can ameliorate undesirable biological outcomes. Downstream modulators of β-arrestin/GPCR signaling are less characterized than their G protein counterparts, and, due to their potential as targets for producing new medical therapies are the subjects of increasing numbers of investigations. Recognized β-arrestin partners include the proteins Src, ERK, and Jnk. Their agonist-induced interactions with β-arrestin are associated with clathrin-compartmentalized signaling and the accumulation of ligand activated β-arrestin/GPCR complexes in clathrin coated pits. The determination as to whether a GPCR ligand is biased towards or against β-arrestin may consequently be evaluated by following these biochemical processes.

In one aspect, compounds described herein are used in the treatment of a disease or condition in a subject that is mediated by neurotensin and/or neurotensin receptor 1.

In one aspect, compounds described herein are used in the treatment of a neurological disease or condition mediated by neurotensin and/or neurotensin receptor 1. In some embodiments, the neurological disease or condition is acute stress disorder, alcohol abuse, alcohol dependence, alcohol withdrawal, alcoholic hallucinosis, alzheimer's disease, amphetamine dependence, amphetamine withdrawal psychosis, anorexia nervosa, anxiety disorder, anxiolytic-related disorders, asperger syndrome, attention deficit disorder, attention deficit hyperactivity disorder, autism, barbiturate dependence, benzodiazepine dependence, benzodiazepine misuse, benzodiazepine withdrawal, bipolar disorder, bipolar I disorder, bipolar II disorder, bulimia nervosa, cannabis dependence, catatonic disorder, catatonic schizophrenia, cocaine dependence, cocaine intoxication, cotard delusion, cyclothymia, delirium tremens, depressive disorder, generalized anxiety disorder, grandiose delusions, hallucinogen-related disorder, hallucinogen persisting perception disorder, huntington's disease, impulse control disorder, intermittent explosive disorder, major depressive disorder, major depressive episode, manic episode, minor depressive disorder, minor depressive episode, munchausen's syndrome, neuroleptic-related disorder, night eating syndrome, obsessive-compulsive disorder (OCD), opioid dependence, pain disorder, panic disorder, paranoid personality disorder, parasomnia, parkinson's disease, partner relational problem, pathological gambling, phencyclidine (or phencyclidine-like)-related disorder, residual schizophrenia, sadomasochism, schizoaffective disorder, schizoid personality disorder, schizophrenia, schizophreniform disorder, schizotypal personality disorder, social anxiety disorder, social phobia, substance-related disorder, tardive dyskinesia, or tourette syndrome.

In some embodiments, compounds described herein are useful in the treatment of amphetamine addiction. In some embodiments, the amphetamine is Methamphetamine, ethylamphetamine, propylamphetamine, isopropylamphetamine, phentermine, phenylpropanolamine (PPA), Cathine, Cathinone, Ortetamine, 2-Fluoroamphetamine (2-FA), 3-Methylamphetamine (3-MA), 3-Fluoroamphetamine (3-FA), Norfenfluramine, 4-Methylamphetamine (4-MA), para-Methoxyamphetamine (PMA), para-Ethoxyamphetamine, 4-Methylthioamphetamine (4-MTA), Norpholedrine (α-Me-TRA), para-Bromoamphetamine (PBA, 4-BA), para-Chloroamphetamine (PCA, 4-CA), para-Fluoroamphetamine (PFA, 4-FA, 4-FMP), para-Iodoamphetamine (PIA, 4-IA), Dimethylamphetamine, Benzphetamine, Selegiline, Mephentermine, Phenpentermine, Ephedrine (EPH), Pseudoephedrine (PSE), Methcathinone, Ethcathinone, Clortermine, Methoxymethylamphetamine (MMA), Fenfluramine, Dexfenfluramine, 4-Methylmethamphetamine (4-MMA), Para-methoxymethamphetamine (PMMA), para-Methoxyethylamphetamine (PMEA), Pholedrine, Chlorphentermine, para-Fluoromethamphetamine (PFMA, 4-FMA), Xylopropamine, alpha-Methyldopamine (alpha-Me-DA), Methylenedioxyamphetamine (MDA), Dimethoxyamphetamine (DMA), Nordefrin (alpha-Me-NE), Oxilofrine, Aleph, Dimethoxybromoamphetamine (DOB), Dimethoxychloroamphetamine (DOC), Dimethoxyfluoroethylamphetamine (DOEF), Dimethoxyethylamphetamine (DOET), Dimethoxyfluoroamphetamine (DOF), Dimethoxyiodoamphetamine (DOI), Dimethoxymethylamphetamine (DOM), Dimethoxynitroamphetamine (DON), Dimethoxypropylamphetamine (DOPR), Dimethoxytrifluoromethylamphetamine (DOTFM), Methylenedioxymethamphetamine (MDMA), Methylenedioxyethylamphetamine (MDEA), Methylenedioxyhydroxyamphetamine (MDOH), 2-Methyl- MDA, 5-Methyl-MDA, Methoxymethylenedioxyamphetamine (MMDA), Trimethoxyamphetamine (TMA), Dimethylcathinone, Diethylcathinone, Bupropion, Mephedrone (4-MMC), Methedrone (PMMC), Brephedrone (4-BMC), Flephedrone (4-FMC). In some embodiments, the amphetamine is methamphetamine.

In certain instances, compounds described herein are used in the treatment of stroke/cerebral ischemia. In certain instances, compounds described herein reduce infarct formation and/or brain cell death. In certain instances, compounds described herein increase patient recovery post-stroke.

In a further aspect, compounds described herein are used in the treatment of neurotensin-dependent pathologies.

In one aspect, compounds described herein are used in the treatment of neuropsychiatric disorders mediated by neurotensin and/or neurotensin receptor 1, for example substance abuse, psychosis, schizophrenia, Parkinson's disease, attention deficit hyperactivity disorder (ADHD), and pain. In some embodiments, compounds described herein are used in the treatment of schizophrenia. In some embodiments, compounds described herein are used in the treatment of Parkinson's disease. In some embodiments, compounds described herein are used in the treatment of pain. In some embodiments, the pain is acute pain or chronic pain. In some embodiments, the pain is neuropathic pain, e.g., chronic neuropathic pain.

In some embodiments, the neuropsychiatric disorder is substance abuse and the substance of abuse is, for example an opiate (e.g., heroin, morphine, codeine), a psychomotor stimulant (e.g., amphetamine, methamphetamine (meth), ephedrine, or pseudoephedrine), a cannabinoids (e.g., tetrahydrocannabinol (THC)), alcohol, nicotine, or a hallucinogen.

In some embodiments, the neuropsychiatric disorder is an eating disorder such as bulimia nervosa, binge eating disorder, compulsive overeating, anxiety, sleep disorder, or bipolar disorder. In some embodiments, compounds described herein are used to reduce food intake and/or increase satiety.

In one other aspect compounds described herein are used in the treatment of a neurodegenerative disease mediated by neurotensin and/or neurotensin receptor 1, for example, Alzheimer's disease, Hungtinton's disease, or Amyotrophic Lateral Sclerosis (ALS or Lou Gehrig's disease).

In one other aspect, compounds described herein are used in the treatment of cancer. In some embodiments, the cancer is a solid tumor. In some embodiments, the cancer is bladder cancer, colon cancer, brain cancer, breast cancer, bone cancer, endometrial cancer, heart cancer, kidney cancer, lung cancer, liver cancer, uterine cancer, ovarian cancer, pancreatic cancer, prostate cancer, thyroid cancer, or skin cancer In one other aspect, compounds described herein are used in the treatment of cardiovascular disorders such as, but not limited to, hypertension, coronary artery disease, cardiomyopathy, or inflammatory heart disease.

Compounds

In one aspect, provided herein is a compound of Formula I, or a pharmaceutically acceptable salt, solvate, tautomer, or N-oxide thereof:

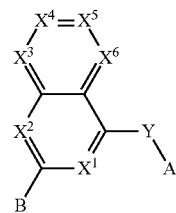

Formula I wherein:
A is $A^1$, —O-$A^1$, —NH-$A^1$, —C(=O)-$A^1$, or —S(=O)$_2$-$A^1$; $A^1$ is selected from the group consisting of optionally substituted phenyl, optionally substituted naphthyl, optionally substituted 5-membered heteroaryl, optionally substituted 6-membered heteroaryl, optionally substituted 9-membered heteroaryl and optionally substituted 10-membered heteroaryl; wherein optional substituents for A are selected from the group consisting of hydrogen, halogen, —CN, —OH, —NO$_2$, —N($R^{13}$)—$R^{14}$, —C(=O)—N($R^{13}$)—$R^{14}$, —N$R^{13}$C(=O)$R^{15}$, —C(=O)—O—$R^{13}$, —O—C(=O)—$R^{15}$, —Se, —S(=O)$R^{15}$, —S(=O)$_2R^{15}$, —N($R^{13}$)S(=O)$_2R^{15}$, —S(=O)$_2$—N($R^{13}$)—$R^{14}$, —C(=O)$R^{13}$, optionally substituted alkyl, optionally substituted cycloalkyl, optionally substituted heterocycloalkyl, optionally substituted alkoxy, optionally substituted haloalkyl, optionally substituted haloalkoxy, optionally substituted phenyl, and optionally substituted 5- or 6-membered heteroaryl;

B is selected from the group consisting of optionally substituted phenyl, optionally substituted 5-membered heteroaryl, optionally substituted 6-membered heteroaryl, optionally substituted alkyl, optionally substituted cycloalkyl and optionally substituted heterocycloalkyl.

Y is selected from optionally substituted heterocyloalkyl, optionally substituted spiroheterocyloalkyl, optionally substituted with alkyl, and —NR$^2$(CH$_2$)NR$^3$—;

n is 2, 3, 4, 5, or 6;

$R^2$ is H or alkyl;

$R^3$ is H or alkyl;

$X^1$ is N or C($R^1$);

$X^2$ is N or C($R^1$);

$X^3$ is N or C($R^4$);

$X^4$ is N or C($R^5$);

$X^5$ is N or C($R^6$);

$X^6$ is N or C($R^7$);

each $R^1$ is independently selected from the group consisting of hydrogen, halogen, —CN, —OH, —NO$_2$, optionally substituted alkyl, optionally substituted alkoxy, optionally substituted haloalkyl, and optionally substituted haloalkoxy;

each of $R^4$, $R^5$, $R^6$, and $R^7$ is independently selected from the group consisting of hydrogen, halogen, —CN, —OH, —NO$_2$, —N($R^{13}$)—$R^{14}$, —C(=O)—N($R^{13}$)—$R^{14}$, —N$R^{13}$C(=O)$R^{15}$, —C(=O)—O—$R^{13}$, —O—C(=O)—$R^{15}$, —S$R^{13}$, —S(=O)$R^{15}$, —S(=O)$_2R^{15}$, —N($R^{13}$)S(=O)$_2R^{15}$, —S(=O)$_2$—N($R^{13}$)—$R^{14}$, —C(=O)$R^{13}$, optionally substituted alkyl, optionally substituted cycloalkyl, optionally substituted heterocycloalkyl, optionally substituted alkoxy, optionally substituted haloalkyl, optionally substituted haloalkoxy, optionally substituted phenyl, and optionally substituted 5- or 6-membered heteroaryl;

or R⁵ and R⁶ are taken together with the atoms connecting R⁵ and R⁶ to form an optionally substituted heterocycloalkyl;

each of R¹³ and R¹⁴ is independently selected from the group consisting of hydrogen, optionally substituted alkyl, optionally substituted cycloalkyl, optionally substituted heterocycloalkyl, optionally substituted alkoxy, optionally substituted haloalkyl, optionally substituted haloalkoxy, optionally substituted phenyl, and optionally substituted 5- or 6-membered heteroaryl;

or R¹³ and R¹⁴, when on the same nitrogen atom, are taken together with the nitrogen atom to which they are attached to form an optionally substituted heterocycloalkyl;

R¹⁵ is selected from the group consisting of optionally substituted alkyl, optionally substituted cycloalkyl, optionally substituted heterocycloalkyl, optionally substituted alkoxy, optionally substituted haloalkyl, optionally substituted haloalkoxy, optionally substituted phenyl, and optionally substituted 5- or 6-membered heteroaryl.

Any combination of the groups described above or below for the various variables is contemplated herein. For example, in some embodiments X¹ is N or C(R¹). In other embodiments X¹ is N. In some other embodiments, X¹ is C(R¹). In some embodiments, X² is N or C(R¹). In other embodiments X² is N. In some other embodiments, X² is C(R¹).

In some embodiments, X¹ is C(R¹); and X² is C(R¹).
In some embodiments, X¹ is N; and X² is C(R¹).
In some embodiments, X¹ is C(R¹); and X² is N.
In some embodiments, X¹ is N; and X² is N.
In some embodiments, X³ is N; X⁴ is C(R⁵); X⁵ is C(R⁶); and X⁶ is N or C(R⁷).
In some embodiments, X³ is C(R⁴); X⁴ is N; X⁵ is C(R⁶); and X⁶ is C(R⁷).
In some embodiments, X³ is C(R⁴); X⁴ is C(R⁵); X⁵ is N; and X⁶ is C(R⁷).
In some embodiments, X³ is N or C(R⁴); X⁴ is C(R⁵); X⁵ is C(R⁶); and X⁶ is N.
In some embodiments, X³ is C(R⁴); X⁴ is C(R⁵); X⁵ is C(R⁶); and X⁶ is C(R⁷).

In some embodiments, the compound of Formula I has the following structure of Formula II, or a pharmaceutically acceptable salt, solvate, tautomer, or N-oxide thereof:

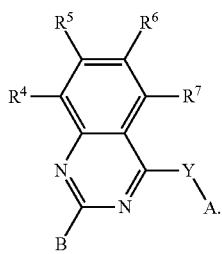

Formula II

In some embodiments, Y is selected from optionally substituted 5-, 6-, 7-, or 8-membered heterocyloalkyl, optionally substituted spiroheterocyloalkyl, and —NR²(CH₂)ₙNR³—.

In some embodiments, Y is an optionally substituted 6-membered heterocyloalkyl.

In some embodiments, Y is an optionally substituted piperidinyl or optionally substituted piperazinyl.

In some embodiments, Y is

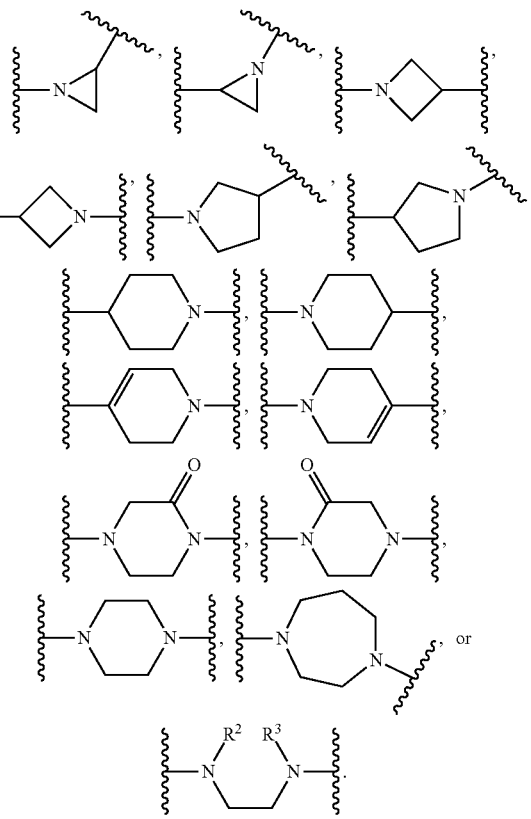

In some embodiments, Y is

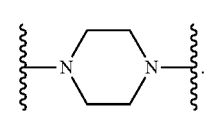

In some embodiments, Y is

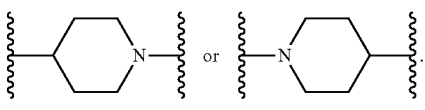

In some embodiments, Y is

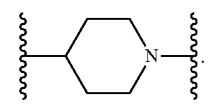

In some embodiments, Y is

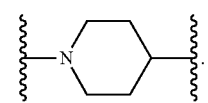

In some embodiments, the compound has the following structure of Formula III, or a pharmaceutically acceptable salt, solvate, tautomer, or N-oxide thereof:

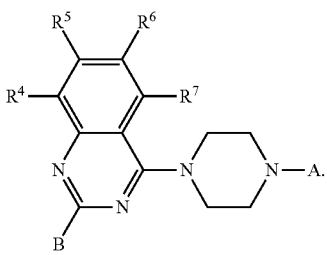

Formula III

In some embodiments, $R^4$ is hydrogen; and $R^7$ is hydrogen.

In some embodiments, the compound has the following structure of Formula IV, or a pharmaceutically acceptable salt, solvate, tautomer, or N-oxide thereof:

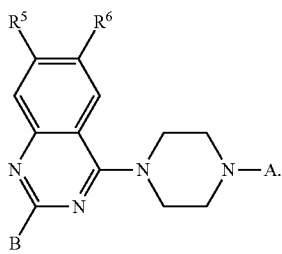

Formula IV

In some embodiments, the compound has the following structure of Formula V, or a pharmaceutically acceptable salt, solvate, tautomer, or N-oxide thereof:

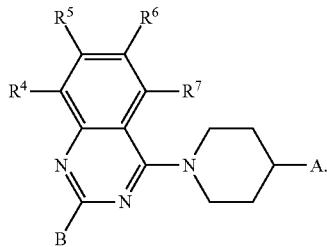

Formula V

In some embodiments, $R^4$ is hydrogen; and $R^7$ is hydrogen.

In some embodiments, the compound has the following structure of Formula VI, or a pharmaceutically acceptable salt, solvate, tautomer, or N-oxide thereof:

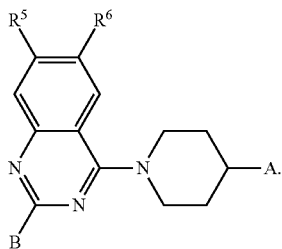

Formula VI

In some embodiments, A is selected from the group consisting of optionally substituted phenyl, optionally substituted naphthyl, optionally substituted furanyl, optionally substituted pyrrolyl, optionally substituted oxazolyl, optionally substituted thiazolyl, optionally substituted imidazolyl, optionally substituted pyrazolyl, optionally substituted triazolyl, optionally substituted tetrazolyl, optionally substituted isoxazolyl, optionally substituted isothiazolyl, optionally substituted oxadiazolyl, optionally substituted thiadiazolyl, optionally substituted pyridinyl, optionally substituted pyrimidinyl, optionally substituted pyrazinyl, optionally substituted pyridazinyl, optionally substituted triazinyl, optionally substituted quinolinyl, optionally substituted isoquinolinyl, optionally substituted quinazolinyl, optionally substituted quinoxalinyl, optionally substituted naphthyridinyl, optionally substituted indolyl, optionally substituted indazolyl, optionally substituted benzoxazolyl, optionally substituted benzisoxazolyl, optionally substituted benzofuranyl, benzothienyl, optionally substituted benzothiazolyl, optionally substituted benzimidazolyl, optionally substituted purinyl, optionally substituted cinnolinyl, optionally substituted phthalazinyl, and optionally substituted pteridinylene.

In some embodiments, A is selected from the group consisting of optionally substituted phenyl, optionally substituted pyridinyl, optionally substituted pyrimidinyl, optionally substituted pyrazinyl, optionally substituted pyridazinyl, and optionally substituted triazinyl.

In some embodiments, A is an optionally substituted phenyl.

In some embodiments, the compound has the following structure of Formula VII, or a pharmaceutically acceptable salt, solvate, tautomer, or N-oxide thereof:

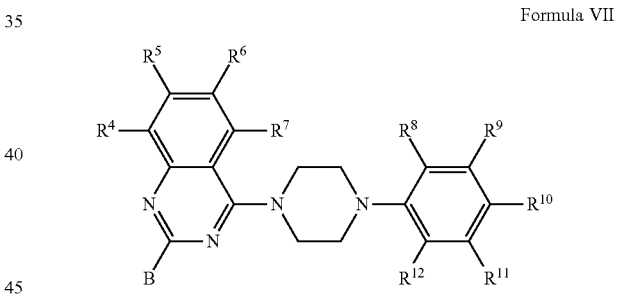

Formula VII wherein:
each of $R^8$, $R^9$, $R^{10}$, $R^{11}$, and $R^{12}$ is independently selected from the group consisting of hydrogen, halogen, —CN, —OH, —NO$_2$, —N(R$^{13}$)—R$^{14}$, —C(=O)—N(R$^{13}$)—R$^{14}$, —NR$^{13}$C(=O)R$^{15}$, —C(=O)—O—R$^{13}$, —O—C(=O)—R$^{15}$, —SR$^{13}$, —S(=O)R$^{15}$, —S(=O)$_2$R$^{15}$, —N(R$^{13}$)S(=O)$_2$R$^{15}$, —S(=O)$_2$—N(R$^{13}$)—R$^{14}$, —C(=O)R$^{13}$, optionally substituted alkyl, optionally substituted cycloalkyl, optionally substituted heterocycloalkyl, optionally substituted alkoxy, optionally substituted haloalkyl, optionally substituted haloalkoxy, optionally substituted phenyl, and optionally substituted 5- or 6-membered heteroaryl.

In some embodiments, at least two of $R^8$, $R^9$, $R^{10}$, $R^{11}$, and $R^{12}$ is hydrogen.

In some embodiments, $R^4$ is hydrogen; $R^7$ is hydrogen; and at least two of $R^8$, $R^9$, $R^{10}$, $R^{11}$, and $R^{12}$ is hydrogen.

In some embodiments, the compound has the following structure of Formula VIII, or a pharmaceutically acceptable salt, solvate, tautomer, or N-oxide thereof:

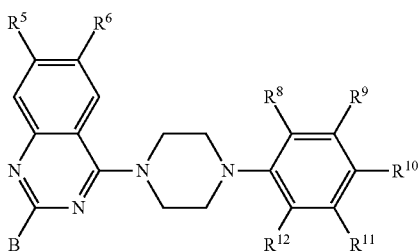

Formula VIII

In some embodiments, the compound has the following structure of Formula IX, or a pharmaceutically acceptable salt, solvate, tautomer, or N-oxide thereof:

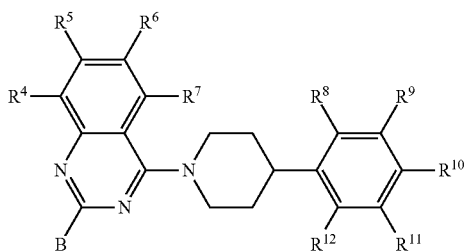

Formula IX wherein:
each of $R^8$, $R^9$, $R^{10}$, $R^{11}$, and $R^{12}$ is independently selected from the group consisting of hydrogen, halogen, —CN, —OH, —NO$_2$, —N(R$^{13}$)—R$^{14}$, —C(=O)—N(R$^{13}$)—R$^{14}$, —NR$^{13}$C(=O)R$^{15}$, —C(=O)—O—R$^{13}$, —O—C(=O)—R$^{15}$, —SR$^{13}$, —S(=O)R$^{15}$, —S(=O)$_2$R$^{15}$, —N(R$^{13}$)S(=O)$_2$R$^{15}$, —S(=O)$_2$—N(R$^{13}$)—R$^{14}$, —C(=O)R$^{13}$, optionally substituted alkyl, optionally substituted cycloalkyl, optionally substituted heterocycloalkyl, optionally substituted alkoxy, optionally substituted haloalkyl, optionally substituted haloalkoxy, optionally substituted phenyl, and optionally substituted 5- or 6-membered heteroaryl.

In some embodiments, at least two of $R^8$, $R^9$, $R^{10}$, $R^{11}$, and $R^{12}$ is hydrogen.

In some embodiments, $R^4$ is hydrogen; $R^7$ is hydrogen; and at least two of $R^8$, $R^9$, $R^{10}$, $R^{11}$, and $R^{12}$ is hydrogen.

In some embodiments, the compound has the following structure of Formula X, or a pharmaceutically acceptable salt, solvate, tautomer, or N-oxide thereof:

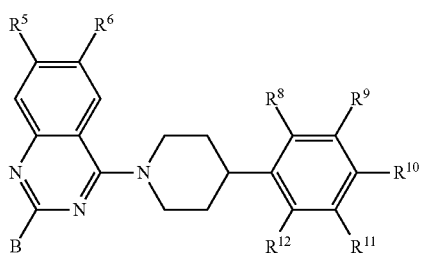

Formula X

In some embodiments, B is selected from the group consisting of optionally substituted phenyl, optionally substituted 5-membered heteroaryl, optionally substituted 6-membered heteroaryl, optionally substituted alkyl, optionally substituted cycloalkyl and optionally substituted heterocyloalkyl.

In some embodiments, B is an optionally substituted cycloalkyl.

In some embodiments, B is an optionally substituted cyclopropyl, an optionally substituted cyclobutyl, an optionally substituted cyclopentyl, or optionally substituted cyclohexyl.

In some embodiments, B is an optionally substituted cyclopropyl.

In some embodiments, B is an optionally cyclobutyl.

In some embodiments, B is methyl; ethyl; propyl; isopropyl; butyl; isobutyl; tert-butyl; vinyl; cyclopropylmethyl; benzyl; 2-(4-(2-methoxyphenyl)piperazin-1-yl)ethyl; N,N-dimethylaminoethyl; cyclopropyl; cyclobutyl; cyclopentyl; cyclohexyl; 2-methyl-cyclopropyl; 4-methyl-cyclohexyl; 4-methoxy-cyclohexyl; piperidin-4-yl; 1-methyl-piperidin-4-yl; tetrahydro-furan-3-yl, tetrahydro-pyran-4-yl; pyrrolidin-3-yl; 4-methyl-pyrrolidin-3-yl; 1,4-dimethyl-pyrrolidin-3-yl; 1-methyl-pyrrolidin-3-yl; 3-chloro-3-methylcyclobutyl; 3-methyl-cyclobutyl; 1-methyl-cyclopropyl; or 1-trifluoromethyl-cyclopropyl.

In some embodiments, the compound has the following structure of Formula XI, or a pharmaceutically acceptable salt, solvate, tautomer, or N-oxide thereof:

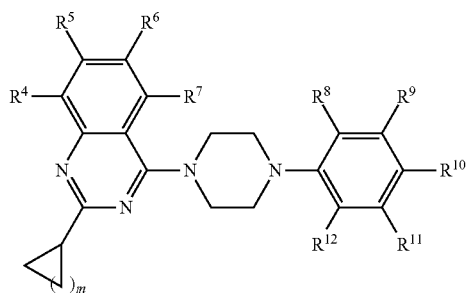

Formula XI wherein:
m is 1, 2, 3, 4, 5, 6, or 7.

In some embodiments, m is 1 or 2; at least two of $R^8$, $R^9$, $R^{10}$, $R^{11}$, and $R^{12}$ is hydrogen.

In some embodiments, $R^4$ is hydrogen; and $R^7$ is hydrogen.

In some embodiments, the compound has the following structure of Formula XII, or a pharmaceutically acceptable salt, solvate, tautomer, or N-oxide thereof:

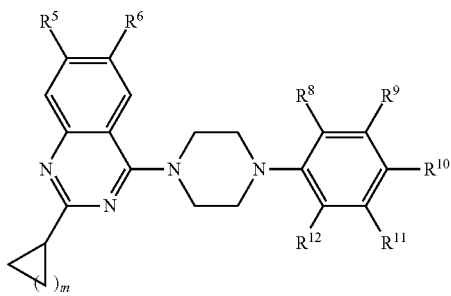

Formula XII

In some embodiments, the compound has the following structure of Formula XIII, or a pharmaceutically acceptable salt, solvate, tautomer, or N-oxide thereof:

Formula XIII

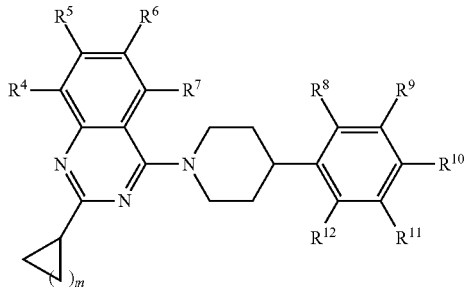

wherein:
m is 1, 2, 3, 4, 5, 6, or 7.

In some embodiments, m is 1 or 2; at least two of $R^8$, $R^9$, $R^{10}$, $R^{11}$, and $R^{12}$ is hydrogen.

In some embodiments, $R^4$ is hydrogen; and $R^7$ is hydrogen.

In some embodiments, the compound has the following structure of Formula XIV, or a pharmaceutically acceptable salt, solvate, tautomer, or N-oxide thereof:

Formula XIV

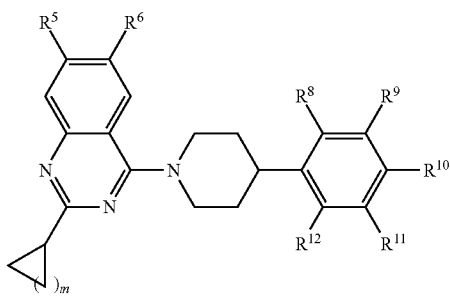

In some embodiments, m is 1.
In some embodiments, m is 2.
In some embodiments, the compound is
2-cyclobutyl-6,7-dimethoxy-4-(4-(2-methoxyphenyl)piperazin-1-yl)quinazoline;
2-phenyl-6,7-dimethoxy-4-(4-(2-methoxyphenyl)piperazin-1-yl)quinazoline;
2-phenyl-6,7-dimethoxy-4-(4-(phenyl)piperazin-1-yl)quinazoline;
2-phenyl-6,7-dimethoxy-4-(4-(2-fluorophenyl)piperazin-1-yl)quinazoline;
2-phenyl-6,7-dimethoxy-4-(4-(4-fluorophenyl)piperazin-1-yl)quinazoline;
2-phenyl-6,7-dimethoxy-4-(4-(2-chlorophenyl)piperazin-1-yl)quinazoline;
2-phenyl-6-ethoxy-7-methoxy-4-(4-(2-methoxyphenyl)piperazin-1-yl)quinazoline;
2-phenyl-6-ethoxy-7-methoxy-4-(4-(phenyl)piperazin-1-yl)quinazoline;
2-phenyl-6-ethoxy-7-methoxy-4-(4-(2-fluorophenyl)piperazin-1-yl)quinazoline;
or a pharmaceutically acceptable salt, solvate, tautomer, or N-oxide thereof.

In some embodiments, the compound has the following structure, or a pharmaceutically acceptable salt, solvate, tautomer, or N-oxide thereof:

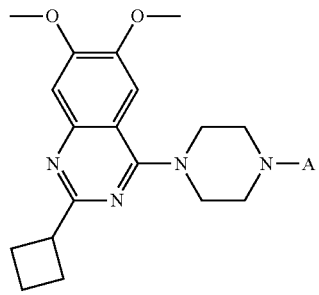

wherein,
A is phenyl, 2-methoxyphenyl, 3-methoxyphenyl, 4-methoxyphenyl, 2,4-dimethoxyphenyl, 2-methylphenyl, 2,6-dimethylphenyl, 2-fluorophenyl, 2-chlorophenyl, pyridin-2-yl, or 2-nitrophenyl.

In some embodiments, the compound has the following structure, or a pharmaceutically acceptable salt, solvate, tautomer, or N-oxide thereof:

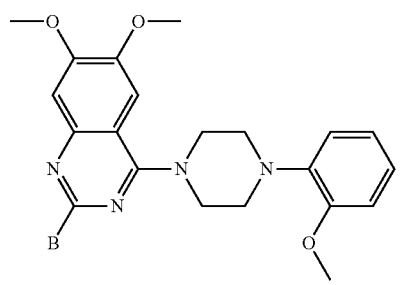

wherein:
B is hydrogen, methyl, ethyl, n-propyl, i-propyl, i-butyl, -vinyl, cyclopropyl, cyclobutyl, cyclopentyl, methylcyclopropyl, —CH$_2$Ph, —CH$_2$CH$_2$NMe$_2$, or

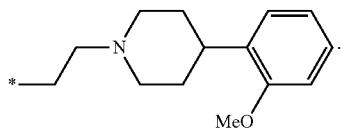

In some embodiments, the compound is
2-cyclobutyl-6,7-dimethoxy-4-(4-(2-methoxyphenyl)piperazin-1-yl)quinazoline;
2-cyclobutyl-6-methoxy-4-(4-(2-methoxyphenyl)piperazin-1-yl)quinazoline;
2-cyclobutyl-7-methoxy-4-(4-(2-methoxyphenyl)piperazin-1-yl)quinazoline;
2-cyclobutyl-4-(4-(2-methoxyphenyl)piperazin-1-yl)quinazoline;
6-cyclobutyl-8-(4-(2-methoxyphenyl)piperazin-1-yl)-[1,3]dioxolo[4,5-g]quinazoline;
2-cyclopropyl-6-methoxy-4-(4-(2-methoxyphenyl)piperazin-1-yl)quinazoline;
or a pharmaceutically acceptable salt, solvate, tautomer, or N-oxide thereof.

In some embodiments, the compound has the following structure, or a pharmaceutically acceptable salt, solvate, tautomer, or N-oxide thereof:

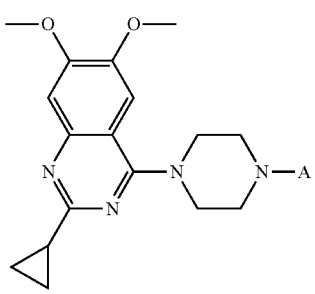

wherein,

A is hydrogen, 2-methoxyphenyl, 2-ethoxyphenyl, 2-chlorophenyl, —SO₂-phenyl, 4-methylbenzyl, 2-methoxybenzyl, benzoyl, and 2-methoxybenzoyl.

In one aspect, described herein is a compound having the following structure, or a pharmaceutically acceptable salt, polymorph, solvate, tautomer, or N-oxide thereof:

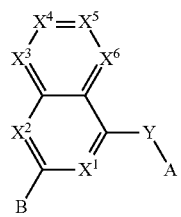

wherein:
- A is selected from the group consisting of optionally substituted phenyl, and optionally substituted 5- or 6-membered heteroaryl.
- B is selected from the group consisting of optionally substituted phenyl, and optionally substituted 5- or 6-membered heteroaryl, or optionally substituted alkyl, cycloalkyl or heterocyloalkyl.
- $X^1$-$X^6$ are independently N or $C(R^1)$
- Y is selected from N or C linked piperidinyl, piperazinyl, homopiperazinyl, optionally substituted with alkyl, —$NR^2(CH_2)_n NR^3$—, wherein n=2-6, and $R^2$ and $R^3$ are H or alkyl.

In some embodiments, $X^1$ and $X^2$ are N and $X^3$-$X^6$ are C as shown in the following structure:

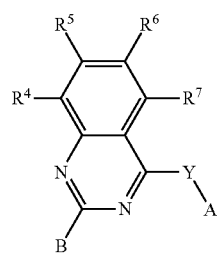

$R^4$-$R^7$ are independently selected from the group consisting of hydrogen, halogen, —CN, —C(O)—N($R^7$)—$R^8$, —C(O)—O—$R^9$, optionally substituted alkyl, optionally substituted cycloalkyl, optionally substituted heterocyloalkyl, optionally substituted alkoxy, haloalkyl, haloalkoxy, optionally substituted phenyl, and optionally substituted 5- or 6-membered heteroaryl.

In some embodiments, Y is piperazinyl and A is substituted phenyl as shown in the following structure:

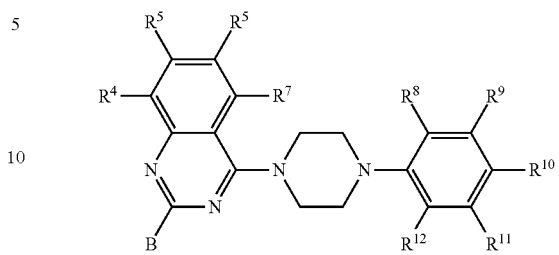

$R^8$-$R^{12}$ are independently selected from the group consisting of hydrogen, halogen, —CN, —C(O)—N($R^7$)—$R^8$, —C(O)—O—$R^9$, optionally substituted alkyl, optionally substituted cycloalkyl, optionally substituted heterocyloalkyl, optionally substituted alkoxy, haloalkyl, haloalkoxy, optionally substituted phenyl, and optionally substituted 5- or 6-membered heteroaryl In some embodiments, B is cycloalkyl as shown in the following structure:

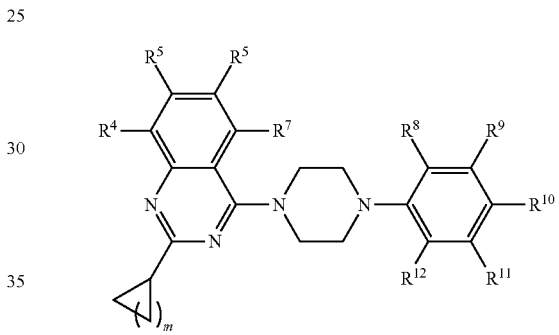

wherein m is 1, 2, 3, 4, 5, 6, or 7.

Any combination of the groups described above or below for the various variables is contemplated herein. Throughout the specification, groups and substituents thereof are chosen by one skilled in the field to provide stable moieties and compounds.

A compound that is:
2-cyclopropyl-4-[4-(4-fluoro-2-methoxy-phenyl)-piperazin-1-yl]-6,7-dimethoxy-quinazoline;
2-cyclopropyl-6,7-dimethoxy-4-[4-(2-methoxy-4-trifluoromethoxy-phenyl)-piperazin-1-yl]-quinazoline;
4-[4-(4-chloro-2-methoxy-phenyl)-piperazin-1-yl]-2-cyclopropyl-6,7-dimethoxy-quinazoline;
2-cyclopropyl-6,7-dimethoxy-4-[4-(2-methoxy-4-nitro-phenyl)-piperazin-1-yl]-quinazoline;
4-[4-(2-cyclopropyl-6,7-dimethoxy-quinazolin-4-yl)-piperazin-1-yl]-3-methoxy-phenylamine;
4-[4-(2-cyclopropyl-6,7-dimethoxy-quinazolin-4-yl)-piperazin-1-yl]-3-methoxy-benzonitrile;
4-[4-(2-cyclopropyl-6,7-dimethoxy-quinazolin-4-yl)-piperazin-1-yl]-3-methoxy-benzoic acid;
4-[4-(2-cyclopropyl-6,7-dimethoxy-quinazolin-4-yl)-piperazin-1-yl]-3-methoxy-benzamide;
{4-[4-(2-cyclopropyl-6,7-dimethoxy-quinazolin-4-yl)-piperazin-1-yl]-3-methoxy-phenyl}-dimethyl-amine;
2-cyclopropyl-6,7-dimethoxy-4-[4-(2-methoxy-4-trifluoromethyl-phenyl)-piperazin-1-yl]-quinazoline;
2-cyclopropyl-4-[4-(2,4-dimethoxy-phenyl)-piperazin-1-yl]-6,7-dimethoxy-quinazoline;

2-cyclopropyl-6,7-dimethoxy-4-[4-(2-methoxy-5-methyl-phenyl)-piperazin-1-yl]-quinazoline;
2-[4-(2-cyclopropyl-6,7-dimethoxy-quinazolin-4-yl)-piperazin-1-yl]-benzonitrile;
2-cyclopropyl-6,7-dimethoxy-4-[4-(2-methoxy-5-nitro-phenyl)-piperazin-1-yl]-quinazoline;
3-[4-(2-cyclopropyl-6,7-dimethoxy-quinazolin-4-yl)-piperazin-1-yl]-4-methoxy-phenylamine;
N-{3-[4-(2-cyclopropyl-6,7-dimethoxy-quinazolin-4-yl)-piperazin-1-yl]-4-methoxy-phenyl}-acetamide;
N-{3-[4-(2-cyclopropyl-6,7-dimethoxy-quinazolin-4-yl)-piperazin-1-yl]-4-methoxy-phenyl}-methanesulfonamide;
{3-[4-(2-cyclopropyl-6,7-dimethoxy-quinazolin-4-yl)-piperazin-1-yl]-4-methoxy-phenyl}-dimethyl-amine;
{3-[4-(2-cyclopropyl-6,7-dimethoxy-quinazolin-4-yl)-piperazin-1-yl]-4-methoxy-phenyl}-methyl-amine;
2-cyclopropyl-4-[4-(2,3-dichloro-phenyl)-piperazin-1-yl]-6,7-dimethoxy-quinazoline;
2-cyclopropyl-4-[4-(2,4-dichloro-phenyl)-piperazin-1-yl]-6,7-dimethoxy-quinazoline;
3-chloro-4-[4-(2-cyclopropyl-6,7-dimethoxy-quinazolin-4-yl)-piperazin-1-yl]-benzonitrile;
4-[4-(2-chloro-4-nitro-phenyl)-piperazin-1-yl]-2-cyclopropyl-6,7-dimethoxy-quinazoline;
3-chloro-4-[4-(2-cyclopropyl-6,7-dimethoxy-quinazolin-4-yl)-piperazin-1-yl]-benzoic acid;
3-chloro-4-[4-(2-cyclopropyl-6,7-dimethoxy-quinazolin-4-yl)-piperazin-1-yl]-benzamide;
3-chloro-4-[4-(2-cyclopropyl-6,7-dimethoxy-quinazolin-4-yl)-piperazin-1-yl]-phenylamine;
N-{3-chloro-4-[4-(2-cyclopropyl-6,7-dimethoxy-quinazolin-4-yl)-piperazin-1-yl]-phenyl}-acetamide;
N-{3-chloro-4-[4-(2-cyclopropyl-6,7-dimethoxy-quinazolin-4-yl)-piperazin-1-yl]-phenyl}-methanesulfonamide;
3-chloro-4-[4-(2-cyclopropyl-6,7-dimethoxy-quinazolin-4-yl)-piperazin-1-yl]-benzoic acid;
4-[4-(2-chloro-4-fluoro-phenyl)-piperazin-1-yl]-2-cyclopropyl-6,7-dimethoxy-quinazoline;
4-[4-(2-chloro-4-trifluoromethyl-phenyl)-piperazin-1-yl]-2-cyclopropyl-6,7-dimethoxy-quinazoline;
4-[4-(2-chloro-4-methyl-phenyl)-piperazin-1-yl]-2-cyclopropyl-6,7-dimethoxy-quinazoline;
4-[4-(2-chloro-4-methoxy-phenyl)-piperazin-1-yl]-2-cyclopropyl-6,7-dimethoxy-quinazoline;
2-[4-(2-cyclopropyl-6,7-dimethoxy-quinazolin-4-yl)-piperazin-1-yl]-benzonitrile;
2-[4-(2-cyclopropyl-6,7-dimethoxy-quinazolin-4-yl)-piperazin-1-yl]-5-methoxy-benzonitrile;
5-chloro-2-[4-(2-cyclopropyl-6,7-dimethoxy-quinazolin-4-yl)-piperazin-1-yl]-benzonitrile;
2-[4-(2-cyclopropyl-6,7-dimethoxy-quinazolin-4-yl)-piperazin-1-yl]-5-nitro-benzonitrile;
5-amino-2-[4-(2-cyclopropyl-6,7-dimethoxy-quinazolin-4-yl)-piperazin-1-yl]-benzonitrile;
2-cyclopropyl-6,7-dimethoxy-4-[4-(2-nitro-phenyl)-piperazin-1-yl]-quinazoline;
2-[4-(2-cyclopropyl-6,7-dimethoxy-quinazolin-4-yl)-piperazin-1-yl]-phenylamine;
2-(4-(2-cyclopropyl-6,7-dimethoxyquinazolin-4-yl)piperazin-1-yl)-N-ethylaniline;
{2-[4-(2-cyclopropyl-6,7-dimethoxy-quinazolin-4-yl)-piperazin-1-yl]-phenyl}-dimethyl-amine;
{2-[4-(2-cyclopropyl-6,7-dimethoxy-quinazolin-4-yl)-piperazin-1-yl]-phenyl}-diethyl-amine;
4-[4-(2-aziridin-1-yl-phenyl)-piperazin-1-yl]-2-cyclopropyl-6,7-dimethoxy-quinazoline;
4-[4-(4-benzyloxy-2-nitro-phenyl)-piperazin-1-yl]-2-cyclopropyl-6,7-dimethoxy-quinazoline;
3-amino-4-[4-(2-cyclopropyl-6,7-dimethoxy-quinazolin-4-yl)-piperazin-1-yl]-phenol;
2-cyclopropyl-6,7-dimethoxy-4-[4-(4-methoxy-2-nitro-phenyl)-piperazin-1-yl]-quinazoline;
2-[4-(2-cyclopropyl-6,7-dimethoxy-quinazolin-4-yl)-piperazin-1-yl]-5-fluoro-phenylamine;
2-[4-(2-cyclopropyl-6,7-dimethoxy-quinazolin-4-yl)-piperazin-1-yl]-5-methoxy-phenylamine;
{5-bromo-2-[4-(2-cyclopropyl-6,7-dimethoxy-quinazolin-4-yl)-piperazin-1-yl]-phenyl}-dimethyl-amine;
{2-[4-(2-cyclopropyl-6,7-dimethoxy-quinazolin-4-yl)-piperazin-1-yl]-5-fluoro-phenyl}-dimethyl-amine;
{5-chloro-2-[4-(2-cyclopropyl-6,7-dimethoxy-quinazolin-4-yl)-piperazin-1-yl]-phenyl}-dimethyl-amine;
{2-[4-(2-cyclopropyl-6,7-dimethoxy-quinazolin-4-yl)-piperazin-1-yl]-5-methoxy-phenyl}-dimethyl-amine;
4-[4-(2-cyclopropyl-6,7-dimethoxy-quinazolin-4-yl)-piperazin-1-yl]-3-dimethylamino-benzoic acid;
{2-[4-(2-cyclopropyl-6,7-dimethoxy-quinazolin-4-yl)-piperazin-1-yl]-phenyl}-phenyl-amine;
2-cyclopropyl-6,7-dimethoxy-4-[4-(2-morpholin-4-yl-phenyl)-piperazin-1-yl]-quinazoline;
2-cyclopropyl-6,7-dimethoxy-4-[4-(2-pyrrolidin-1-yl-phenyl)-piperazin-1-yl]-quinazoline;
4-[4-(2-azetidin-1-yl-phenyl)-piperazin-1-yl]-2-cyclopropyl-6,7-dimethoxy-quinazoline;
2-cyclopropyl-6,7-dimethoxy-4-[4-(2-piperidin-1-yl-phenyl)-piperazin-1-yl]-quinazoline;
2-Cyclopropyl-6,7-dimethoxy-4-{4-[2-(4-methyl-piperazin-1-yl)-phenyl]-piperazin-1-yl}-quinazoline;
5-amino-2-[4-(2-cyclopropyl-6,7-dimethoxy-quinazolin-4-yl)-piperazin-1-yl]-phenol;
4-(4-(2-cyclopropyl-6,7-dimethoxyquinazolin-4-yl)piperazin-1-yl)-N,N-dimethylaniline;
{4-[4-(2-cyclopropyl-6,7-dimethoxy-quinazolin-4-yl)-piperazin-1-yl]-phenyl}-diethyl-amine;
3-(4-(2-cyclopropyl-6,7-dimethoxyquinazolin-4-yl)piperazin-1-yl)-N,N-dimethylaniline;
{3-[4-(2-cyclopropyl-6,7-dimethoxy-quinazolin-4-yl)-piperazin-1-yl]-phenyl}-diethyl-amine;
N-(2-cyclopropyl-6,7-dimethoxy-quinazolin-5-yl)-N'-(2-methoxy-phenyl)-ethane-1,2-diamine;
N'-(2-cyclopropyl-6,7-dimethoxy-quinazolin-5-yl)-N-(2-methoxy-phenyl)-N-methyl-ethane-1,2-diamine;
2-cyclopropyl-6,7-dimethoxy-4-[4-(2-methoxy-phenyl)-2-methyl-piperazin-1-yl]-quinazoline;
N-(2-cyclopropyl-6,7-dimethoxy-quinazolin-4-yl)-N'-phenyl-ethane-1,2-diamine;
N-(2-cyclopropyl-6,7-dimethoxy-quinazolin-4-yl)-N'-(2-methoxy-phenyl)-propane-1,3-diamine;
N-(2-cyclopropyl-6,7-dimethoxy-quinazolin-4-yl)-N'-(2-methoxy-phenyl)-N,N'-dimethyl-ethane-1,2-diamine;
2-cyclopropyl-6,7-dimethoxy-4-[4-(2-methoxy-phenyl)-[1,4]diazepan-1-yl]-quinazoline;
[1-(2-cyclopropyl-6,7-dimethoxy-quinazolin-4-yl)-piperidin-4-yl]-(2-methoxy-phenyl)-amine;
2-(2-cyclopropyl-6,7-dimethoxy-quinazolin-4-ylamino)-N-(2-methoxy-phenyl)-acetamide;
2-Cyclopropyl-6,7-dimethoxy-4-[4-(2-methoxy-phenyl)-piperidin-1-yl]-quinazoline;
{2-[1-(2-Cyclopropyl-6,7-dimethoxy-quinazolin-4-yl)-piperidin-4-yl]-phenyl}-dimethyl-amine;
2-cyclopropyl-6,7-dimethoxy-4-[4-(2-methoxy-phenyl)-3,6-dihydro-2H-pyridin-1-yl]-quinazoline;

2-cyclopropyl-6,7-dimethoxy-4-(3-phenyl-pyrrolidin-1-yl)-quinazoline;
2-cyclopropyl-6,7-dimethoxy-4-[3-(2-methoxy-phenyl)-pyrrolidin-1-yl]-quinazoline;
{2-[1-(2-cyclopropyl-6,7-dimethoxy-quinazolin-4-yl)-pyrrolidin-3-yl]-phenyl}-dimethyl-amine;
2-cyclopropyl-6,7-dimethoxy-4-[3-(3-methoxy-phenyl)-cyclopentyl]-quinazoline;
{3-[1-(2-cyclopropyl-6,7-dimethoxy-quinazolin-4-yl)-pyrrolidin-3-yl]-phenyl}-dimethyl-amine;
1-(2-cyclopropyl-6,7-dimethoxy-quinazolin-4-yl)-3-phenyl-pyrrolidin-3-ol;
1-(2-cyclopropyl-6,7-dimethoxy-quinazolin-4-yl)-3-(2-dimethylamino-phenyl)-pyrrolidin-3-ol;
1-(2-cyclopropyl-6,7-dimethoxy-quinazolin-4-yl)-3-(3-methoxy-phenyl)-pyrrolidin-3-ol;
2-cyclopropyl-4-(3-fluoro-3-phenyl-pyrrolidin-1-yl)-6,7-dimethoxy-quinazoline;
{2-[1-(2-cyclopropyl-6,7-dimethoxy-quinazolin-4-yl)-3-fluoro-pyrrolidin-3-yl]-phenyl}-dimethyl-amine;
2-cyclopropyl-4-[3-fluoro-3-(3-methoxy-phenyl)-pyrrolidin-1-yl]-6,7-dimethoxy-quinazoline;
2-cyclopropyl-6,7-dimethoxy-4-(3-methyl-4-phenyl-piperazin-1-yl)-quinazoline;
2-cyclopropyl-6,7-dimethoxy-4-[1-(2-methoxy-phenyl)-piperidin-4-yl]-quinazoline;
6,7-dimethoxy-4-[4-(2-methoxy-phenyl)-piperazin-1-yl]-2-piperidin-4-yl-quinazoline;
6,7-dimethoxy-4-[4-(2-methoxy-phenyl)-piperazin-1-yl]-2-(1-methyl-piperidin-4-yl)-quinazoline;
6,7-dimethoxy-4-[4-(2-methoxy-phenyl)-piperazin-1-yl]-2-(4-methyl-cyclohexyl)-quinazoline;
4-{6,7-dimethoxy-4-[4-(2-methoxy-phenyl)-piperazin-1-yl]-quinazolin-2-yl}-piperidine-1-carboxylic acid benzyl ester;
6,7-dimethoxy-4-[4-(2-methoxy-phenyl)-piperazin-1-yl]-2-(tetrahydro-pyran-4-yl)-quinazoline;
6,7-dimethoxy-4-[4-(2-methoxy-phenyl)-piperazin-1-yl]-2-(tetrahydro-furan-3-yl)-quinazoline;
6,7-dimethoxy-4-[4-(2-methoxy-phenyl)-piperazin-1-yl]-2-(2-methyl-cyclopropyl)-quinazoline;
cis-6,7-dimethoxy-2-(4-methoxy-cyclohexyl)-4-[4-(2-methoxy-phenyl)-piperazin-1-yl]-quinazoline;
trans-6,7-dimethoxy-2-(4-methoxy-cyclohexyl)-4-[4-(2-methoxy-phenyl)-piperazin-1-yl]-quinazoline;
6,7-dimethoxy-4-[4-(2-methoxy-phenyl)-piperazin-1-yl]-2-(4-methyl-pyrrolidin-3-yl)-quinazoline;
2-(1,4-dimethyl-pyrrolidin-3-yl)-6,7-dimethoxy-4-[4-(2-methoxy-phenyl)-piperazin-1-yl]-quinazoline;
6,7-dimethoxy-4-[4-(2-methoxy-phenyl)-piperazin-1-yl]-2-pyrrolidin-3-yl-quinazoline;
6,7-dimethoxy-4-[4-(2-methoxy-phenyl)-piperazin-1-yl]-2-(1-methyl-pyrrolidin-3-yl)-quinazoline;
2-((1R,3R)-3-chloro-3-methylcyclobutyl)-6,7-dimethoxy-4-(4-(2-methoxyphenyl)piperazin-1-yl)quinazoline;
2-((1S,3S)-3-chloro-3-methylcyclobutyl)-6,7-dimethoxy-4-(4-(2-methoxyphenyl)piperazin-1-yl)quinazoline;
6,7-dimethoxy-4-[4-(2-methoxy-phenyl)-piperazin-1-yl]-2-(3-methyl-cyclobutyl)-quinazoline;
2-cyclohexyl-6,7-dimethoxy-4-[4-(2-methoxy-phenyl)-piperazin-1-yl]-quinazoline;
2-tert-Butyl-6,7-dimethoxy-4-[4-(2-methoxy-phenyl)-piperazin-1-yl]-quinazoline;
2-tert-Butyl-6,7-dimethoxy-4-[4-(2-methoxy-phenyl)-piperidin-1-yl]-quinazoline;
6,7-dimethoxy-4-[4-(2-methoxy-phenyl)-piperazin-1-yl]-2-(1-methyl-cyclopropyl)-quinazoline;
6,7-dimethoxy-4-[4-(2-methoxy-phenyl)-piperidin-1-yl]-2-(1-methyl-cyclopropyl)-quinazoline;
6,7-dimethoxy-4-[4-(2-methoxy-phenyl)-piperazin-1-yl]-2-(1-trifluoromethyl-cyclopropyl)-quinazoline;
6,7-dimethoxy-4-[4-(2-methoxy-phenyl)-piperidin-1-yl]-2-(1-trifluoromethyl-cyclopropyl)-quinazoline;
[4-[4-(2-Methoxy-phenyl)-piperidin-1-yl]-2-(1-methyl-cyclopropyl)-quinazolin-6-yl]-methyl-(2-morpholin-4-yl-ethyl)-amine;
7-chloro-2-cyclopropyl-6-methoxy-4-[4-(2-methoxy-phenyl)-piperazin-1-yl]-quinazoline;
2-cyclopropyl-4-[4-(2-methoxy-phenyl)-piperazin-1-yl]-pyrido[2,3-d]pyrimidine;
2-cyclopropyl-6,8-dimethoxy-4-[4-(2-methoxy-phenyl)-piperazin-1-yl]-quinazoline;
2-cyclopropyl-6-methoxy-4-[4-(2-methoxy-phenyl)-piperazin-1-yl]-7-methyl-quinazoline;
2-cyclopropyl-7-fluoro-6-methoxy-4-[4-(2-methoxy-phenyl)-piperazin-1-yl]-quinazoline;
6-bromo-2-cyclopropyl-4-[4-(2-methoxy-phenyl)-piperazin-1-yl]-quinazoline;
{2-cyclopropyl-4-[4-(2-methoxy-phenyl)-piperazin-1-yl]-quinazolin-6-yl}-dimethylamine;
6-bromo-2-cyclopropyl-7-fluoro-4-[4-(2-methoxy-phenyl)-piperazin-1-yl]-quinazoline;
{2-cyclopropyl-7-fluoro-4-[4-(2-methoxy-phenyl)-piperazin-1-yl]-quinazolin-6-yl}-dimethyl-amine;
{2-cyclopropyl-7-fluoro-4-[4-(2-methoxy-phenyl)-piperazin-1-yl]-quinazolin-6-yl}-diethyl-amine;
6-bromo-7-chloro-2-cyclopropyl-4-[4-(2-methoxy-phenyl)-piperazin-1-yl]-quinazoline;
{7-chloro-2-cyclopropyl-4-[4-(2-methoxy-phenyl)-piperazin-1-yl]-quinazolin-6-yl}-dimethyl-amine;
{7-chloro-2-cyclopropyl-4-[4-(2-methoxy-phenyl)-piperazin-1-yl]-quinazolin-6-yl}-diethyl-amine;
6-bromo-2-cyclopropyl-4-[4-(2-methoxy-phenyl)-piperazin-1-yl]-7-methyl-quinazoline;
{2-cyclopropyl-4-[4-(2-methoxy-phenyl)-piperazin-1-yl]-7-methyl-quinazolin-6-yl}-dimethyl-amine;
{2-cyclopropyl-4-[4-(2-methoxy-phenyl)-piperazin-1-yl]-7-methyl-quinazolin-6-yl}-ethyl-methyl-amine;
6-bromo-2-cyclopropyl-4-[4-(2-methoxy-phenyl)-piperidin-1-yl]-7-methyl-quinazoline;
{2-cyclopropyl-4-[4-(2-methoxy-phenyl)-piperidin-1-yl]-7-methyl-quinazolin-6-yl}-diethyl-amine;
2-cyclopropyl-6-methoxy-4-[4-(2-methoxy-phenyl)-piperazin-1-yl]-pyrido[3,4-d]pyrimidine;
6-bromo-2-cyclopropyl-4-[4-(2-methoxy-phenyl)-piperidin-1-yl]-7-methyl-quinazoline;
{2-cyclopropyl-4-[4-(2-methoxy-phenyl)-piperidin-1-yl]-7-methyl-quinazolin-6-yl}-diethyl-amine;
{2-cyclopropyl-4-[4-(2-methoxy-phenyl)-piperazin-1-yl]-quinazolin-7-yl}-dimethyl-amine;
{2-cyclopropyl-4-[4-(2,5-dimethoxy-phenyl)-piperazin-1-yl]-quinazolin-6-yl}-dimethyl-amine;
2-cyclopropyl-4-[4-(2-methoxy-phenyl)-piperazin-1-yl]-6-piperidin-1-yl-quinazoline;
{2-cyclopropyl-4-[4-(2-methoxy-phenyl)-piperazin-1-yl]-quinazolin-6-yl}-diethyl-amine;
2-cyclopropyl-4-[4-(2-methoxy-phenyl)-piperazin-1-yl]-6-morpholin-4-yl-quinazoline;
2-cyclopropyl-4-[4-(2-methoxy-phenyl)-piperazin-1-yl]-6-pyrrolidin-1-yl-quinazoline;
{2-cyclopropyl-4-[4-(2-methoxy-phenyl)-piperazin-1-yl]-quinazolin-6-yl}-phenyl-amine;
{2-cyclopropyl-4-[4-(2-methoxy-phenyl)-piperidin-1-yl]-quinazolin-6-yl}-dimethyl-amine;

{2-cyclopropyl-4-[4-(2-methoxy-phenyl)-piperidin-1-yl]-quinazolin-6-yl}-ethyl-methyl-amine;
{7-chloro-2-cyclopropyl-4-[4-(2-methoxyphenyl)piperidyl]quinazolin-6-yl}dimethylamine;
2-cyclopropyl-4-[4-(2-methoxy-phenyl)-piperazin-1-yl]-6-piperazin-1-yl-quinazoline;
2-cyclopropyl-4-[4-(2-methoxy-phenyl)-piperazin-1-yl]-6-(4-methyl-piperazin-1-yl)-quinazoline;
2-cyclopropyl-6,7-difluoro-4-[4-(2-methoxy-phenyl)-piperazin-1-yl]-quinazoline;
{2-cyclopropyl-6-fluoro-4-[4-(2-methoxy-phenyl)-piperazin-1-yl]-quinazolin-7-yl}-dimethyl-amine;
{2-cyclopropyl-6-fluoro-4-[4-(2-methoxy-phenyl)-piperazin-1-yl]-quinazolin-7-yl}-diethyl-amine;
2-cyclopropyl-6-fluoro-7-methoxy-4-[4-(2-methoxy-phenyl)-piperazin-1-yl]-quinazoline;
{2-cyclopropyl-4-[4-(2-methoxy-phenyl)-piperazin-1-yl]-quinazolin-6-yl}-methyl-propyl-amine;
{2-cyclopropyl-4-[4-(2-methoxy-phenyl)-piperazin-1-yl]-quinazolin-6-yl}-methyl-(2-morpholin-4-yl-ethyl)-amine;
2-cyclopropyl-4-(4-(2-methoxyphenyl)piperazin-1-yl)-N-methyl-N-(2-morpholino ethyl)quinazolin-6-amine;
2,2'-((2-cyclopropyl-4-(4-(2-methoxyphenyl)piperazin-1-yl)quinazolin-6-yl)azanediyl)diethanol;
2-({2-cyclopropyl-4-[4-(2-methoxy-phenyl)-piperazin-1-yl]-quinazolin-6-yl}-methyl-amino)-ethanol;
{2-cyclopropyl-4-[4-(2-methoxy-phenyl)-piperazin-1-yl]-quinazolin-6-yl}-(2-methoxy-ethyl)-methyl-amine;
2-({2-cyclopropyl-4-[4-(2-methoxy-phenyl)-piperidin-1-yl]-quinazolin-6-yl}-methyl-amino)-ethanol;
{2-cyclopropyl-4-[4-(2-methoxy-phenyl)-piperidin-1-yl]-quinazolin-6-yl}-(2-methoxy-ethyl)-methyl-amine;
{2-cyclopropyl-4-[4-(2-methoxy-phenyl)-piperidin-1-yl]-quinazolin-6-yl}-methyl-propyl-amine;
{2-cyclopropyl-4-[4-(2-methoxy-phenyl)-piperidin-1-yl]-quinazolin-6-yl}-methyl-(2-morpholin-4-yl-ethyl)-amine;
2-cyclopropyl-5,8-dimethoxy-4-[4-(2-methoxy-phenyl)-piperazin-1-yl]-quinazoline;
2-cyclopropyl-4-[4-(2-methoxy-phenyl)-piperazin-1-yl]-quinazoline;
2-cyclopropyl-5,6-dimethoxy-4-[4-(2-methoxy-phenyl)-piperazin-1-yl]-quinazoline;
2-cyclopropyl-5-methoxy-4-[4-(2-methoxy-phenyl)-piperazin-1-yl]-quinazoline;
2-cyclopropyl-8-methoxy-4-[4-(2-methoxy-phenyl)-piperazin-1-yl]-quinazoline;
2-cyclopropyl-6,7-dimethoxy-4-[4-(2-methoxy-phenyl)-piperazin-1-yl]-quinoline;
3-cyclopropyl-6,7-dimethoxy-1-[4-(2-methoxy-phenyl)-piperazin-1-yl]-isoquinoline;
3-chloro-4-(4-(2-cyclopropyl-6-(dimethylamino)quinazolin-4-yl)piperazin-1-yl)benzonitrile;
3-chloro-4-[4-(2-cyclopropyl-6-dimethylamino-quinazolin-4-yl)-piperazin-1-yl]-benzamide;
3-{3-chloro-4-[4-(2-cyclopropyl-6-dimethylamino-quinazolin-4-yl)-piperazin-1-yl]-phenyl}-1,1-dimethyl-urea;
6-bromo-2-cyclopropyl-4-[4-(2,5-dimethoxy-phenyl)-piperazin-1-yl]-quinazoline;
{2-cyclopropyl-4-[4-(2,5-dimethoxy-phenyl)-piperazin-1-yl]-quinazolin-6-yl}-dimethyl-amine;
6-bromo-2-cyclopropyl-4-[4-(2-methoxy-5-methyl-phenyl)-piperazin-1-yl]-quinazoline;
{2-cyclopropyl-4-[4-(2-methoxy-5-methyl-phenyl)-piperazin-1-yl]-quinazolin-6-yl}-dimethyl-amine;
6-bromo-2-cyclopropyl-4-[4-(4-fluoro-2-methoxy-phenyl)-piperazin-1-yl]-quinazoline;
{2-cyclopropyl-4-[4-(4-fluoro-2-methoxy-phenyl)-piperazin-1-yl]-quinazolin-6-yl}-dimethyl-amine;
4-[4-(6-bromo-2-cyclopropyl-quinazolin-4-yl)-piperazin-1-yl]-3-methoxy-benzonitrile;
4-[4-(2-cyclopropyl-6-dimethylamino-quinazolin-4-yl)-piperazin-1-yl]-3-methoxy-benzonitrile;
6-bromo-2-cyclopropyl-4-[4-(2-methoxy-4-trifluoromethoxy-phenyl)-piperazin-1-yl]-quinazoline;
{2-cyclopropyl-4-[4-(2-methoxy-4-trifluoromethoxy-phenyl)-piperazin-1-yl]-quinazolin-6-yl}-dimethyl-amine;
6-bromo-4-[4-(2-chloro-4-fluoro-phenyl)-piperazin-1-yl]-2-cyclopropyl-quinazoline;
{4-[4-(2-chloro-4-fluoro-phenyl)-piperazin-1-yl]-2-cyclopropyl-quinazolin-6-yl}-dimethyl-amine;
6-bromo-4-[4-(2-chloro-4-methyl-phenyl)-piperazin-1-yl]-2-cyclopropyl-quinazoline;
{4-[4-(2-chloro-4-methyl-phenyl)-piperazin-1-yl]-2-cyclopropyl-quinazolin-6-yl}-dimethyl-amine;
6-bromo-4-[4-(4-chloro-2-methoxy-phenyl)-piperazin-1-yl]-2-cyclopropyl-quinazoline;
{4-[4-(4-chloro-2-methoxy-phenyl)-piperazin-1-yl]-2-cyclopropyl-quinazolin-6-yl}-dimethyl-amine;
6-bromo-2-cyclopropyl-4-[4-(4-methoxy-phenyl)-piperazin-1-yl]-quinazoline;
{2-cyclopropyl-4-[4-(4-methoxy-phenyl)-piperazin-1-yl]-quinazolin-6-yl}-dimethyl-amine;
6-bromo-2-cyclopropyl-4-[4-(3-methoxy-phenyl)-piperazin-1-yl]-quinazoline;
{2-cyclopropyl-4-[4-(3-methoxy-phenyl)-piperazin-1-yl]-quinazolin-6-yl}-dimethyl-amine;
6-bromo-2-cyclopropyl-4-(4-o-tolyl-piperazin-1-yl)-quinazoline;
[2-cyclopropyl-4-(4-o-tolyl-piperazin-1-yl)-quinazolin-6-yl]-dimethyl-amine;
6-bromo-2-cyclopropyl-4-[4-(2-fluoro-phenyl)-piperazin-1-yl]-quinazoline;
6-bromo-4-[4-(2-chloro-phenyl)-piperazin-1-yl]-2-cyclopropyl-quinazoline;
{2-cyclopropyl-4-[4-(2-fluoro-phenyl)-piperazin-1-yl]-quinazolin-6-yl}-dimethyl-amine;
{4-[4-(2-chloro-phenyl)-piperazin-1-yl]-2-cyclopropyl-quinazolin-6-yl}-dimethyl-amine;
2-[4-(6-Bromo-2-cyclopropyl-quinazolin-4-yl)-piperazin-1-yl]-benzonitrile;
2-[4-(2-cyclopropyl-6-dimethylamino-quinazolin-4-yl)-piperazin-1-yl]-benzonitrile;
2-[4-(2-cyclopropyl-6-dimethylamino-quinazolin-4-yl)-piperazin-1-yl]-benzamide;
{4-[4-(2-azetidin-1-yl-phenyl)-piperazin-1-yl]-2-cyclopropyl-quinazolin-6-yl}-dimethyl-amine;
{4-[4-(2-azetidin-1-yl-phenyl)-piperazin-1-yl]-2-cyclopropyl-quinazolin-6-yl}-ethyl-methyl-amine;
{4-[4-(2-azetidin-1-yl-phenyl)-piperidin-1-yl]-2-cyclopropyl-quinazolin-6-yl}-dimethyl-amine;
2-cyclopropyl-6,7-dimethoxy-4-(4-(2-methoxyphenyl)piperazin-1-yl)quinazoline;
6,7-dimethoxy-4-(4-(2-methoxyphenyl)piperazin-1-yl)-2-methylquinazoline;
2-benzyl-6,7-dimethoxy-4-(4-(2-methoxyphenyl)piperazin-1-yl)quinazoline;
2-ethyl-6,7-dimethoxy-4-(4-(2-methoxyphenyl)piperazin-1-yl)quinazoline;
6,7-dimethoxy-4-(4-(2-methoxyphenyl)piperazin-1-yl)-2-propylquinazoline;

2-isopropyl-6,7-dimethoxy-4-(4-(2-methoxyphenyl)piperazin-1-yl)quinazoline;
2-isobutyl-6,7-dimethoxy-4-(4-(2-methoxyphenyl)piperazin-1-yl)quinazoline;
6,7-dimethoxy-4-(4-(2-methoxyphenyl)piperazin-1-yl)-2-vinylquinazoline;
6,7-dimethoxy-4-(4-(2-methoxyphenyl)piperazin-1-yl)-2-(2-(4-(2-methoxyphenyl)piperazin-1-yl)ethyl)quinazoline;
2-cyclopentyl-6,7-dimethoxy-4-(4-(2-methoxyphenyl)piperazin-1-yl)quinazoline;
2-(cyclopropylmethyl)-6,7-dimethoxy-4-(4-(2-methoxyphenyl)piperazin-1-yl)quinazoline;
2-(6,7-dimethoxy-4-(4-(2-methoxyphenyl)piperazin-1-yl)quinazolin-2-yl)-N,N-dimethylethanamine;
2-cyclobutyl-6,7-dimethoxy-4-(4-(2-methoxyphenyl)piperazin-1-yl)quinazoline;
2-cyclobutyl-6,7-dimethoxy-4-(4-phenylpiperazin-1-yl)quinazoline;
2-cyclobutyl-6,7-dimethoxy-4-(4-(o-tolyl)piperazin-1-yl)quinazoline;
2-cyclobutyl-4-(4-(2-fluorophenyl)piperazin-1-yl)-6,7-dimethoxyquinazoline;
4-(4-(2-chlorophenyl)piperazin-1-yl)-2-cyclobutyl-6,7-dimethoxyquinazoline;
2-cyclobutyl-6,7-dimethoxy-4-(4-(pyridin-2-yl)piperazin-1-yl)quinazoline;
2-cyclobutyl-6,7-dimethoxy-4-(4-(2-nitrophenyl)piperazin-1-yl)quinazoline;
2-cyclobutyl-6,7-dimethoxy-4-(4-(3-methoxyphenyl)piperazin-1-yl)quinazoline;
2-cyclobutyl-6,7-dimethoxy-4-(4-(4-methoxyphenyl)piperazin-1-yl)quinazoline;
2-cyclobutyl-4-(4-(2,4-dimethoxyphenyl)piperazin-1-yl)-6,7-dimethoxyquinazoline;
2-cyclobutyl-4-(4-(2,6-dimethylphenyl)piperazin-1-yl)-6,7-dimethoxyquinazoline;
2-cyclobutyl-6-methoxy-4-(4-(2-methoxyphenyl)piperazin-1-yl)quinazoline;
2-cyclobutyl-7-methoxy-4-(4-(2-methoxyphenyl)piperazin-1-yl)quinazoline;
2-cyclobutyl-4-(4-(2-methoxyphenyl)piperazin-1-yl)quinazoline;
6-cyclobutyl-8-(4-(2-methoxyphenyl)piperazin-1-yl)-[1,3]dioxolo[4,5-g]quinazoline;
2-cyclopropyl-6-methoxy-4-(4-(2-methoxyphenyl)piperazin-1-yl)quinazoline;
2-cyclopropyl-4-(4-(2-ethoxyphenyl)piperazin-1-yl)-6,7-dimethoxyquinazoline;
4-(4-(2-chlorophenyl)piperazin-1-yl)-2-cyclopropyl-6,7-dimethoxyquinazoline;
2-cyclopropyl-6,7-dimethoxy-4-(4-(phenylsulfonyl)piperazin-1-yl)quinazoline;
2-cyclopropyl-6,7-dimethoxy-4-(4-(4-methylbenzyl)piperazin-1-yl)quinazoline;
2-cyclopropyl-6,7-dimethoxy-4-(4-(2-methoxybenzyl)piperazin-1-yl)quinazoline;
(4-(2-cyclopropyl-6,7-dimethoxyquinazolin-4-yl)piperazin-1-yl) (phenyl)methanone;
(4-(2-cyclopropyl-6,7-dimethoxyquinazolin-4-yl)piperazin-1-yl) (2-methoxyphenyl)methanone;
2-cyclopropyl-6,7-dimethoxy-4-(piperazin-1-yl)quinazoline trifluoroacetate;
2-cyclopropyl-6-methoxy-4-(4-(2-methoxyphenyl)piperazin-1-yl)-7-(trifluoromethyl)quinazoline;
or a pharmaceutically acceptable salt, solvate, tautomer, or N-oxide thereof.

Further Forms of Compounds

In one aspect, the compound of Formula I, possesses one or more stereocenters and each stereocenter exists independently in either the R or S configuration. The compounds presented herein include all diastereomeric, enantiomeric, and epimeric forms as well as the appropriate mixtures thereof. The compounds and methods provided herein include all cis, trans, syn, anti, entgegen (E), and zusammen (Z) isomers as well as the appropriate mixtures thereof. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In one aspect, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. In some embodiments, the design of a prodrug increases the effective water solubility. An example, without limitation, of a prodrug is a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

In one aspect, prodrugs are designed to alter the metabolic stability or the transport characteristics of a drug, to mask side effects or toxicity, to improve the flavor of a drug or to alter other characteristics or properties of a drug. By virtue of knowledge of pharmacokinetic, pharmacodynamic processes and drug metabolism in vivo, once a pharmaceutically active compound is known, the design prodrugs of the compound is possible. (see, for example, Nogrady (1985) *Medicinal Chemistry A Biochemical Approach*, Oxford University Press, New York, pages 388-392; Silverman (1992), The Organic Chemistry of Drug Design and Drug Action, Academic Press, Inc., San Diego, pages 352-401, Rooseboom et al., *Pharmacological Reviews*, 56:53-102, 2004; Aesop Cho, "Recent Advances in Oral Prodrug Discovery", *Annual Reports in Medicinal Chemistry*, Vol. 41, 395-407, 2006; T. Higuchi and V. Stella, *Pro-drugs as Novel Delivery Systems*, Vol. 14 of the A.C.S. Symposium Series).

In some cases, some of the herein-described compounds may be a prodrug for another derivative or active compound.

In some embodiments, sites on the aromatic ring portion of compounds described herein are susceptible to various metabolic reactions Therefore incorporation of appropriate substituents on the aromatic ring structures will reduce, minimize or eliminate this metabolic pathway. In specific embodiments, the appropriate substituent to decrease or eliminate the susceptibility of the aromatic ring to metabolic reactions is, by way of example only, a halogen, or an alkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine and chlorine, such as, for example, $^2$H, $^3$H, $^{13}$C, $^{14}$C, $^{15}$N, $^{18}$O, $^{17}$O, $^{35}$S, $^{18}$F, $^{36}$Cl. In one aspect, isotopically-labeled compounds described herein, for example those into which radioactive isotopes such as $^3$H and $^{14}$C are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In additional or further embodiments, the compounds described herein are metabolized upon administration to an organism in need to produce a metabolite that is then used to produce a desired effect, including a desired therapeutic effect.

"Pharmaceutically acceptable" as used herein, refers a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutically acceptable salt" refers to a formulation of a compound that does not cause significant irritation to an organism to which it is administered and does not abrogate the biological activity and properties of the compound. In some embodiments, pharmaceutically acceptable salts are obtained by reacting a compound of Formula I with acids. Pharmaceutically acceptable salts are also obtained by reacting a compound of Formula I with a base to form a salt.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g. lithium, sodium, potassium), an alkaline earth ion (e.g. magnesium, or calcium), or an aluminum ion. In some cases, compounds described herein may coordinate with an organic base, such as, but not limited to, ethanolamine, diethanolamine, triethanolamine, tromethamine, N-methylglucamine, dicyclohexylamine, tris(hydroxymethyl)methylamine. In other cases, compounds described herein may form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

It should be understood that a reference to a pharmaceutically acceptable salt includes the solvent addition forms, particularly solvates. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

Synthesis of Compounds

In some embodiments, the synthesis of compounds described herein are accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich, FisherScientific (Fisher Chemicals), and AcrosOrganics.

In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey and Sundberg, Advanced Organic Chemistry 4$^{th}$ Ed., Vols. A and B (Plenum 2000, 2001), and Green and Wuts, Protective Groups in Organic Synthesis 3$^{rd}$ Ed., (Wiley 1999) (all of which are incorporated by reference for such disclosure). General methods for the preparation of compounds as disclosed herein may be derived from reactions and the reactions may be modified by the use of appropriate reagents and conditions, for the introduction of the various moieties found in the formulae as provided herein. As a guide the following synthetic methods may be utilized.

In the reactions described, it may be necessary to protect reactive functional groups, for example hydroxy, amino, imino, thio or carboxy groups, where these are desired in the final product, in order to avoid their unwanted participation in reactions. A detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure).

In some embodiments, compounds described herein are prepared as shown in Scheme A.

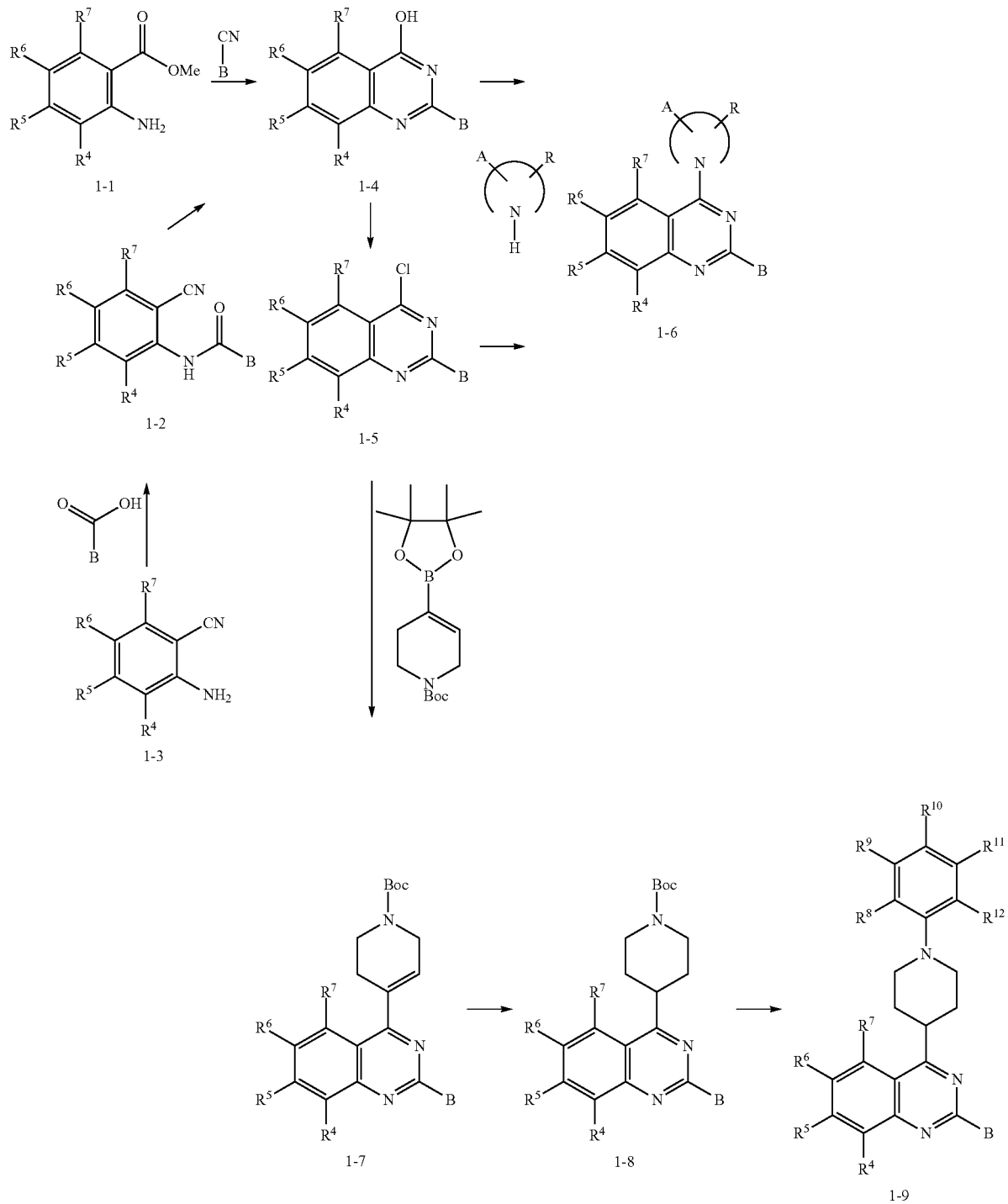

In some embodiments, the synthesis of quinazoline-derived compounds 1-6 described herein is accomplished starting from suitably substituted methyl anthranilates 1-1 as shown in Scheme A. Acid catalyzed (i.e. HCl) condensation of substituted methyl anthranilates (1-1) with substituted carbonitrile affords 4-hydroxyquinazoline intermediates (1-4). Chlorination (i.e. POCl$_3$) of the 4-hydroxyquinazoline intermediates followed by amination of the resulting 4-chloroquinazoline intermediates (1-5) with various substituted aryl piperidines, piperazines or pyrrolidines affords quinazoline analogs 1-6. In some embodiments, the 4-hydroxyquinazoline intermediates (1-4) are directly reacted with various substituted aryl piperidines, piperazines or pyrrolidines using a coupling reagent (i.e. BOP) and a base (i.e. DBU) to afford quinazoline analogs 1-6. In some embodiments, the synthesis of the 4-hydroxyquinazoline intermediates (1-4) is accomplished in two steps by 1) amide condensation of a substituted anthranilonitrile (1-3) and a substituted carboxylic acid using an amide coupling reagent (i.e HATU) to afford N-(2-cyanophenyl)amide derivatives 1-2 and 2) cyclization under basic (i.e. NaOH) and oxidative (i.e. H$_2$O$_2$) conditions to afford 4-hydroxyquinazoline intermediates (1-4).

In some embodiments, 4-chloroquinazoline compound 1-5 are used to prepare quinazoline-derived compounds 1-9 as shown in Scheme A. In some embodiments, the 4-chloroquinazoline compound 1-5 is reacted with a pinacol ester in a Suzuki type reaction to afford C-linked quinazoline derivatives 1-7. In some embodiments, the C-linked quinazoline derivative 1-7 is hydrogenated to provide compound 1-8, the Boc protecting group is removed and a palladium catalyzed Buchwald type amination is performed with an optionally substituted aryl halide to afford substituted quinazoline 1-9.

In some embodiments, compounds described herein are prepared as shown in Scheme B.

Scheme B:

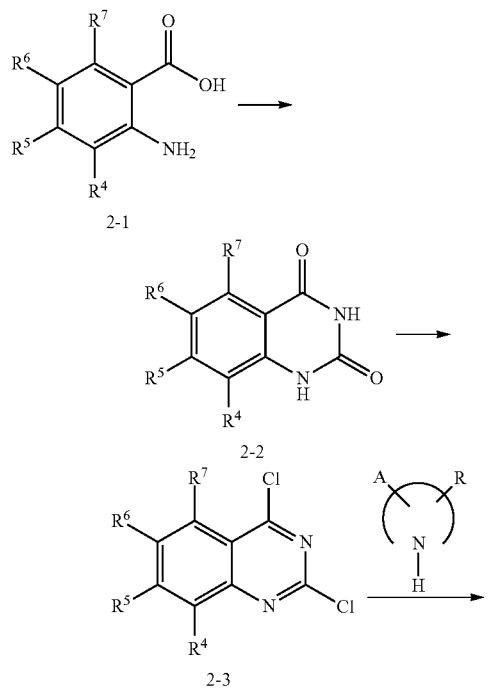

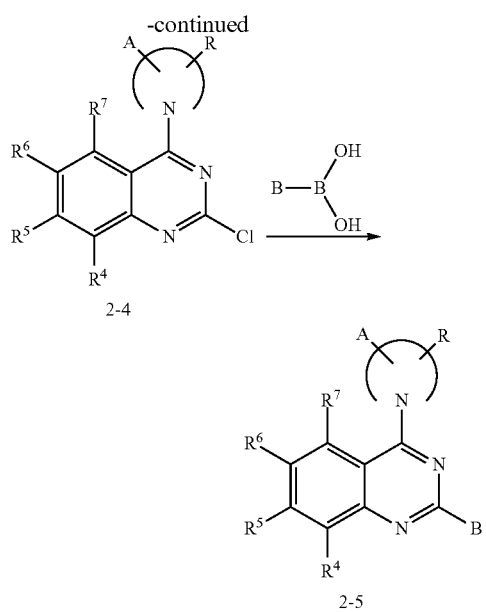

In some embodiments, suitably substituted anthranilic acids 2-1 are used to prepare quinazoline compounds 2-5 as shown in Scheme B. In some embodiments, cyclization of anthranilic acid 2-1 with a cyanate salt (i.e. KOCN) affords quinazoline-(1H,3H)-dione compound 2-2. In some embodiments, quinazoline-(1H,3H)-dione compound 2-2 is chlorinated to yield 2,4-dichloroquinazoline compound 2-3. In some embodiments, the chlorinating agent is POCl$_3$. In some embodiments, dichloroquinazoline compound 2-3 are selectively aminated at the 4-position using an optionally substituted aryl piperidine, aryl piperazines or aryl pyrrolidines to yield compounds of structure 2-4. In some embodiments, a palladium catalyzed Suzuki type reaction with compounds of structure 2-4 and a suitably substituted boronic acid afforded the quinazoline analogs 2-5.

It will be understood that the reactions shown above are illustrative.

In one aspect, compounds are synthesized as described in the Examples section.

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"Amino" refers to the —NH₂ radical.
"Cyano" refers to the —CN radical.
"Hydroxy" or "hydroxyl" refers to the —OH radical.
"Nitro" refers to the —NO₂ radical.
"Oxo" refers to the =O substituent.
"Thioxo" refers to the =S substituent.

"Alkyl" refers to a straight or branched hydrocarbon chain radical, having from one to thirty carbon atoms, and which is attached to the rest of the molecule by a single bond. Alkyls comprising any number of carbon atoms from 1 to 10 are included. An alkyl comprising up to 10 carbon atoms is referred to as a $C_1$-$C_{10}$ alkyl, likewise, for example, an alkyl comprising up to 6 carbon atoms is a $C_1$-$C_6$ alkyl. Alkyls (and other moieties defined herein) comprising other numbers of carbon atoms are represented similarity. Alkyl groups include, but are not limited to, $C_1$-$C_{10}$ alkyl, $C_1$-$C_9$ alkyl, $C_1$-$C_8$ alkyl, $C_1$-$C_7$ alkyl, $C_1$-$C_6$ alkyl, $C_1$-$C_5$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, n-propyl, 1-methylethyl (iso-propyl), n-butyl, i-butyl, s-butyl, n-pentyl, 1,1-dimethylethyl (t-butyl), 3-methylhexyl, 2-methylhexyl, and the like. Unless stated otherwise specifically in the specification, an alkyl group may be optionally substituted as described below. "Alkylene" or "alkylene chain" refers to a straight or branched divalent hydrocarbon chain linking the rest of the molecule to a radical group.

"Alkoxy" refers to a radical of the formula —OR where R is an alkyl radical as defined. Unless stated otherwise specifically in the specification, an alkoxy group may be optionally substituted as described below.

"Heteroalkylene" refers to an alkyl radical as described above where one or more carbon atoms of the alkyl is replaced with a O, N or S atom. "Heteroalkylene" or "heteroalkylene chain" refers to a straight or branched divalent heteroalkyl chain linking the rest of the molecule to a radical group. Unless stated otherwise specifically in the specification, the heteroalkyl or heteroalkylene group may be optionally substituted as described below. Representative heteroalkyl groups include, but are not limited to —OCH₂CH₂OMe, —OCH₂CH₂OCH₂CH₂NH₂, or —OCH₂CH₂OCH₂CH₂OCH₂CH₂N(Me)₂. Representative heteroalkylene groups include, but are not limited to —OCH₂CH₂O—, —OCH₂CH₂OCH₂CH₂O—, or —OCH₂CH₂OCH₂CH₂OCH₂CH₂O—.

"Alkylamino" refers to a radical of the formula —NHR or —NRR where each R is, independently, an alkyl radical as defined above. Unless stated otherwise specifically in the specification, an alkylamino group may be optionally substituted as described below.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused or bridged ring systems. Aryl radicals include, but are not limited to, aryl radicals derived from the hydrocarbon ring systems of benzene, indane, indene, and naphthalene. Unless stated otherwise specifically in the specification, the term "aryl" or the prefix "ar-" (such as in "aralkyl") is meant to include aryl radicals that are optionally substituted.

"Carboxy" refers to —CO₂H. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to,

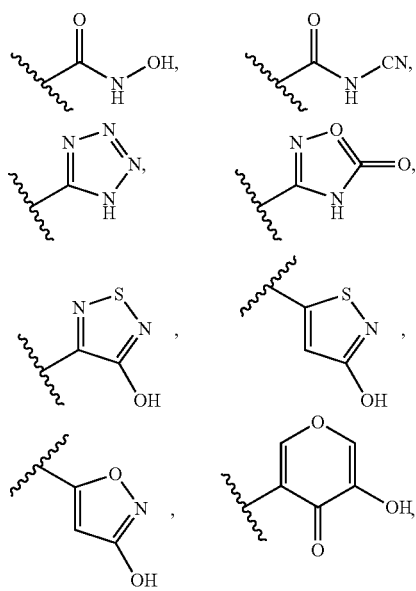

and the like.

"Cycloalkyl" refers to a stable, non-aromatic, monocyclic or polycyclic carbocyclic ring, which may include fused or bridged ring systems, which is saturated or unsaturated, and attached to the rest of the molecule by a single bond. Representative cycloalkyls include, but are not limited to, cycloaklyls having from three to fifteen carbon atoms, from three to ten carbon atoms, from three to eight carbon atoms, from three to six carbon atoms, from three to five carbon atoms, or three to four carbon atoms. Monocyclic cycloalkyl radicals include, for example, cyclopropyl, cyclobutyl, cyclopentyl, cyclohexyl, cycloheptyl, and cyclooctyl. Polycyclic radicals include, for example, adamantyl, norbornyl, decalinyl, and 7,7-dimethyl-bicyclo[2.2.1]heptanyl. Unless otherwise stated specifically in the specification, a cycloalkyl group may be optionally substituted. Illustrative examples of cycloalkyl groups include, but are not limited to, the following moieties:

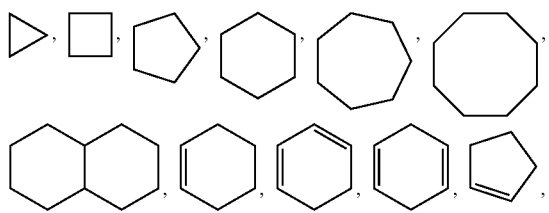

-continued

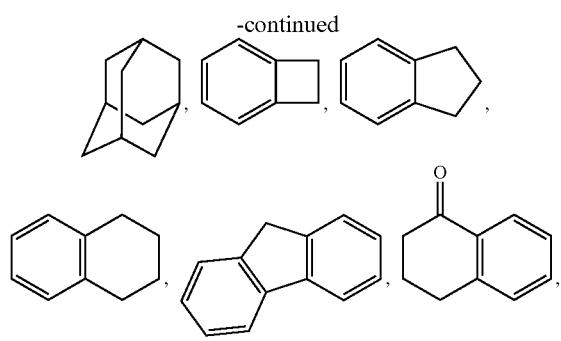

and the like.

"Fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Perhalo" or "perfluoro" refers to a moiety in which each hydrogen atom has been replaced by a halo atom or fluorine atom, respectively.

"Heterocyclyl" or "heterocyclic ring" or "heterocycloalkyl" refers to a stable 3- to 14-membered non-aromatic ring radical comprising 2 to 13 carbon atoms and from one to 6 heteroatoms selected from the group consisting of nitrogen, oxygen, and sulfur. Unless stated otherwise specifically in the specification, the heterocyclyl radical may be a monocyclic, or bicyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl. Unless stated otherwise specifically in the specification, a heterocyclyl group may be optionally substituted. Illustrative examples of heterocycloalkyl groups, also referred to as non-aromatic heterocycles, include:

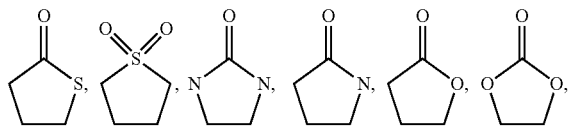

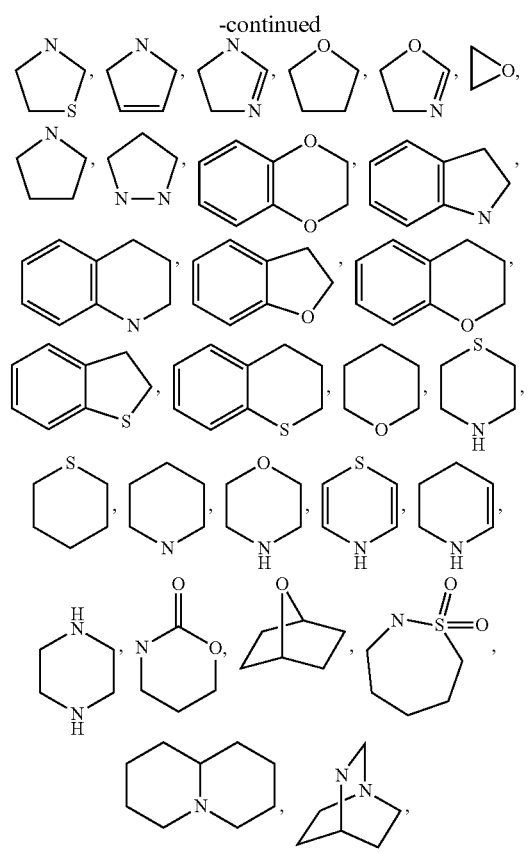

and the like. The term heterocycloalkyl also includes all ring forms of the carbohydrates, including but not limited to the monosaccharides, the disaccharides and the oligosaccharides. Unless otherwise noted, heterocycloalkyls have from 2 to 10 carbons in the ring. In some embodiments, heterocycloalkyls have from 2 to 8 carbons in the ring. In some embodiments, heterocycloalkyls have from 2 to 8 carbons in the ring and 1 or 2 N atoms. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen, phosphorous and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxirinyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group may be optionally substituted.

All the above groups may be either substituted or unsubstituted. The term "substituted" as used herein means any of the above groups may be further functionalized wherein at least one hydrogen atom is replaced by a bond to a non-hydrogen atom substituent. Unless stated specifically in the specification, a substituted group may include one or more substituents selected from: oxo, $-CO_2H$, nitrile, nitro, hydroxyl, thiooxy, alkyl, alkylene, alkoxy, alkoxyalkyl, alkylcarbonyl, alkyloxycarbonyl, aryl, aralkyl, arylcarbonyl, aryloxycarbonyl, aralkylcarbonyl, aralkyloxycarbonyl, aryloxy, cycloalkyl, cycloalkylalkyl, cycloalkylcarbonyl, cycloalkylalkylcarbonyl, cycloalkyloxycarbonyl, heterocyclyl, heterocyclalkyl, dialkylamines, arylamines, alkylarylamines, diarylamines, perfluoroalkyl or perfluoroalkoxy, for example, trifluoromethyl or trifluoromethoxy. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with $-NR_gC(=O)NR_gR_h$, $-NR_gC(=O)OR_h$, $-NR_gSO_2R_h$, $-OC(=O)NR_gR_h$, $-OR_g$, $-SR_g$, $-SOR_g$, $-SO_2R_g$, $-OSO_2R_g$, $-SO_2OR_g$, $=NSO_2R_g$, and $-SO_2NR_gR_h$. "Substituted" also means any of the above groups in which one or more hydrogen atoms are replaced with $-C(=O)R_g$, $-C(=O)OR_g$, $-CH_2SO_2R_g$, $-CH_2SO_2NR_gR_h$, $-SH$, $-SR_g$ or $-SSR_g$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, heterocyclylalkyl, heteroaryl, and/or heteroarylalkyl. In addition, each of the foregoing substituents may also be optionally substituted with one or more of the above substituents. In some embodiments, optional substituents are independently selected from hydrogen, halogen, $-CN$, $-OH$, $-NO_2$, $-N(R^{13})-R^{14}$, $-C(=O)-N(R^{13})-R^{14}$, $-NR^{13}C(=O)R^{15}$, $-C(=O)-O-R^{13}$, $-O-C(=O)-R^{15}$, $-SR^{13}$, $-S(=O)R^{15}$, $-S(=O)_2R^{15}$, $-N(R^{13})S(=O)_2R^{15}$, $-S(=O)_2-N(R^{13})-R^{14}$, $-C(=O)R^{13}$, optionally substituted alkyl, optionally substituted cycloalkyl, optionally substituted heterocycloalkyl, optionally substituted alkoxy, optionally substituted haloalkyl, optionally substituted haloalkoxy, optionally substituted phenyl, and optionally substituted 5- or 6-membered heteroaryl; each of $R^{13}$ and $R^{14}$ is independently selected from the group consisting of hydrogen, optionally substituted alkyl, optionally substituted cycloalkyl, optionally substituted heterocycloalkyl, optionally substituted alkoxy, optionally substituted haloalkyl, optionally substituted haloalkoxy, optionally substituted phenyl, and optionally substituted 5- or 6-membered heteroaryl; or $R^{13}$ and $R^{14}$, when on the same nitrogen atom, are taken together with the nitrogen atom to which they are attached to form an optionally substituted heterocycloalkyl; $R^{15}$ is selected from the group consisting of optionally substituted alkyl, optionally substituted cycloalkyl, optionally substituted heterocycloalkyl, optionally substituted alkoxy, optionally substituted haloalkyl, optionally substituted haloalkoxy, optionally substituted phenyl, and optionally substituted 5- or 6-membered heteroaryl. In some embodiments, optional substituents are independently selected from hydrogen, halogen, $-CN$, $-OH$, $-NO_2$, $-N(R^{13})-R^{14}$, $-C(=O)-N(R^{13})-R^{14}$, $-NR^{13}C(=O)R^{15}$, $-C(=O)-O-R^{13}$, $-O-C(=O)-R^{15}$, $-SR^{13}$, $-S(=O)R^{15}$, $-S(=O)_2R^{15}$, $-N(R^{13})S(=O)_2R^{15}$, $-S(=O)_2-N(R^{13})-R^{14}$, $-C(=O)R^{13}$, alkyl, cycloalkyl, heterocycloalkyl, alkoxy, haloalkyl, haloalkoxy, phenyl, and 5- or 6-membered heteroaryl; each of $R^{13}$ and $R^{14}$ is independently selected from the group consisting of hydrogen, alkyl, cycloalkyl, heterocycloalkyl, alkoxy, haloalkyl, haloalkoxy, phenyl, and 5- or 6-membered heteroaryl; or $R^{13}$ and $R^{14}$, when on the same nitrogen atom, are taken together with the nitrogen atom to which they are attached to form an optionally substituted heterocycloalkyl; $R^{15}$ is selected from the group consisting of alkyl, cycloalkyl, heterocycloalkyl, alkoxy, haloalkyl, haloalkoxy, phenyl, and 5- or 6-membered heteroaryl.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "subject" or "patient" encompasses mammals. Examples of mammals include, but are not limited to, humans. In one embodiment, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

Forms and Drug Delivery Systems, Seventh Ed. (Lippincott Williams & Wilkins 1999), herein incorporated by reference for such disclosure.

A pharmaceutical composition, as used herein, refers to a mixture of a compound of Formula I with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism.

Pharmaceutical formulations described herein are administrable to a subject in a variety of ways by multiple

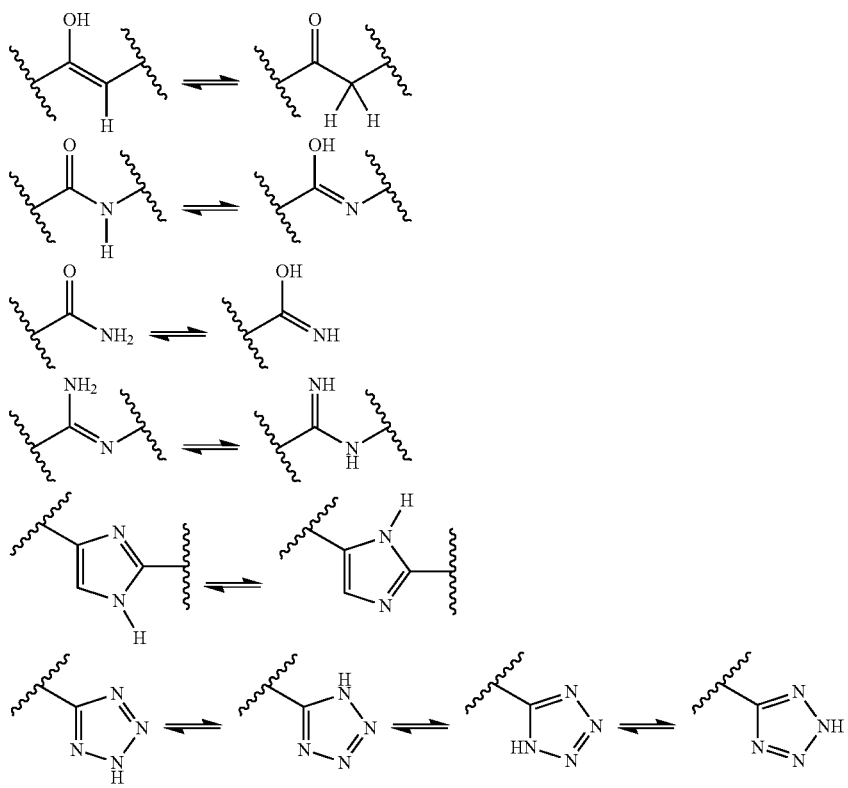

Administration and Pharmaceutical Composition

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage administration routes, including but not limited to, oral, parenteral (e.g., intravenous, subcutaneous, intramuscular, intramedullary injections, intrathecal, direct intraventricular, intraperitoneal, intralymphatic, intranasal injections), intranasal, buccal, topical or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, the compounds of Formula I are administered orally.

In some embodiments, the compounds of Formula I are administered topically. In such embodiments, the compound of Formula I is formulated into a variety of topically administrable compositions, such as solutions, suspensions, lotions, gels, pastes, shampoos, scrubs, rubs, smears, medicated sticks, medicated bandages, balms, creams or ointments. In one aspect, the compounds of Formula I are administered topically to the skin.

In another aspect, the compounds of Formula I are administered by inhalation.

In another aspect, the compounds of Formula I are formulated for intranasal administration. Such formulations include nasal sprays, nasal mists, and the like.

In another aspect, the compounds of Formula I are formulated as eye drops.

In any of the aforementioned aspects are further embodiments in which the effective amount of the compound of Formula I is: (a) systemically administered to the mammal; and/or (b) administered orally to the mammal; and/or (c) intravenously administered to the mammal; and/or (d) administered by inhalation to the mammal; and/or (e) administered by nasal administration to the mammal; or and/or (f) administered by injection to the mammal; and/or (g) administered topically to the mammal; and/or (h) administered by ophthalmic administration; and/or (i) administered rectally to the mammal; and/or (j) adminstered non-systemically or locally to the mammal.

In any of the aforementioned aspects are further embodiments comprising single administrations of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In certain embodiments, a compound as described herein is administered in a local rather than systemic manner.

In some embodiments, the compound described herein is administered topically. In some embodiments, the compound described herein is administered systemically.

In some embodiments, the pharmaceutical formulation is in the form of a tablet. In other embodiments, pharmaceutical formulations of the compounds of Formula I are in the form of a capsule.

In one aspect, liquid formulation dosage forms for oral administration are in the form of aqueous suspensions or solutions selected from the group including, but not limited to, aqueous oral dispersions, emulsions, solutions, elixirs, gels, and syrups.

For administration by inhalation, a compound of Formula I is formulated for use as an aerosol, a mist or a powder.

For buccal or sublingual administration, the compositions may take the form of tablets, lozenges, or gels formulated in a conventional manner.

In some embodiments, compounds of Formula I are prepared as transdermal dosage forms.

In one aspect, a compound of Formula I is formulated into a pharmaceutical composition suitable for intramuscular, subcutaneous, or intravenous injection.

In some embodiments, the compounds described herein may be administered topically and can be formulated into a variety of topically administrable compositions, such as solutions, suspensions, lotions, gels, pastes, medicated sticks, balms, creams or ointments.

In some embodiments, the compounds of Formula I are formulated in rectal compositions such as enemas, rectal gels, rectal foams, rectal aerosols, suppositories, jelly suppositories, or retention enemas.

Methods of Dosing and Treatment Regimens

In one embodiment, the compounds of Formula I are used in the preparation of medicaments for the treatment of diseases or conditions described herein. In addition, a method for treating any of the diseases or conditions described herein in a subject in need of such treatment, involves administration of pharmaceutical compositions that include at least one compound of Formula I or a pharmaceutically acceptable salt, active metabolite, prodrug, or solvate thereof, in therapeutically effective amounts to said subject.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In prophylactic applications, compositions containing the compounds described herein are administered to a patient susceptible to or otherwise at risk of a particular disease, disorder or condition.

In certain embodiments, the dose of drug being administered may be temporarily reduced or temporarily suspended for a certain length of time (i.e., a "drug holiday").

Doses employed for adult human treatment are typically in the range of 0.01 mg-5000 mg per day or from about 1 mg to about 1000 mg per day. In one embodiment, the desired dose is conveniently presented in a single dose or in divided doses.

Combination Treatments

In certain instances, it is appropriate to administer at least one compound of Formula I in combination with another therapeutic agent.

In one specific embodiment, a compound of Formula I is co-administered with a second therapeutic agent, wherein the compound of Formula I and the second therapeutic agent modulate different aspects of the disease, disorder or condition being treated, thereby providing a greater overall benefit than administration of either therapeutic agent alone.

For combination therapies described herein, dosages of the co-administered compounds vary depending on the type of co-drug(s) employed, on the specific drug(s) employed, on the disease or condition being treated and so forth. In additional embodiments, when co-administered with one or more other therapeutic agents, the compound provided herein is administered either simultaneously with the one or more other therapeutic agents, or sequentially.

If administration is simultaneous, the multiple therapeutic agents are, by way of example only, provided in a single, unified form, or in multiple forms.

In some embodiments, compounds of Formula I are administered to a mammal in combination with an anti-inflammatory agent. In some embodiments, compounds of Formula I are administered in combination with an antipsychotic agent. In some embodiments, compounds of Formula I are administered to a mammal in combination with a neuroleptic. In some embodiments, compounds of Formula I are administered to a mammal in combination with an atypical antipsychotic. In some embodiments, compounds of Formula I are administered in combination with a dopamine agonist. In some embodiments, compounds of Formula I are administered in combination with an anticholinergic. In some embodiments, compounds of Formula I are administered in combination with a COMT inhibitor. In some embodiments, compounds of Formula I are administered to a mammal in combination with an analgesic. In some embodiments, compounds of Formula I are administered to a mammal in combination with an antidepressant.

In some embodiments, compounds of Formula I are administered to a mammal in combination with an NSAID, COX-2 inhibitor, opiate, morphinomimetic, or combinations thereof.

In some embodiments, compounds of Formula I are administered in combination with an anti-schizophrenia drug. In some embodiments, compounds of Formula I are administered to a mammal in combination with thorazine, haloperidol, fluphenazine, tiotixene, trifluoperazine, perphenazine, thioridazine, clozapine, aripiprazole, ziprasidone, paliperidone, lurasidone, risperidone, asenapine, quetiapine, olanzapine, dihydrexidine, roxindole or combinations thereof.

In some embodiments, compounds of Formula I are administered in combination with an anti-Parkinson's drug. In some embodiments, compounds of Formula I are administered in combination with L-DOPA, carbidopa, carbidopa/L-DOPA, ropinirole, pramipexole, rotigotine, amantadine, trihexyphenidyl, benzatropine, selegiline, rasagiline, tolcapone, entacapone, apomorphine, bromocriptine, dihydrexidine, dinapsoline, lisuride, pergolide, piribedil, roxindole, sumanirole, or combinations thereof.

In some embodiments, compounds of Formula I are administered to a mammal in combination with other therapeutics used in the treatment of drug abuse.

In some embodiments, compounds of Formula I are administered to a mammal in combination with a stroke treatment. In some embodiments, compounds of Formula I are administered to a mammal in combination with a thrombolytic. In some embodiments, compounds of Formula I are administered to a mammal in combination with tissue plasminogen activator (tPA), or a recombinant tissue plasminogen activator. In some embodiments, compounds of Formula I are administered to a mammal in combination with alteplase, reteplase, tenecteplase, or combinations thereof.

In some embodiments, compounds of Formula I are administered to a mammal in combination with a treatment for neuropathic pain. In some embodiments, compounds of Formula I are administered to a mammal in combination with duloxetine, venlafaxine, and milnacipran, amitriptyline, nortriptyline, desipramine, bupropion, pregabalin, gabapentin, carbamazepine, oxcarbazepine, lamotrigine, methadone, ketobemidone, lidocaine, gallium maltolate, capsaicin, botulinum toxin type A, ketamine, dextromethorphan, memantine, alpha lipoic acid, benfotiamine, and combinations thereof.

EXAMPLES

The following examples are intended to illustrate but not limit the disclosed embodiments.

All reactions involving air and moisture-sensitive reagents and solvents were performed under a nitrogen atmosphere using standard chemical techniques. Anhydrous solvents were purchased and freshly used from Sigma-Aldrich or EMD Biosciences. All organic reagents were used as purchased. Analytical thin-layer chromatography was performed on Partisil K6F silica gel 60 Å, 250 μm. Microwave-assisted reactions were performed using a CEM Discover system. $^1$H and $^{13}$C chemical shifts are reported in δ values in ppm in the corresponding solvent. All solvents used for chromatography on the synthetic materials were Fisher Scientific HPLC grade, and the water was Millipore Milli-Q PP filtered. LCMS analysis of synthetic materials was completed on a Waters Autopurification system, which consists of a 2767 sample manager, a 2545 binary gradient module, a system fluidics organizer, a 2489 UV/vis detector, and a 3100 mass detector, all controlled with MassLynx software. A Sunfire Analytical C18 5 μm column (4.6×50 mm) and stepwise gradient {10% [(MeCN+0.1% TFA) in (water+0.1% TFA)] to 98% [(MeCN+0.1% TFA) in (water+0.1% TFA)] for 9 min.} was used for analytical LCMS of final compounds. The final compounds were purified by silica gel flash chromatography with ethyl acetate/hexanes as the eluant. All NMR spectra for the synthetic materials were recorded on a Bruker Avance II 400 or DRX-500 MHz instrument. The MestReNova 7 program was used to process and interpret NMR spectra. High Resolution Mass Spectrometry (HRMS) spectra were carried out on an Agilent 6224A Accurate-Mass Time-of-Flight (TOF) LC/MS system with electron spray ionization (ESI).

Scheme 1:

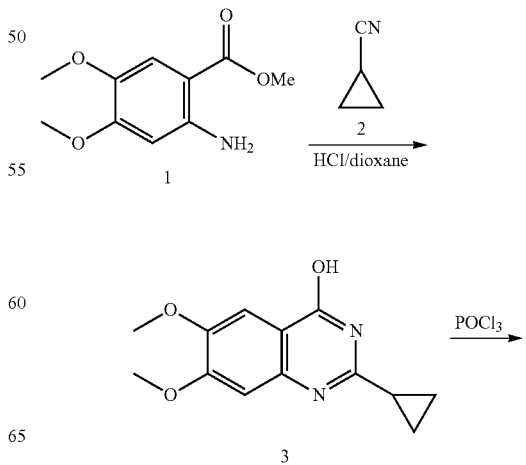

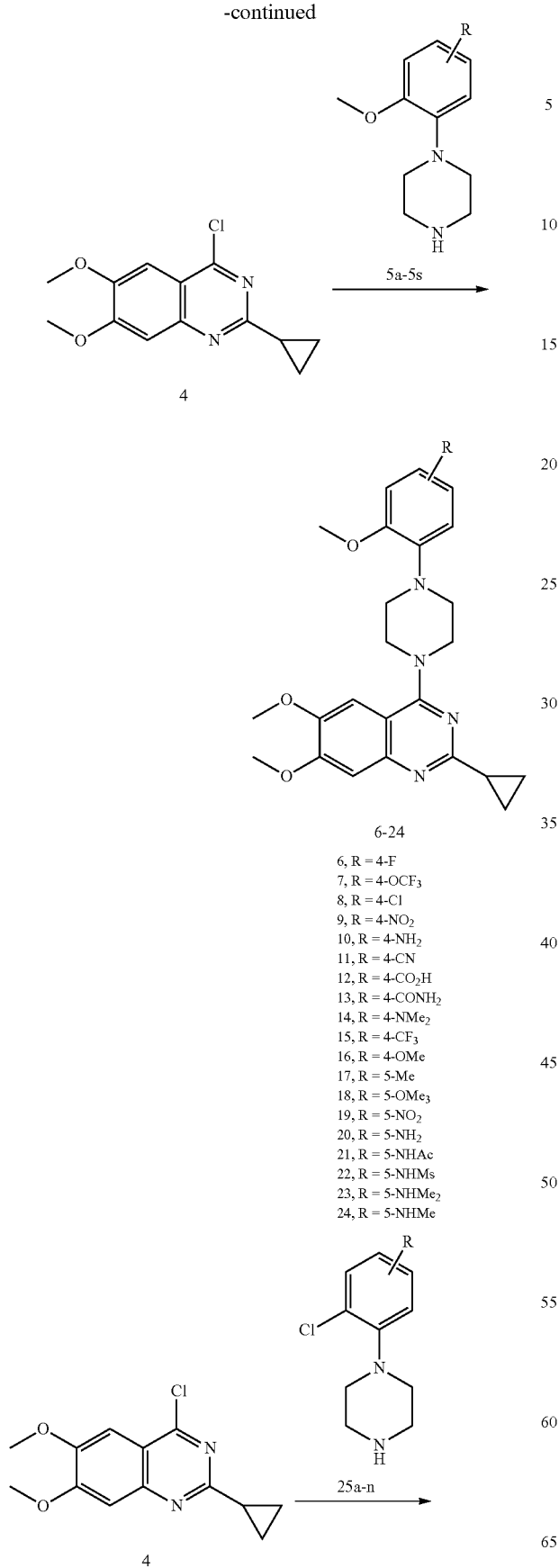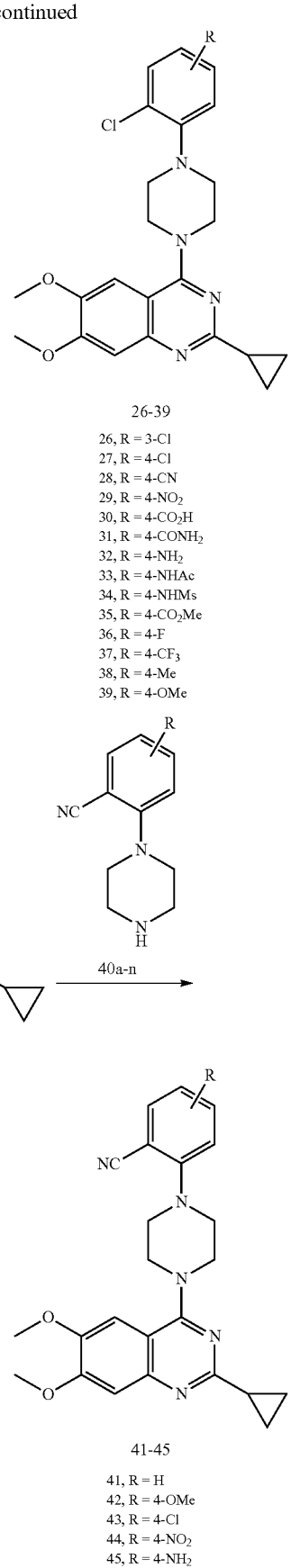

Example 1: 2-cyclopropyl-4-[4-(4-fluoro-2-methoxy-phenyl)-piperazin-1-yl]-6,7-dimethoxy-quinazoline (6)

Compound (1) (10 g, 47.3 mmol) and (2) (9.5 g 142 mmol) were weighted into reaction flask and 4M HCl in 1,4-dioxane was added. The mixture was stirred at 100° C. for overnight. The mixture was cooled to rt and poured carefully into cold saturated $Na_2CO_3$ solution (100 mL). The resulting solid was collected by filtration and washed with water to give compound (3) (10.8 g, yield: 93%) as a white solid $^1$H NMR (300 MHz, DMSO-$d_6$): δ 12.28 (brs, 1H), 7.37 (s, 1H), 6.93 (s, 1H), 3.86 (s, 3H), 3.83 (s, 3H), 2.11-2.04 (m, 1H), 1.07-0.95 (m, 4H). MS: m/z 247 (M–H$^+$).

Compound (3) (11 g, 45 mmol) was suspended in $POCl_3$ (40 mL) and the mixture was stirred at 110° C. for overnight. During the time, the suspension turned brown. The reaction mixture was cooled to rt and added into ice water dropwise. The reaction was extracted with EtOAc (30 mL×2). The organic layer was concentrated under reduced pressure. The crude product was purified by silica gel column chromatography (DCM) to give compound (4) (6.2 g, yield: 53%) as a white solid.

$^1$H NMR (400 MHz, DMSO-$d_6$): δ 7.29 (s, 1H), 3.99 (s, 3H), 3.96 (s, 3H), 2.27-2.20 (m, 1H), 1.11-1.06 (m, 4H). MS: m/z 265 (M–H$^+$).

A suspension of compound (4) (54 mg, 0.20 mmol), 1-(4-fluoro-2-methoxyphenyl)piperazine HCl salt (50 mg, 0.20 mmol), $K_2CO_3$ (83 mg, 0.60 mmol) in DMF (5 mL) was stirred at 70° C. for 17 h. After cooled to room temperature, 10 mL of water was added and the resulting solid was collected by filtration. The solid was purified by prep-HPLC (0.5% TFA as additive) to give compound (6) (24 mg, yield: 27%) as white solid.

$^1$H NMR (400 MHz, CDCl$_3$): δ=7.19 (s, 1H), 7.10 (s, 1H), 6.91 (d, J=8.0 Hz, 1H), 6.71-6.59 (m, 2H), 4.01 (s, 3H), 3.97 (s, 3H), 3.88 (s, 3H), 3.84-3.75 (m, 4H), 3.23-3.15 (m, 4H), 2.24-2.14 (m, 1H), 1.22-1.11 (m, 2H), 1.06-0.95 (m, 2H). MS: m/z 439.2 (M+H$^+$).

Example 2: 2-cyclopropyl-6,7-dimethoxy-4-[4-(2-methoxy-4-trifluoromethoxy-phenyl)-piperazin-1-yl]-quinazoline (7)

The title compound was prepared as described for compound (6), except that 1-(4-fluoro-2-methoxy-phenyl)-piperazine was substituted for 1-(2-methoxy-4-trifluoromethoxy-phenyl)-piperazine in step 3 of that route.

$^1$H NMR (400 MHz, CDCl$_3$): δ=7.22 (s, 1H), 7.10 (s, 1H), 6.94 (d, J=8.4 Hz, 1H), 6.82 (dd, J=8.8 Hz, 1H), 6.75 (d, J=1.6 Hz, 1H), 4.02 (s, 3H), 3.97 (s, 3H), 3.91 (s, 3H), 3.88-3.77 (m, 4H), 3.38-3.20 (m, 4H), 2.25-2.15 (m, 1H), 1.19-1.13 (m, 2H), 1.05-0.96 (m, 2H). MS: m/z 505.2 (M+H$^+$).

Example 3: 4-[4-(4-chloro-2-methoxy-phenyl)-piperazin-1-yl]-2-cyclopropyl-6,7-dimethoxy-quinazoline (8)

The title compound was prepared as described for compound (6), except that 1-(4-fluoro-2-methoxy-phenyl)-piperazine was substituted for 1-(4-chloro-2-methoxy-phenyl)-piperazine in step 3 of that route.

$^1$H NMR (400 MHz, CDCl$_3$): δ=7.33 (s, 1H), 7.08 (s, 1H), 6.96-6.83 (m, 3H), 4.02 (s, 3H), 3.97 (s, 3H), 3.94 (s, 3H), 3.93-3.81 (m, 4H), 3.30-3.22 (m, 4H), 2.33-2.21 (m, 1H), 1.23-1.15 (m, 2H), 1.08-0.97 (m, 2H). MS: m/z 455.2 (M+H$^+$).

Example 4: 2-cyclopropyl-6,7-dimethoxy-4-[4-(2-methoxy-4-nitro-phenyl)-piperazin-1-yl]-quinazoline (9)

The title compound was prepared as described for compound (6), except that 1-(4-fluoro-2-methoxy-phenyl)-piperazine was substituted for 1-(2-methoxy-4-nitro-phenyl)-piperazine in step 3 of that route.

$^1$H NMR (400 MHz, CDCl$_3$): δ=7.89 (d, J=8.4 Hz, 1H), 7.75 (s, 1H), 7.20 (s, 1H), 7.09 (s, 1H), 6.95 (d, J=8.0 Hz, 1H), 4.06-3.89 (m, 9H), 3.86-3.73 (m, 4H), 3.48-3.36 (m, 4H), 2.26-2.16 (m, 1H), 1.20-1.10 (m, 2H), 1.08-0.93 (m, 2H). MS: m/z 466.2 (M+H$^+$).

Example 5: 4-[4-(2-cyclopropyl-6,7-dimethoxy-quinazolin-4-yl)-piperazin-1-yl]-3-methoxy-phenylamine (10)

The title compound was prepared as described for compound (6), except that 1-(4-fluoro-2-methoxy-phenyl)-piperazine was substituted for 3-methoxy-4-piperazin-1-yl-phenylamine in step 3 of that route.

$^1$H NMR (400 HMz, DMSO-$d_6$): δ=7.13-7.08 (m, 2H), 6.69 (d, J=8.4 Hz, 1H), 6.26 (d, J=2.0 Hz, 1H), 6.09 (dd, J=8.4, 2.0 Hz, 1H), 4.76 (brs, 2H), 3.90 (s, 3H), 3.88 (s, 3H), 3.71 (s, 3H), 3.70-3.58 (m, 4H), 3.08-2.96 (m, 4H), 2.10-2.00 (m, 1H), 1.09-0.99 (m, 2H), 0.98-0.88 (m, 2H). MS: m/z 436.3 (M+H$^+$).

Example 6: 4-[4-(2-cyclopropyl-6,7-dimethoxy-quinazolin-4-yl)-piperazin-1-yl]-3-methoxy-benzonitrile (11)

The title compound was prepared as described for compound (6), except that 1-(4-fluoro-2-methoxy-phenyl)-piperazine was substituted for 3-methoxy-4-piperazin-1-yl-benzonitrile in step 3 of that route.

$^1$H NMR (300 MHz, DMSO-$d_6$): δ=7.44-7.32 (m, 2H), 7.20-7.10 (m, 2H), 7.06 (d, J=8.7 Hz, 1H), 3.98-3.82 (m, 9H), 3.76-3.63 (m, 4H), 3.34-3.26 (m, 4H), 2.16-2.02 (m, 1H), 1.08-0.98 (m, 2H), 0.98-0.89 (m, 2H). MS: m/z 446.2 (M+H$^+$).

Example 7: 4-[4-(2-cyclopropyl-6,7-dimethoxy-quinazolin-4-yl)-piperazin-1-yl]-3-methoxy-benzoic acid (12)

The title compound was prepared as described for compound (6), except that 1-(4-fluoro-2-methoxy-phenyl)-piperazine was substituted for 3-methoxy-4-piperazin-1-yl-benzoic acid in step 3 of that route.

$^1$H NMR (400 MHz, CDCl$_3$): δ=7.75 (d, J=8.0 Hz, 1H), 7.62 (s, 1H), 7.44 (s, 1H), 7.08 (s, 1H), 6.99 (d, J=8.0 Hz, 1H), 4.43-4.23 (m, 4H), 4.06 (s, 3H), 3.98 (s, 6H), 3.52-3.36 (m, 4H), 2.42-2.28 (m, 1H), 1.41-1.25 (m, 4H). MS: m/z 465.2 (M+H$^+$).

Example 8: 4-[4-(2-cyclopropyl-6,7-dimethoxy-quinazolin-4-yl)-piperazin-1-yl]-3-methoxy-benzamide (13)

The title compound was prepared as described for compound (6), except that 1-(4-fluoro-2-methoxy-phenyl)-piperazine was substituted for 3-methoxy-4-piperazin-1-yl-benzamide in step 3 of that route.

¹H NMR (400 MHz, CDCl₃): δ=7.63 (s, 1H), 7.50 (s, 1H), 7.34 (d, J=8.4 Hz, 1H), 7.06 (s, 1H), 6.91 (d, J=8.0 Hz, 1H), 6.62 (brs, 1H), 6.42 (brs, 1H), 4.30-4.20 (m, 4H), 4.06 (s, 3H), 3.98 (s, 6H), 3.42-3.28 (m, 4H), 2.50-2.39 (m, 1H), 1.39-1.25 (m, 4H). MS: m/z 464.3 (M+H⁺).

Example 9: {4-[4-(2-cyclopropyl-6,7-dimethoxy-quinazolin-4-yl)-piperazin-1-yl]-3-methoxy-phenyl}-dimethyl-amine (14)

The title compound was prepared as described for compound (6), except that 1-(4-fluoro-2-methoxy-phenyl)-piperazine was substituted for (3-methoxy-4-piperazin-1-yl-phenyl)-dimethyl-amine in step 3 of that route.

¹H NMR (400 MHz, CDCl₃): δ=7.24 (s, 1H), 7.10 (s, 1H), 6.91 (d, J=8.8 Hz, 1H), 6.37 (d, J=2.4 Hz, 1H), 6.32 (dd, J=8.1, 2.0 Hz, 1H), 4.01 (s, 3H), 3.96 (s, 3H), 3.90 (s, 3H), 3.89-3.76 (m, 4H), 3.26-3.13 (m, 4H), 2.93 (s, 6H), 2.28-2.18 (m, 1H), 1.21-1.12 (m, 2H), 1.08-0.93 (m, 2H). MS: m/z 464.3 (M+H⁺).

Example 10: 2-cyclopropyl-6,7-dimethoxy-4-[4-(2-methoxy-4-trifluoromethyl-phenyl)-piperazin-1-yl]-quinazoline (15)

The title compound was prepared as described for compound (6), except that 1-(4-fluoro-2-methoxy-phenyl)-piperazine was substituted for 1-(2-methoxy-4-trifluoromethyl-phenyl)-piperazine in step 3 of that route.

¹H NMR (400 MHz, CDCl₃): δ=7.26-7.19 (m, 2H), 7.10-7.06 (m, 2H), 7.00 (d, J=8.0 Hz, 1H), 4.02 (s, 3H), 3.97 (s, 3H), 3.95 (s, 3H), 3.88-3.78 (m, 4H), 3.33-3.25 (m, 4H), 2.28-2.16 (m, 1H), 1.19-1.11 (m, 2H), 1.06-0.89 (m, 2H). MS: m/z 489.3 (M+H⁺).

Example 11: 2-cyclopropyl-4-[4-(2,4-dimethoxy-phenyl)-piperazin-1-yl]-6,7-dimethoxy-quinazoline (16)

The title compound was prepared as described for compound (6), except that 1-(4-fluoro-2-methoxy-phenyl)-piperazine was substituted for 1-(2,4-dimethoxy-phenyl)-piperazine in step 3 of that route.

¹H NMR (400 MHz, CDCl₃): δ=7.19 (s, 1H), 7.11 (s, 1H), 6.91 (d, J=8.8 Hz, 1H), 6.52 (d, J=2.8 Hz, 1H), 6.45 (dd, J=8.8, 2.8 Hz, 1H), 4.01 (s, 3H), 3.97 (s, 3H), 3.88 (s, 3H), 3.86-3.76 (m, 7H), 3.26-3.16 (m, 4H), 2.26-2.13 (m, 1H), 1.23-1.12 (m, 2H), 1.04-0.91 (m, 2H). MS: m/z 451.2 (M+H⁺).

Example 12: 2-cyclopropyl-6,7-dimethoxy-4-[4-(2-methoxy-5-methyl-phenyl)-piperazin-1-yl]-quinazoline (17)

The title compound was prepared as described for compound (6), except that 1-(4-fluoro-2-methoxy-phenyl)-piperazine was substituted for 1-(2-methoxy-5-methyl-phenyl)-piperazine in step 3 of that route.

¹H NMR (300 MHz, CDCl₃): δ=7.21 (s, 1H), 7.12 (s, 1H), 6.83-6.79 (m, 3H), 4.02 (s, 3H), 3.99 (s, 3H), 3.89 (s, 3H), 3.83-3.80 (m, 4H), 3.24 (t, J=4.5 Hz, 4H), 2.32 (s, 3H), 2.11-2.04 (m, 1H), 1.20-1.15 (m, 2H), 1.03-0.95 (m, 2H) MS: m/z 435.2 (M−H⁺).

Example 13: 2-[4-(2-cyclopropyl-6,7-dimethoxy-quinazolin-4-yl)-piperazin-1-yl]-benzonitrile (18)

The title compound was prepared as described for compound (6), except that 1-(4-fluoro-2-methoxy-phenyl)-piperazine was substituted for 1-(2,5-dimethoxy-phenyl)-piperazine in step 3 of that route.

¹H NMR (300 MHz, CDCl₃): δ=7.21 (s, 1H), 7.11 (s, 1H), 6.82 (d, J=8.7 Hz, 1H), 6.59 (d, J=3.0 Hz, 1H) 6.53 (dd, J=8.7, 3.0 Hz, 1H), 4.02 (s, 3H), 3.99 (s, 3H), 3.89 (s, 3H), 3.87-3.76 (m, 7H), 3.24 (t, J=4.5 Hz, 4H), 2.21-2.16 (m, 1H), 1.18-1.14 (m, 2H), 1.03-0.95 (m, 2H) MS: m/z 451.2 (M−H⁺).

Example 14: 2-cyclopropyl-6,7-dimethoxy-4-[4-(2-methoxy-5-nitro-phenyl)-piperazin-1-yl]-quinazoline (19)

The title compound was prepared as described for compound (6), except that 1-(4-fluoro-2-methoxy-phenyl)-piperazine was substituted for 1-(2-methoxy-5-nitro-phenyl)-piperazine in step 3 of that route.

¹H NMR (400 MHz, CDCl₃): δ=8.05-7.99 (m, 2H), 7.80 (d, J=2.4 Hz, 1H), 7.05 (s, 1H), 6.97 (d, J=8.8 Hz, 1H), 4.29-4.15 (m, 4H), 4.10 (s, 3H), 4.03 (s, 3H), 3.99 (s, 3H), 3.38-3.26 (m, 4H), 2.69-2.54 (m, 1H), 1.38-1.24 (m, 4H). MS: m/z 466.2 (M+H⁺).

Example 15: 3-[4-(2-cyclopropyl-6,7-dimethoxy-quinazolin-4-yl)-piperazin-1-yl]-4-methoxy-phenylamine (20)

The title compound was prepared as described for compound (6), except that 1-(4-fluoro-2-methoxy-phenyl)-piperazine was substituted for 4-methoxy-3-piperazin-1-yl-phenylamine in step 3 of that route.

¹H NMR (400 MHz, DMSO-d₆): δ=10.29 (brs, 2H), 7.46 (s, 1H), 7.35 (s, 1H), 7.08 (d, J=8.8 Hz, 1H), 7.05-6.95 (m, 2H), 4.36-4.18 (m, 4H), 3.96 (s, 3H), 3.95 (s, 3H), 3.85 (s, 3H), 3.26-3.15 (m, 4H), 2.46-2.34 (m, 1H), 1.33-1.22 (m, 4H). MS: m/z 436.3 (M+H⁺).

Example 16: N-{3-[4-(2-cyclopropyl-6,7-dimethoxy-quinazolin-4-yl)-piperazin-1-yl]-4-methoxy-phenyl}-acetamide (21)

The title compound was prepared as described for compound (6), except that 1-(4-fluoro-2-methoxy-phenyl)-piperazine was substituted for N-(4-methoxy-3-piperazin-1-yl-phenyl)-acetamide in step 3 of that route.

¹H NMR (300 MHz, CDCl₃): δ=7.26-7.18 (m, 2H), 7.16-7.00 (m, 3H), 6.82 (d, J=8.7 Hz, 1H), 4.01 (s, 3H), 3.97 (s, 3H), 3.88 (s, 3H), 3.85-3.74 (m, 4H), 3.38-3.21 (m, 4H), 2.26-2.11 (m, 4H), 1.22-1.11 (m, 2H), 1.06-0.90 (m, 2H). MS: m/z 478.3 (M+H⁺).

Example 17: N-{3-[4-(2-cyclopropyl-6,7-dimethoxy-quinazolin-4-yl)-piperazin-1-yl]-4-methoxy-phenyl}-methanesulfonamide (22)

The title compound was prepared as described for compound (6), except that 1-(4-fluoro-2-methoxy-phenyl)-piperazine was substituted for N-(4-methoxy-3-piperazin-1-yl-phenyl)-methanesulfonamide in step 3 of that route.

¹H NMR (300 MHz, CDCl₃): δ=7.25 (s, 1H), 7.10 (s, 1H), 6.98-6.82 (m, 3H), 4.02 (s, 3H), 3.99 (s, 3H), 3.91 (s, 3H), 3.89-3.76 (m, 4H), 3.29-3.22 (m, 4H), 3.98 (s, 3H), 2.28-2.15 (m, 1H), 1.25-1.13 (m, 2H), 1.09-0.92 (m, 2H). MS: m/z 514.2 (M+H$^+$).

Example 18: {3-[4-(2-cyclopropyl-6,7-dimethoxy-quinazolin-4-yl)-piperazin-1-yl]-4-methoxy-phenyl}-dimethyl-amine (23)

The title compound was prepared as described for compound (6), except that 1-(4-fluoro-2-methoxy-phenyl)-piperazine was substituted for (4-methoxy-3-piperazin-1-yl-phenyl)-dimethyl-amine in step 3 of that route.
$^1$H NMR (300 MHz, CDCl$_3$): δ=7.20 (s, 1H), 7.11 (s, 1H), 6.82 (d, J=8.7 Hz, 1H), 6.51-6.38 (m, 2H), 4.01 (s, 3H), 3.97 (s, 3H), 3.91-3.79 (m, 7H), 3.28-3.20 (m, 4H), 2.88 (s, 6H), 2.26-2.13 (m, 1H), 1.24-1.11 (m, 2H), 1.04-0.92 (m, 2H). MS: m/z 464.3 (M+H$^+$).

Example 19: {3-[4-(2-cyclopropyl-6,7-dimethoxy-quinazolin-4-yl)-piperazin-1-yl]-4-methoxy-phenyl}-methyl-amine (24)

The title compound was prepared as described for compound (6), except that 1-(4-fluoro-2-methoxy-phenyl)-piperazine was substituted for (4-methoxy-3-piperazin-1-yl-phenyl)-methyl-amine in step 3 of that route.
$^1$H NMR (400 MHz, CDCl$_3$): δ=7.19 (s, 1H), 7.10 (s, 1H), 6.78 (d, J=8.8 Hz, 1H), 6.35-6.25 (m, 2H), 4.01 (s, 3H), 3.96 (s, 3H), 3.88-3.76 (m, 7H), 3.28-3.20 (m, 4H), 2.82 (s, 3H), 2.23-2.12 (m, 1H), 1.22-1.14 (m, 2H), 1.04-0.92 (m, 2H). MS: m/z 450.3 (M+H$^+$).

Example 20: 2-cyclopropyl-4-[4-(2,3-dichloro-phenyl)-piperazin-1-yl]-6,7-dimethoxy-quinazoline (26)

The title compound was prepared as described for compound (6), except that 1-(4-fluoro-2-methoxy-phenyl)-piperazine was substituted for 1-(2,3-dichloro-phenyl)-piperazine in step 3 of that route.
$^1$H NMR (400 MHz, CDCl$_3$): δ=7.25-7.14 (m, 3H), 7.09 (s, 1H), 7.01 (dd, J=7.2, 2.0 Hz, 1H), 4.01 (s, 3H), 3.97 (s, 3H), 3.89-3.75 (m, 4H), 3.28-3.18 (m, 4H), 2.48-2.12 (m, 1H), 1.19-1.12 (m, 2H), 1.10-0.93 (m, 2H). MS: m/z 459.2 (M+H$^+$).

Example 21: 2-cyclopropyl-4-[4-(2,4-dichloro-phenyl)-piperazin-1-yl]-6,7-dimethoxy-quinazoline (27)

The title compound was prepared as described for compound (6), except that 1-(4-fluoro-2-methoxy-phenyl)-piperazine was substituted for 1-(2,4-dichloro-phenyl)-piperazine in step 3 of that route.
$^1$H NMR (400 MHz, CDCl$_3$): δ=7.31 (d, J=8.8 Hz, 1H), 7.20 (s, 1H), 7.08 (s, 1H), 7.01 (d, J=2.8 Hz, 1H), 6.80 (dd, J=8.8, 2.8 Hz, 1H), 4.01 (s, 3H), 3.97 (s, 3H), 3.79-3.71 (m, 4H), 3.40-3.32 (m, 4H), 2.28-2.15 (m, 1H), 1.19-1.11 (m, 2H), 1.04-0.93 (m, 2H). MS: m/z 459.1 (M+H$^+$).

Example 22: 3-chloro-4-[4-(2-cyclopropyl-6,7-dimethoxy-quinazolin-4-yl)-piperazin-1-yl]-benzonitrile (28)

The title compound was prepared as described for compound (6), except that 1-(4-fluoro-2-methoxy-phenyl)-piperazine was substituted for 3-chloro-4-piperazin-1-yl-benzonitrile in step 3 of that route.

$^1$H NMR (400 MHz, DMSO-d$_6$): δ=8.00 (d, J=2.0 Hz, 1H), 7.79 (d, J=8.4, 2.0 Hz, 1H), 7.33 (d, J=8.4 Hz, 1H), 7.16-7.10 (m, 2H), 3.92 (s, 3H), 3.90 (s, 3H), 3.86-3.70 (m, 4H), 3.40-3.29 (m, 4H), 2.16-2.02 (m, 1H), 1.09-1.02 (m, 2H), 1.00-0.93 (m, 2H). MS: m/z 450.2 (M+H$^+$).

Example 23: 4-[4-(2-chloro-4-nitro-phenyl)-piperazin-1-yl]-2-cyclopropyl-6,7-dimethoxy-quinazoline (29)

The title compound was prepared as described for compound (6), except that 1-(4-fluoro-2-methoxy-phenyl)-piperazine was substituted for 1-(2-chloro-4-nitro-phenyl)-piperazine in step 3 of that route.
$^1$H NMR (400 MHz, CDCl$_3$): δ=8.29 (d, J=2.8 Hz, 1H), 8.13 (dd, J=8.8, 2.8 Hz, 1H), 7.21 (s, 1H), 7.20-7.05 (m, 2H), 4.02 (s, 3H), 3.98 (s, 3H), 3.89-3.78 (m, 4H), 3.43-3.35 (m, 4H), 2.48-2.15 (m, 1H), 1.19-1.12 (m, 2H), 1.06-0.94 (m, 2H). MS: m/z 470.0 (M+H$^+$).

Example 24: 3-chloro-4-[4-(2-cyclopropyl-6,7-dimethoxy-quinazolin-4-yl)-piperazin-1-yl]-benzoic acid (30)

The title compound was prepared as described for compound (6), except that 1-(4-fluoro-2-methoxy-phenyl)-piperazine was substituted for 3-chloro-4-piperazin-1-yl-benzoic acid in step 3 of that route.
$^1$H NMR (400 MHz, DMSO-d$_6$): δ=13.06 (brs, 1H), 7.91 (s, 1H), 7.87 (d, J=8.8 Hz, 1H), 7.35 (s, 1H), 7.27 (d, J=8.4 Hz, 1H), 7.18 (s, 1H), 4.29-4.10 (m, 4H), 3.98 (s, 3H), 3.95 (s, 3H), 3.40-3.26 (m, 4H), 2.25-2.20 (m, 1H), 1.35-1.26 (m, 4H). MS: m/z 469.2 (M+H$^+$).

Example 25: 3-chloro-4-[4-(2-cyclopropyl-6,7-dimethoxy-quinazolin-4-yl)-piperazin-1-yl]-benzamide (31)

The title compound was prepared as described for compound (6), except that 1-(4-fluoro-2-methoxy-phenyl)-piperazine was substituted for 3-chloro-4-piperazin-1-yl-benzamide in step 3 of that route.
$^1$H NMR (300 MHz, DMSO-d$_6$): δ=7.98 (brs, 1H), 7.95 (s, 1H), 7.83 (dd, J=8.1, 1.5 Hz, 1H), 7.37 (brs, 1H), 7.27 (d, J=8.7 Hz, 1H), 7.15-7.12 (m, 2H), 3.91 (s, 6H), 3.80-3.76 (m, 4H), 3.28-3.246 (m, 4H), 2.09-2.07 (m, 1H), 1.05-0.93 (m, 4H), MS: m/z 468 (M−H$^{11}$).

Example 26: 3-chloro-4-[4-(2-cyclopropyl-6,7-dimethoxy-quinazolin-4-yl)-piperazin-1-yl]-phenylamine (32)

The title compound was prepared as described for compound (6), except that 1-(4-fluoro-2-methoxy-phenyl)-piperazine was substituted for 3-chloro-4-piperazin-1-yl-phenylamine in step 3 of that route.
$^1$H NMR (400 MHz, DMSO-d$_6$): δ=7.25-7.14 (m, 2H), 6.96 (d, J=8.4 Hz, 1H), 6.66 (s, 1H), 6.50 (dd, J=8.4, 2.0 Hz, 1H), 3.99-3.75 (m, 10H), 3.05-2.96 (m, 4H), 2.20-2.11 (m, 1H), 1.19-0.96 (m, 4H). MS: m/z 440.2 (M+H$^+$).

Example 27: N-{3-chloro-4-[4-(2-cyclopropyl-6,7-dimethoxy-quinazolin-4-yl)-piperazin-1-yl]-phenyl}-acetamide (33)

The title compound was prepared as described for compound (6), except that 1-(4-fluoro-2-methoxy-phenyl)-piperazine was substituted for N-(3-chloro-4-piperazin-1-yl-phenyl)-acetamide in step 3 of that route.

¹H NMR (400 MHz, CDCl₃): δ=7.67 (brs, 1H), 7.57 (s, 1H), 7.34 (dd, J=8.4, 2.0 Hz, 1H), 7.21 (s, 1H), 7.01 (s, 1H), 6.94 (d, J=8.4 Hz, 1H), 3.93 (s, 3H), 3.90 (s, 3H), 3.82-3.76 (m, 4H), 3.20-3.06 (m, 4H), 2.20-2.11 (m, 1H), 2.10 (s, 3H), 1.13-1.06 (m, 2H), 0.98-0.90 (m, 2H). MS: m/z 482.2 (M+H⁺).

Example 28: N-{3-chloro-4-[4-(2-cyclopropyl-6,7-dimethoxy-quinazolin-4-yl)-piperazin-1-yl]-phenyl}-methanesulfonamide (34)

The title compound was prepared as described for compound (6), except that 1-(4-fluoro-2-methoxy-phenyl)-piperazine was substituted for N-(3-chloro-4-piperazin-1-yl-phenyl)-methanesulfonamide in step 3 of that route.

¹H NMR (400 MHz, CDCl₃): δ=7.31-7.26 (m, 2H), 7.12 (dd, J=8.8, 2.8 Hz, 1H), 7.06-6.95 (m, 2H), 3.94 (s, 3H), 3.90 (s, 3H), 3.86-3.73 (m, 4H), 3.20-3.06 (m, 4H), 2.95 (s, 3H), 2.24-2.13 (m, 1H), 1.14-1.06 (m, 2H), 0.99-0.91 (m, 2H). MS: m/z 518.2 (M+H⁺).

Example 29: 3-chloro-4-[4-(2-cyclopropyl-6,7-dimethoxy-quinazolin-4-yl)-piperazin-1-yl]-benzoic acid (35)

The title compound was prepared as described for compound (6), except that 1-(4-fluoro-2-methoxy-phenyl)-piperazine was substituted for 3-chloro-4-piperazin-1-yl-benzoic acid methyl ester in step 3 of that route.

¹H NMR (400 MHz, CDCl₃): δ=8.08 (d, J=1.6 Hz, 1H), 7.93 (dd, J=8.4, 1.6 Hz, 1H), 7.87 (s, 1H), 7.08-7.01 (m, 2H), 4.29-4.20 (m, 4H), 4.09 (s, 3H), 3.98 (s, 3H), 3.91 (s, 3H), 3.35-3.26 (m, 4H), 2.58-2.50 (m, 1H), 1.35-1.26 (m, 4H). MS: m/z 483.2 (M+H⁺).

Example 30: 4-[4-(2-chloro-4-fluoro-phenyl)-piperazin-1-yl]-2-cyclopropyl-6,7-dimethoxy-quinazoline (36)

The title compound was prepared as described for compound (6), except that 1-(4-fluoro-2-methoxy-phenyl)-piperazine was substituted for 1-(2-chloro-4-fluoro-phenyl)-piperazine in step 3 of that route.

¹H NMR (400 MHz, CDCl₃): δ=7.23 (s, 1H), 7.16 (dd, J=8.4, 3.2 Hz, 1H), 7.11-7.01 (m, 2H), 7.00-6.93 (m, 1H), 4.01 (s, 3H), 3.97 (s, 3H), 3.84-3.75 (m, 4H), 3.20-3.11 (m, 4H), 2.20-2.11 (m, 1H), 1.22-1.11 (m, 2H), 1.07-0.95 (m, 2H). MS: m/z 443.2 (M+H⁺).

Example 31: 4-[4-(2-chloro-4-trifluoromethyl-phenyl)-piperazin-1-yl]-2-cyclopropyl-6,7-dimethoxy-quinazoline (37)

The title compound was prepared as described for compound (6), except that 1-(4-fluoro-2-methoxy-phenyl)-piperazine was substituted for 1-(2-chloro-4-trifluoromethyl-phenyl)-piperazine in step 3 of that route.

¹H NMR (400 MHz, CDCl₃): δ=7.65 (s, 1H), 7.50 (d, J=7.6 Hz, 1H), 7.22 (s, 1H), 7.14 (d, J=8.4 Hz, 1H), 7.09 (s, 1H), 4.02 (s, 3H), 3.98 (s, 3H), 3.85-3.78 (m, 4H), 3.34-3.25 (m, 4H), 2.26-2.14 (m, 1H), 1.22-1.11 (m, 2H), 1.07-0.95 (m, 2H). MS: m/z 493.2 (M+H⁺).

Example 32: 4-[4-(2-chloro-4-methyl-phenyl)-piperazin-1-yl]-2-cyclopropyl-6,7-dimethoxy-quinazoline (38)

The title compound was prepared as described for compound (6), except that 1-(4-fluoro-2-methoxy-phenyl)-piperazine was substituted for 1-(2-chloro-4-methyl-phenyl)-piperazine in step 3 of that route.

¹H NMR (400 MHz, CDCl₃): δ=7.26-7.18 (m, 2H), 7.10 (s, 1H), 7.05 (d, 1H), 6.98 (d, J=8.4 Hz, 1H), 4.01 (s, 3H), 3.97 (s, 3H), 3.85-3.78 (m, 4H), 3.26-3.15 (m, 4H), 2.30 (s, 3H), 2.26-2.12 (m, 1H), 1.20-1.13 (m, 2H), 1.06-0.94 (m, 2H). MS: m/z 439.2 (M+H⁺).

Example 33: 4-[4-(2-chloro-4-methoxy-phenyl)-piperazin-1-yl]-2-cyclopropyl-6,7-dimethoxy-quinazoline (39)

The title compound was prepared as described for compound (6), except that 1-(4-fluoro-2-methoxy-phenyl)-piperazine was substituted for 1-(2-chloro-4-methoxy-phenyl)-piperazine in step 3 of that route.

¹H NMR (400 MHz, CDCl₃): δ=7.29 (s, 1H), 7.09 (s, 1H), 7.03 (d, J=8.4 Hz, 1H), 6.99 (d, J=2.8 Hz, 1H), 6.80 (dd, J=8.8, 2.8 Hz, 1H), 4.02 (s, 3H), 3.97 (s, 3H), 3.95-3.79 (m, 4H), 3.78 (s, 3H), 3.21-3.10 (m, 4H), 2.29-2.18 (m, 1H), 1.19-1.13 (m, 2H), 1.09-0.96 (m, 2H). MS: m/z 455.2 (M+H⁺).

Example 34: 2-[4-(2-cyclopropyl-6,7-dimethoxy-quinazolin-4-yl)-piperazin-1-yl]-benzonitrile (41)

The title compound was prepared as described for compound (6), except that 1-(4-fluoro-2-methoxy-phenyl)-piperazine was substituted for 2-piperazin-1-yl-benzonitrile in step 3 of that route.

¹H NMR (300 MHz, DMSO-d₆): δ=7.74 (dd, J=7.5, 1.2 Hz, 1H), 7.67-7.60 (m, 1H), 7.25 (d, J=8.1 Hz, 1H), 7.16-7.10 (m, 3H), 3.90 (s, 6H), 3.77-3.73 (m, 4H), 3.38-3.30 (m, 4H), 2.11-2.04 (m, 1H), 1.06-1.00 (m, 2H), 0.99-0.90 (m, 2H) MS: m/z 416.2 (M+H⁺).

Example 35: 2-[4-(2-cyclopropyl-6,7-dimethoxy-quinazolin-4-yl)-piperazin-1-yl]-5-methoxy-benzonitrile (42)

The title compound was prepared as described for compound (6), except that 1-(4-fluoro-2-methoxy-phenyl)-piperazine was substituted for 5-methoxy-2-piperazin-1-yl-benzonitrile in step 3 of that route.

¹H NMR (400 MHz, CDCl₃): δ=8.00 (s, 1H), 7.16-7.06 (m, 2H), 7.06-6.98 (m, 2H), 4.29-4.19 (m, 4H), 4.10 (s, 3H), 3.98 (s, 3H), 3.81 (s, 3H), 3.26-3.13 (m, 4H), 2.64-2.53 (m, 1H), 1.38-1.24 (m, 4H). MS: m/z 446.3 (M+H⁺).

Example 36: 5-chloro-2-[4-(2-cyclopropyl-6,7-dimethoxy-quinazolin-4-yl)-piperazin-1-yl]-benzonitrile (43)

The title compound was prepared as described for compound (6), except that 1-(4-fluoro-2-methoxy-phenyl)-piperazine was substituted for 5-chloro-2-piperazin-1-yl-benzonitrile in step 3 of that route.

¹H NMR (400 MHz, CDCl₃): δ=8.02 (s, 1H), 7.60 (d, J=2.4 Hz, 1H), 7.51 (dd, J=8.8, 2.4 Hz, 1H), 7.03 (s, 1H), 6.98 (d, J=8.8 Hz, 1H), 4.29-4.19 (m, 4H), 4.10 (s, 3H), 3.98

(s, 3H), 3.38-3.28 (m, 4H), 2.69-2.54 (m, 1H), 1.41-1.23 (m, 4H). MS: m/z 450.2 (M+H⁺).

Example 37: 2-[4-(2-cyclopropyl-6,7-dimethoxy-quinazolin-4-yl)-piperazin-1-yl]-5-nitro-benzonitrile (44)

The title compound was prepared as described for compound (6), except that 1-(4-fluoro-2-methoxy-phenyl)-piperazine was substituted for 5-nitro-2-piperazin-1-yl-benzonitrile in step 3 of that route.

¹H NMR (300 MHz, CDCl₃): δ=8.50 (d, J=2.7 Hz, 1H), 8.33 (dd, J=9.6, 2.7 Hz, 1H), 7.27 (s, 1H), 7.11-7.01 (m, 2H), 4.04 (s, 1H), 4.00 (s, 1H), 3.98-3.88 (m, 4H), 3.78-3.59 (m, 4H), 2.19-2.16 (m, 1H), 1.20-1.11 (m, 2H), 1.10-0.96 (m, 2H). MS: m/z 461.2 (M+H⁺).

Example 38: 5-amino-2-[4-(2-cyclopropyl-6,7-dimethoxy-quinazolin-4-yl)-piperazin-1-yl]-benzonitrile (45)

The title compound was prepared as described for compound (6), except that 1-(4-fluoro-2-methoxy-phenyl)-piperazine was substituted for 5-amino-2-piperazin-1-yl-benzonitrile in step 3 of that route.

¹H NMR (400 MHz, CDCl₃): δ=7.19 (s, 1H), 7.00 (s, 1H), 6.93-6.80 (m, 2H), 6.80-6.72 (m, 1H), 3.94 (s, 3H), 3.90 (s, 3H), 3.88-3.78 (m, 4H), 3.62 (brs, 2H), 3.21-3.06 (m, 4H), 2.23-2.10 (m, 1H), 1.14-1.05 (m, 2H), 1.00-0.88 (m, 2H). MS: m/z 431.3 (M+H⁺).

Scheme 2:

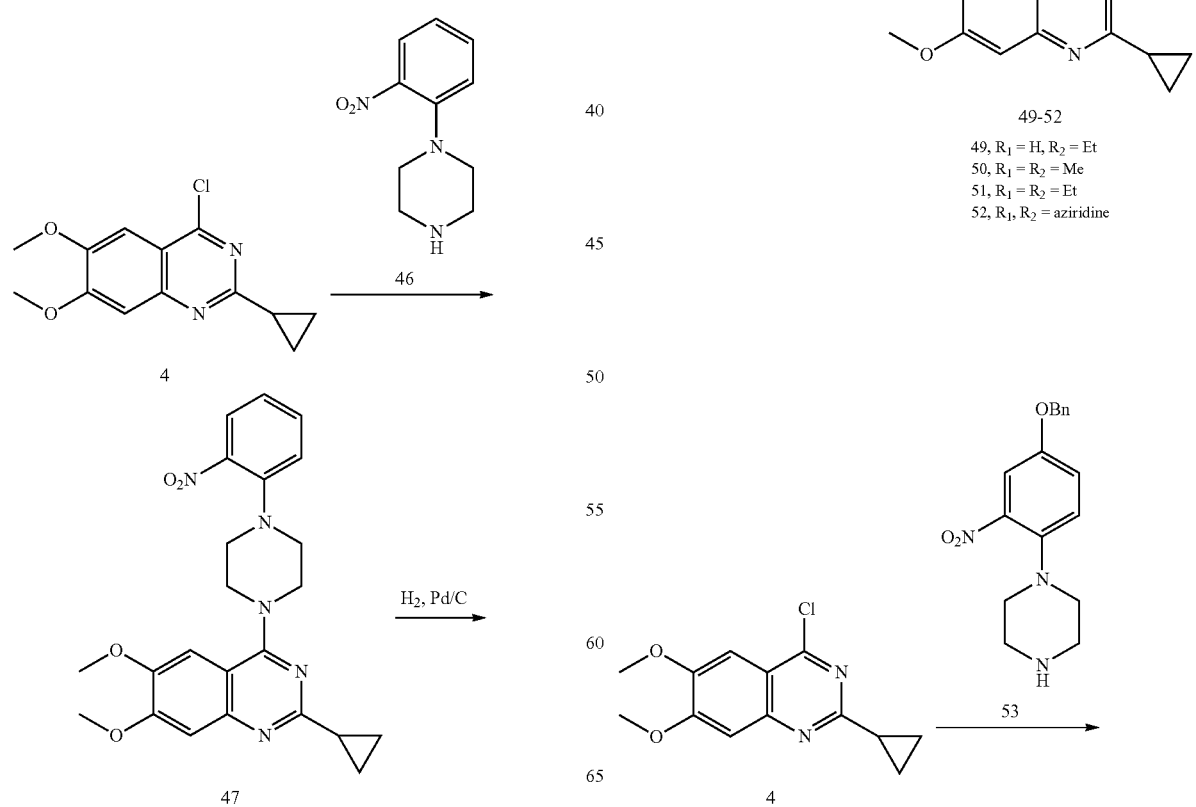

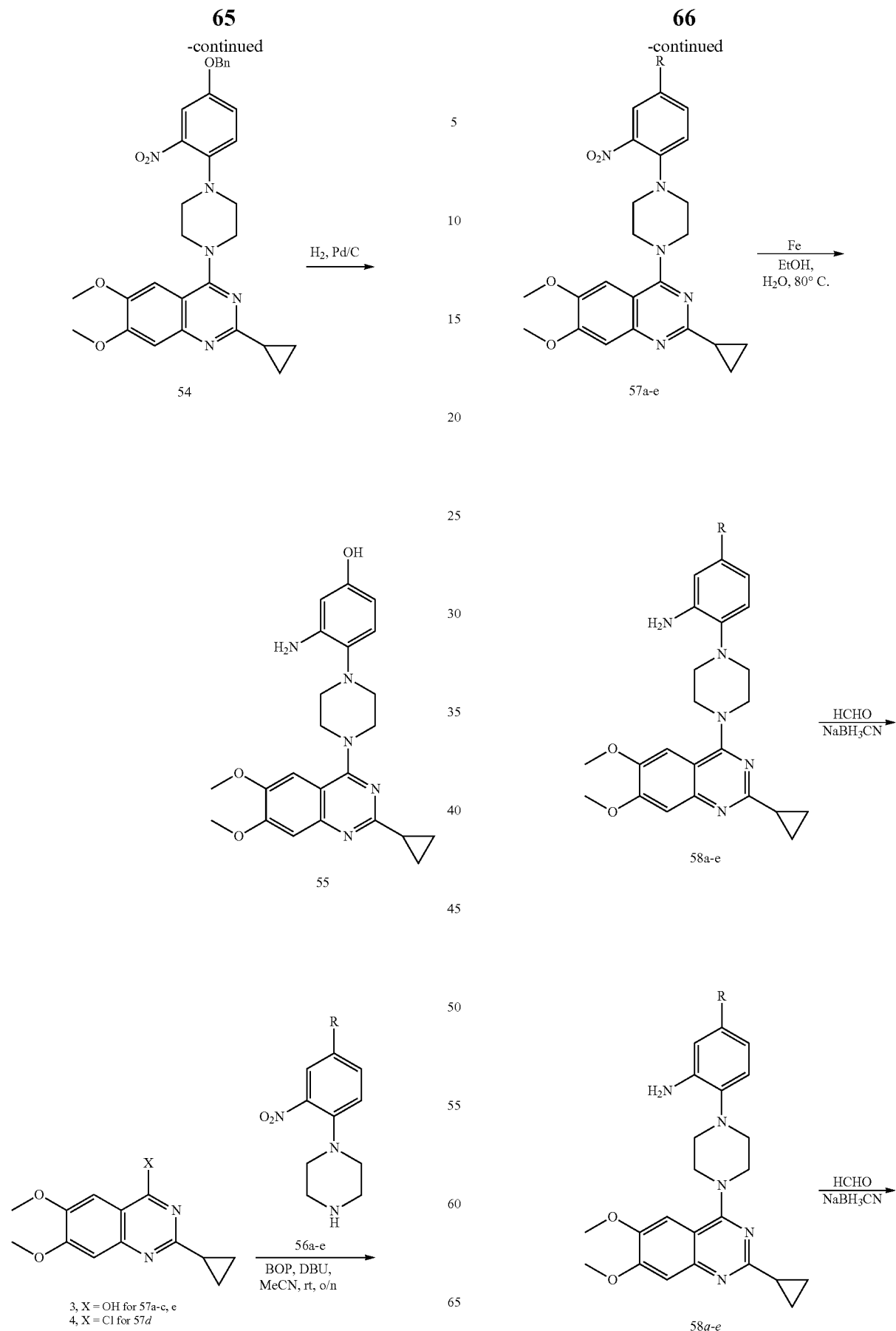

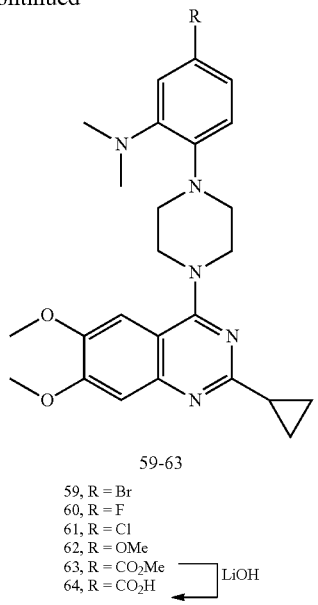

59, R = Br
60, R = F
61, R = Cl
62, R = OMe
63, R = CO₂Me
64, R = CO₂H  ⎤ LiOH

Example 39: 2-cyclopropyl-6,7-dimethoxy-4-[4-(2-nitro-phenyl)-piperazin-1-yl]-quinazoline (47)

A mixture of 1-(2-nitro-phenyl)-piperazine hydrochloride (534 mg, 2 mmol), 4-chloro-2-cyclopropyl-6,7-dimethoxy-quinazoline (486 mg, 2 mmol) and K₂CO₃ (828 mg, 6 mmol) in DMF (5 mL) was stirred at 70° C. for 16 h. The reaction mixture was cooled to room temperature, diluted with water (50 mL) and the aqueous suspension was extracted with EtOAc (40 mL×2). The combined organic layers were washed with brine (30 mL×2), dried over anhydrous Na₂SO₄ and filtered. The filtrate was evaporated in vacuum to residue, which was purified by silica gel column chromatography (from PE/EtOAc=10/1, PE/EtOAc=5/1, to PE/EtOAc=3/1) to give compound (47) (145 mg, yield: 17%) as yellow solid.

¹H NMR (400 MHz, CDCl₃): δ=7.82 (dd, J=8.0, 1.2 Hz, 1H), 7.52 (t, J=7.2 Hz, 1H), 7.25-7.16 (m, 2H), 7.16-7.04 (m, 2H), 4.01 (s, 3H), 3.97 (s, 3H), 3.86-3.78 (m, 4H), 3.28-3.18 (m, 4H), 2.23-2.12 (m, 1H), 1.28-1.13 (m, 2H), 1.04-0.95 (m, 2H). MS: m/z 436.2 (M+H⁺).

Example 40: 2-[4-(2-cyclopropyl-6,7-dimethoxy-quinazolin-4-yl)-piperazin-1-yl]-phenylamine (48)

A mixture of compound (47) (20 mg, 0.046 mmol), active iron powder (26 mg, 0.46 mmol) and NH₄Cl (25 mg, 0.46 mmol) in EtOH/H₂O (8 mL/2 mL) was refluxed under N₂ for 2 h. The reaction mixture was cooled to room temperature, diluted with DCM (30 mL) and filtered. The filtrate was evaporated under reduced pressure to residue, which was suspended in DCM (20 mL) for 10 min and then filtered. The filtrate was evaporated under reduced pressure to residue, which was purified by prep-TLC (PE/EtOAc=1/1) to afford compound (48) (12 mg, yield: 66%) as white solid.

¹H NMR (400 MHz, DMSO-d₆): δ=7.18-7.09 (m, 2H), 6.96 (d, J=7.2 Hz, 1H), 6.83 (t, J=8.0 Hz, 1H), 6.69 (d, J=6.8 Hz, 1H), 6.56 (t, J=7.2 Hz, 1H), 4.85 (brs, 2H), 3.91 (s, 3H), 3.89 (s, 3H), 3.80-3.68 (m, 4H), 3.08-2.91 (m, 4H), 2.12-2.06 (m, 1H), 1.11-1.00 (m, 2H), 1.00-0.89 (m, 2H). MS: m/z 406.2 (M+H⁺).

Example 41: 2-(4-(2-cyclopropyl-6,7-dimethoxyquinazolin-4-yl)piperazin-1-yl)-N-ethylaniline (49)

A mixture of compound (48) (60 mg, 0.15 mmol), s-trioxane (0.5 mL, excess) and AcOH (3 drops) in MeOH (5 mL) was stirred at room temperature for 1 h. Then to the mixture was added NaBH₃CN (200 mg, excess) at 0° C. The reaction mixture was allowed to warm to room temperature and stirred for a further 2 h. The mixture was diluted with EtOAc (60 mL). It was further washed with sat.NaHCO₃ (30 mL), brine (30 mL×2), dried over anhydrous Na₂SO₄ and filtered. The filtrate was evaporated under reduced pressure to residue, which was purified by prep-TLC (PE/EtOAc=1/1, 0.5% NH₃.H₂O as additive) to afford compound (49) (11 mg, yield: 16%) as white solid.

¹H NMR (400 MHz, CDCl₃): δ=7.20 (s, 1H), 7.11 (s, 1H), 7.08-7.03 (m, 2H), 6.72-6.64 (m, 2H), 4.62 (brs, 1H), 4.06 (s, 3H), 3.96 (s, 3H), 3.96-3.58 (m, 4H), 3.18 (q, J=7.2 Hz, 2H), 3.21-2.14 (m, 4H), 2.24-2.15 (m, 1H), 1.30 (t, J=7.2 Hz, 3H), 1.20-1.14 (m, 2H), 1.03-0.96 (m, 2H). MS: m/z 434.3 (M+H⁺).

Example 42: {2-[4-(2-cyclopropyl-6,7-dimethoxy-quinazolin-4-yl)-piperazin-1-yl]-phenyl}-dimethyl-amine (50)

A mixture of compound (48) (106 mg, 0.26 mmol), aq. formaldehyde (2 drops, 40% aq.) and AcOH (1 drop) in MeOH (5 mL) was stirred at room temperature for 1 h. Then to the mixture was added NaBH₃CN (6 mg, 0.1 mmol) at 0° C. The reaction mixture was warmed to room temperature for a further 2 h and diluted with EtOAc (60 mL). The mixture was washed with sat. NaHCO₃ (30 mL), brine (30 mL×2), dried over anhydrous Na₂SO₄ and filtered. The filtrate was evaporated under reduced pressure to residue, which was purified by prep-TLC (PE/EtOAc=1/1) to afford compound (50) (11 mg, yield: 10%) as white solid.

¹H NMR (400 MHz, CDCl₃): δ=7.19 (s, 1H), 7.12 (s, 1H), 7.02-6.92 (m, 4H), 4.01 (s, 3H), 3.96 (s, 3H), 3.80-3.68 (m, 4H), 3.36-3.30 (m, 4H), 2.92 (s, 6H), 2.22-2.15 (m, 1H), 1.21-1.13 (m, 2H), 1.02-0.95 (m, 2H). MS: m/z 434.3 (M+H⁺).

Example 43: {2-[4-(2-cyclopropyl-6,7-dimethoxy-quinazolin-4-yl)-piperazin-1-yl]-phenyl}-diethyl-amine (51)

The title compound was prepared as described for compound (50), except that {2-[4-(2-cyclopropyl-6,7-dimethoxy-quinazolin-4-yl)-piperazin-1-yl]-phenyl}-dimethyl-amine was substituted for {2-[4-(2-cyclopropyl-6,7-dimethoxy-quinazolin-4-yl)-piperazin-1-yl]-phenyl}-diethyl-amine in step 3 of that route.

¹H NMR (400 MHz, CDCl₃): δ=7.51 (s, 1H), 7.10 (s, 1H), 7.09-6.92 (m, 4H), 4.05 (s, 3H), 3.97 (s, 3H), 3.96-3.80 (m, 4H), 3.35-3.4 (m, 8H), 2.50-2.31 (m, 1H), 1.22-1.00 (m, 10H). MS: m/z 462.3 (M+H⁺).

Example 44: 4-[4-(2-aziridin-1-yl-phenyl)-piperazin-1-yl]-2-cyclopropyl-6,7-dimethoxy-quinazoline (52)

A mixture of compound (48) (60 mg, 0.15 mmol), chloroacetaldehyde (63 mg, 20% aq., 0.16 mmol) and AcOH (1 drop) in MeOH (5 mL) was stirred at room temperature for 1 h. Then to the mixture was added NaBH₃CN (4 mg, 0.06 mmol) at 0° C. The reaction mixture was warmed to room temperature for a further 2 h and diluted with EtOAc (30 mL). The mixture was washed with sat.NaHCO₃ (30 mL), brine (30 mL×2), dried over anhydrous Na₂SO₄ and filtered. The filtrate was evaporated under reduced pressure to residue, which was purified by prep-TLC (DCM/MeOH=20/1) to afford (2-chloro-ethyl)-{2-[4-(2-cyclopropyl-6,7-dimethoxy-quinazolin-4-yl)-piperazin-1-yl]-phenyl}-amine (31 mg, yield: 45%) as yellow oil.

$^1$H NMR (300 MHz, CDCl₃): δ=7.38 (s, 1H), 7.12-7.03 (m, 3H), 6.75 (t, J=7.5 Hz, 1H), 6.66 (d, J=8.1 Hz, 1H), 5.27 (brs, 1H), 4.08-3.95 (m, 4H), 4.07 (s, 3H), 3.97 (s, 3H), 3.79 (t, J=6.0 Hz, 1H), 3.58-3.52 (m, 2H), 3.08-2.91 (m, 4H), 2.32-2.25 (m, 1H), 1.26-1.10 (m, 4H).

To a mixture of (2-chloro-ethyl)-{2-[4-(2-cyclopropyl-6,7-dimethoxy-quinazolin-4-yl)-piperazin-1-yl]-phenyl}-amine (31 mg, 0.07 mmol) and K₂CO₃ (18 mg, 0.13 mmol) in DMF (2 mL) was added NaH (5 mg, 60%, 0.13 mmol) at 0° C. The mixture was heated at 80° C. for 16 h and cooled to room temperature, diluted with water (10 mL). The suspension was purified by prep-HPLC to afford compound (52), (5 mg, yield: 18%) as white solid.

$^1$H NMR (300 MHz, CDCl₃): δ=7.19 (s, 1H), 7.12 (s, 1H), 7.00-6.96 (m, 4H), 4.01 (s, 3H), 3.96 (s, 3H), 3.80-3.74 (m, 4H), 3.36-3.30 (m, 4H), 2.23-2.12 (m, 5H), 1.20-1.13 (m, 2H), 1.02-0.96 (m, 2H). MS: m/z 432.3 (M+H⁺).

Example 45: 4-[4-(4-benzyloxy-2-nitro-phenyl)-piperazin-1-yl]-2-cyclopropyl-6,7-dimethoxy-quinazoline (54)

The title compound was prepared as described for compound (6), except that 1-(4-fluoro-2-methoxy-phenyl)-piperazine was substituted for 1-(4-benzyloxy-2-nitro-phenyl)-piperazine in step 3 of that route.

$^1$H NMR (400 MHz, DMSO-d₆): δ=7.42-7.34 (m, 6H), 7.22-7.14 (m, 3H), 7.06 (s, 1H), 5.08 (s, 2H), 4.01 (s, 3H), 3.96 (s, 3H), 3.83-3.79 (m, 4H), 3.15-3.13 (m, 4H), 2.24-2.20 (m, 1H), 1.16-1.15 (m, 2H), 1.02-1.00 (m, 2H). MS: m/z 542.3 (M+H⁺).

Example 46: 3-amino-4-[4-(2-cyclopropyl-6,7-dimethoxy-quinazolin-4-yl)-piperazin-1-yl]-phenol (55)

To a mixture of (54) (54 mg, 0.1 mmol) in EtOH (8 mL) was added Pd/C (10 mg). The mixture was stirred under H₂ at rt for 16 h. The mixture was diluted with water (10 mL). The suspension was filtered and the filtrate was evaporated under reduced pressure to residue, which was purified by prep-HPLC to afford compound (55), (20 mg, yield: 50%) as white solid.

$^1$H NMR (400 MHz, DMSO-d₆): δ=8.71 (brs, 1H), 7.16-7.10 (m, 2H), 6.77 (d, J=8.4 Hz, 1H), 6.14 (d, J=2.4 Hz, 1H), 5.95 (dd, J=8.4, 2.4 Hz, 1H), 4.87 (brs, 2H), 3.91 (s, 3H), 3.89 (s, 3H), 3.88-3.58 (m, 4H), 3.96-2.79 (m, 4H), 2.13-2.02 (m, 1H), 1.10-1.00 (m, 2H), 0.99-0.89 (m, 2H). MS: m/z 422.3 (M+H⁺).

Example 47: 2-cyclopropyl-6,7-dimethoxy-4-[4-(4-methoxy-2-nitro-phenyl)-piperazin-1-yl]-quinazoline (57d)

A mixture of 1-(4-methoxy-2-nitro-phenyl)-piperazine hydrochloride (410 mg, 1.5 mmol), (4) (400 mg, 1.5 mmol) and TEA (454 mg, 4.5 mmol) in DMF (5 mL) was stirred at room temperature for 16 h. The reaction mixture was diluted with EtOAc (80 mL) and the suspension was washed with water (50 mL), brine (30 mL×3), dried over anhydrous Na₂SO₄ and filtered. The filtrate was evaporated in vacuum to residue, which was purified by silica gel column chromatography (from DCM to DCM/MeOH=50/1) to give compound (57d), (430 mg, yield: 61%) as yellow solid.

$^1$H NMR (400 MHz, CDCl₃): δ=7.36 (s, 1H), 7.29 (d, J=3.0 Hz, 1H), 7.21 (d, J=8.7 Hz, 1H), 7.11-7.05 (m, 2H), 4.01 (s, 3H), 3.97 (s, 3H), 3.88-3.85 (m, 4H), 3.84 (s, 3H), 3.14-3.10 (m, 4H), 2.33-2.25 (m, 1H), 1.19-1.12 (m, 2H), 1.10-0.93 (m, 2H). MS: m/z 466.2 (M+H⁺).

Example 48: 2-[4-(2-cyclopropyl-6,7-dimethoxy-quinazolin-4-yl)-piperazin-1-yl]-5-fluoro-phenylamine (58b)

To a mixture of 1-(4-fluoro-2-nitrophenyl)piperazine HCl salt (800 mg, 3.06 mmol), DBU (360 mg, 2.37 mmol) and BOP (1.04 g, 2.35 mmol) was added compound (3) (300 mg, 1.22 mmol), and the mixture was stirred at room temperature overnight. The solution was concentrated to dryness in vacuum and the residue was dissolved in EtOAc. The mixture was washed with brine and dried over Na₂SO₄. The crude product was purified by silica gel column chromatography (PE/EtOAc=1/1) to give 57b (200 mg, yield: 36%) as yellow solid. MS: m/z 454.2 (M+H⁺).

A mixture of (57b) (200 mg, 0.44 mmol), iron (74 mg, 1.32 mmol) and 2 drops of concentrated HCl in EtOH/H₂O (10 mL/1 mL) was heated at reflux for 3 hours. The mixture was filtered and the filtrate was concentrated to dryness in vacuum. The residue was dissolved in EtOAc and the mixture was washed with brine and dried over Na2SO4. The solution was concentrated to dryness in vacuum and the crude product was purified by silica gel column chromatography (PE/EtOAc=2/1) to give (58b), (100 mg, yield: 52%) as yellow solid.

$^1$H NMR (300 MHz, CDCl₃): δ=7.21 (s, 1H), 7.11 (s, 1H), 7.04-6.98 (m, 1H), 6.50-6.40 (m, 2H), 4.20 (brs, 2H), 4.02 (s, 3H), 3.98 (s, 3H), 3.75-3.65 (m, 4H), 2.22-2.17 (m, 1H), 1.20-1.15 (m, 2H), 1.13-0.99 (m, 2H). MS: m/z 424.3 (M+H⁺).

Example 49: 2-[4-(2-cyclopropyl-6,7-dimethoxy-quinazolin-4-yl)-piperazin-1-yl]-5-methoxy-phenylamine (58d)

A mixture of (57d) (430 mg, 0.92 mmol), active iron powder (259 mg, 4.63 mmol) and NH₄Cl (99 mg, 1.85 mmol) in EtOH/H₂O (10 mL/2 mL) was refluxed under N₂ for 2 h. The reaction mixture was cooled to room temperature, diluted with DCM (30 mL) and filtered. The filtrate was evaporated under reduced pressure to residue, which was purified by silica gel column chromatography (from DCM to DCM/MeOH=20/1) to give compound (58d), (295 mg, yield: 73%) as white solid.

$^1$H NMR (400 MHz, CDCl₃): δ=7.26 (d, J=6.8 Hz, 1H), 7.09 (s, 1H), 6.97 (d, J=8.4 Hz, 1H), 6.36-6.26 (m, 2H), 4.01 (s, 3H), 3.95 (s, 3H), 3.97-3.70 (m, 7H), 3.06-3.00 (m, 4H), 2.27-2.20 (m, 1H), 1.20-1.12 (m, 2H), 1.05-0.96 (m, 2H). MS: m/z 436.2 (M+H⁺).

Example 50: {5-bromo-2-[4-(2-cyclopropyl-6,7-dimethoxy-quinazolin-4-yl)-piperazin-1-yl]-phenyl}-dimethyl-amine (59)

The title compound was prepared as described for compound (50), except that {2-[4-(2-cyclopropyl-6,7-dimethoxy-quinazolin-4-yl)-piperazin-1-yl]-phenyl}-dimethylamine was substituted for 5-bromo-2-[4-(2-cyclopropyl-6,7-dimethoxy-quinazolin-4-yl)-piperazin-1-yl]-phenylamine in step 3 of that route.

¹H NMR (400 MHz, CDCl₃): δ=7.20 (s, 1H), 7.11 (s, 1H), 7.05-7.00 (m, 2H), 6.80 (d, J=8.0 Hz, 1H), 4.01 (s, 3H), 3.97 (s, 3H), 3.76-3.73 (m, 4H), 3.29-3.27 (m, 4H), 2.86 (s, 6H), 2.21-2.17 (m, 1H), 1.19-1.15 (m, 2H), 1.02-0.99 (m, 2H). MS: m/z 512.2 (M+H⁺).

Example 51: {2-[4-(2-cyclopropyl-6,7-dimethoxy-quinazolin-4-yl)-piperazin-1-yl]-5-fluoro-phenyl}-dimethyl-amine (60)

The title compound was prepared as described for compound (50), except that {2-[4-(2-cyclopropyl-6,7-dimethoxy-quinazolin-4-yl)-piperazin-1-yl]-phenyl}-dimethyl-amine was substituted for 2-[4-(2-cyclopropyl-6,7-dimethoxy-quinazolin-4-yl)-piperazin-1-yl]-5-fluoro-phenylamine in step 3 of that route.

¹H NMR (300 MHz, CDCl₃): δ=7.26 (s, 1H), 7.12 (s, 1H), 6.90-6.87 (m, 1H), 6.69-6.60 (m, 2H), 4.03 (s, 3H), 3.97 (s, 3H), 3.79-3.74 (m, 4H), 3.28-3.22 (m, 4H), 2.86 (s, 6H), 2.20-2.10 (m, 1H), 1.19-1.17 (m, 2H), 1.04-1.00 (m, 2H). MS: m/z 452.3 (M+H⁺).

Example 52: {5-chloro-2-[4-(2-cyclopropyl-6,7-dimethoxy-quinazolin-4-yl)-piperazin-1-yl]-phenyl}-dimethyl-amine (61)

The title compound was prepared as described for compound (50), except that {2-[4-(2-cyclopropyl-6,7-dimethoxy-quinazolin-4-yl)-piperazin-1-yl]-phenyl}-dimethyl-amine was substituted for 5-chloro-2-[4-(2-cyclopropyl-6,7-dimethoxy-quinazolin-4-yl)-piperazin-1-yl]-phenylamine in step 3 of that route.

¹H NMR (300 MHz, CDCl₃): δ=7.21 (s, 1H), 7.11 (s, 1H), 6.90-6.87 (m, 3H), 4.02 (s, 3H), 3.97 (s, 3H), 3.77-3.74 (m, 4H), 3.30-3.27 (m, 4H), 2.88 (s, 6H), 2.20-2.10 (m, 1H), 1.19-1.17 (m, 2H), 1.04-1.00 (m, 2H). MS: m/z 468.3 (M+H⁺).

Example 53: {2-[4-(2-cyclopropyl-6,7-dimethoxy-quinazolin-4-yl)-piperazin-1-yl]-5-methoxy-phenyl}-dimethyl-amine (62)

A mixture of 2-[4-(2-cyclopropyl-6,7-dimethoxy-quinazolin-4-yl)-piperazin-1-yl]-5-methoxy-phenylamine (280 mg, 0.64 mmol), aq. formaldehyde (0.5 mL, 40% aq.) and AcOH (1 drop) in MeOH (5 mL) was stirred at room temperature for 1 h. Then to the mixture was added NaBH₃CN (40 mg, 0.64 mmol) at 0° C. The reaction mixture was warmed to room temperature for a further 2 h and diluted with EtOAc (100 mL). The mixture was washed with sat. NaHCO₃ (30 mL), brine (30 mL×2), dried over anhydrous Na₂SO₄ and filtered. The filtrate was evaporated under reduced pressure to residue, which was purified by silica gel column chromatography (from DCM to DCM/MeOH=50/1) and then prep-HPLC to afford compound (62), (56 mg, yield: 19%) as white solid.

¹H NMR (400 MHz, DMSO-d₆): δ=7.18 (s, 1H), 7.11 (s, 1H), 6.87 (d, J=7.6 Hz, 1H), 6.52 (d, J=3.0 Hz, 1H), 6.45 (dd, J=8.7, 2.7 Hz, 1H), 4.00 (s, 3H), 3.95 (s, 3H), 3.80-3.70 (m, 4H), 3.26-3.19 (m, 4H), 2.21-2.14 (m, 1H), 1.21-1.13 (m, 2H), 1.02-0.93 (m, 2H). MS: m/z 464.3 (M+H⁺).

Example 54: 4-[4-(2-cyclopropyl-6,7-dimethoxy-quinazolin-4-yl)-piperazin-1-yl]-3-dimethylamino-benzoic acid (64)

A mixture of methyl 3-amino-4-(4-(2-cyclopropyl-6,7-dimethoxyquinazolin-4-yl)piperazin-1-yl)benzoate (58e) (520 mg, 1.12 mmol), aq. formaldehyde (1 mL) and AcOH (10 drops) in MeOH (10 mL) was stirred at room temperature for 1 h. Then to the mixture was added NaBH₃CN (71 mg, 1.12 mmol) at 0° C. The reaction mixture was warmed to room temperature and stirred for a further 2 hours. The mixture was quenched with saturated aqueous NaHCO₃ (10 mL) and the aqueous phase was extracted with DCM (60 mL×2). The extracts were washed with brine (60 mL), dried over anhydrous Na₂SO₄ and filtered. The filtrate was evaporated under reduced pressure to residue, which was purified by prep-HPLC to afford compound (63) (300 mg, yield: 54%) as yellow solid. MS: m/z 464.2 (M+H⁺).

To a solution of compound (63) (300 mg, 0.61 mmol) in THF/H₂O (12 mL/3 mL) was added LiOH (103 mg, 2.44 mmol) and the mixture was stirred at room temperature for 5 hours. The mixture was evaporated to remove most of THF in vacuum. The residue was acidified with 6 M HCl at 0° C. to pH=5-6. The resulting solid was collected by filtration to give compound (64), (100 mg, yield: 34%) as white solid.

¹H NMR (400 MHz, DMSO-d₆): δ=12.51 (brs, 1H), 7.53 (dd, J=8.4, 2.0 Hz, 1H), 7.47 (d, J=2.0 Hz, 1H), 7.15-7.12 (m, 2H), 7.01 (d, J=8.4 Hz, 1H), 3.91 (s, 3H), 3.90 (s, 3H), 3.76-3.72 (m, 4H), 3.39-3.35 (m, 4H), 2.81 (s, 6H), 2.10-2.08 (m, 1H), 1.06-1.01 (m, 2H), 0.96-0.93 (m, 2H). MS: m/z 478.2 (M+H⁺).

Scheme 3:

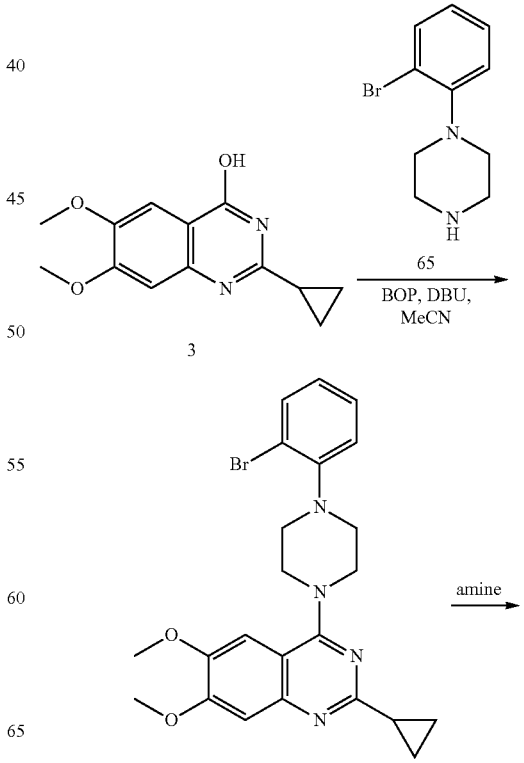

-continued

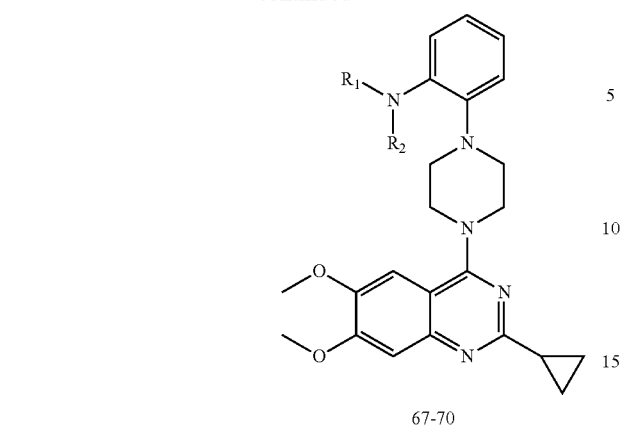

67-70

67, R₁ = H, R₂ = Ph
68, R₁, R₂ = morpholine
69, R₁, R₂ = pyrrolidine
70, R₁, R₂ = azetidine

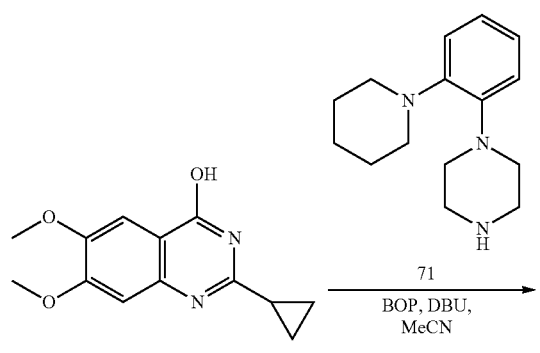

3 → 71, BOP, DBU, MeCN

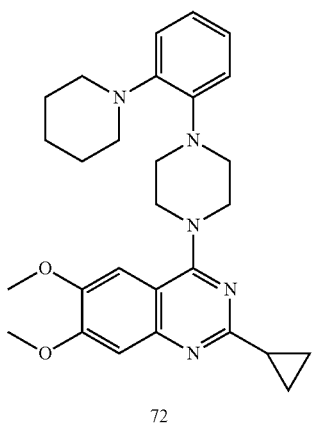

72

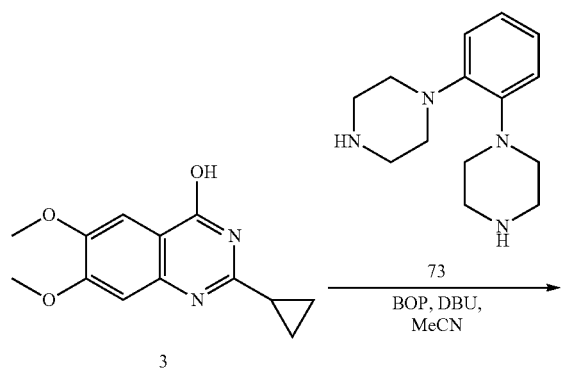

3 → 73, BOP, DBU, MeCN

-continued

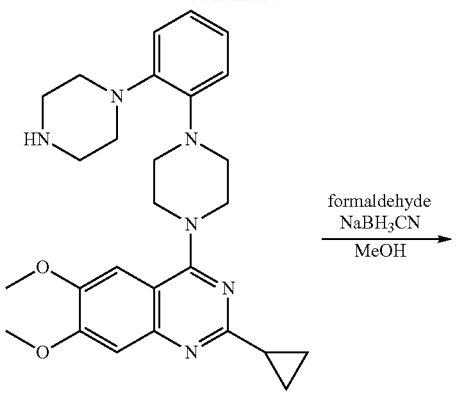

74 formaldehyde
NaBH₃CN
————
MeOH

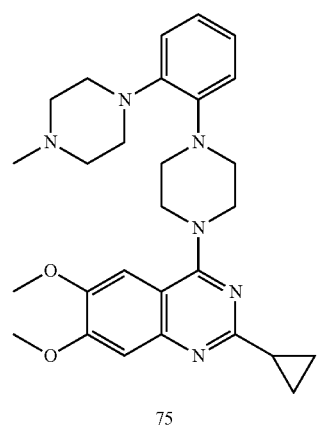

75

Example 55: {2-[4-(2-cyclopropyl-6,7-dimethoxy-quinazolin-4-yl)-piperazin-1-yl]-phenyl}-phenyl-amine (67)

To a mixture of compound (66) (100 mg, 0.21 mmol), phenylamine (60 mg, 0.64 mmol) and t-BuONa (41 mg, 0.43 mmol) in anhydrous toluene (10 mL) was added BINAP (7 mg, 0.01 mmol) and Pd₂(dba)₃ (7 mg, 0.05 mmol). The mixture was refluxed under N₂ for 16 h. After cooled to room temperature, the suspension was filtered. The filtrate was evaporated in vacuum to residue, which was purified by silica gel column chromatography (DCM/MeOH=20/1) and then prep-HPLC to afford compound (67), (13 mg, 13%) as brown oil.

$^1$H NMR (400 MHz, CDCl₃): δ=7.46-7.28 (m, 3H), 7.25-7.19 (m, 4H), 7.09 (s, 1H), 7.06 (td, J=8.0, 1.6 Hz, 1H), 6.95 (t, J=7.2 Hz, 1H), 6.87 (td, J=7.6, 1.2 Hz, 1H), 6.62 (brs, 1H), 4.01 (s, 3H), 3.96 (s, 3H), 3.82-3.72 (m, 4H), 3.22-3.09 (m, 4H), 2.26-2.16 (m, 1H), 1.23-1.19 (m, 2H), 1.09-0.92 (m, 2H). MS: m/z 482.3 (M+H⁺).

Example 56: 2-cyclopropyl-6,7-dimethoxy-4-[4-(2-morpholin-4-yl-phenyl)-piperazin-1-yl]-quinazoline (68)

The title compound was prepared as described for compound (67), except that phenylamine was substituted for morpholine in step 2 of that route.

¹H NMR (400 MHz, CDCl₃): δ=7.34 (s, 1H), 7.10 (s, 1H), 7.09-6.94 (m, 4H), 4.02 (s, 3H), 3.97 (s, 3H), 3.96-3.71 (m, 8H), 3.48-3.30 (m, 4H), 3.30-3.13 (m, 4H), 2.38-2.22 (m, 1H), 1.20-1.11 (m, 2H), 1.10-0.96 (m, 2H). MS: m/z 476.3 (M+H⁺).

Example 57: 2-cyclopropyl-6,7-dimethoxy-4-[4-(2-pyrrolidin-1-yl-phenyl)-piperazin-1-yl]-quinazoline (69)

The title compound was prepared as described for compound (67), except that phenylamine was substituted for pyrrolidine in step 2 of that route.

¹H NMR (400 MHz, CDCl₃): δ=7.70 (s, 1H), 7.58-7.36 (m, 4H), 7.06 (s, 1H), 4.50-4.23 (m, 4H), 4.07 (s, 3H), 4.02-3.79 (m, 7H), 3.09-2.91 (m, 4H), 2.56-2.43 (m, 1H), 2.42-2.30 (m, 4H). MS: m/z 460.3 (M+H⁺).

Example 58: 4-[4-(2-azetidin-1-yl-phenyl)-piperazin-1-yl]-2-cyclopropyl-6,7-dimethoxy-quinazoline (70)

The title compound was prepared as described for compound (67), except that phenylamine was substituted for azetidine in step 2 of that route.

¹H NMR (400 MHz, CDCl₃): δ=7.19 (s, 1H), 7.10 (s, 1H), 7.06-6.98 (m, 2H), 6.81 (t, J=7.6 Hz, 1H), 6.53 (d, J=8.0 Hz, 1H), 4.00 (s, 3H), 4.00-3.90 (m, 7H), 3.86-3.68 (m, 4H), 3.23-3.08 (m, 4H), 2.29-2.14 (m, 3H), 1.20-1.13 (m, 2H), 1.03-0.94 (m, 2H). MS: m/z 446.3 (M+H⁺).

Example 59: 2-cyclopropyl-6,7-dimethoxy-4-[4-(2-piperidin-1-yl-phenyl)-piperazin-1-yl]-quinazoline (72)

The title compound was prepared as described for compound (58b), except that 1-(4-methoxy-2-nitro-phenyl)-piperazine was substituted for 1-(4-fluoro-2-nitrophenyl)piperazine in step 1 of that route.

¹H NMR (400 MHz, CDCl₃): δ=7.25 (s, 1H), 7.12 (s, 1H), 7.06-6.88 (m, 4H), 3.98 (s, 3H), 3.96 (s, 3H), 3.88-3.74 (m, 4H), 3.48-3.36 (m, 4H), 3.19-3.00 (m, 4H), 2.56-2.46 (m, 1H), 1.76-1.66 (m, 4H), 1.60-1.53 (m, 2H), 1.26-1.20 (m, 2H), 1.08-0.96 (m, 2H). MS: m/z 474.3 (M+H⁺).

Example 60: 2-Cyclopropyl-6,7-dimethoxy-4-{4-[2-(4-methyl-piperazin-1-yl)-phenyl]-piperazin-1-yl}-quinazoline (75)

The title compound was prepared as described for compound (50), using the similar procedure.

¹H NMR (400 MHz, CDCl₃): δ=7.20 (s, 1H), 7.12 (s, 1H), 7.09-6.89 (m, 4H), 4.01 (s, 3H), 3.97 (s, 3H), 3.79-3.68 (m, 4H), 3.48-3.09 (m, 8H), 2.78-2.46 (m, 4H), 2.36 (s, 3H), 2.26-2.13 (m, 1H), 1.26-1.18 (m, 2H), 1.09-0.92 (m, 2H). MS: m/z 489.4 (M+H⁺).

Scheme 4:

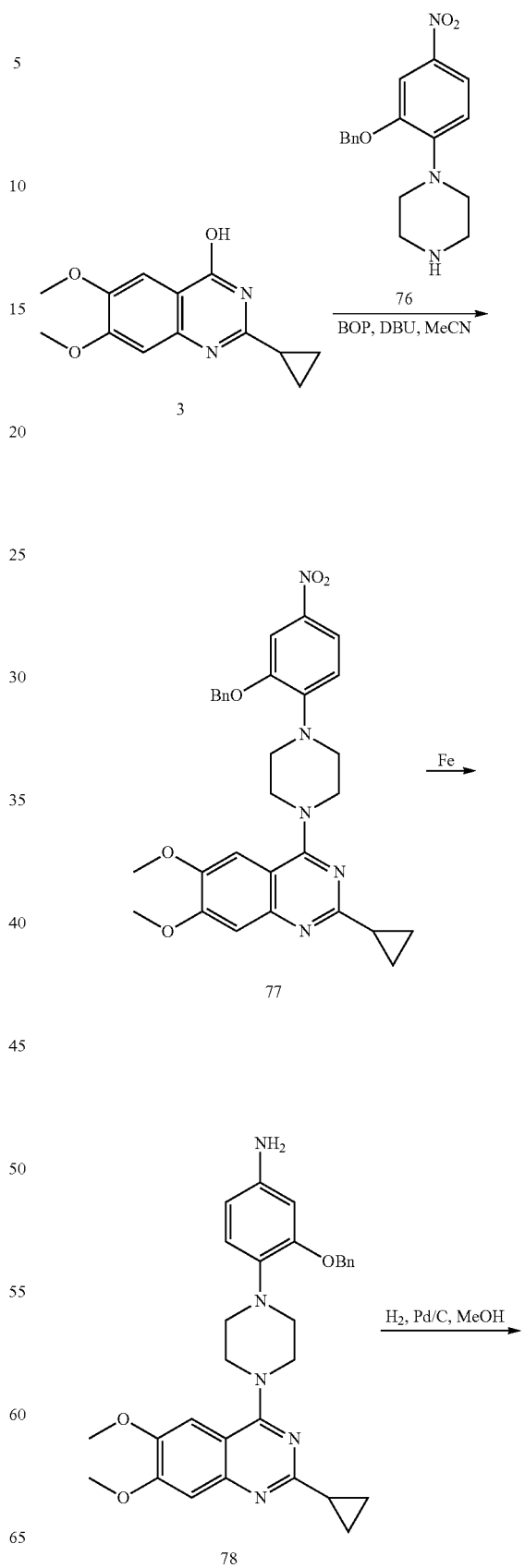

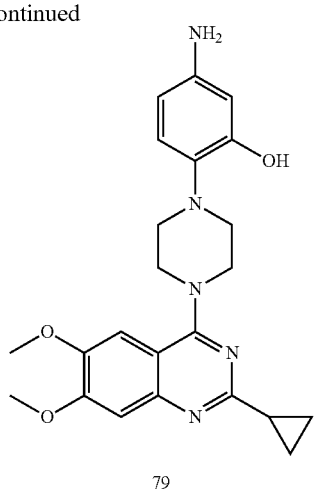

79

Example 61: 5-amino-2-[4-(2-cyclopropyl-6,7-di-methoxy-quinazolin-4-yl)-piperazin-1-yl]-phenol (79)

The title compound was prepared as described for compound (55), using the similar route and procedure.

$^1$H NMR (300 MHz, DMSO-$d_6$): δ=7.38 (s, 1H), 7.35 (s, 1H), 7.00 (d, J=8.7 Hz, 1H), 6.90 (s, 1H), 6.72 (d, J=7.8 Hz, 1H), 4.50 (brs, 2H), 4.36-4.20 (m, 4H), 3.97 (s, 3H), 3.95 (s, 3H), 3.28-3.16 (m, 4H), 2.43-2.38 (m, 1H), 1.36-1.22 (m, 4H). MS: m/z 422.2 (M+H$^+$).

Scheme 5:

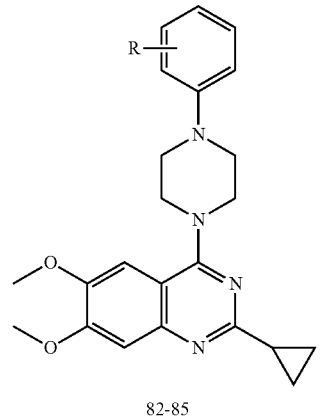

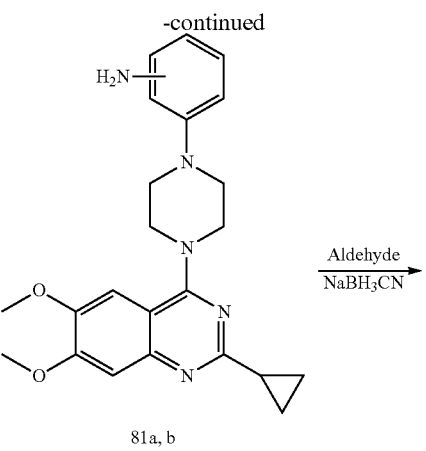

82-85
82, R = 4-NMe$_2$
83, R = 4-NEt$_2$
84, R = 3-NMe$_2$
85, R = 3-NEt$_2$

Example 62: 4-(4-(2-cyclopropyl-6,7-dimethoxyquinazolin-4-yl)piperazin-1-yl)-N,N-dimethylaniline (82)

A mixture of compound 3 (369 mg, 1.50 mmol), 1-(4-nitrophenyl)piperazine HCl salt (730 mg, 3.00 mmol), DBU (684 mg, 4.50 mmol) and BOP (862 mg, 7.95 mmol) was stirred at room temperature overnight. The solution was concentrated to dryness in vacuum and the residue was triturated with EtOAc (10 mL) to form a large amount of solid. The solid collected by filtration was washed with water (20 mL) and air-dried to give compound (80a) (405 mg, yield: 65%) as yellow solid.

$^1$H NMR (400 MHz, DMSO-$d_6$): δ=8.10 (d, J=9.6 Hz, 2H), 7.17 (s, 1H), 7.13 (s, 1H), 7.04 (d, J=9.2 Hz, 2H), 3.91 (s, 3H), 3.89 (s, 3H), 3.82-3.78 (m, 4H), 3.74-3.70 (m, 4H), 2.08-2.06 (m, 1H), 1.03-0.93 (m, 4H).

A mixture of compound (80a) (405 mg, 0.93 mmol), active iron powder (260 mg, 4.66 mmol) and NH$_4$Cl (100 mg, 01.86 mmol) in EtOH/H$_2$O (20 mL/4 mL) was refluxed under N$_2$ for 2 h. The reaction mixture was cooled to room temperature and filtered. The filtrate was diluted with EtOAc (20 mL). The organic layer was separated and washed with water (30 mL), brine (30 mL×2) and dried over Na$_2$SO$_4$. The solution was concentrated to give compound (81a) (358 mg, yield: 95%) as yellow solid.

$^1$HNMR (400 MHz, DMSO-$d_6$): δ=7.13 (s, 1H), 7.12 (s, 1H), 6.77 (d, J=8.4 Hz, 1H), 6.53 (d, J=8.4 Hz, 1H), 5.04

(brs, 2H), 4.04 (s, 3H), 4.02 (s, 3H), 3.91-3.86 (m, 4H), 3.14-3.10 (m, 4H), 2.11-2.06 (m, 1H), 1.03-0.93 (m, 4H).

A mixture of compound (81a) (162 mg, 0.40 mmol), aq. formaldehyde (3 drops, 40% aq.) and AcOH (1 drop) in MeOH (10 mL) was stirred at room temperature for 2 h. Then to the mixture was added NaBH$_3$CN (10 mg, 0.16 mmol) at 0° C. The reaction mixture was stirred at room temperature for a further 2 h. The solvent was removed in vacuum. The residue was diluted with DCM (20 mL). The mixture was washed with sat. NaHCO$_3$ (10 mL), brine (15 mL), dried over anhydrous Na$_2$SO$_4$ and filtered. The filtrate was evaporated under reduced pressure to residue, which was purified by prep-HPLC to afford compound (82), (80 mg, yield: 47%) as white solid.

$^1$H NMR (300 MHz, CDCl$_3$): δ=7.23 (s, 1H), 7.11 (s, 1H), 6.97 (d, J=9.0 Hz, 2H), 6.79 (d, J=9.0 Hz, 2H), 4.02 (s, 3H), 3.98 (s, 3H), 3.81-3.77 (m 4H), 3.27-3.24 (m, 4H), 2.91 (s, 6H), 2.22-2.19 (m, 1H), 1.18-1.15 (m, 2H), 1.03-0.99 (m, 2H). LC-MS: 434.3 (M+H$^+$).

Example 63: {4-[4-(2-cyclopropyl-6,7-dimethoxy-quinazolin-4-yl)-piperazin-1-yl]-phenyl}-diethyl-amine (83)

The title compound was prepared as described for compound (82), using the similar route and procedure.

$^1$HNMR (400 MHz, CDCl$_3$): δ=7.21 (s, 1H), 7.12 (s, 1H), 6.95 (d, J=8.7 Hz, 2H), 6.73-6.72 (m, 2H), 4.02 (s, 3H), 3.98 (s, 3H), 3.79-3.73 (m, 4H), 3.36-3.22 (m, 8H), 2.21-2.18 (m, 1H), 1.20-0.95 (m, 10H). LC-MS: 462.3 (M+H$^+$).

Example 64: 3-(4-(2-cyclopropyl-6,7-dimethoxyquinazolin-4-yl)piperazin-1-yl)-N,N-dimethylaniline (84)

The title compound was prepared as described for compound (82), using the similar route and procedure.

$^1$HNMR (400 MHz, CDCl$_3$): δ=7.27 (s, 1H), 7.17 (t, J=8.0 Hz, 1H), 7.10 (s, 1H), 6.39-6.32 (m, 3H), 4.03 (s, 3H), 3.97 (s, 3H), 3.89-3.87 (m, 4H), 3.39-3.36 (m, 4H), 2.97 (s, 6H), 2.22-2.18 (m, 1H), 1.21-1.18 (m, 2H), 1.09-1.06 (m, 2H). LC-MS: 434.3 (M+H$^+$).

Example 65: {3-[4-(2-cyclopropyl-6,7-dimethoxy-quinazolin-4-yl)-piperazin-1-yl]-phenyl}-diethyl-amine (85)

The title compound was prepared as described for compound (82), using the similar route and procedure.

$^1$HNMR (400 MHz, CDCl$_3$): δ=7.19 (s, 1H), 7.09-7.03 (m, 2H), 6.25-6.21 (m, 3H), 3.96 (s, 3H), 3.90 (s, 3H), 3.82-3.76 (m, 4H), 3.31-3.26 (m, 8H), 2.27-2.24 (m, 1H), 1.26-1.24 (m, 2H), 1.18-1.08 (m, 6H), 0.98-0.97 (m, 2H). LC-MS: 462.3 (M+H$^+$).

Scheme 6:

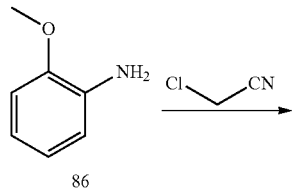

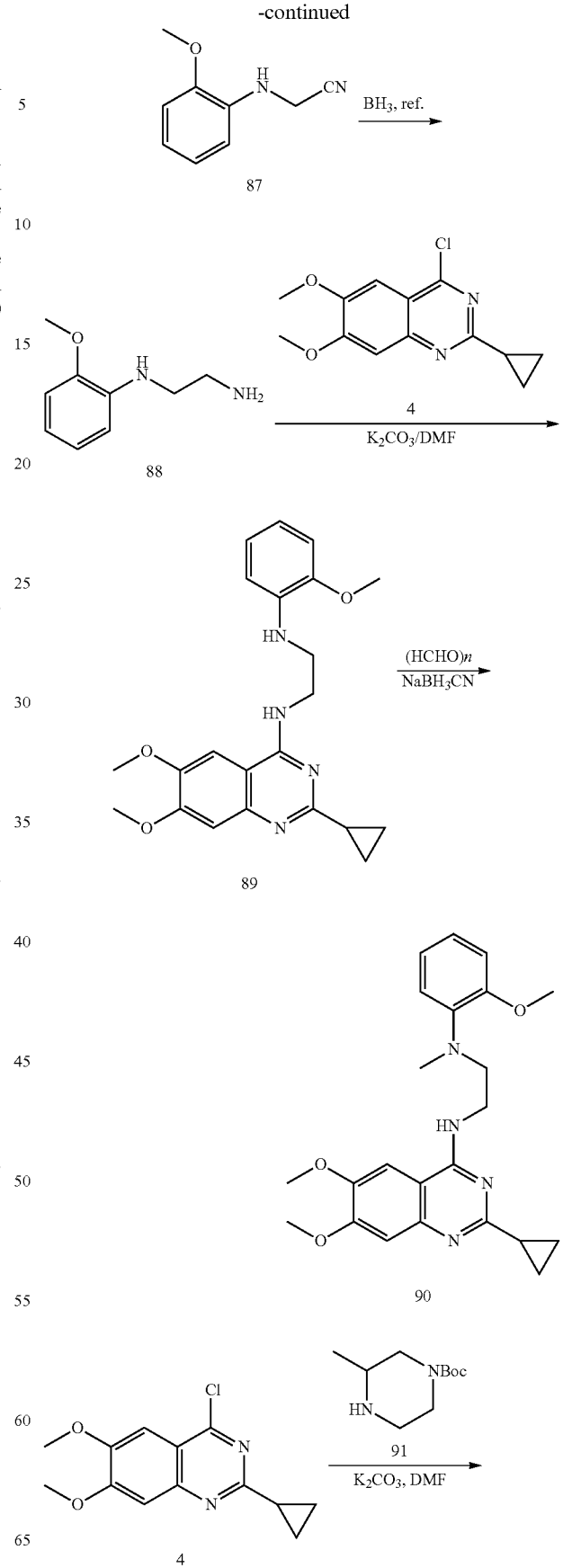

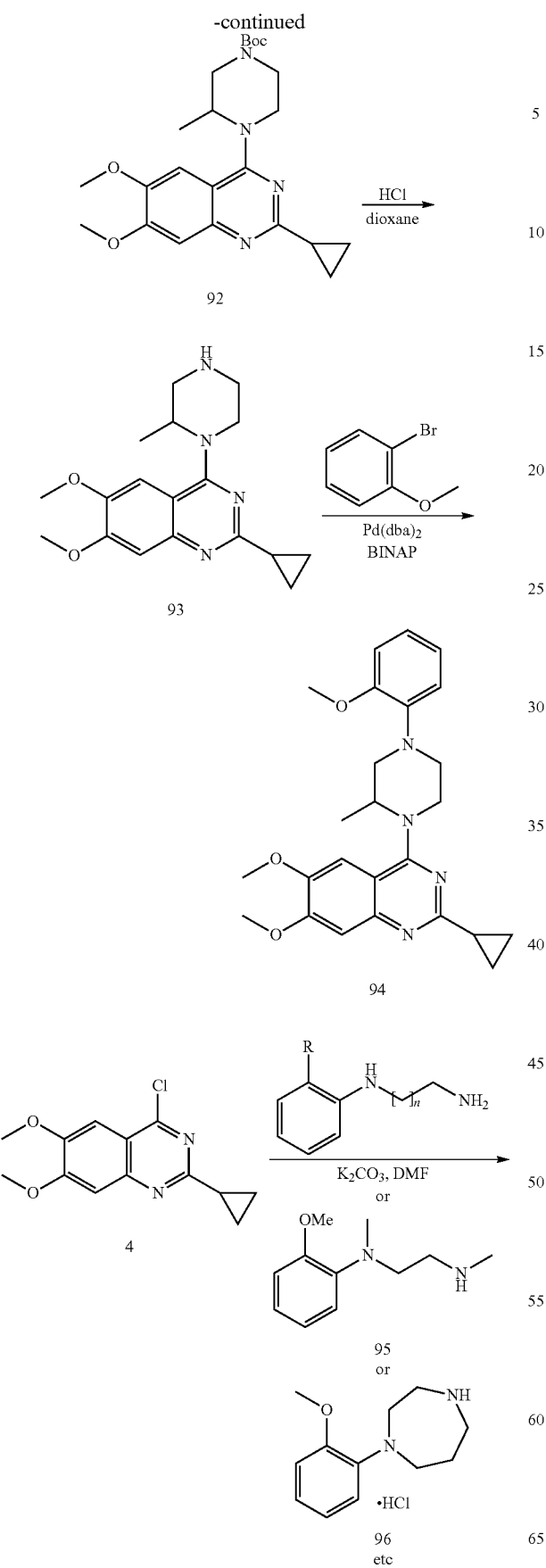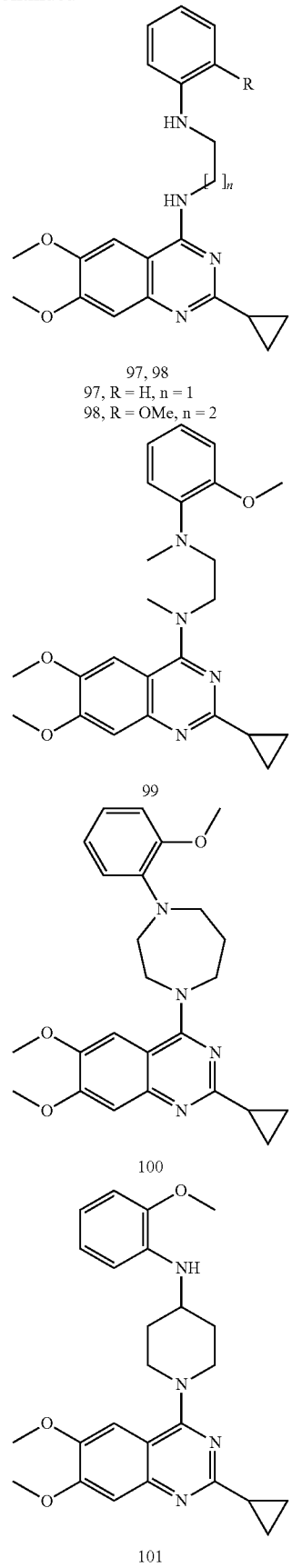

-continued

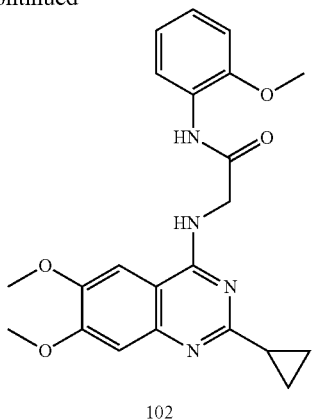

102

Example 66: N-(2-cyclopropyl-6,7-dimethoxy-quinazolin-5-yl)-N'-(2-methoxy-phenyl)-ethane-1,2-diamine (89)

A mixture of 2-methoxy-phenylamine (500 mg, 4.1 mmol), chloro-acetonitrile (305 mg, 4.0 mmol), NaI (300 mg, 2.0 mmol) and NaHCO$_3$ (504 mg, 6.0 mmol) in acetone (15 mL) was refluxed for 16 h. The mixture was cooled to room temperature and filtered. The filtrate was evaporated under reduced pressure to residue, which was suspended in Et$_2$O (10 mL). The resulting solid was filtered and the cake was washed with Et$_2$O (5 mL×2). The combined Et$_2$O solution was evaporated under reduced pressure to give compound (87) (540 mg, yield: 82%) as yellow solid.

$^1$H NMR (400 MHz, CDCl$_3$): δ=7.00-6.91 (m, 1H), 6.86-6.71 (m, 2H), 6.71 (d, J=8.0 Hz, 1H), 4.57 (brs, 1H), 4.14 (d, J=6.8 Hz, 2H), 3.86 (s, 3H).

To a solution of (2-methoxy-phenylamino)-acetonitrile (540 mg, 3.33 mmol) in THF (5 mL) was added 0.5 mL of BH$_3$ (10M in Me$_2$S, 5 mmol) at 0° C. and the mixture was stirred at reflux for 12 h. The mixture was cooled to room temperature, quenched with MeOH (2 mL) and 1 mL of aq. HCl (2M) and evaporated under reduced pressure to dryness. The residue was diluted with water (10 mL) and adjusted with aq. NaHCO$_3$ to pH=8. The mixture was extracted with DCM (30 mL×2). The extracts were washed with brine (30 mL×2), dried over anhydrous Na$_2$SO$_4$ and filtered. The filtrate was evaporated in vacuum to give compound (88) (310 mg, yield: 56%) as gray solid.

MS: m/z 167.1 (M+H$^+$).

A mixture of N$^1$-(2-methoxy-phenyl)-ethane-1,2-diamine (63 mg, 0.38 mmol), 4-chloro-2-cyclopropyl-6,7-dimethoxy-quinazoline (100 mg, 0.38 mmol) and K$_2$CO$_3$ (78 mg, 0.57 mmol) in DMF (3 mL) was stirred at 80° C. for 16 h. The reaction mixture was cooled to room temperature, diluted with water (50 mL) and the aqueous mixture was extracted with DCM (30 mL×2). The extracts were washed with brine (30 mL×2), dried over anhydrous Na$_2$SO$_4$ and filtered. The filtrate was evaporated in vacuum to residue, which was purified by prep-HPLC (0.5% TFA as additive) to give compound (89), (16 mg, yield: 22%) as gray solid.

$^1$H NMR (400 MHz, CDCl$_3$): δ=7.15 (s, 1H), 6.88 (dd, J=8.4, 1.2 Hz, 1H), 6.82-6.65 (m, 4H), 3.97 (s, 3H), 3.92 (s, 3H), 3.92-3.86 (m, 2H), 3.81 (s, 3H), 3.50 (t, J=8.0 Hz, 2H), 2.21-2.11 (m, 1H), 1.26-1.10 (m, 2H), 1.06-0.94 (m, 2H). MS: m/z 395.3 (M+H$^+$).

Example 67: N'-(2-cyclopropyl-6,7-dimethoxy-quinazolin-5-yl)-N-(2-methoxy-phenyl)-N-methyl-ethane-1,2-diamine (90)

To a stirred solution of N-(2-cyclopropyl-6,7-dimethoxy-quinazolin-5-yl)-N'-(2-methoxy-phenyl)-ethane-1,2-diamine (20 mg, 0.05 mmol) in MeOH (2 mL) was added formaldehyde (0.5 mL) and AcOH (1 drop). The mixture was stirred at 25° C. for 1 h and NaBH$_3$CN (10 mg, 0.16 mmol) was added. The mixture was stirred for another 2 h and quenched with aq. NaHCO$_3$ (30 mL). The aqueous mixture was extracted with DCM (30 mL×2). The extracts were washed with brine (20 mL×2), dried over anhydrous Na$_2$SO$_4$, filtered and the filtrate was evaporated in vacuum to dryness. The residue was purified by prep-HPLC to give compound (90), (10 mg, yield: 50%) as brown solid. Its structure was confirmed by NOESY.

$^1$H NMR (400 MHz, CDCl$_3$): δ=7.91 (brs, 1H), 7.22 (s, 1H), 7.10-7.00 (m, 2H), 7.00-6.91 (m, 2H), 6.84 (d, J=8.4 Hz, 1H), 3.94 (s, 3H), 3.91 (s, 3H), 3.81 (s, 3H), 3.74-3.66 (m, 2H), 3.27 (t, J=6.4 Hz, 2H), 2.83 (s, 3H), 2.26-2.13 (m, 1H), 1.21-1.12 (m, 2H), 1.06-0.96 (m, 2H). MS: m/z 409.3 (M+H$^+$).

Example 68: 2-cyclopropyl-6,7-dimethoxy-4-[4-(2-methoxy-phenyl)-2-methyl-piperazin-1-yl]-quinazoline (94)

A mixture of 3-methyl-piperazine-1-carboxylic acid tert-butyl ester (374 mg, 1.87 mmol), 4-chloro-2-cyclopropyl-6,7-dimethoxy-quinazoline (500 mg, 1.87 mmol) and K$_2$CO$_3$ (516 mg, 3.74 mmol) in DMF (5 mL) was stirred at 100° C. for 16 h. The reaction mixture was cooled to room temperature, diluted with water (50 mL), and extracted with DCM (30 mL×2). The extracts were washed with brine (20 mL×2), dried over anhydrous Na$_2$SO$_4$ and filtered. The filtrate was evaporated in vacuum to residue, which was purified by silica gel column chromatography (from PE/EtOAc=10/1 to PE/EtOAc=1/1) to afford 4-(2-cyclopropyl-6,7-dimethoxy-quinazolin-4-yl)-3-methyl-piperazine-1-carboxylic acid tert-butyl ester (92) (430 mg, yield: 54%) as white solid. MS: m/z 429.2 (M+H$^+$).

A mixture of 4-(2-cyclopropyl-6,7-dimethoxy-quinazolin-4-yl)-3-methyl-piperazine-1-carboxylic acid tert-butyl ester (430 mg, 1 mmol) suspended in HCl/dioxane (3 mL, 4M) was stirred at room temperature for 1 h. The mixture was filtered and the solid cake was washed with EtOAc (2 mL×3). The solid was dried under evaporation in vacuum to afford 2-cyclopropyl-6,7-dimethoxy-4-(2-methyl-piperazin-1-yl)-quinazoline hydrochloride (93) (260 mg, yield: 71%) as yellow solid and HCl salt.

$^1$H NMR (400 HMz, DMSO-d$_6$): δ=9.93 (brs, 1H), 9.55 (brs, 1H), 7.46 (s, 1H), 7.18 (s, 1H), 4.58-4.49 (d, J=14.8 Hz, 1H), 3.97 (s, 3H), 3.96 (s, 3H), 3.83-3.71 (m, 2H), 3.43-3.11 (m, 4H), 2.48-2.38 (m, 1H), 1.63 (d, J=6.8 Hz, 3H), 1.38-1.23 (m, 4H).

To a mixture of 1-bromo-2-methoxy-benzene (77 mg, 0.412 mmol), 2-cyclopropyl-6,7-dimethoxy-4-(2-methyl-piperazin-1-yl)-quinazoline hydrochloride (93) (100 mg, 0.275 mmol) and t-BuONa (53 mg, 0.55 mmol) in anhydrous toluene (10 mL) was added BINAP (18 mg, 0.027 mmol) and Pd$_2$(dba)$_3$ (8 mg, 0.014 mmol). The mixture was refluxed under N$_2$ for 17 h. After cooled to room temperature, the reaction solution was filtered and the filtered cake was washed with DCM/MeOH (20 mL, v/v=20/1). The combined filtrate was evaporated in vacuum to residue, which was purified by silica gel chromatography (from PE, PE/EtOAc=3/1 to PE/EtOAc=1/1) to afford compound (94), (30 mg, yield: 25%) as white solid.

$^1$H NMR (400 MHz, CDCl$_3$): δ=7.26-7.04 (m, 2H), 7.03-6.80 (m, 4H), 4.48-4.37 (m, 1H), 4.11-3.89 (m, 7H), 3.87 (s, 3H), 3.79-3.66 (m, 1H), 3.42-3.25 (m, 2H), 3.22-3.04 (m, 1H), 3.03-2.89 (m, 1H), 2.25-2.10 (m, 1H), 1.54 (d, J=6.8 Hz, 3H), 1.24-1.06 (m, 2H), 1.04-0.89 (m, 2H). MS: m/z 435.3 (M+H$^+$).

Example 69: N-(2-cyclopropyl-6,7-dimethoxy-quinazolin-4-yl)-N'-phenyl-ethane-1,2-diamine (97)

A mixture of N$^1$-phenyl-ethane-1,2-diamine (40 mg, 0.29 mmol), 4-chloro-2-cyclopropyl-6,7-dimethoxy-quinazoline (77 mg, 0.29 mmol) and K$_2$CO$_3$ (61 mg, 0.44 mmol) in DMF (3 mL) was stirred at 60° C. for 17 h. The reaction mixture was cooled to room temperature, diluted with EtOAc (80 mL) and the suspension was stirred for another 10 minutes. The suspension was washed with water (30 mL), brine (30 mL×2), dried over anhydrous Na$_2$SO$_4$ and filtered. The filtrate was evaporated in vacuum to residue, which was purified by prep-TLC (PE/EtOAc=1/2, 0.5% TEA as additive) to give compound (97), (25 mg, yield: 24%) as white solid.

$^1$H NMR (300 HMz, DMSO-d$_6$): δ=7.93 (brs, 1H), 7.51 (s, 1H), 7.09 (m, J=7.5 Hz, 2H), 6.99 (s, 1H), 6.68 (d, J=7.8 Hz, 2H), 6.53 (t, J=7.2 Hz, 1H), 5.82 (brs, 1H), 3.87 (s, 3H), 3.85 (s, 3H), 3.71-3.60 (m, 2H), 3.33-3.20 (m, 2H), 2.06-1.93 (m, 1H), 1.08-1.00 (m, 2H), 0.95-0.84 (m, 2H). MS: m/z 365.2 (M+H$^+$).

Example 70: N-(2-cyclopropyl-6,7-dimethoxy-quinazolin-4-yl)-N'-(2-methoxy-phenyl)-propane-1,3-diamine (98)

The title compound was prepared as described for compound (97), except that N'-(2-methoxyphenyl)propane-1,3-diamine was substituted for N'-phenyl-ethane-1,2-diamine.

$^1$H NMR (400 MHz, CDCl$_3$): δ=7.12 (s, 1H), 6.91-6.80 (m, 1H), 6.78-6.65 (m, 4H), 5.96 (brs, 1H), 4.36 (brs, 1H), 3.97 (s, 3H), 3.89-3.72 (m, 8H), 3.38-3.29 (m, 2H), 2.23-2.00 (m, 3H), 1.23-1.14 (m, 2H), 0.99-0.89 (m, 2H). MS: m/z 409.3 (M+H$^+$).

Example 71: N-(2-cyclopropyl-6,7-dimethoxy-quinazolin-4-yl)-N'-(2-methoxy-phenyl)-N,N'-dimethyl-ethane-1,2-diamine (99)

The title compound was prepared as described for compound (97), except that N-(2-methoxy-phenyl)-N,N'-dimethyl-ethane-1,2-diamine was substituted for N'-phenyl-ethane-1,2-diamine.

$^1$H NMR (400 HMz, CDCl$_3$): δ=7.14 (s, 1H), 7.11 (s, 1H), 6.98-6.76 (m, 4H), 3.99 (s, 3H), 3.95-3.78 (m, 5H), 3.74 (s, 3H), 3.56-3.42 (m, 2H), 3.20 (s, 3H), 2.90 (s, 3H), 2.21-2.08 (m, 1H), 1.18-1.10 (m, 2H), 1.00-0.90 (m, 2H). MS: m/z 423.3 (M+H$^+$).

Example 72: 2-cyclopropyl-6,7-dimethoxy-4-[4-(2-methoxy-phenyl)-[1,4]diazepan-1-yl]-quinazoline (100)

The title compound was prepared as described for compound (97), except that 1-(2-methoxy-phenyl)-[1,4]diazepane hydrochloride was substituted for N'-phenyl-ethane-1,2-diamine.

$^1$H NMR (400 MHz, CDCl$_3$): δ=7.25 (s, 1H), 7.05 (s, 1H), 6.99-6.78 (m, 4H), 4.13-3.98 (m, 2H), 3.98-3.91 (m, 2H), 3.89 (s, 3H), 3.85 (s, 3H), 3.72 (s, 3H), 3.48-3.36 (m, 2H), 3.32-3.20 (m, 2H), 2.20-2.08 (m, 2H), 2.06-1.96 (m, 1H), 1.01-0.91 (m, 2H), 0.91-0.82 (m, 2H). MS: m/z 435.3 (M+H$^+$).

Example 73: [1-(2-cyclopropyl-6,7-dimethoxy-quinazolin-4-yl)-piperidin-4-yl]-(2-methoxy-phenyl)-amine (101)

The title compound was prepared as described for compound (97), except that (2-methoxy-phenyl)-piperidin-4-yl-amine hydrochloride was substituted for N-phenyl-ethane-1,2-diamine.

$^1$H NMR (400 MHz, DMSO-d$_6$): δ=7.09 (s, 1H), 7.06 (s, 1H), 6.84-6.75 (m, 2H), 6.68 (d, J=8.4 Hz, 1H), 6.55 (t, J=8.0 Hz, 1H), 4.56 (d, J=7.6 Hz, 1H), 4.08 (d, J=13.2 Hz, 2H), 3.90 (s, 3H), 3.87 (s, 3H), 3.77 (s, 3H), 3.68-3.55 (m, 1H), 3.25-3.12 (t, J=12.0 Hz, 2H), 2.12-1.98 (m, 3H), 1.71-1.54 (m, 2H), 1.04-0.97 (m, 2H), 0.98-0.88 (m, 2H). MS: m/z 435.3 (M+H$^+$).

Example 74: 2-(2-cyclopropyl-6,7-dimethoxy-quinazolin-4-ylamino)-N-(2-methoxy-phenyl)-acetamide (102)

The title compound was prepared as described for compound (97), except that 2-amino-N-(2-methoxy-phenyl)-acetamide hydrochloride was substituted for N-phenyl-ethane-1,2-diamine.

$^1$H NMR (400 MHz, CDCl$_3$): δ=8.60 (brs, 1H), 8.33 (d, J=8.0 Hz, 1H), 7.15 (s, 1H), 7.10-7.02 (m, 1H), 7.01-6.89 (m, 2H), 6.84 (d, J=8.0 Hz, 1H), 6.62 (brs, 1H), 4.42 (d, J=5.2 Hz, 2H), 3.99 (s, 3H), 3.91 (s, 3H), 3.79 (s, 3H), 2.22-2.14 (m, 1H), 1.18-1.11 (m, 2H), 1.02-0.89 (m, 2H). MS: m/z 409.2 (M+H$^+$).

Scheme 7:

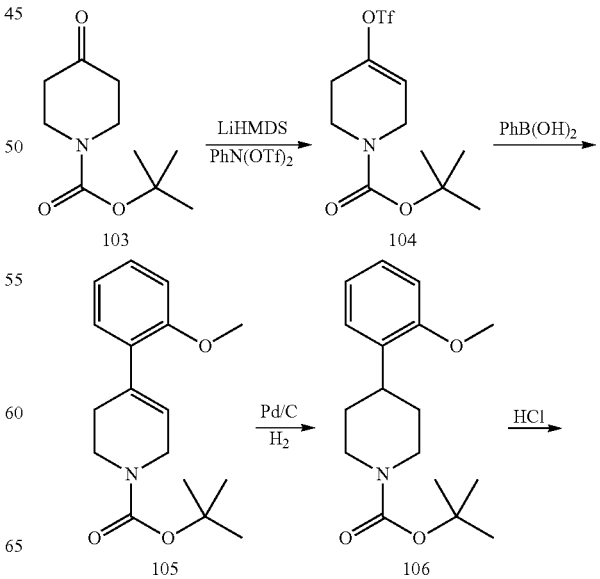

-continued

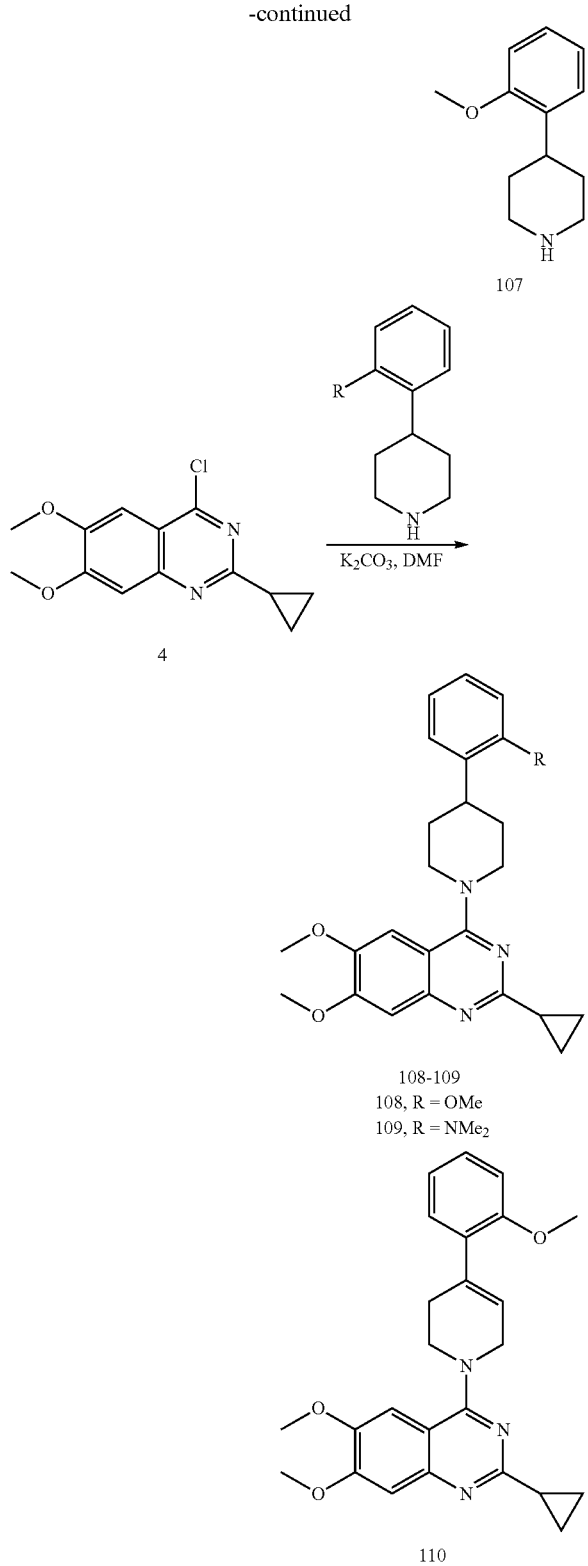

108-109
108, R = OMe
109, R = NMe₂

110

Example 75: 2-Cyclopropyl-6,7-dimethoxy-4-[4-(2-methoxy-phenyl)-piperidin-1-yl]-quinazoline (108)

To a solution of (103) (400 mg, 2 mmol) in 10 mL of THF at −78° C. was dropwise added LiHMDS (1.6 M in THF, 2.5 mL, 4 mmol), then the mixture was stirred for 1 h at −78° C. before the addition of PhN(OTf)₂ (357 mg, 2 mmol) at −78° C. The reaction was allowed to warm to room temperature and stirred overnight. The solution was quenched with water and the aqueous phase was extracted with EtOAc. The extracts were washed with brine and dried over NaSO₄. The solution was evaporated in vacuum to give compound (104) as yellow oil, which was used for next step without further purification.

A suspension of compound (104) (166 mg, 0.5 mmol), PhB(OH)₂ (114 mg, 0.75 mmol), KCO₃ (207 mg, 0.75 mmol), Pd(PPh₃)₄ (58 mg, 0.05 mmol) in 3 mL of dioxane was degassed and bubbled with N₂. Then it was exposed under microwave irradiation at 80° C. for 1.5 h. The solution was evaporated to dryness in vacuum and the residue was purified by Prep-TLC (PE/EtOAc=19/1) to give compound (105) (70 mg, yield: 48%) as colorless oil.

$^1$H NMR (300 MHz, CDCl₃): δ=7.27-7.22 (m, 1H), 7.18-7.14 (m, 1H), 7.01-6.81 (m, 2H), 5.77-5.75 (m, 1H), 4.08-4.05 (m, 2H), 3.83 (s, 3H), 3.61 (t, J=5.4 Hz, 2H), 2.52-2.49 (m, 2H), 1.51 (s, 9H).

A solution of compound (105) (70 mg, 0.24 mmol) and 10% wet Pd/C (10 mg) in 10 mL of EtOAc was purged with N₂ for three times and then it was stirred under H₂ atmosphere (50 psi) overnight. The suspension was filtered and the filtrate was evaporated in vacuum to give compound (106) (70 mg, yield: 99%) as colorless oil. A solution of compound 106 (70 mg, 0.24 mmol) in 5 mL of HCl/Dioxane was stirred at room temperature overnight. The solution was evaporated in vacuum to dryness. The solid was washed with ether to give compound (107) (35 mg, yield: 76%) as white solid.

A mixture of 4-(2-methoxyphenyl)piperidine (35 mg, 0.18 mmol), 4-chloro-2-cyclopropyl-6,7-dimethoxy-quinazoline (50 mg, 0.19 mmol), KCO₃ (75 mg, 0.54 mmol) in DMF (5 mL) was stirred at 70° C. overnight. The solution was quenched with water. The resulting solid was filtered and purified by Pre-TLC (PE/EtOAc=1/1) to give compound (108), (21 mg, yield: 27%) as yellow solid.

$^1$H NMR (400 MHz, DMSO-d₆): δ=7.38-7.22 (m, 3H), 7.18 (s, 1H), 7.05 (d, J=8.0 Hz, 1H), 7.03-6.93 (m, 1H), 4.62-4.35 (m, 2H), 3.99 (s, 3H), 3.96 (s, 3H), 3.88 (s, 3H), 3.37-3.20 (m, 3H), 2.20-2.17 (m, 1H), 2.04-1.83 (m, 4H), 1.24-0.97 (m, 4H). MS: m/z 420.2 (M+H⁺).

Example 76: {2-[1-(2-Cyclopropyl-6,7-dimethoxy-quinazolin-4-yl)-piperidin-4-yl]-phenyl}-dimethyl-amine (109)

The title compound was prepared as described for compound (108), except that N,N-dimethyl-2-(piperidin-4-yl)aniline was substituted for 4-(2-methoxyphenyl)piperidine.

$^1$H NMR (400 MHz, DMSO-d₆): δ=7.31-7.23 (m, 2H), 7.19-7.16 (m, 2H), 7.14 (s, 1H), 7.08-7.00 (m, 1H), 4.69-4.49 (m, 2H), 3.96 (s, 3H), 3.91 (s, 3H), 3.58-3.46 (m, 1H), 3.45-3.29 (m, 2H), 2.65 (s, 6H), 2.24-2.11 (m, 1H), 1.92-1.79 (m, 4H), 1.21-1.08 (m, 4H). MS: m/z 433.3 (M+H⁺).

Example 77: 2-cyclopropyl-6,7-dimethoxy-4-[4-(2-methoxy-phenyl)-3,6-dihydro-2H-pyridin-1-yl]-quinazoline (110)

The title compound was prepared as described for compound (108), except that 4-(2-methoxyphenyl)-1,2,3,6-tetrahydropyridine was substituted for 4-(2-methoxyphenyl)piperidine.

¹H NMR (400 MHz, DMSO-d₆): δ=7.31-7.23 (m, 2H), 7.20-7.16 (m, 2H), 7.01 (d, J=8.4 Hz, 1H), 6.92 (t, J=7.2 Hz, 1H), 5.89 (s, 1H), 4.60-4.50 (m, 2H), 4.06-4.00 (m, 2H), 3.95 (s, 3H), 3.93 (s, 3H), 3.75 (s, 3H), 2.74-2.70 (m, 2H), 2.18-2.16 (m, 1H), 1.23-1.17 (m, 4H), MS: m/z 418.3 (M+H⁺).
Scheme 8:
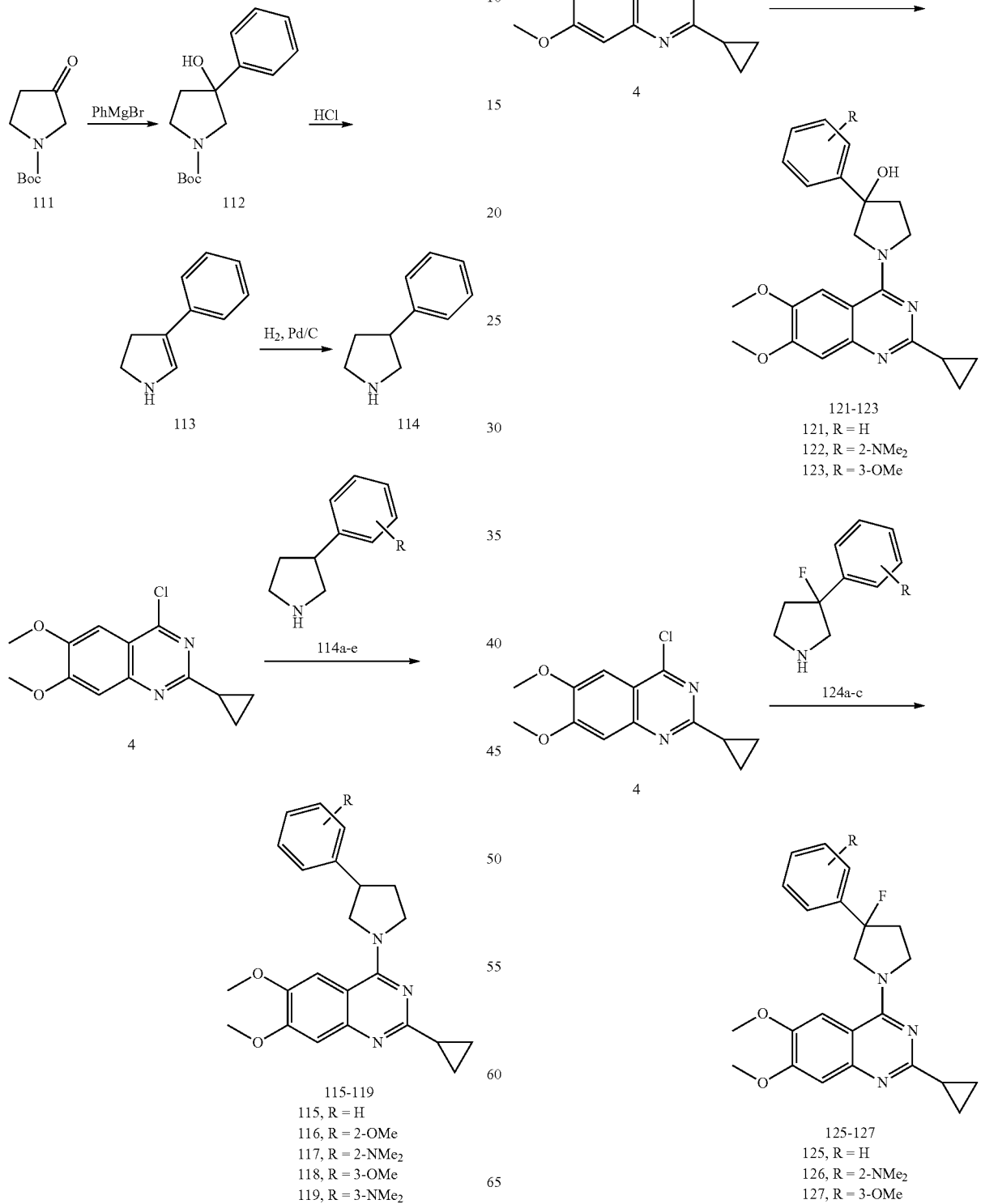

Example 78: 2-cyclopropyl-6,7-dimethoxy-4-(3-phenyl-pyrrolidin-1-yl)-quinazoline (115)

To a solution of 3-oxo-pyrrolidine-1-carboxylic acid tert-butyl ester (0.5 g, 2.7 mmol) in THF (30 mL) was added phenylmagnesium bromide (13.5 mL, 1 M in THF) drop-wise at room temperature under $N_2$. The mixture was stirred at room temperature overnight. The reaction was quenched with aq. $NH_4Cl$ solution (10 mL) and the mixture was extracted with EtOAc (30 mL). The extracts were washed with brine, dried over anhydrous $Na_2SO_4$. The solvent was removed and the residue was purified by silica gel column chromatography (PE/EtOAc=10/1) to give 3-hydroxy-3-phenyl-pyrrolidine-1-carboxylic acid tert-butyl ester (112) (267 mg, yield: 37%) as white solid.

$^1$H NMR (400 MHz, $CDCl_3$): δ=7.49-7.30 (m, 5H), 3.77-3.57 (m, 4H), 2.33-2.27 (m, 2H), 1.43 (s, 9H).

The mixture of 3-hydroxy-3-phenyl-pyrrolidine-1-carboxylic acid tert-butyl ester (112) (267 mg, 1.02 mmol) in HCl (5 mL, 12 M) was heated to reflux for 2 h. Most of the solvent was removed. The residue was basified with aq. $Na_2CO_3$ solution to pH=8 and the mixture was extracted with EtOAc (15 mL×3). The extracts were washed with brine (30 mL) and dried with anhydrous $Na_2SO_4$. The solvent was removed to give crude compound (113) (119 mg, yield: 37%) as yellow oil. MS: m/z 146.1 ($M+H^+$).

A suspension of 4-phenyl-2,3-dihydro-1H-pyrrole (119 mg, 0.82 mmol) and wet 10% Pd/C (20 mg) in MeOH (10 mL) was purged with $H_2$ for several times. Then it was stirred at room temperature under $H_2$ balloon pressure for 3 hours. The mixture was filtered and the filtrate was evaporated in vacuo to give crude compound (114) (120 mg, yield: 98%) as yellow oil. MS: m/z 148.1 (M+H+).

This step proceeded as described for compound (108), except that 3-phenylpyrrolidine was substituted for 4-(2-methoxyphenyl)piperidine to afford compound (115).

$^1$H NMR (400 MHz, $CDCl_3$): δ=7.41-7.28 (m, 7H), 4.31-4.27 (m, 1H), 4.10-4.06 (m, 2H), 4.02 (s, 3H), 3.95 (s, 3H), 3.53-3.50 (m, 1H), 2.46-2.44 (m, 1H), 2.28-2.17 (m, 3H), 1.25-1.15 (m, 2H), 1.01-0.98 (m, 2H). MS: m/z 376.2 ($M+H^+$).

Example 79: 2-cyclopropyl-6,7-dimethoxy-4-[3-(2-methoxy-phenyl)-pyrrolidin-1-yl]-quinazolin (116)

The title compound was prepared as described for compound (108), except that 3-(2-methoxyphenyl)pyrrolidine was substituted for 4-(2-methoxyphenyl)piperidine.

$^1$H NMR (400 MHz, $CDCl_3$): δ=7.41 (s, 1H), 7.29-7.25 (m, 2H), 7.16 (s, 1H), 6.99-6.91 (m, 2H), 4.29-4.28 (m, 1H), 4.03-3.98 (m, 5H), 3.90-3.82 (m, 8H), 2.22-2.18 (m, 3H), 1.16-1.12 (m, 2H), 0.93-0.88 (m, 2H). MS: m/z 406.3.2 ($M+H^+$).

Example 80: {2-[1-(2-cyclopropyl-6,7-dimethoxy-quinazolin-4-yl)-pyrrolidin-3-yl]-phenyl}-dimethyl-amine (117)

The title compound was prepared as described for compound (108), except that 3-(2-methoxyphenyl)pyrrolidine was substituted for 4-(2-methoxyphenyl)piperidine.

$^1$H NMR (400 MHz, $CDCl_3$): δ=7.77 (s, 1H), 7.39-7.29 (m, 5H), 4.55-4.23 (m, 3H), 4.06 (s, 3H), 3.95-3.92 (m, 4H), 2.95-2.90 (m, 6H), 2.55-2.45 (m, 2H), 2.21-2.19 (m, 1H), 1.27-1.19 (m, 4H). MS: m/z 419 ($M+H^+$).

Example 81: 2-cyclopropyl-6,7-dimethoxy-4-[3-(3-methoxy-phenyl)-cyclopentyl]-quinazoline (118)

The title compound was prepared as described for compound (108), except that 3-(3-methoxyphenyl)pyrrolidine was substituted for 4-(2-methoxyphenyl)piperidine.

$^1$H NMR (400 MHz, $CDCl_3$): δ=7.41 (s, 1H), 7.33-7.24 (m, 2H), 6.93-6.83 (m, 3H), 4.29-4.23 (m, 1H), 4.10-4.07 (m, 2H), 4.02 (s, 3H), 3.97-3.93 (m, 4H), 3.83 (s, 3H), 3.50-3.46 (m, 1H), 2.44-2.40 (m, 1H), 2.22-2.15 (m, 2H), 1.17-1.14 (m, 2H), 0.98-0.96 (m, 2H). LC-MS: 406.2 (M+1).

Example 82: {3-[1-(2-cyclopropyl-6,7-dimethoxy-quinazolin-4-yl)-pyrrolidin-3-yl]-phenyl}-dimethyl-amine (119)

The title compound was prepared as described for compound (108), except that N,N-dimethyl-3-(pyrrolidin-3-yl)aniline was substituted for 4-(2-methoxyphenyl)piperidine.

$^1$H NMR (300 MHz, $CDCl_3$): δ=8.00 (s, 1H), 7.46 (s, 1H), 7.36-7.19 (m, 2H), 6.73-6.62 (m, 3H), 4.50-4.11 (m, 2H), 4.10-3.93 (m, 8H), 3.52-3.47 (m, 1H), 2.98 (s, 6H), 2.76-2.72 (m, 1H), 2.65-2.49 (m, 1H), 2.47-2.39 (m, 1H), 1.32-1.20 (m, 4H). MS: m/z 419.3 ($M+H^+$).

Example 83: 1-(2-cyclopropyl-6,7-dimethoxy-quinazolin-4-yl)-3-phenyl-pyrrolidin-3-ol (121)

The title compound was prepared as described for compound (108), except that 3-phenylpyrrolidin-3-ol was substituted for 4-(2-methoxyphenyl)piperidine.

$^1$H NMR (400 MHz, $CDCl_3$): δ=7.70-7.62 (m, 2H), 7.47-7.7.25 (m, 5H), 4.49-4.38 (m, 1H), 4.35-4.05 (m, 3H), 3.99 (s, 3H), 3.90 (s, 3H), 2.60-2.40 (m, 2H), 2.35-2.00 (m, 1H), 1.26-1.00 (m, 2H), 0.96-0.0.86 (m, 2H). LC-MS: 392.4 (M+1).

Example 84: 1-(2-cyclopropyl-6,7-dimethoxy-quinazolin-4-yl)-3-(2-dimethylamino-phenyl)-pyrrolidin-3-ol (122)

The title compound was prepared as described for compound (108), except that 3-(2-(dimethylamino)phenyl)pyrrolidin-3-ol was substituted for 4-(2-methoxyphenyl)piperidine.

$^1$H NMR (400 MHz, $CDCl_3$): δ=7.65-7.46 (m, 5H), 7.39 (d, J=8.0 Hz, 1H), 4.90-4.10 (m, 4H), 4.02 (s, 3H), 3.95 (s, 3H), 3.16 (s, 6H), 2.83-2.47 (m, 2H), 2.40-2.26 (m, 1H), 1.36-1.08 (m, 4H). MS: m/z 435.3 ($M+H^+$).

Example 85: 1-(2-cyclopropyl-6,7-dimethoxy-quinazolin-4-yl)-3-(3-methoxy-phenyl)-pyrrolidin-3-ol (123)

The title compound was prepared as described for compound (108), except that 3-(3-methoxyphenyl)pyrrolidin-3-ol was substituted for 4-(2-methoxyphenyl)piperidine.

$^1$HNMR (400 MHz, $CDCl_3$): δ=7.37-7.32 (m, 2H), 7.19-7.15 (m, 3H), 6.91-6.88 (m, 1H), 4.36-4.32 (m, 1H), 4.12 (s, 2H), 4.10-4.06 (m, 1H), 3.96 (s, 3H), 3.90 (s, 3H), 3.85 (s, 3H), 2.48-2.45 (m, 1H), 2.43-2.34 (m, 1H), 2.08-2.06 (m, 1H), 1.07-1.04 (m, 2H), 0.90-0.87 (m, 2H). MS: m/z 422.3 ($M+H^+$).

Example 86: 2-cyclopropyl-4-(3-fluoro-3-phenyl-pyrrolidin-1-yl)-6,7-dimethoxy-quinazoline (125)

To a solution of compound (112) (197 mg, 0.75 mmol) in DCM (10 mL) was added DAST (120 mg, 0.75 mmol)

dropwise at 0° C. and the mixture was stirred at this temperature for 1 hour. LCMS showed it gave a mixture of desired tert-butyl 3-fluoro-3-phenylpyrrolidine-1-carboxylate and dehydrated byproduct tert-butyl 3-phenyl-2,5-dihydro-1H-pyrrole-1-carboxylate. The reaction was quenched with saturated aqueous Na$_2$CO$_3$ and the organic layer was dried over Na$_2$SO$_4$. The solution was concentrated to dryness and the residue was purified by silica gel column chromatography (PE/EtOAc=20/1) to give 105 mg of mixture of desired tert-butyl 3-fluoro-3-phenylpyrrolidine-1-carboxylate and dehydrated byproduct tert-butyl 3-phenyl-2,5-dihydro-1H-pyrrole-1-carboxylate as yellow oil. MS: m/z 266.1 (M+H$^+$).

The above mixture in HCl/EtOAc (10 mL) was stirred at room temperature for 1 hour. LCMS showed all the starting material was consumed and the solvent was concentrated to give 66 mg of crude mixture of 3-fluoro-3-phenylpyrrolidine (124a) and 3-phenyl-2,5-dihydro-1H-pyrrole.

To the above mixture of mixture of 3-fluoro-3-phenylpyrrolidine and 3-phenyl-2,5-dihydro-1H-pyrrole as HCl salt (66 mg) in MeCN was added 2-cyclopropyl-6,7-dimethoxyquinazolin-4-ol (98 mg, 0.40 mmol), DBU (182 mg, 1.20 mmol), BOP (230 mg, 0.52 mmol), and the mixture was stirred at room temperature overnight. The solution was concentrated to dryness in vacuum and the residue was purified by prep-HPLC to give compound (125) (7.4 mg, 3-step yield: 2.5%) as yellow solid.

$^1$H NMR (400 MHz, CDCl$_3$): δ=7.55-7.40 (m, 5H), 7.28 (s, 1H), 7.20 (s, 1H), 4.42-4.33 (m, 4H), 4.01 (s, 3H), 3.95 (s, 3H), 2.64-2.57 (m, 1H), 2.14-2.11 (m, 1H), 1.31-1.28 (m, 1H), 1.16-1.09 (m, 2H), 0.96-0.93 (m, 2H). LC-MS: 394.2 (M+H$^+$).

Example 87: {2-[1-(2-cyclopropyl-6,7-dimethoxyquinazolin-4-yl)-3-fluoro-pyrrolidin-3-yl]-phenyl}-dimethyl-amine (126)

The title compound was prepared as described for compound (125), using the similar route and procedure.

$^1$H NMR (300 MHz, CDCl$_3$): δ=7.63 (s, 1H), 7.58-7.26 (m, 4H), 6.32-6.12 (s, 1H), 5.50-4.80 (m, 4H), 4.13 (s, 6H), 4.04-3.87 (m, 2H), 3.10-2.84 (m, 6H), 2.48-2.39 (m, 1H), 1.46-1.15 (m, 4H). MS: m/z 417.3 (M–HF+H$^+$).

Example 88: 2-cyclopropyl-4-[3-fluoro-3-(3-methoxy-phenyl)-pyrrolidin-1-yl]-6,7-dimethoxy-quinazoline (127)

The title compound was prepared as described for compound (125), using the similar route and procedure.

$^1$HNMR (400 MHz, CDCl$_3$): δ=7.39-7.37 (m, 2H), 7.20 (s, 1H), 7.08-7.06 (m, 2H), 6.95-6.92 (m, 1H), 4.41-4.34 (m, 1H), 4.29 (s, 2H), 4.24-4.20 (m, 1H), 4.02 (s, 3H), 3.94 (s, 3H), 3.87 (s, 3H), 2.60-2.55 (m, 2H), 2.13-2.12 (m, 1H), 1.14-1.10 (m, 2H), 0.93-0.92 (m, 2H). LC-MS: 424.3 (M+1).

Scheme 9:

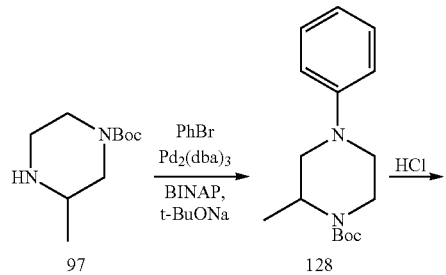

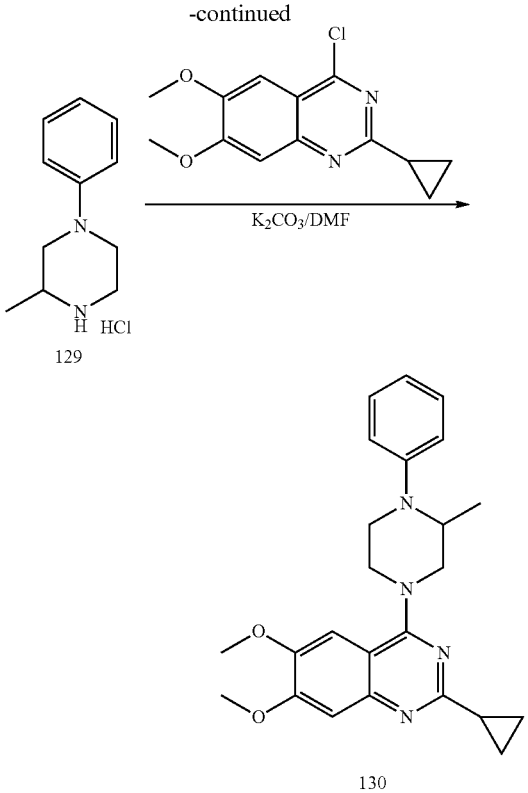

Example 89: 2-cyclopropyl-6,7-dimethoxy-4-(3-methyl-4-phenyl-piperazin-1-yl)-quinazoline (130)

To a mixture of bromobenzene (312 mg, 2 mmol), 3-methyl-piperazine-1-carboxylic acid tert-butyl ester (480 mg, 2.4 mmol) and t-BuONa (576 mg, 6 mmol) in anhydrous toluene (10 mL) was added BINAP (62 mg, 0.1 mmol) and Pd$_2$(dba)$_3$ (57 mg, 0.1 mmol). The mixture was refluxed under N$_2$ for 17 h. After cooled to room temperature, the reaction solution was filtered. The filtrate was evaporated in vacuum to residue, which was purified by silica gel chromatography (from PE to PE/EtOAc=20/1) to afford compound (128) (223 mg, yield: 40%) as brown oil. MS: m/z 277.2 (M+H$^+$).

To a stirred solution of 2-methyl-4-phenyl-piperazine-1-carboxylic acid tert-butyl ester (223 mg, about 81% purity by LCMS) in 1,4-dioxane (3 mL) was added HCl/dioxane (5 mL, 4M) and the mixture was stirred at 25° C. for 4 h. The reaction mixture was evaporated in vacuum to dryness to afford (161 mg, yield: 94%) of 3-methyl-1-phenyl-piperazine hydrochloride as brown oil. MS: m/z 177.1 (M+H$^+$).

A mixture of 3-methyl-1-phenyl-piperazine hydrochloride (50 mg, 0.23 mmol), 4-chloro-2-cyclopropyl-6,7-dimethoxy-quinazoline (69 mg, 0.26 mmol) and K$_2$CO$_3$ (97 mg, 0.7 mmol) in DMF (5 mL) was stirred at 70° C. for 17 h. The reaction mixture was cooled to room temperature, diluted with water (30 mL) and the new suspension was filtered. The solid cake was dissolved with DMF (1 mL) and then purified by prep-HPLC to afford compound (130), (14 mg, yield: 15%) as white solid.

¹H NMR (400 MHz, CDCl₃): δ=7.46-7.26 (m, 2H), 7.25-7.16 (m, 2H), 7.02-6.94 (m, 2H), 6.93-6.83 (m, 1H), 4.16-4.00 (m, 5H), 3.99 (s, 3H), 3.94-3.86 (m, 1H), 3.63-3.52 (m, 1H), 3.50-3.31 (m, 3H), 2.24-2.13 (m, 1H), 1.21-1.14 (m, 5H), 1.07-0.95 (m, 2H). MS: m/z 405.2 (M+H⁺).

Scheme 10:

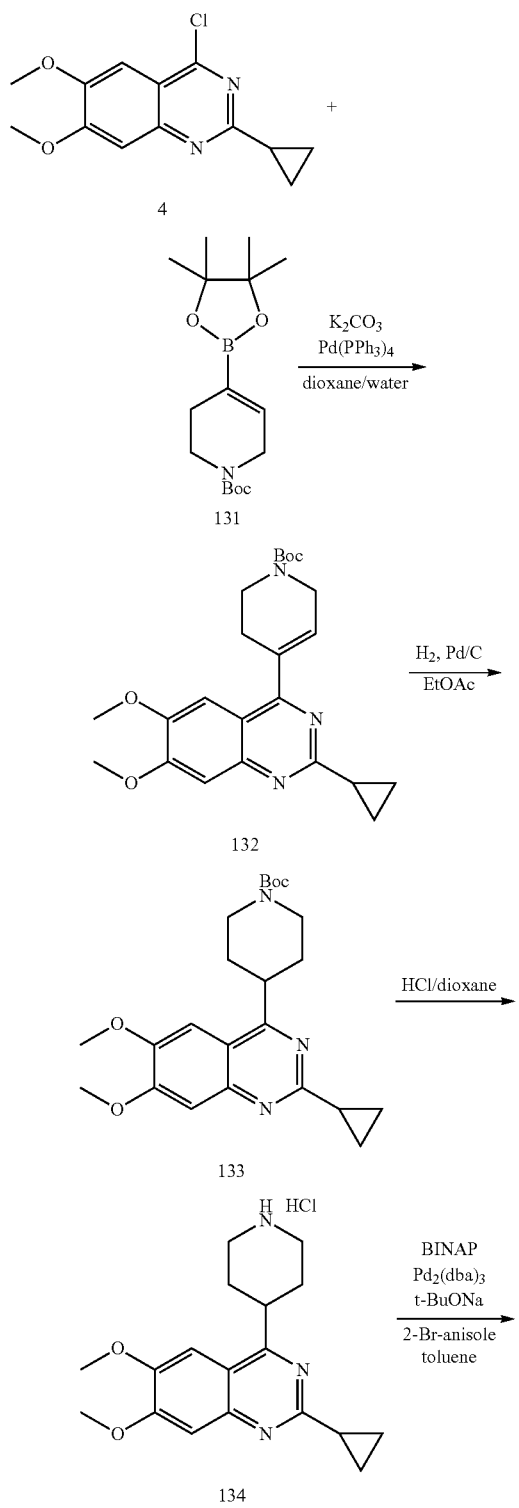

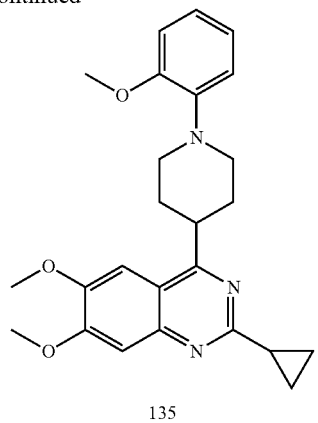

135

Example 90: 2-cyclopropyl-6,7-dimethoxy-4-[1-(2-methoxy-phenyl)-piperidin-4-yl]-quinazoline (135)

To a mixture of compound (4) (144 mg, 0.53 mmol), 131 (150 mg, 0.48 mmol) and K₂CO₃ (135 mg, 0.96 mmol) in dioxane/water (10 mL/3 mL) was added Pd(PPh₃)₄ (54 mg, 0.05 mmol). The mixture was stirred at reflux under N₂ for 16 h. The reaction mixture was cooled to room temperature and diluted with EtOAc (30 mL). The organic layer was separated and dried over anhydrous Na₂SO₄. The solution was evaporated in vacuum to residue, which was purified by prep-TLC (PE/EtOAc=1/1) to give compound (132) (42 mg, yield: 21%) as white solid.

A suspension of compound (132) (42 mg, 0.1 mmol) and wet 10% Pd/C (10 mg) in EtOAc (5 mL) was stirred under H₂ balloon for 2 hours. The mixture was filtered and the filtrate was evaporated in vacuum to dryness to afford compound 133 (42 mg, yield: 100%) as white solid.

¹H NMR (300 MHz, CDCl₃): δ=7.25 (s, 1H), 7.19 (s, 1H), 4.42-4.19 (m, 2H), 4.09-3.99 (m, 6H), 3.50-3.38 (m, 1H), 3.10-2.88 (m, 2H), 2.32-2.20 (m, 1H), 2.05-1.75 (m, 4H), 1.52 (s, 9H), 1.26-1.19 (m, 2H), 1.11-0.99 (m, 2H).

A mixture of 4-(2-cyclopropyl-6,7-dimethoxy-quinazolin-4-yl)-piperidine-1-carboxylic acid tert-butyl ester (133) (50 mg, 0.12 mmol) in HO/dioxane (5 mL, 4M) was stirred at room temperature for 2 hours. The mixture was evaporated in vacuum to dryness to afford compound 134 (42 mg, yield: 100%) as brown solid.

To a mixture of compound 134 (42 mg, 0.12 mmol), 1-bromo-2-methoxy-benzene (45 mg, 0.24 mmol) and t-BuONa (192 mg, 2 mmol) in anhydrous toluene (10 mL) was added BINAP (7 mg, 0.01 mmol) and Pd₂(dba)₃ (7 mg, 0.01 mmol). The mixture was refluxed under N₂ for 17 h. After cooled to room temperature, the reaction solution was filtered. The filtrate was evaporated in vacuum to residue, which was purified by prep-TLC (PE/EtOAc=3/1) to afford compound 135 (6 mg, yield: 12%) as brown solid.

¹H NMR (400 HMz, CDCl₃): δ=7.30-7.22 (m, 2H), 7.10-6.88 (m, 4H), 4.05 (s, 6H), 3.93 (s, 3H), 3.75-3.62 (m, 2H), 3.45 (t, J=10.4 Hz, 1H), 2.84 (t, J=11.2 Hz, 2H), 2.46-2.23 (m, 3H), 2.05-1.89 (m, 2H), 1.16-1.00 (m, 2H), 0.93-0.82 (m, 2H). MS: m/z 420.2 (M+H⁺).

Scheme 11:
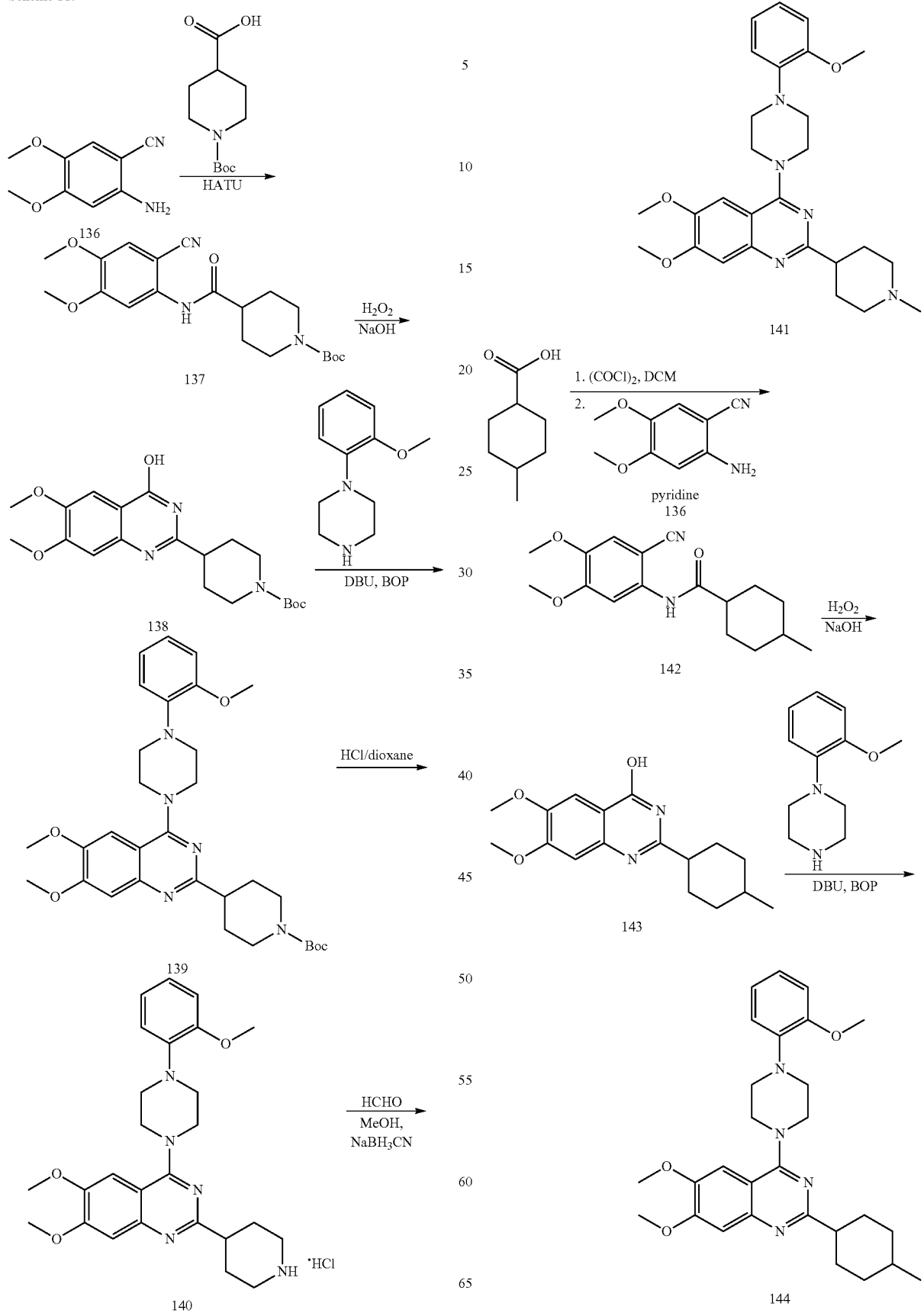

Example 91: 6,7-dimethoxy-4-[4-(2-methoxy-phenyl)-piperazin-1-yl]-2-piperidin-4-yl-quinazoline (140)

To a solution of piperidine-1,4-dicarboxylic acid mono-tert-butyl ester (378 mg, 1.65 mmol) in DMF (10 mL) were added DIEPA (580 mg, 4.50 mmol), 2-amino-4,5-dimethoxy-benzonitrile 136 (267 mg, 1.50 mmol). The mixture was stirred at 50° C. overnight. The solvent was removed in vacuum and the residue was dissolved in EtOAc (20 mL). The mixture was washed with water (10 mL) and dried over anhydrous $Na_2SO_4$. The solvent was removed and the residue was purified by silica gel column chromatography (EtOAc/PE=1/8) to give compound (137) (184 mg, yield: 32%) as yellow solid.

$^1$HNMR (400 MHz, $CDCl_3$): δ=8.07 (s, 1H), 7.57 (brs, 1H), 6.95 (s, 1H), 4.22-4.18 (m, 2H), 3.96 (s, 3H) 3.88 (s, 3H), 2.85-2.79 (m, 2H), 2.49-2.43 (m, 1H), 2.00-1.96 (m, 2H), 1.80-1.70 (m, 2H), 1.47 (s, 9H).

To a solution of compound (137) (298 mg, 0.77 mmol) in EtOH (20 mL) were added NaOH (34 mg, 0.84 mmol) and $H_2O_2$ (2 mL). The mixture was stirred at 80° C. for 2 h. The solvent was removed to give crude compound (138) (368 mg, yield: 100%) as yellow solid.

$^1$HNMR (400 MHz, DMSO-$d_6$): δ=7.40 (s, 1H), 7.05 (s, 1H), 4.05-4.02 (m, 2H), 3.89 (s, 3H), 3.86 (s, 3H), 2.77-2.72 (m, 3H), 1.67-1.62 (m, 4H), 1.45 (s, 9H).

To a solution of 4-(4-hydroxy-6,7-dimethoxy-quinazolin-2-yl)-piperidine-1-carboxylic acid tert-butyl ester (138) (298 mg, 0.77 mmol) in MeCN (25 mL) were added 1-(2-methoxy-phenyl)-piperazine (441 mg, 2.30 mmol), DBU (233 mg, 1.53 mmol) and BOP (440 mg, 0.99 mmol). The mixture was stirred at 50° C. overnight. The solvent was removed and the residue was dissolved in EtOAc (20 mL). The mixture was washed with water (30 mL) and dried over anhydrous $Na_2SO_4$. The solvent was removed and the residue was purified by silica gel column chromatography (EtOAc/PE=1/2) to give compound (139) (144 mg, yield: 33%) as brown oil.

$^1$HNMR (400 MHz, $CDCl_3$): δ=7.22 (s, 1H), 7.14 (s, 1H), 7.05-6.91 (m, 4H), 4.25-4.15 (m, 2H), 4.02 (s, 3H), 3.98 (s, 3H), 3.91 (s, 3H), 3.91-3.86 (m, 4H), 3.29-3.25 (m, 4H), 2.90-2.83 (m, 3H), 2.00-1.98 (m, 2H), 1.58-1.56 (m, 2H), 1.48 (s, 9H).

The mixture of compound (139) (140 mg, 0.25 mmol) in HCl/dioxane (4 M) was stirred at room temperature overnight. The resulting mixture was filtered. The solid was dried to give compound (140), (100 mg, yield: 80%) as white solid.

$^1$HNMR (400 MHz, DMSO-$d_6$): δ=9.09 (brs, 1H), 8.95 (brs, 1H), 7.51 (s, 1H), 7.39 (s, 1H), 7.02-6.89 (m, 4H), 4.31-4.27 (m, 4H), 3.97 (s, 6H), 3.83 (s, 3H), 3.41-3.00 (m, 9H), 2.22-2.06 (m, 4H). MS: m/z 464.3 (M+H$^+$).

Example 92: 6,7-dimethoxy-4-[4-(2-methoxy-phenyl)-piperazin-1-yl]-2-(1-methyl-piperidin-4-yl)-quinazoline (141)

To a solution of 6,7-dimethoxy-4-[4-(2-methoxy-phenyl)-piperazin-1-yl]-2-piperidin-4-yl-quinazoline (68 mg, 0.14 mmol) in MeOH (10 mL) were added $NaBH_3CN$ (68 mg, 0.68 mmol) and aq. HCHO (0.5 mL). The mixture was stirred at room temperature for 1 h. The solvent was removed and the residue was dissolved in EtOAc (20 mL). The mixture was washed with brine (10 mL×2) and dried over anhydrous $Na_2SO_4$. The solution was concentrated to dryness in vacuum and the residue was purified by prep-HPLC to give compound (141) (11 mg, yield: 16%) as yellow solid.

$^1$HNMR (400 MHz, $CDCl_3$): δ=7.54 (s, 1H), 7.13 (s, 1H), 7.08-6.91 (m, 4H), 4.18-4.06 (m, 4H), 4.06 (s, 3H), 4.00 (s, 3H), 3.92 (s, 3H), 3.65-3.46 (m, 2H), 3.45-3.28 (m, 4H), 3.01-2.70 (m, 6H), 2.69-2.63 (m, 2H), 2.34-2.31 (m, 2H). MS: m/z 478.3 (M+H$^+$).

Example 93: 6,7-dimethoxy-4-[4-(2-methoxy-phenyl)-piperazin-1-yl]-2-(4-methyl-cyclohexyl)-quinazoline (144)

To a solution of 4-methyl-cyclohexanecarboxylic acid (284 mg, 2.0 mmol) in DCM (15 mL) was added 1 drop of DMF and oxalyl chloride (305 mg, 2.4 mmol) dropwise at 0° C. The mixture was stirred at room temperature for 2 h. A solution of 2-amino-4,5-dimethoxy-benzonitrile 136 (356 mg, 2.0 mmol) in pyridine (3 mL) was added to the reaction mixture at 0° C. The resulting mixture was stirred at room temperature overnight. The mixture was washed with 1N HCl (1 mL), water (20 mL) and brine (20 mL). The organic layer was separated and dried over anhydrous $Na_2SO_4$. The solution was concentrated in vacuum to give compound (142) (600 mg, yield: 99%) as yellow solid.

$^1$HNMR (400 MHz, $CDCl_3$): δ=8.14 (s, 1H), 7.68 (brs, 1H), 6.94 (s, 1H), 3.96 (s, 3H,) 3.89 (s, 3H), 2.50-2.49 (m, 1H), 2.02-1.96 (m, 2H), 1.76-1.42 (m, 7H), 0.97 (d, J=6.8 Hz, 3H).

6,7-dimethoxy-2-(4-methyl-cyclohexyl)-3H-quinazolin-4-one (143) was prepared as similar as the intermediate 4-(4-hydroxy-6,7-dimethoxy-quinazolin-2-yl)-piperidine-1-carboxylic acid tert-butyl ester (138).

6,7-dimethoxy-4-[4-(2-methoxy-phenyl)-piperazin-1-yl]-2-(4-methyl-cyclohexyl)-quinazoline (144) was prepared as similar as for 4-{6,7-dimethoxy-4-[4-(2-methoxy-phenyl)-piperazin-1-yl]-quinazolin-2-yl}-piperidine-1-carboxylic acid tert-butyl ester (139).

$^1$HNMR (400 MHz, $CDCl_3$): δ=7.24 (s, 1H), 7.15 (s, 1H), 7.07-6.90 (m, 4H), 4.02 (s, 3H), 4.01 (s, 3H), 3.98 (s, 3H), 3.91-3.87 (m, 4H), 3.29-3.28 (m, 4H), 2.93-2.90 (m, 1H), 2.19-2.01 (m, 2H), 1.84-1.50 (m, 7H), 1.00 (d, J=6.8 Hz, 3H). MS: m/z 477.3 (M+H$^+$).

Example 94: 4-{6,7-dimethoxy-4-[4-(2-methoxy-phenyl)-piperazin-1-yl]-quinazolin-2-yl}-piperidine-1-carboxylic acid benzyl ester (145)

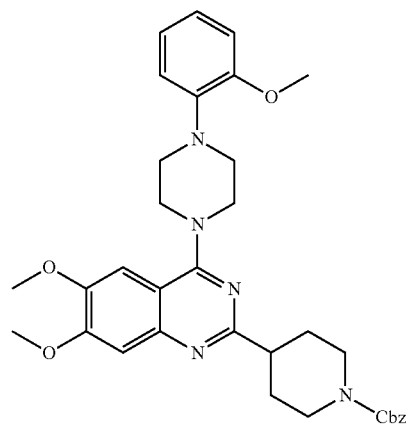

145

The title compound was prepared as similar as for compound (139) starting from material 1-((benzyloxy)carbonyl)piperidine-4-carboxylic acid instead of 1-(tert-butoxycarbonyl)piperidine-4-carboxylic acid.

¹HNMR (400 MHz, CDCl₃): δ=8.10 (s, 1H), 7.38-7.30 (m, 5H), 7.11-7.08 (m, 2H), 6.99-6.93 (m, 3H), 5.16 (s, 2H), 4.29-4.24 (m, 6H), 4.11 (s, 3H), 3.98 (s, 3H), 3.93 (s, 3H), 3.64-3.61 (m, 1H), 3.28-3.24 (m, 4H), 3.07-3.02 (m, 2H), 2.10-2.04 (m, 2H), 1.68-1.54 (m, 2H). MS: m/z 598.4 (M+H⁺).

Example 95: 6,7-dimethoxy-4-[4-(2-methoxy-phenyl)-piperazin-1-yl]-2-(tetrahydro-pyran-4-yl)-quinazoline (146)

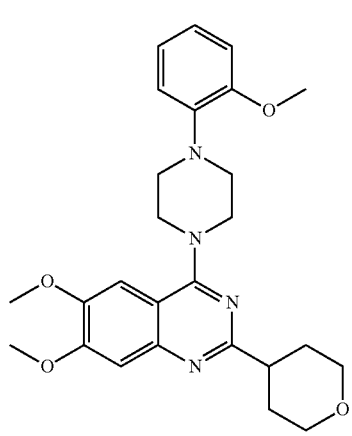

146

The title compound was prepared as similar as for compound (139) starting from material tetrahydro-2H-pyran-4-carboxylic acid instead of 1-(tert-butoxycarbonyl)piperidine-4-carboxylic acid.

¹HNMR (400 MHz, DMSO-d₆): δ=7.18 (s, 1H), 7.16 (s, 1H), 6.99-6.90 (m, 4H), 3.96-3.91 (m, 8H), 3.81-3.78 (m, 7H), 3.49-3.43 (m, 2H), 3.19-3.16 (m, 4H), 2.98-2.95 (m, 1H), 1.90-1.84 (m, 4H). MS: m/z 465.3 (M+H⁺).

Example 96: 6,7-dimethoxy-4-[4-(2-methoxy-phenyl)-piperazin-1-yl]-2-(tetrahydro-furan-3-yl)-quinazoline (147)

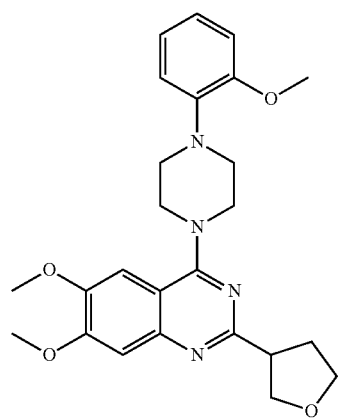

147

The title compound was prepared as similar as for compound (139) starting from material tetrahydrofuran-3-carboxylic acid instead of 1-(tert-butoxycarbonyl)piperidine-4-carboxylic acid.

¹HNMR (400 MHz, CDCl₃): δ=7.22 (s, 1H), 7.14 (s, 1H), 7.03-6.90 (m, 4H), 4.30-4.25 (m, 1H), 4.17-4.06 (m, 2H), 4.02 (s, 3H), 3.99 (s, 3H), 3.96 (s, 3H), 3.91-3.87 (m, 4H), 3.71-3.67 (m, 1H), 3.28-3.26 (m, 4H), 2.45-2.36 (m, 2H). MS: m/z 451.3 (M+H⁺).

Example 97: 6,7-dimethoxy-4-[4-(2-methoxy-phenyl)-piperazin-1-yl]-2-(2-methyl-cyclopropyl)-quinazoline (148)

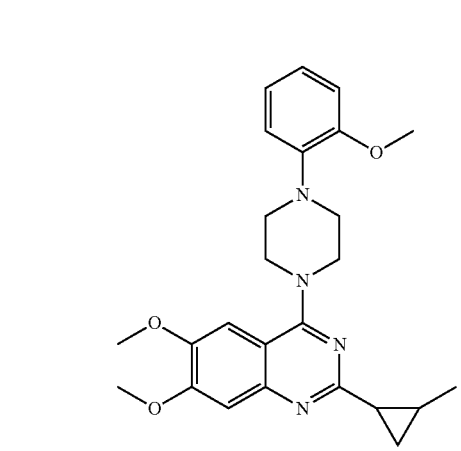

148

The title compound was prepared as for compound (139) starting from material 2-methylcyclopropanecarboxylic acid instead of 1-(tert-butoxycarbonyl)piperidine-4-carboxylic acid.

¹HNMR (400 MHz, CDCl₃): δ=7.19 (s, 1H), 7.10 (s, 1H), 7.07-6.90 (m, 4H), 4.01 (s, 3H), 3.97 (s, 3H), 3.90 (s, 3H), 3.86-3.81 (m, 4H), 3.26-3.23 (m, 4H), 1.92-1.88 (m, 1H), 1.55-1.50 (m, 1H), 1.37-1.25 (m, 1H), 1.23-1.21 (d, J=6.0 Hz, 3H). MS: m/z 435.3 (M+H⁺).

Scheme 12:

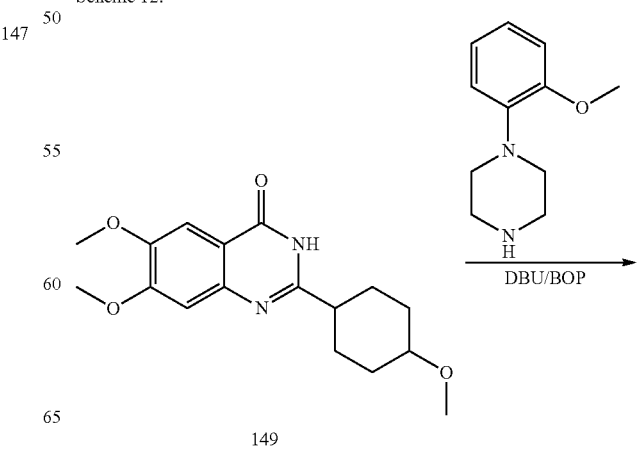

149

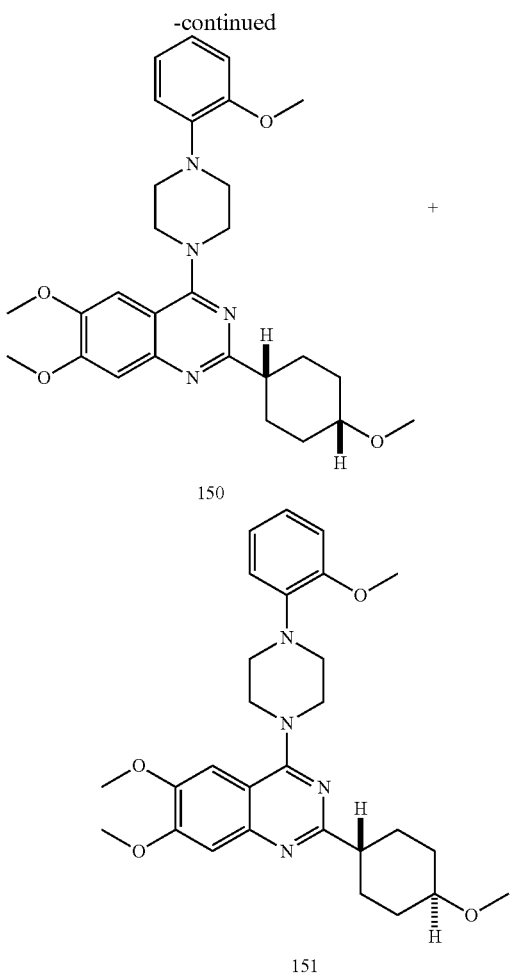

150

151

Examples 98 and 99: cis-6,7-dimethoxy-2-(4-methoxy-cyclohexyl)-4-[4-(2-methoxy-phenyl)-piperazin-1-yl]-quinazoline (150) and trans-6,7-dimethoxy-2-(4-methoxy-cyclohexyl)-4-[4-(2-methoxy-phenyl)-piperazin-1-yl]-quinazoline (151)

The title compounds were prepared as similar as for compound (139) starting from material 4-methoxycyclohexanecarboxylic acid instead of 1-(tert-butoxycarbonyl)piperidine-4-carboxylic acid. Each of them was isolated by silica gel column chromatography (from PE/EA=2/1 to PE/EA=1/2) to give 120 mg of cis-6,7-dimethoxy-2-(4-methoxy-cyclohexyl)-4-[4-(2-methoxy-phenyl)-piperazin-1-yl]-quinazoline (150) as yellow solid and 80 mg of trans-6,7-dimethoxy-2-(4-methoxy-cyclohexyl)-4-[4-(2-methoxy-phenyl)-piperazin-1-yl]-quinazoline (151) yellow solid from 296 mg of 6,7-dimethoxy-2-(4-methoxycyclohexyl)quinazolin-4(3H)-one.

cis-6,7-dimethoxy-2-(4-methoxy-cyclohexyl)-4-[4-(2-methoxy-phenyl)-piperazin-1-yl]-quinazoline (150): $^1$HNMR (400 MHz, CDCl$_3$): δ=7.23 (s, 1H), 7.14 (s, 1H), 7.07-6.90 (m, 4H), 4.01 (s, 3H), 3.98 (s, 3H), 3.90 (s, 3H), 3.89-3.86 (m, 4H), 3.51 (m, 1H), 3.41 (s, 3H), 3.36-3.26 (m, 4H), 2.90-2.85 (m, 1H), 2.17-2.01 (m, 4H), 1.83-1.65 (m, 2H), 1.64-1.57 (m, 2H). MS: m/z 493.3 (M+H$^+$).

trans-6,7-dimethoxy-2-(4-methoxy-cyclohexyl)-4-[4-(2-methoxy-phenyl)-piperazin-1-yl]-quinazoline (151): $^1$HNMR (300 MHz, CDCl$_3$): δ=7.24 (s, 1H), 7.17 (s, 1H), 7.14-6.91 (m, 4H), 4.02 (s, 3H), 3.92 (s, 3H), 3.91 (s, 3H), 3.89-3.87 (m, 4H), 3.53-3.50 (m, 1H), 3.38 (s, 3H), 3.35-3.25 (m, 4H), 3.10-3.07 (m, 1H), 2.82-2.77 (m, 1H), 2.25-2.10 (m, 4H), 1.85-1.72 (m, 2H), 1.46-1.26 (m, 2H). MS: m/z 493.3 (M+H$^+$).

Example 100: 6,7-dimethoxy-4-[4-(2-methoxy-phenyl)-piperazin-1-yl]-2-(4-methyl-pyrrolidin-3-yl)-quinazoline (152)

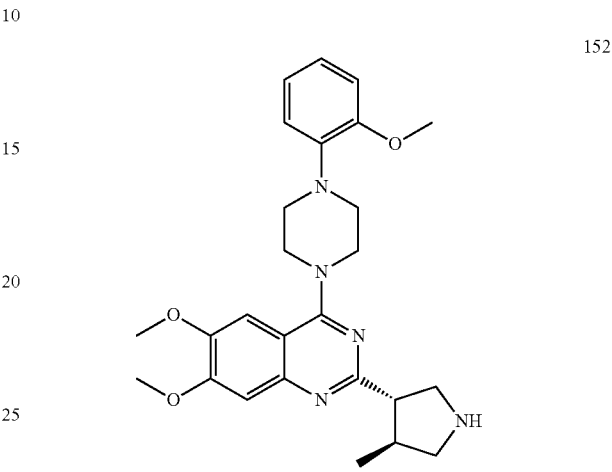

152

The title compound was prepared as similar as for compound (140) starting from material (3S,4S)-1-(tert-butoxycarbonyl)-4-methylpyrrolidine-3-carboxylic acid instead of 1-(tert-butoxycarbonyl)piperidine-4-carboxylic acid.

$^1$HNMR (400 MHz, DMSO-d$_6$): δ=9.96 (brs, 1H), 9.78 (brs, 1H), 7.56 (s, 1H), 7.10-7.05 (m, 3H), 6.97-6.93 (m, 1H), 440-4.38 (m, 4H), 3.98 (s, 6H), 3.97 (s, 3H), 3.65-3.53 (m, 2H), 3.51-3.46 (m, 2H), 3.36-3.31 (m, 4H), 2.99-2.95 (m, 1H), 2.69-2.66 (m, 1H), 1.17-1.15 (d, J=6.8 Hz, 3H). MS: m/z 464.3 (M+H$^+$).

Example 101: 2-(1,4-dimethyl-pyrrolidin-3-yl)-6,7-dimethoxy-4-[4-(2-methoxy-phenyl)-piperazin-1-yl]-quinazoline (153)

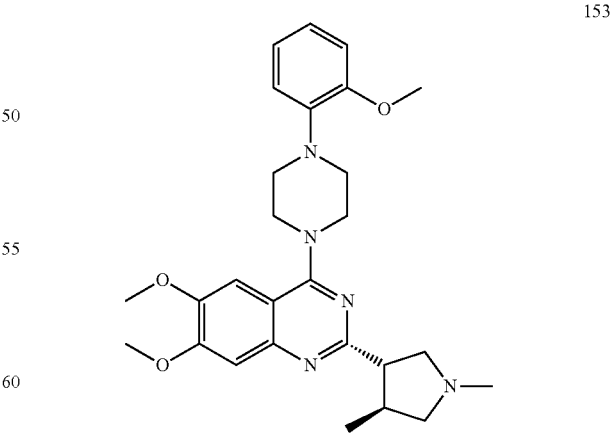

153

The title compound was prepared as similar as for compound (141), starting from material (3S,4S)-1-(tert-butoxycarbonyl)-4-methylpyrrolidine-3-carboxylic acid instead of 1-(tert-butoxycarbonyl)piperidine-4-carboxylic acid.

¹HNMR (400 MHz, CDCl₃): δ=7.23 (s, 1H), 7.21 (s, 1H), 7.07-6.91 (m, 4H), 4.04 (s, 3H), 4.02 (s, 3H), 3.99 (s, 3H), 3.91-3.86 (m, 4H), 3.29-3.25 (m, 7H), 3.02-3.01 (m, 1H), 2.79-2.75 (m, 1H), 2.62-2.54 (m, 1H), 2.52 (s, 3H), 1.25-1.23 (d, J=6.8 Hz, 3H). MS: m/z 478.3 (M+H⁺).

Example 102: 6,7-dimethoxy-4-[4-(2-methoxy-phenyl)-piperazin-1-yl]-2-pyrrolidin-3-yl-quinazoline (154)

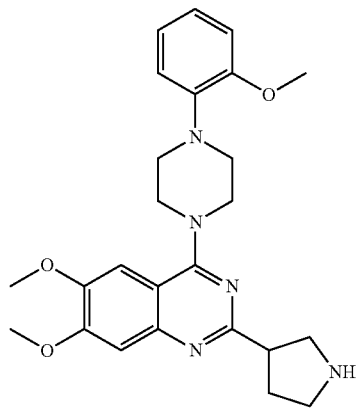

154

The title compound was prepared as similar as for compound (140), starting from material 1-(tert-butoxycarbonyl)pyrrolidine-3-carboxylic acid instead of 1-(tert-butoxycarbonyl)piperidine-4-carboxylic acid.

¹HNMR (400 MHz, CDCl₃): δ=7.23 (s, 1H), 7.13 (s, 1H), 7.10-7.05 (m, 4H), 7.06-6.91 (m, 4H), 4.02 (s, 3H), 4.00 (s, 3H), 3.99 (s, 3H), 3.91-3.90 (m, 4H), 3.58-3.54 (m, 1H), 3.44-3.40 (m, 1H), 3.30-3.26 (m, 6H), 3.14-3.10 (m, 1H), 2.33-2.29 (m, 1H), 2.19-2.16 (m, 1H). MS: m/z 450.3 (M+H⁺).

Example 103: 6,7-dimethoxy-4-[4-(2-methoxy-phenyl)-piperazin-1-yl]-2-(1-methyl-pyrrolidin-3-yl)-quinazoline (155)

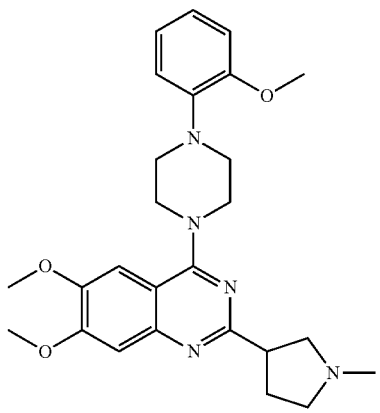

155

The title compound was prepared as similar as for compound (141) starting from material 1-(tert-butoxycarbonyl)pyrrolidine-3-carboxylic acid instead of 1-(tert-butoxycarbonyl)piperidine-4-carboxylic acid.

¹HNMR (400 MHz, CDCl₃): δ=7.22 (s, 1H), 7.14 (s, 1H), 7.07-6.91 (m, 4H), 4.05 (s, 3H), 4.04 (s, 3H), 4.01 (s, 3H), 3.89-3.86 (m, 4H), 3.72-3.68 (m, 1H), 3.29-3.24 (m, 4H), 2.95-2.93 (m, 1H), 2.86-2.84 (m, 1H), 2.67-2.64 (m, 1H), 2.48 (s, 3H), 2.37-2.33 (m, 2H), 1.75-1.63 (m, 2H). MS: m/z 464.3 (M+H⁺).

Scheme 13:

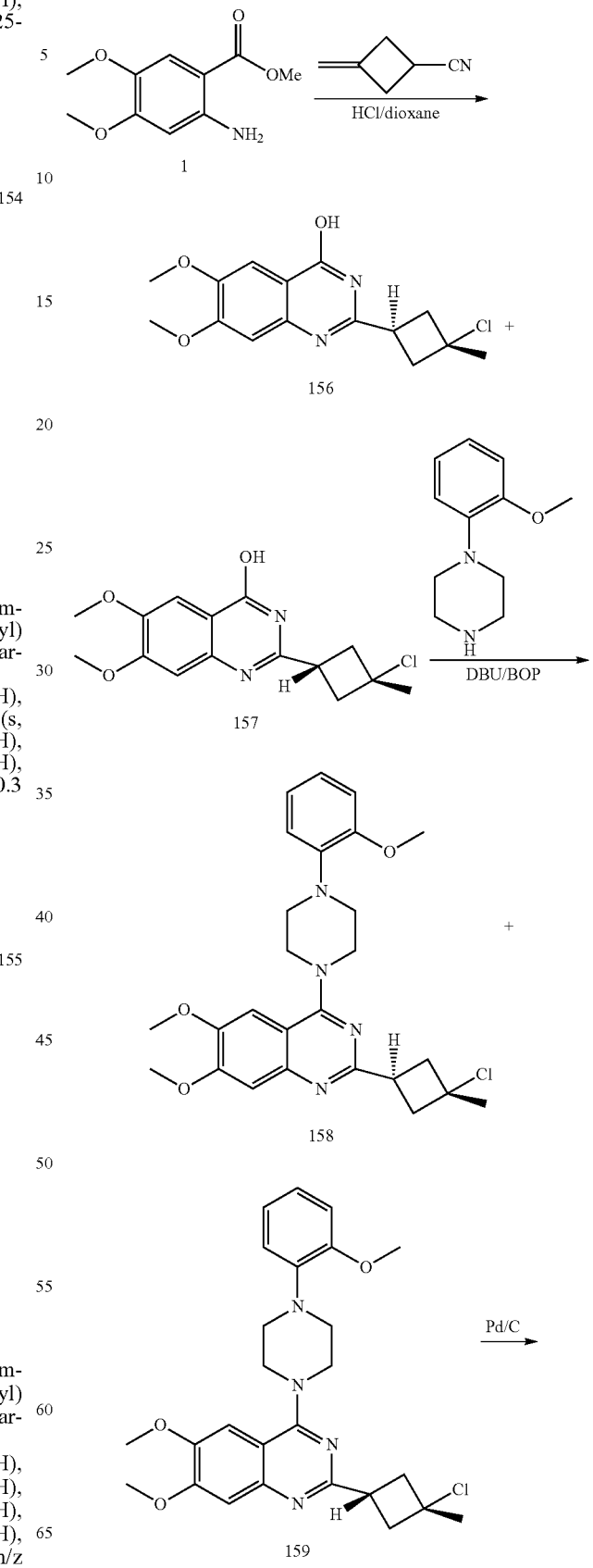

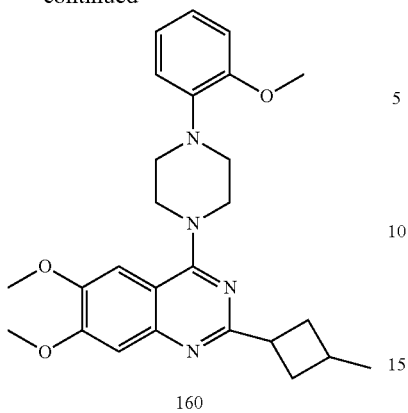

160

Example 104 and 105 2-((1R,3R)-3-chloro-3-methylcyclobutyl)-6,7-dimethoxy-4-(4-(2-methoxyphenyl)piperazin-1-yl)quinazoline (158), and 2-((1S,3S)-3-chloro-3-methylcyclobutyl)-6,7-dimethoxy-4-(4-(2-methoxyphenyl)piperazin-1-yl)quinazoline (159)

To a solution of 2-amino-4,5-dimethoxy-benzoic acid methyl ester 1 (422 mg, 2 mmol) and 3-methylene-cyclobutanecarbonitrile (558 mg, 6 mmol) in 1,4-dioxane (3 mL) was added 4N HCl in 1,4-dioxane (8 mL). The mixture was stirred at 100° C. overnight. The resulting mixture was cooled to room temperature and poured into chilly NaHCO₃ solution (20 mL) to give a precipitate. The solid was collected by filtration, washed with water (30 mL) and dried to give a mixture of compound (156) and (157) (440 mg, yield: 72%). MS: m/z 307.1 (M–H⁺).

To a solution of the above mixture of compound (156) and (157) (440 mg, 1.43 mmol) in MeCN (25 mL) were added 1-(2-methoxy-phenyl)-piperazine (441 mg, 2.30 mmol), DBU (650 mg, 4.28 mmol) and BOP (821 mg, 1.86 mmol). The mixture was stirred at 50° C. overnight. The solvent was removed and the residue was dissolved in EtOAc (20 mL). The mixture was washed with water (30 mL) and dried over anhydrous Na₂SO₄. The solution was concentrated to dryness and the residue was purified by silica gel column chromatography (from EtOAc/PE=1/4 to EtOAc/PE=1/2) to give compound (158), (303 mg, yield: 44%) as yellow solid and compound (159), (172 mg, yield: 25%) as yellow solid.

2-((1R,3R)-3-chloro-3-methylcyclobutyl)-6,7-dimethoxy-4-(4-(2-methoxyphenyl)piperazin-1-yl)quinazoline (158): ¹HNMR (400 MHz, CDCl₃): δ=7.22 (s, 1H), 7.14 (s, 1H), 7.06-6.91 (m, 4H), 4.06-4.39 (m, 7H), 3.92-3.89 (m, 7H), 3.30 (m, 4H), 2.93-2.86 (m, 4H), 1.80 (s, 3H). MS: m/z 483.3 (M+H⁺).

2-((1S,3S)-3-chloro-3-methylcyclobutyl)-6,7-dimethoxy-4-(4-(2-methoxyphenyl)piperazin-1-yl)quinazoline (159): ¹HNMR (400 MHz, CDCl₃): δ=7.22 (s, 1H), 7.15 (s, 1H), 7.05-6.91 (m, 4H), 4.01 (s, 3H), 3.99 (s, 3H), 3.94-3.92 (m, 7H), 3.54-3.50 (m, 1H), 3.30-3.28 (m, 4H), 3.16-3.11 (m, 2H), 2.75-2.70 (m, 2H), 1.88 (s, 3H). MS: m/z 483.3 (M+H⁺).

Example 106: 6,7-dimethoxy-4-[4-(2-methoxy-phenyl)-piperazin-1-yl]-2-(3-methyl-cyclobutyl)-quinazoline (160)

To a mixture of pyridine (231 mg, 2.93 mmol), EtOAc (6.4 mL), water (3 mL) and 2-(3-chloro-3-methyl-cyclobutyl)-6,7-dimethoxy-4-[4-(2-methoxy-phenyl)-piperazin-1-yl]-quinazoline (131 mg, 0.27 mmol) was added wet 10% Pd/C (100 mg). The mixture was purged with N₂ for three times and then it was hydrogenated under 40 psi of H₂ for 48 h. The mixture was filtered. The filtrate was purified by prep-HPLC to give compound (160), (18 mg, yield: 15%) as white solid.

¹HNMR (400 MHz, CDCl₃): δ=7.24 (s, 1H), 7.14 (s, 1H), 7.08-6.91 (m, 4H), 4.01 (s, 3H), 3.98 (s, 3H), 3.97-3.92 (m, 7H), 3.56-3.51 (m, 1H), 3.30 (brs, 4H), 2.52-239 (m, 3H), 2.13-2.08 (m, 2H), 1.14-1.13 (d, J=6.0 Hz, 3H). MS: m/z 449.3 (M+H⁺).

Example 107: 2-cyclohexyl-6,7-dimethoxy-4-[4-(2-methoxy-phenyl)-piperazin-1-yl]-quinazoline (161)

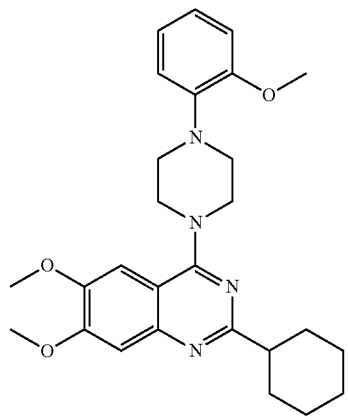

161

The title compound was prepared as similar as for compound (144), starting from material cyclohexanecarboxylic acid instead of 4-methyl-cyclohexanecarboxylic acid.

¹HNMR (400 MHz, CDCl₃): δ=7.23 (s, 1H), 7.14 (s, 1H), 7.06-6.90 (m, 4H), 4.01 (s, 3H), 3.98 (s, 3H), 3.89 (s, 3H), 3.91-3.87 (m, 4H), 3.28 (t, J=9.2 Hz, 4H), 2.83-2.77 (m, 1H), 2.02 (d, J=12.0 Hz, 2H), 1.87 (d, J=12.8 Hz, 2H), 1.77-1.69 (m, 3H), 1.37-1.24 (m, 3H). MS: m/z 463.3 (M+H⁺).

Example 108: 2-tert-Butyl-6,7-dimethoxy-4-[4-(2-methoxy-phenyl)-piperazin-1-yl]-quinazoline (162)

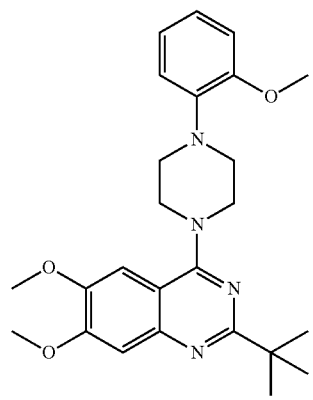

162

The title compound was prepared as similar as for compound (144), starting from material 2,2-dimethyl-propionic acid instead of 4-methyl-cyclohexanecarboxylic acid.

¹H NMR (400 MHz, DMSO-d₆): δ=7.16 (d, J=6.8 Hz, 1H) 6.98 (d, J=13.2 Hz, 3H), 6.92-6.87 (m, 1H), 3.93 (s, 1H), 3.90 (s, 3H), 3.82 (s, 3H), 3.82 (s, 4H), 3.82 (s, 3H), 1.38 (s, 6H). MS: m/z 437.2 (M+H⁺).

Example 109: 2-tert-Butyl-6,7-dimethoxy-4-[4-(2-methoxy-phenyl)-piperidin-1-yl]-quinazoline (163)

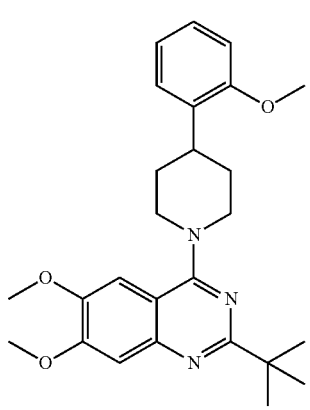

163

The title compound was prepared as similar as for compound (144), starting from material 2,2-dimethyl-propionic acid instead of 4-methyl-cyclohexanecarboxylic acid.

¹H NMR (400 MHz, DMSO-d₆): δ=7.24-7.18 (m, 2H), 7.14 (d, J=8.8 Hz, 2H), 6.98 (d, J=8.4 Hz, 1H), 6.92 (t, J=14.4 Hz, 1H), 4.29 (d, J=12.8 Hz, 2H), 3.93 (s, 3H), 3.89 (s, 3H), 3.81 (s, 3H), 3.24-3.12 (m, 3H), 1.87 (s, 4H), 1.38 (s, 9H). MS: m/z 436.2 (M+H⁺).

Example 110: 6,7-dimethoxy-4-[4-(2-methoxy-phenyl)-piperazin-1-yl]-2-(1-methyl-cyclopropyl)-quinazoline (164)

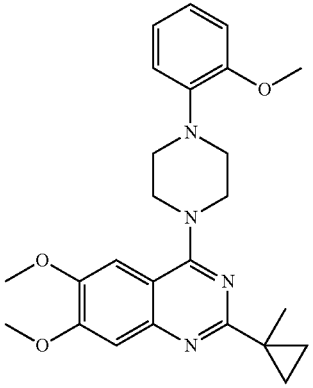

164

The title compound was prepared as similar as for compound (144), starting from material 1-methyl-cyclopropanecarboxylic acid instead of 4-methyl-cyclohexanecarboxylic acid.

¹H NMR (400 MHz, DMSO-d₆): δ=7.13 (s, 1H), 6.98-6.95 (m, 3H), 6.92-6.88 (m, 1H), 3.92 (s, 3H), 3.89 (s, 3H), 3.81 (s, 3H), 3.70 (s, 4H), 3.17 (s, 4H), 1.53 (s, 3H), 1.32-1.30 (m, 2H), 0.81-0.79 (m, 2H). MS: m/z 435.2 (M+H⁺).

Example 111: 6,7-dimethoxy-4-[4-(2-methoxy-phenyl)-piperidin-1-yl]-2-(1-methyl-cyclopropyl)-quinazoline (165)

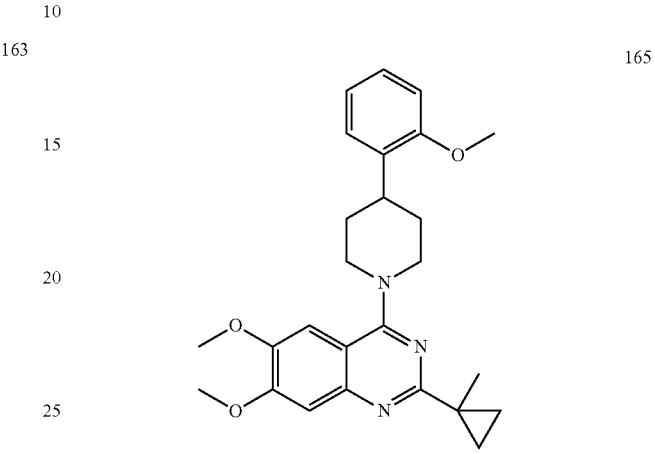

165

The title compound was prepared as similar as for compound (144), starting from material 1-methyl-cyclopropanecarboxylic acid instead of 4-methyl-cyclohexanecarboxylic acid.

¹H NMR (400 MHz, CDCl₃): δ=7.25-7.19 (m, 3H), 7.11 (s, 1H), 6.96 (t, J=15.2 Hz, 1H), 6.92 (d, J=8.4 Hz, 1H) 4.27 (d, J=13.2 Hz, 2H), 4.02 (s, 3H), 3.96 (s, 3H), 3.86 (s, 3H), 3.28-3.25 (m, 1H), 3.15 (t, J=14.0 Hz, 2H), 1.97-1.89 (m, 4H), 1.61 (s, 3H) 1.44-1.40 (m, 2H), 0.82-0.79 (m, 2H). MS: m/z 434.2 (M+H⁺).

Scheme 14:

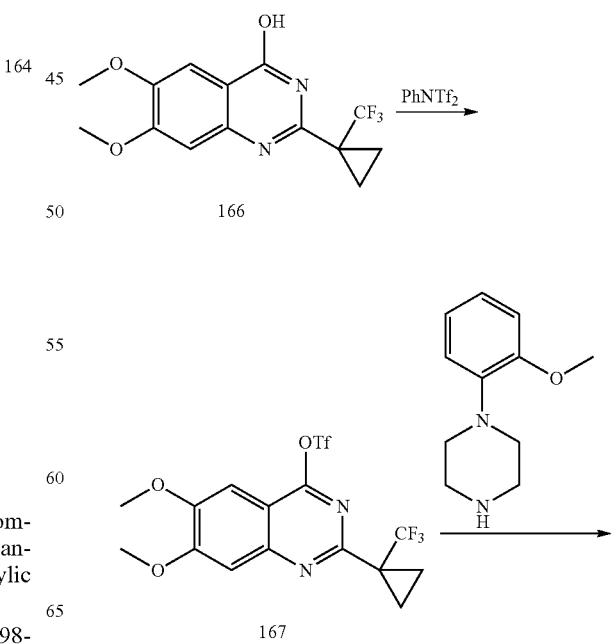

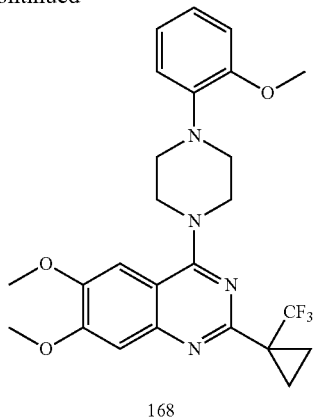

168

Example 112: 6,7-dimethoxy-4-[4-(2-methoxy-phenyl)-piperazin-1-yl]-2-(1-trifluoromethyl-cyclopropyl)-quinazoline (168)

A solution of compound 166 (prepared similar to compound (138), 150 mg, 0.48 mmol), PhNTf$_2$ (171 mg, 0.48 mmol) DBU (73 mg, 0.48 mmol) and DMAP (6 mg, 0.048 mmol) in DCM (5 mL) was stirred at room temperature for 2 hours. The mixture was concentrated to dryness under reduced pressure. The residue was diluted with water (20 mL) and extracted with EtOAc (50 mL×3). The extracts were washed with brine (20 mL) and dried over Na$_2$SO$_4$. The solution was concentrated under reduced pressure to give crude compound (167) as white solid.

To a solution of compound (131) (80 mg, 0.17 mmol) in DMF (5 mL) was added excessive 1-(2-methoxyphenyl)piperazine (665 mg, 3.46 mmol) and the mixture was stirred at 70° C. for 3 hours. The mixture was concentrated under reduced pressure. The residue was diluted with water (20 mL) and the mixture was extracted with EtOAc (50 mL×3). The extracts were washed with brine (20 mL) and dried over Na$_2$SO$_4$. The solution was concentrated under reduced pressure and the residue was purified by prep-HPLC to give compound (168), (20 mg, 16%) as yellow oil.

$^1$H NMR (300 MHz, DMSO-d$_6$): δ=7.15 (s, 1H), 7.13 (s, 1H), 6.98-6.90 (m, 4H), 3.94 (s, 3H), 3.92 (s, 3H), 3.81 (s, 3H), 3.80-3.78 (m, 4H), 3.18-3.14 (s, 4H), 1.61-1.57 (m, 2H), 1.45-1.41 (m, 2H). MS: m/z 489.2 (M+H$^+$).

Example 113: 6,7-dimethoxy-4-[4-(2-methoxy-phenyl)-piperidin-1-yl]-2-(1-trifluoromethyl-cyclopropyl)-quinazoline (169)

169

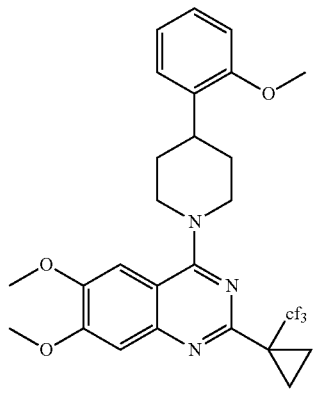

The title compound was prepared as described for compound (168), except that 1-(2-methoxy-phenyl)-piperazine was substituted for 4-(2-methoxy-phenyl)-piperidine.

$^1$H NMR (400 MHz, CDCl$_3$): δ=7.21 (t, J=15.6 Hz, 3H), 7.11 (s, 1H), 6.98-6.94 (m, 1H), 6.89 (d, J=8.0 Hz, 1H), 4.33 (d, J=13.6 Hz, 2H), 4.02 (s, 3H), 3.96 (s, 3H), 3.86 (s, 3H), 3.32-3.16 (m, 3H), 1.98-1.89 (m, 4H), 1.62-1.58 (m, 2H), 1.46-1.43 (m, 2H). MS: m/z 488.1 (M+H$^+$).

Scheme 15:

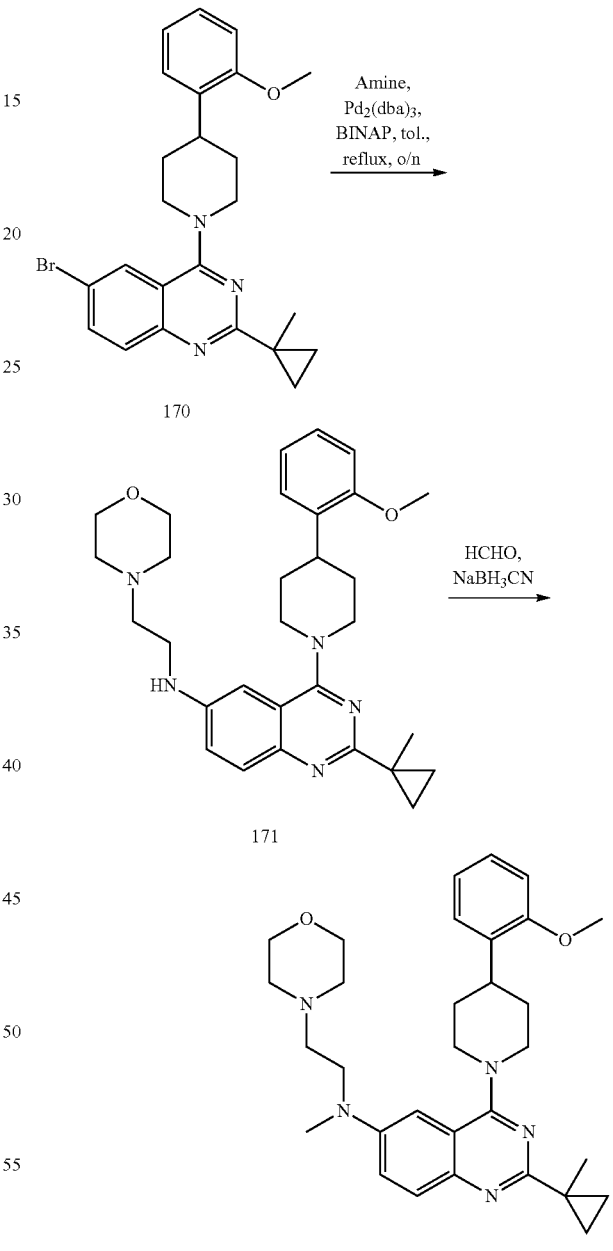

Example 114: [4-[4-(2-Methoxy-phenyl)-piperidin-1-yl]-2-(1-methyl-cyclopropyl)-quinazolin-6-yl]-methyl-(2-morpholin-4-yl-ethyl)-amine (172)

To a solution of compound 170 (prepared similar to compound (144), 200 mg, 0.44 mmol), t-BuONa (85 mg, 0.88 mmol) and BINAP (30 mg, 0.044 mmol) and 2-morpholin-4-yl-ethylamine (86 mg, 0.66 mmol) in anhydrous toluene (10 mL) was added Pd$_2$(dba)$_3$ (20 mg, 0.0221 mmol). The mixture was degassed with N$_2$ for 3 times and stirred at 110° C. under N$_2$ overnight. After cooled to room temperature, the mixture was concentrated to dryness under reduced pressure. The residue was diluted with water (5 mL). The aqueous phase was extracted with DCM (20 mL×3). The extracts were washed with brine (10 mL×2) and dried over Na$_2$SO$_4$. The solution was concentrated under reduced pressure and the crude product was purified by prep-TLC (DCM/MeOH=10/1) to give compound (171) (40 mg, 18%) as yellow oil. MS: m/z 502.0 (M+H$^+$).

To a solution of compound (171) (30 mg, 0.060 mmol) in MeOH (10 mL) was added 30% aq. HCHO (2 mL) and the mixture was stirred at room temperature for 2 h. NaCNBH$_3$ was added and the mixture was stirred at room temperature overnight. The mixture was concentrated to dryness under reduced pressure. The residue was diluted with water (5 mL) and the aqueous phase was extracted with DCM (20 mL×3). The extracts were washed with brine (20 mL×2) and dried over Na$_2$SO$_4$. The solution was concentrated under reduced pressure and the crude product was purified by prep-HPLC to give compound (172), (10 mg, 33%) as yellow solid.

$^1$H NMR (300 MHz, CDCl$_3$): δ=7.75 (d, J=9.0 Hz, 1H), 7.33-7.21 (m, 3H), 7.00 (t, J=7.2 Hz, 1H), 6.96-6.87 (m, 2H), 4.33 (d, J=13.8 Hz, 2H), 3.87 (s, 3H), 3.72-3.69 (m, 4H), 3.60-3.55 (m, 2H), 3.13-3.08 (m, 3H), 3.05 (s, 3H), 2.60-2.50 (m, 6H), 1.97-1.89 (m, 4H), 1.65 (s, 3H) 1.42 (s, 2H), 0.82-0.79 (m, 2H). MS: m/z 516.0 (M+H$^+$).

Scheme 16:

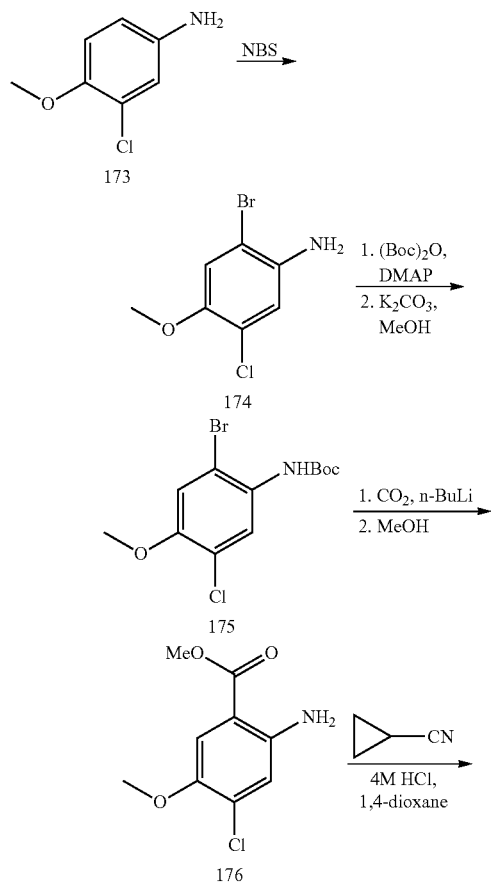

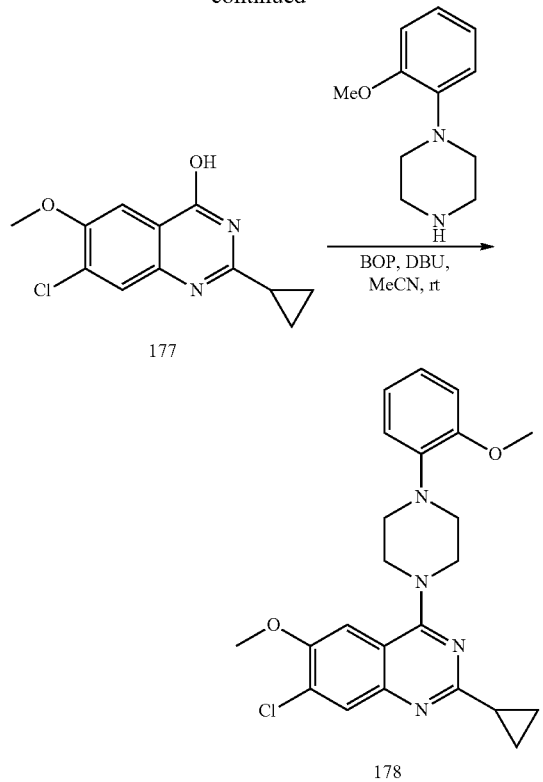

Example 115: 7-chloro-2-cyclopropyl-6-methoxy-4-[4-(2-methoxy-phenyl)-piperazin-1-yl]-quinazoline (178)

To a solution of 3-chloro-4-methoxy-phenylamine (173) (3.15 g, 20 mmol) in THF (30 mL) was added NBS (3.56 g, 20 mmol). The mixture was stirred at room temperature for 4 h. The reaction solution was diluted with EtOAc (150 mL) and the mixture was washed with aq. Na$_2$S$_2$O$_3$ solution (100 aq. NaHCO$_3$ solution (100 mL) and brine (100 mL). The organic layer was separated and dried over anhydrous Na$_2$SO$_4$. The solvent was removed in vacuum and the residue was purified by silica gel column chromatography (EtOAc/PE=1/20) to give compound (174) (2.75 g, yield: 58%) as white solid. $^1$HNMR (400 MHz, CDCl$_3$): δ=7.01 (s, 1H), 6.84 (s, 1H), 3.82 (brs, 5H).

To a solution of 2-bromo-5-chloro-4-methoxy-phenylamine (174) (2.75 g, 11.63 mmol) in THF (50 mL) were added DMAP (0.14 g, 1.16 mmol) and (Boc)$_2$O (7.53 g, 34.89 mmol). The mixture was stirred at reflux for 4 h. After cooled to room temperature, the reaction solution was diluted with EtOAc (100 mL). The mixture was washed with 0.5 N HCl (30 mL), brine (150 mL). The organic layer was separated and dried over anhydrous Na$_2$SO$_4$. The solvent was removed to give di-Boc protected product. The residue was dissolved in MeOH (100 mL). K$_2$CO$_3$ (4.8 g, 34.89 mmol) was added and the mixture was stirred at reflux for 4 h. The solvent was removed and the residue was dissolved in EtOAc (100 mL). The solution was washed with 0.5 N HCl (30 mL), brine (150 mL) and dried over anhydrous Na$_2$SO$_4$. The solvent was removed in vacuum and the residue was purified by silica gel column chromatography (EtOAc/PE=1/40) to give compound (175) (2.74 g, yield: 70%) as white solid.

¹HNMR (400 MHz, CDCl₃): δ=8.20 (brs, 1H), 7.06 (s, 1H), 6.74 (s, 1H), 3.86 (s, 3H), 1.53 (s, 9H).

To a solution of compound (175) (1.77 g, 5.15 mmol) in THF (50 mL) under N₂ was added n-BuLi (2.5 M, 4.12 mL) dropwise at −78° C. and the mixture was stirred for 1 h. CO₂ was bubbled into the reaction solution for 0.5 h. The mixture was allowed to warm to room temperature and stirred overnight. The reaction was quenched with water (20 mL) and the mixture was extracted with Et₂O (20 mL). The aqueous layer was acidified with 37% HCl to pH=4 and extracted with EtOAc (20 mL×2). The extracts were dried over Na₂SO₄. The solvent was removed in vacuum to give 2-tert-butoxycarbonylamino-4-chloro-5-methoxy-benzoic acid (0.99 g, yield: 64%) as yellow solid. MS: m/z 300.0 (M−H⁺).

The above acid was dissolved in MeOH (30 mL) and SOCl₂ (1.95 g, 16.41 mmol) was added. The mixture was stirred at reflux overnight. The solvent was removed and the residue was dissolved in EtOAc (20 mL). The mixture was washed with Na₂CO₃ solution to pH=8. The organic layer was separated and washed with brine (30 mL). The organic layer was dried over anhydrous Na₂SO₄. The solvent was removed to give compound (176) (0.8 g, yield: 77%) as white solid. ¹HNMR (400 MHz, CDCl₃): δ=7.38 (brs, 1H), 6.76 (s, 1H), 5.42 (brs, 2H), 3.88 (s, 3H), 3.84 (s, 3H).

To the mixture of compound (176) (290 mg, 1.17 mmol) in 1,4-dioxane (5 mL) was added cyclopropanecarbonitrile (390 mg, 5.84 mmol) and HCl in 1,4-dioxane (4 M, 15 mL). The mixture was stirred at 100° C. for 12 h. The mixture was cooled to room temperature and filtered. The solid was dried to give crude compound (177) (224 mg, yield: 77%) as white solid, which was used for next step without further purification. MS: m/z 251.0 (M+H⁺).

To a mixture of 1-(2-methoxyphenyl)piperazine (516 mg, 2.69 mmol), DBU (272 mg, 1.79 mmol), BOP (515 mg, 1.17 mmol) was added compound (177) (224 mg, 0.90 mmol), and the mixture was stirred at room temperature overnight. The solution was concentrated to dryness in vacuum and the residue was dissolved in EtOAc (15 mL). The mixture was washed with brine (15 mL×2) and dried over Na₂SO₄. The crude product was purified by prep-TLC (PE/EtOAc=5/1) to give compound (178), (59.4 mg, yield: 36%) as yellow solid.

¹HNMR (400 MHz, CDCl₃): δ=7.92 (s, 1H), 7.17 (s, 1H), 7.06-6.90 (m, 4H), 4.01 (s, 3H), 3.96 (s, 3H), 3.91-3.84 (m, 4H), 3.26-3.24 (m, 4H), 2.22 (m, 1H), 1.25-1.15 (m, 2H), 1.04-1.02 (m, 2H). MS: m/z 425.2 (M+H⁺).

Example 116: 2-cyclopropyl-4-[4-(2-methoxy-phenyl)-piperazin-1-yl]-pyrido[2,3-d]pyrimidine (179)

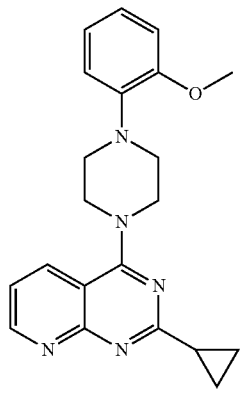

179

The title compound was prepared as described for compound (178), using the similar route and procedure.

¹H NMR (400 MHz, CDCl₃): δ=8.95 (dd, J=4.4, 2.0 Hz, 1H), 8.20 (dd, J=8.0, 1.6 Hz, 1H), 7.25-7.23 (m, 1H), 7.06-7.03 (m, 1H), 6.97-6.90 (m, 3H), 4.00-3.96 (m, 4H), 3.90 (s, 3H), 3.25-3.22 (m, 4H), 2.31-2.26 (m, 1H), 1.28-1.24 (m, 2H), 1.06-1.02 (m, 2H). MS: m/z 326.2 (M+H⁺).

Example 117: 2-cyclopropyl-6,8-dimethoxy-4-[4-(2-methoxy-phenyl)-piperazin-1-yl]-quinazoline (180)

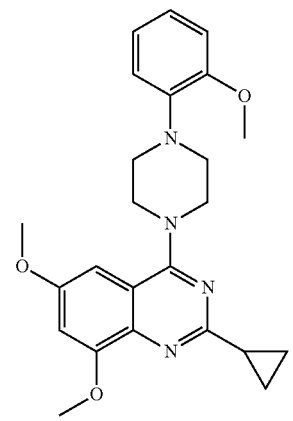

180

The title compound was prepared as described for compound (178), using the similar route and procedure.

¹H NMR (400 MHz, DMSO-d₆): δ=6.96-6.86 (m, 5H), 6.72 (s, 1H), 3.89 (s, 3H), 3.87 (s, 3H), 3.81 (s, 3H), 2.13-2.09 (m, 1H), 1.02-0.92 (m, 4H). LC-MS: 421.2 (M+1).

Example 118: 2-cyclopropyl-6-methoxy-4-[4-(2-methoxy-phenyl)-piperazin-1-yl]-7-methyl-quinazoline (181)

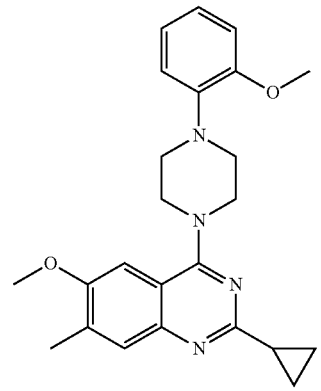

181

The title compound was prepared as described for compound (178), using the similar route and procedure.

¹HNMR (400 MHz, CDCl₃): δ=7.60 (s, 1H), 7.04 (s, 1H), 7.03-6.90 (m, 4H), 3.91 (s, 6H), 3.86-3.82 (m, 4H), 3.26-3.24 (m, 4H), 2.37 (s, 3H), 2.22-2.19 (m, 1H), 1.16-1.15 (m, 2H), 0.99-0.96 (m, 2H). MS: m/z 405.3 (M+H⁺).

Example 119: 2-cyclopropyl-7-fluoro-6-methoxy-4-[4-(2-methoxy-phenyl)-piperazin-1-yl]-quinazoline (182)

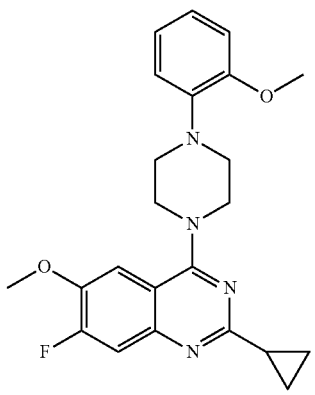

The title compound was prepared as described for compound (178), using the similar route and procedure.

¹HNMR (400 MHz, CDCl₃): δ=7.48 (d, J=12 Hz, 1H), 7.22 (d, J=8.8 Hz, 1H), 7.05-6.90 (m, 4H), 3.97 (s, 3H), 3.91 (s, 3H), 3.83-3.82 (m, 4H), 3.26-3.24 (m, 4H), 2.19-2.17 (m, 1H), 1.18-1.14 (m, 2H), 1.02-0.99 (m, 2H). MS: m/z 409.3 (M+H⁺).

Example 120: 6-bromo-2-cyclopropyl-4-[4-(2-methoxy-phenyl)-piperazin-1-yl]-quinazoline (183)

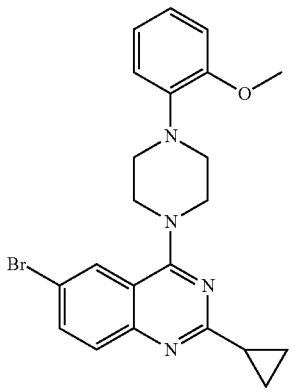

The title compound was prepared as described for compound (178), using the similar route and procedure.

¹H NMR (400 MHz, CDCl₃): δ=7.99 (s, 1H), 7.75-7.72 (m, 1H), 7.67 (d, J=8.8 Hz, 1H), 7.10-6.82 (m, 4H), 4.02-3.83 (m, 7H), 3.28-3.16 (m, 4H), 2.25-2.14 (m, 1H), 1.22-1.14 (m, 2H), 1.12-0.96 (m, 2H). MS: m/z 441.1 (M+H⁺).

Scheme 17:

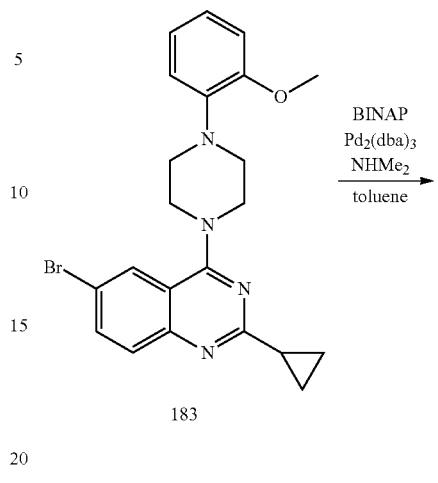

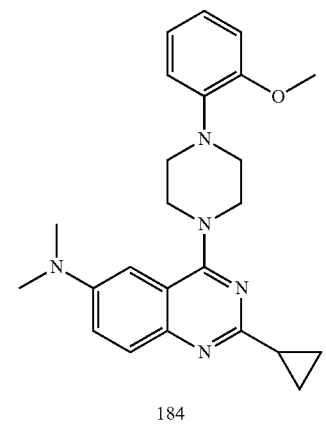 [SMILES: COc1cc2nc(C3CC3)nc(N3CC=C(c4ccccc4OC)CC3)c2cc1OC]

Example 121: {2-cyclopropyl-4-[4-(2-methoxy-phenyl)-piperazin-1-yl]-quinazolin-6-yl}-dimethyl-amine (184)

To a mixture of (183) (100 mg, 0.23 mmol), t-BuONa (67 mg, 0.7 mmol) and BINAP (7 mg, 0.01 mmol) in anhydrous toluene (10 mL) was added a solution of Me₂NH in THF (0.1 mL, 2M) and Pd₂(dba)₃ (7 mg, 0.01 mmol). The mixture was stirred at 116° C. under N₂ for 16 h. After cooled to room temperature, the mixture was filtered. The filtrate was evaporated in vacuum to residue, which was purified by prep-TLC (DCM/MeOH=20/1) and then prep-HPLC to afford compound (184), (9 mg, yield: 10%) as yellow solid.

¹H NMR (400 MHz, CDCl₃): δ=7.76 (d, J=8.8 Hz, 1H), 7.36-7.33 (m, 1H), 7.10-6.80 (m, 4H), 3.90 (s, 3H), 3.92-3.76 (m, 4H), 3.29-3.20 (m, 4H), 3.04 (s, 6H), 2.24-2.16 (m, 1H), 1.19-1.12 (m, 2H), 1.01-0.91 (m, 2H). MS: m/z 404.3 (M+H⁺).

Example 122: 6-bromo-2-cyclopropyl-7-fluoro-4-[4-(2-methoxy-phenyl)-piperazin-1-yl]-quinazoline (185)

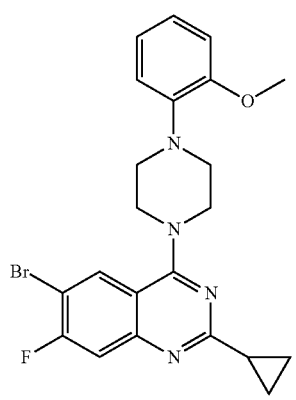

The title compound was prepared as described for compound (178), using the similar route and procedure.

¹HNMR (400 MHz, CDCl₃): δ=8.07 (d, J=7.2 Hz, 1H), 7.48 (d, J=9.6 Hz, 1H), 7.08-6.90 (m, 4H), 3.93-3.90 (m, 7H), 3.24-3.22 (m, 4H), 2.19-2.16 (m, 1H), 1.20-1.16 (m, 2H), 1.05-1.00 (m, 2H). MS: m/z 457.2 (M+H⁺).

Example 123: {2-cyclopropyl-7-fluoro-4-[4-(2-methoxy-phenyl)-piperazin-1-yl]-quinazolin-6-yl}-dimethyl-amine (186)

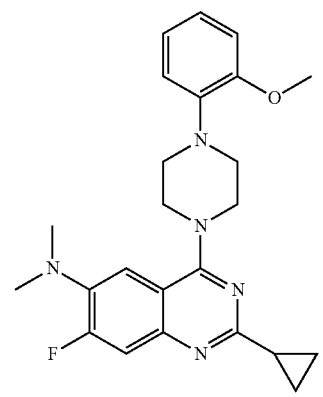

The title compound was prepared as described for compound (184), using the similar route and procedure.

¹HNMR (300 MHz, CDCl₃): δ=7.46 (d, J=13.8 Hz, 1H), 7.17 (d, J=9.3 Hz, 1H), 7.09-6.91 (m, 4H), 3.92 (s, 3H), 3.86-3.81 (m, 4H), 3.27-3.23 (m, 4H), 2.93 (s, 6H), 2.22-2.17 (m, 1H), 1.28-1.25 (m, 2H), 1.03-1.00 (m, 2H). MS: m/z 422.3 (M+H⁺).

Example 124: {2-cyclopropyl-7-fluoro-4-[4-(2-methoxy-phenyl)-piperazin-1-yl]-quinazolin-6-yl}-diethyl-amine (187)

The title compound was prepared as described for compound (184), using the similar route and procedure.

¹HNMR (300 MHz, CDCl₃): δ=7.41 (d, J=14.0 Hz, 1H), 7.19 (d, J=9.2 Hz, 1H), 7.07-6.90 (m, 4H), 3.91 (s, 3H), 3.82-3.80 (m, 4H), 3.31-3.23 (m, 8H), 2.17-2.16 (m, 1H), 1.17-1.12 (m, 8H), 1.00-0.99 (m, 2H). MS: m/z 450.3 (M+H⁺).

Example 125: 6-bromo-7-chloro-2-cyclopropyl-4-[4-(2-methoxy-phenyl)-piperazin-1-yl]-quinazoline (188)

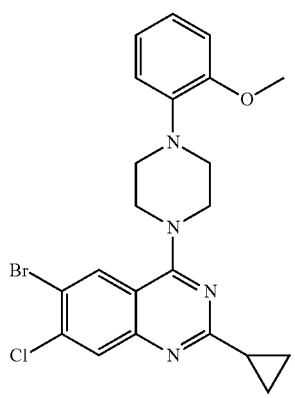

The title compound was prepared as described for compound (178), using the similar route and procedure.

¹HNMR (400 MHz, DMSO-d₆): δ=8.26 (s, 1H), 7.92 (s, 1H), 7.00-6.89 (m, 4H), 3.90-3.87 (m, 4H), 3.81 (s, 3H), 3.13-3.12 (m, 4H), 2.11-2.08 (m, 1H), 1.08-1.05 (m, 2H), 1.02-0.98 (m, 2H). MS: m/z 473.1 (M+H⁺).

Example 126: {7-chloro-2-cyclopropyl-4-[4-(2-methoxy-phenyl)-piperazin-1-yl]-quinazolin-6-yl}-dimethyl-amine (189)

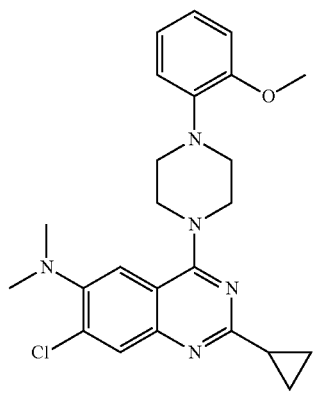

189

The title compound was prepared as described for compound (184), using the similar route and procedure.

¹HNMR (300 MHz, CDCl₃): δ=7.87 (s, 1H), 7.37 (s, 1H), 7.09-6.91 (m, 4H), 3.92 (s, 3H), 3.89-3.86 (m, 4H), 3.28-3.25 (m, 4H), 2.88 (s, 6H), 2.20-2.17 (m, 1H), 1.20-1.15 (m, 2H), 1.04-0.98 (m, 2H). MS: m/z 438.3 (M+H⁺).

Example 127: {7-chloro-2-cyclopropyl-4-[4-(2-methoxy-phenyl)-piperazin-1-yl]-quinazolin-6-yl}-diethyl-amine (190)

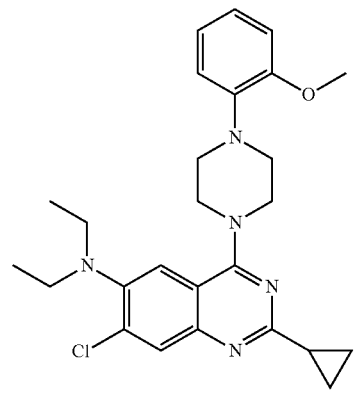

190

The title compound was prepared as described for compound (184), using the similar route and procedure.

¹HNMR (400 MHz, CDCl₃): δ=7.86 (s, 1H), 7.36 (s, 1H), 7.07-6.90 (m, 4H), 3.91 (s, 3H), 3.85-3.82 (m, 4H), 3.25-3.16 (m, 8H), 2.19-2.16 (m, 1H), 1.17-1.14 (m, 2H), 1.10-1.01 (m, 6H), 1.01-0.98 (m, 2H). MS: m/z 466.3 (M+H⁺).

Example 128: 6-bromo-2-cyclopropyl-4-[4-(2-methoxy-phenyl)-piperazin-1-yl]-7-methyl-quinazoline (191)

191

The title compound was prepared as described for compound (178), using the similar route and procedure.

¹HNMR (400 MHz, CDCl₃): δ=8.04 (s, 1H), 7.67 (s, 1H), 7.05-6.90 (m, 4H), 3.92-3.91 (m, 4H), 3.89 (s, 3H), 3.24-3.22 (m, 4H), 2.53 (s, 3H), 2.19-2.15 (m, 1H), 1.18-1.15 (m, 2H), 1.02-0.99 (m, 2H). MS: m/z 453.2 (M+H⁺).

Example 129: {2-cyclopropyl-4-[4-(2-methoxy-phenyl)-piperazin-1-yl]-7-methyl-quinazolin-6-yl}-dimethyl-amine (192)

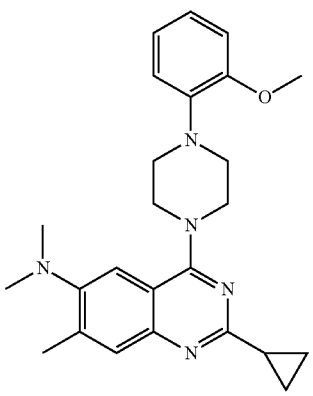

192

The title compound was prepared as described for compound (184), using the similar route and procedure.

¹HNMR (400 MHz, CDCl₃): δ=7.88-7.86 (m, 1H), 7.28 (s, 1H), 7.08-6.91 (m, 4H), 4.09-4.07 (m, 4H), 3.91 (s, 3H), 3.26-3.23 (m, 4H), 2.75 (s, 6H), 2.46 (s, 3H), 1.77-1.72 (m, 1H), 1.22-1.12 (m, 2H), 1.10-0.98 (m, 2H). MS: m/z 418.3 (M+H⁺).

Example 130: {2-cyclopropyl-4-[4-(2-methoxy-phenyl)-piperazin-1-yl]-7-methyl-quinazolin-6-yl}-ethyl-methyl-amine (193)

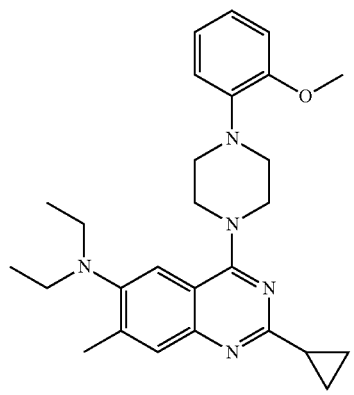

193

The title compound was prepared as described for compound (184), using the similar route and procedure.

¹HNMR (300 MHz, CDCl₃): δ=7.65 (s, 1H), 7.38 (s, 1H), 7.06-6.91 (m, 4H), 3.92 (s, 3H), 3.86-3.83 (m, 4H), 3.28-3.24 (m, 4H), 3.06 (q, J=7.2 Hz, 4H), 2.45 (s, 3H), 2.21-2.17 (m, 1H), 1.96-1.15 (m, 2H), 1.05 (t, J=7.2 Hz, 6H), 1.00-0.95 (m, 2H). MS: m/z 446.4 (M+H⁺).

Example 131: 6-bromo-2-cyclopropyl-4-[4-(2-methoxy-phenyl)-piperidin-1-yl]-7-methyl-quinazoline (194)

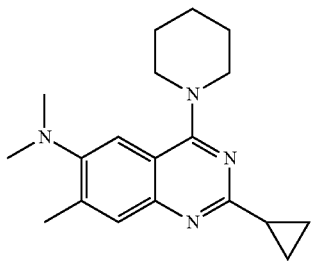

194

The title compound was prepared as described for compound (184), using the similar route and procedure.

¹HNMR (400 MHz, CDCl₃): δ=7.73 (s, 1H), 7.51 (s, 1H), 4.03-3.98 (m, 4H), 2.94 (s, 6H), 2.55 (s, 3H), 2.33-2.30 (m, 1H), 1.86-1.80 (m, 6H), 1.28-1.27 (m, 4H). MS: m/z 311.3 (M+H⁺).

Example 132: {2-cyclopropyl-4-[4-(2-methoxy-phenyl)-piperidin-1-yl]-7-methyl-quinazolin-6-yl}-diethyl-amine (195)

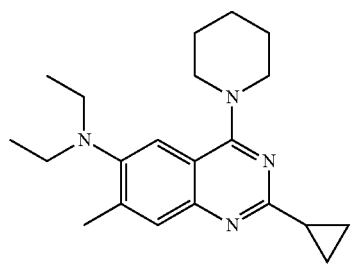

195

The title compound was prepared as described for compound (184), using the similar route and procedure.

¹H NMR (300 MHz, CDCl₃): δ=7.61 (s, 1H), 7.32 (s, 1H), 3.59-3.55 (m, 4H), 3.04 (q, J=7.2 Hz, 4H), 2.42 (s, 3H), 2.17-2.16 (m, 1H), 1.76-1.72 (m, 6H), 1.16-1.13 (m, 2H), 1.04 (t, J=7.2 Hz, 6H), 0.98-0.93 (m, 2H). MS: m/z 339.3 (M+H⁺).

Example 133: 2-cyclopropyl-6-methoxy-4-[4-(2-methoxy-phenyl)-piperazin-1-yl]-pyrido[3,4-d]pyrimidine (196)

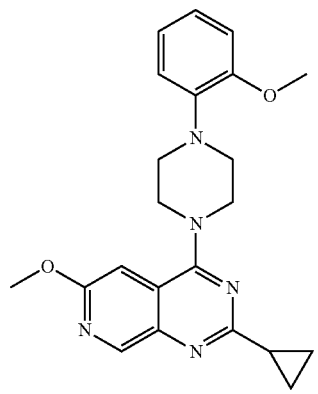

196

The title compound was prepared as described for compound (178), using the similar route and procedure.

¹H NMR (400 MHz, CDCl₃): δ=9.17 (s, 1H), 7.14-6.94 (m, 5H), 4.39-4.35 (m, 4H), 4.05 (s, 3H), 3.92 (s, 3H), 3.34-3.30 (m, 4H), 2.53-2.51 (m, 1H), 1.34-1.23 (m, 4H). MS: m/z 392.3 (M+H⁺).

Example 134: 6-bromo-2-cyclopropyl-4-[4-(2-methoxy-phenyl)-piperidin-1-yl]-7-methyl-quinazoline (197)

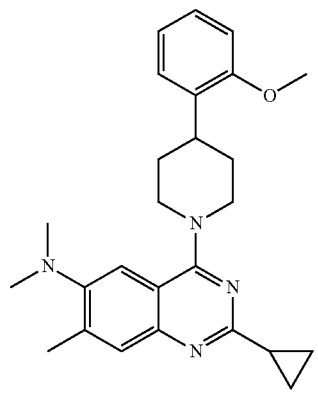

197

The title compound was prepared as described for compound (184), using the similar route and procedure.

¹H NMR (400 MHz, CDCl₃): δ=7.61 (s, 1H), 7.32 (s, 1H), 7.24-7.21 (m, 2H), 7.01-6.91 (m, 2H), 4.42-4.41 (m, 2H), 3.87 (s, 3H), 3.30-3.12 (m, 3H), 2.77 (s, 6H), 2.48 (s, 3H), 2.19-2.15 (m, 1H), 2.00-1.89 (m, 4H), 1.18-1.15 (m, 2H), 0.99-0.96 (m, 2H). MS: m/z 417.3 (M+H⁺).

Example 135: {2-cyclopropyl-4-[4-(2-methoxy-phenyl)-piperidin-1-yl]-7-methyl-quinazolin-6-yl}-diethyl-amine (198)

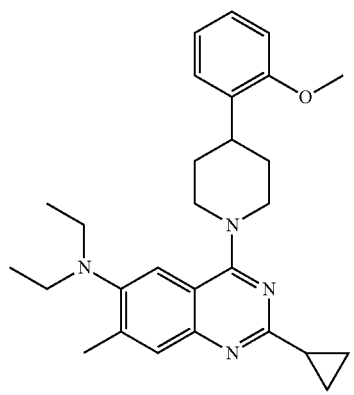

The title compound was prepared as described for compound (184), using the similar route and procedure.

¹H NMR (300 MHz, CDCl₃): δ=7.63 (s, 1H), 7.37 (s, 1H), 7.25-7.21 (m, 2H), 7.01-6.90 (m, 2H), 4.38-4.32 (m, 2H), 3.87 (s, 3H), 3.39-3.02 (m, 7H), 2.44 (s, 3H), 2.19-2.18 (m, 1H), 1.98-1.89 (m, 4H), 1.19-1.15 (m, 2H), 1.06-0.96 (m, 8H). MS: m/z 445.3 (M+H⁺).

Example 136: {2-cyclopropyl-4-[4-(2-methoxy-phenyl)-piperazin-1-yl]-quinazolin-7-yl}-dimethyl-amine (199)

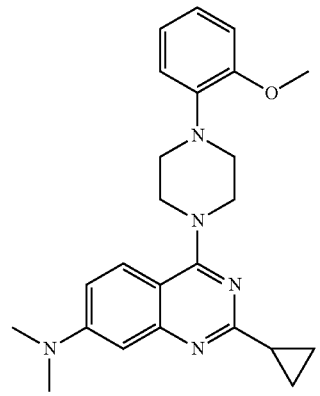

The title compound was prepared as described for compound (184), using the similar route and procedure.

¹H NMR (400 HMz, CDCl₃): δ=7.71 (d, J=9.6 Hz, 1H), 6.97-6.85 (m, 6H), 3.90 (s, 3H), 3.87-3.83 (m, 4H), 3.25-3.17 (m, 4H), 3.09 (s, 6H), 2.18 (m, 1H), 1.17-1.13 (m, 2H), 0.97-0.92 (m, 2H). MS: m/z 404.3 (M+H⁺).

Example 137: {2-cyclopropyl-4-[4-(2,5-dimethoxy-phenyl)-piperazin-1-yl]-quinazolin-6-yl}-dimethyl-amine (200)

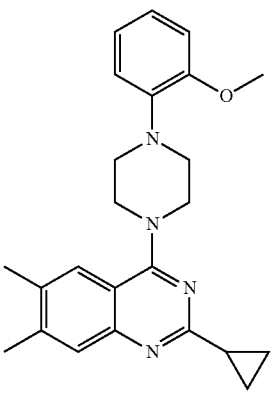

The title compound was prepared as described for compound (178), using the similar route and procedure.

¹H NMR (400 MHz, CDCl₃): δ=7.61-7.57 (m, 2H), 7.08-6.88 (m, 5H), 4.02-3.83 (m, 7H), 3.26-3.18 (m, 4H), 2.40 (s, 3H), 2.39 (s, 3H), 2.23-2.13 (m, 1H), 1.20-1.14 (m, 2H), 1.05-0.92 (m, 2H). MS: m/z 389.3 (M+H⁺).

Example 138: 2-cyclopropyl-4-[4-(2-methoxy-phenyl)-piperazin-1-yl]-6-piperidin-1-yl-quinazoline (201)

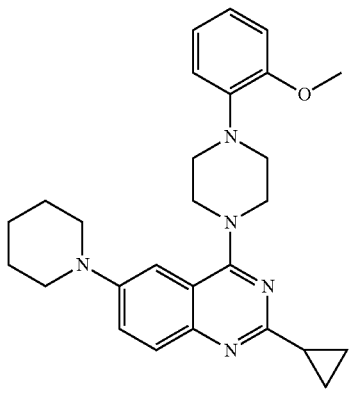

The title compound was prepared as described for compound (184), using the similar route and procedure.

¹H NMR (400 MHz, CDCl₃): δ=8.13 (d, J=9.2 Hz, 1H), 7.69-7.66 (m, 1H), 7.49 (s, 1H), 7.20-7.05 (m, 1H), 7.02-6.89 (m, 3H), 3.34-3.26 (m, 4H), 3.91 (s, 3H), 3.45-3.24 (m, 8H), 2.53-2.48 (m, 1H), 1.93-1.78 (m, 4H), 1.75-1.65 (m, 2H), 1.37-1.26 (m, 4H). MS: m/z 444.3 (M+H⁺).

Example 139: {2-cyclopropyl-4-[4-(2-methoxy-phenyl)-piperazin-1-yl]-quinazolin-6-yl}-diethyl-amine (202)

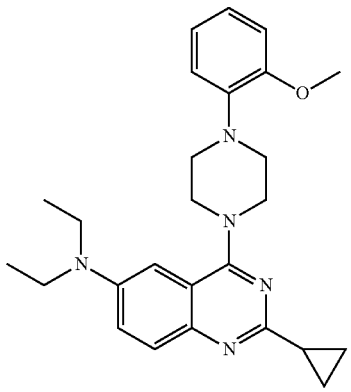

The title compound was prepared as described for compound (184), using the similar route and procedure.

$^1$HNMR (400 MHz, CDCl$_3$): δ=8.08 (d, J=10.0 Hz, 1H), 7.44 (d, J=7.6 Hz, 1H), 7.21-7.09 (m, 2H), 7.08-6.89 (m, 3H), 4.33-4.25 (m, 4H), 3.91 (s, 3H), 3.51-3.42 (m, 4H), 3.40-3.30 (m, 4H), 2.50-2.43 (m, 1H), 1.37-1.08 (m, 10H). MS: m/z 432.3 (M+H$^+$).

Example 140: 2-cyclopropyl-4-[4-(2-methoxy-phenyl)-piperazin-1-yl]-6-morpholin-4-yl-quinazoline (203)

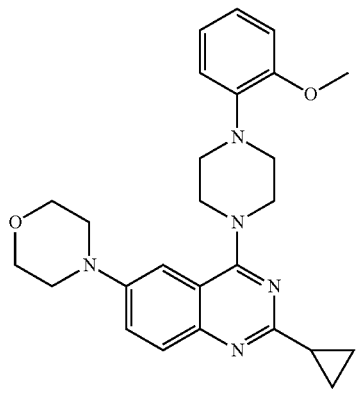

The title compound was prepared as described for compound (184), using the similar route and procedure.

$^1$H NMR (400 MHz, CDCl$_3$): δ=7.80 (d, J=8.8 Hz, 1H), 7.48-7.45 (m, 1H), 7.10-7.05 (m, 1H), 7.02-6.86 (m, 5H), 4.01-3.76 (m, 1H), 3.29-3.19 (m, 8H), 2.58-2.46 (m, 1H), 1.21-1.14 (m, 2H), 1.08-0.91 (m, 2H). MS: m/z 446.3 (M+H$^+$).

Example 141: 2-cyclopropyl-4-[4-(2-methoxy-phenyl)-piperazin-1-yl]-6-pyrrolidin-1-yl-quinazolin (204)

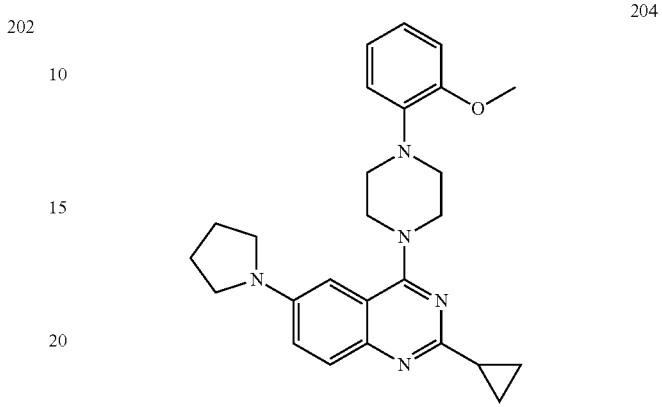

The title compound was prepared as described for compound (184), using the similar route and procedure.

$^1$H NMR (400 MHz, CDCl$_3$): δ=8.15 (d, J=9.2 Hz, 1H), 7.23-7.20 (m, 1H), 7.12-7.02 (m, 1H), 7.00-6.89 (m, 3H), 6.58 (d, J=2.8 Hz, 1H), 4.25-4.39 (m, 4H), 3.92 (s, 3H), 3.46-3.39 (m, 4H), 3.25-3.18 (m, 4H), 2.70-2.59 (m, 1H), 2.19-2.03 (m, 4H), 1.28-1.21 (m, 4H). MS: m/z 430.3 (M+H$^+$).

Example 142: {2-cyclopropyl-4-[4-(2-methoxy-phenyl)-piperazin-1-yl]-quinazolin-6-yl}-phenyl-amine (205)

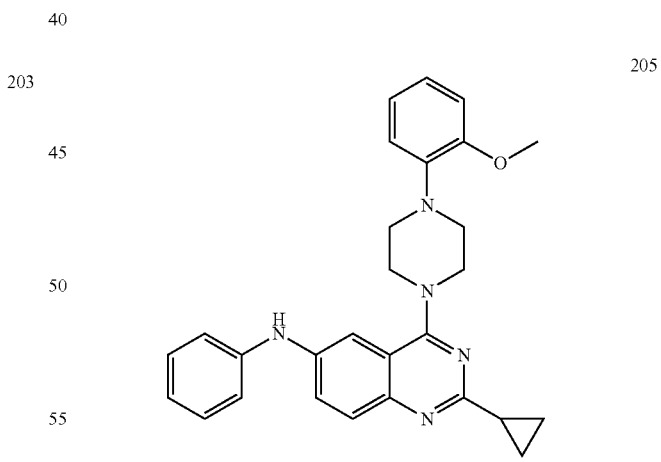

The title compound was prepared as described for compound (184), using the similar route and procedure.

$^1$H NMR (400 MHz, CDCl$_3$): δ=7.76 (d, J=8.8 Hz, 1H), 7.48-7.39 (m, 2H), 7.36-7.26 (m, 2H), 7.12 (d, J=7.2 Hz, 2H), 7.08-6.86 (m, 5H), 5.96 (brs, 1H), 3.89 (s, 3H), 3.84-3.76 (m, 4H), 3.30-3.10 (m, 4H), 2.50-2.16 (m, 1H), 1.21-1.12 (m, 2H), 1.02-0.96 (m, 2H). MS: m/z 452.3 (M+H$^+$).

Example 143: {2-cyclopropyl-4-[4-(2-methoxy-phenyl)-piperidin-1-yl]-quinazolin-6-yl}-dimethyl-amine (206)

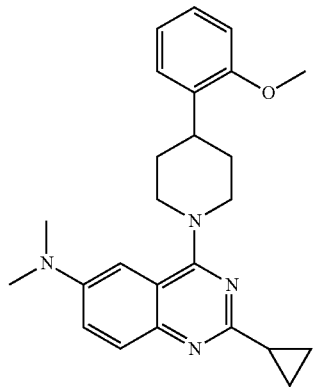

The title compound was prepared as described for compound (184), using the similar route and procedure.

¹H NMR (400 MHz, CDCl₃): δ=7.74 (d, J=6.0 Hz, 1H), 7.33 (dd, J=9.2, 2.8 Hz, 1H), 7.27-7.18 (m, 2H), 7.00-6.93 (m, 1H), 6.91-6.83 (m, 2H), 4.38 (d, J=12.8 Hz, 2H), 3.86 (s, 3H), 3.35-3.22 (m, 1H), 3.14 (t, J=12.0 Hz, 2H), 3.02 (s, 6H), 2.24-2.16 (m, 1H), 2.00-1.79 (m, 4H), 1.20-1.12 (m, 2H), 1.03-0.91 (m, 2H). MS: m/z 404.3 (M+H⁺).

Example 144: {2-cyclopropyl-4-[4-(2-methoxy-phenyl)-piperidin-1-yl]-quinazolin-6-yl}-ethyl-methyl-amine (207)

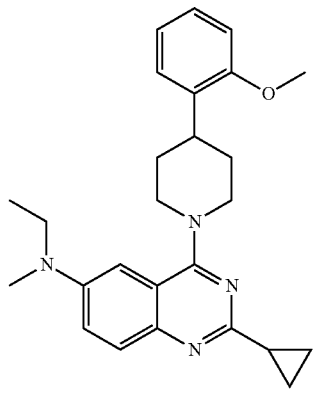

The title compound was prepared as described for compound (184), using the similar route and procedure.

¹H NMR (400 MHz, CDCl₃): δ=7.77 (d, J=9.2 Hz, 1H), 7.31 (dd, J=9.2, 2.4 Hz, 1H), 7.30-7.20 (m, 2H), 6.99-6.95 (m, 1H), 6.89 (d, J=8.0 Hz, 1H), 6.84 (d, J=2.4 Hz, 1H), 4.40 (d, J=12.4 Hz, 2H), 3.86 (s, 3H), 3.47 (q, J=7.2 Hz, 2H), 3.35-3.23 (m, 1H), 3.22-3.08 (m, 2H), 2.98 (s, 3H), 2.25-2.18 (m, 1H), 2.02-1.79 (m, 4H), 1.19-1.12 (m, 5H), 1.02-0.91 (m, 2H). MS: m/z 417.3 (M+H⁺).

Example 145: {7-chloro-2-cyclopropyl-4-[4-(2-methoxyphenyl)piperidyl]quinazolin-6-yl}dimethylamine (208)

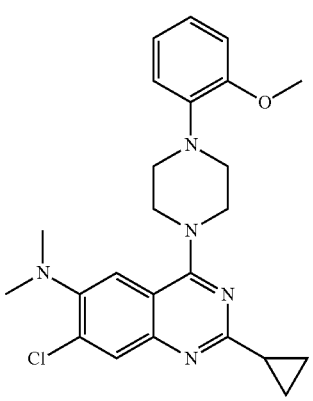 [SMILES: COc1cc2c(N3CCN(c4ccccc4OC)CC3)nc(C3CC3)nc2cc1F]

The title compound was prepared as described for compound (184), using the similar route and procedure.

¹H NMR (400 MHz, MeOD): δ=7.75 (s, 1H), 7.50 (s, 1H), 7.27-7.15 (m, 2H), 7.01-6.88 (m, 2H), 4.60-4.49 (m, 2H), 3.87 (s, 3H), 3.44-3.33 (m, 3H), 2.90 (s, 6H), 2.20-2.04 (m, 1H), 2.07-1.86 (m, 4H), 1.25-1.15 (m, 2H), 1.12-1.00 (m, 2H). MS: m/z 437.3 (M+H⁺).

Example 146: 2-cyclopropyl-4-[4-(2-methoxy-phenyl)-piperazin-1-yl]-6-piperazin-1-yl-quinazoline (209)

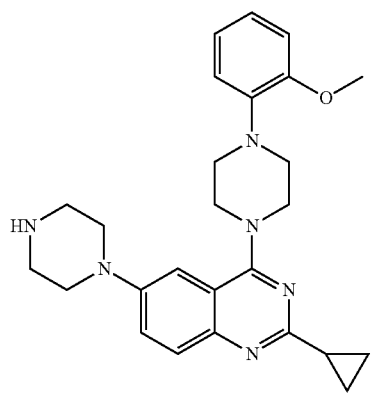

The title compound as HCl salt was prepared as described for compound (178), using the similar route and procedure.

¹H NMR (400 MHz, DMSO-d₆): δ=9.32 (brs, 2H), 7.89-7.80 (m, 2H), 7.27 (s, 1H), 7.08-6.82 (m, 4H), 4.35-4.20 (m, 4H), 3.82 (s, 3H), 3.60-3.49 (m, 4H), 3.34-3.15 (m, 8H), 2.40-2.30 (m, 1H), 1.30-1.22 (m, 4H). MS: m/z 445.3 (M+H⁺).

Example 147: 2-cyclopropyl-4-[4-(2-methoxy-phenyl)-piperazin-1-yl]-6-(4-methyl-piperazin-1-yl)-quinazoline (210)

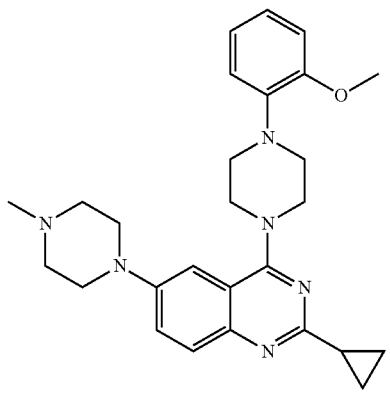

210

The title compound as HCl salt was prepared as described for compound (178), using the similar route and procedure.

$^1$H NMR (400 MHz, DMSO-$d_6$): δ=10.13 (brs, 1H), 7.84 (d, J=7.6 Hz, 1H), 7.71 (d, J=9.6 Hz, 1H), 7.32 (s, 1H), 7.04-6.97 (m, 2H), 6.97-6.85 (m, 2H), 4.34-4.23 (m, 4H), 4.06-3.96 (m, 2H), 3.82 (s, 3H), 3.63-3.51 (m, 2H), 3.39-3.05 (m, 8H), 2.89 (s, 3H), 2.26-2.20 (m, 1H), 1.46-1.26 (m, 4H). MS: m/z 459.3 (M+H+).

Example 148: 2-cyclopropyl-6,7-difluoro-4-[4-(2-methoxy-phenyl)-piperazin-1-yl]-quinazoline (211)

211

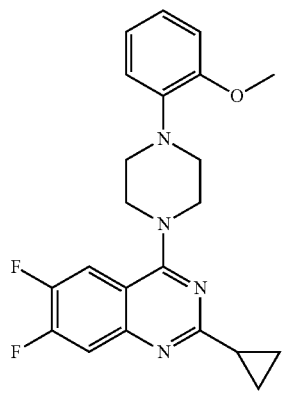

The title compound was prepared as described for compound (178), using the similar route and procedure.

$^1$H NMR (400 MHz, CDCl$_3$): δ=7.64-7.52 (m, 2H), 7.08-7.03 (m, 1H), 6.98-6.90 (m, 3H), 3.90 (s, 3H), 3.86 (t, J=9.2 Hz, 4H), 3.23 (t, J=9.6 Hz, 4H), 2.32 (s, 3H), 2.19-2.15 (m, 1H), 1.19-1.145 (m, 2H), 1.04-0.99 (m, 2H). MS: m/z 397.2 (M+H$^+$).

Scheme 18:

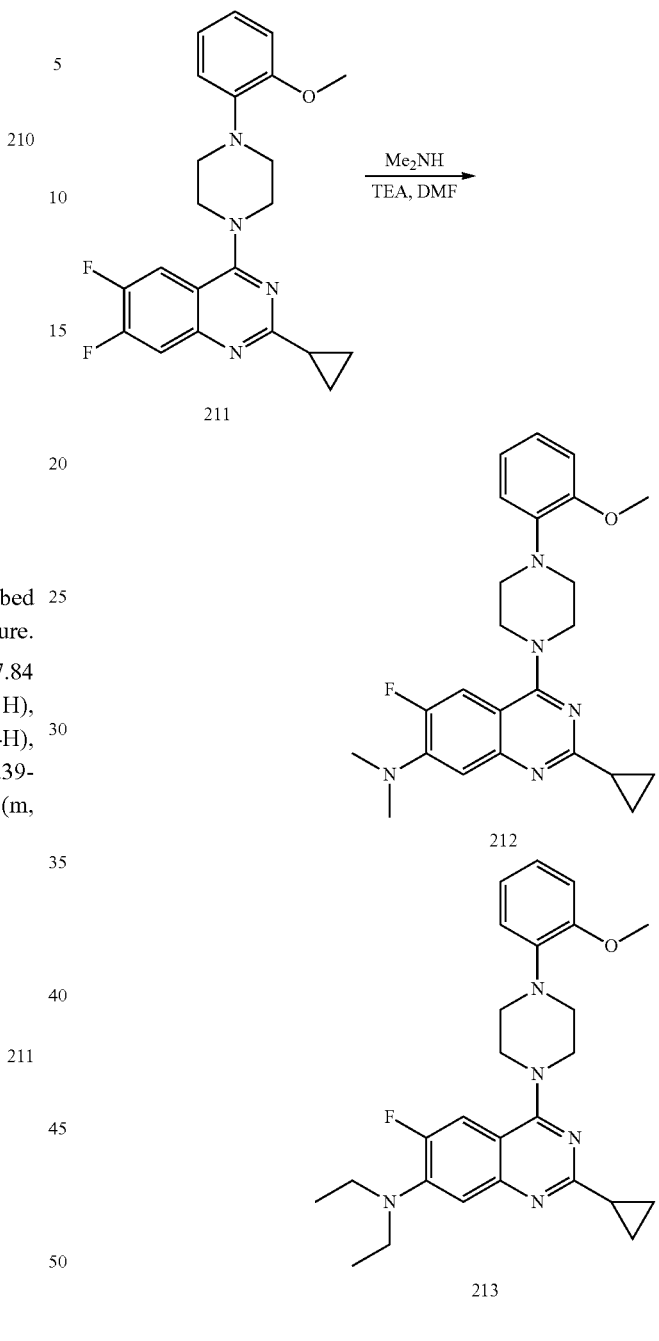

Example 149 and 150 {2-cyclopropyl-6-fluoro-4-[4-(2-methoxy-phenyl)-piperazin-1-yl]-quinazolin-7-yl}-dimethyl-amine (212) and {2-cyclopropyl-6-fluoro-4-[4-(2-methoxy-phenyl)-piperazin-1-yl]-quinazolin-7-yl}-diethyl-amine (213)

A solution of compound (211) (200 mg, 0.51 mmol), diethylamine (40 mg, 0.56 mmol) and TEA (102 mg, 1.01 mmol) in DMF (10 mL) in sealed tube was heated at 120° C. overnight. The mixture was diluted with water (20 mL) and extracted with EtOAc (10 mL 2). The extracts were washed with brine (10 mL×2) and dried over Na$_2$SO$_4$. The solution was concentrated under reduced pressure and the crude was purified by prep-HPLC to give compound (212), (20 mg, yield: 18%) as white solid and compound (213), (30 mg, yield: 38%) as white solid.

{2-cyclopropyl-6-fluoro-4-[4-(2-methoxy-phenyl)-piperazin-1-yl]-quinazolin-7-yl}-dimethyl-amine (212) $^1$H NMR (400 MHz, DMSO-d6): δ=7.55 (d, J=14.8 Hz, 1H), 6.98-6.89 (m, 5H), 3.81 (s, 3H), 3.74-3.70 (m, 4H), 3.15-3.11 (m, 4H), 2.96 (s, 6H), 2.09-2.07 (m, 1H), 1.02 (m, 2H), 0.94-0.91 (m, 2H). MS: m/z 422.3 (M+H[+]).

{2-cyclopropyl-6-fluoro-4-[4-(2-methoxy-phenyl)-piperazin-1-yl]-quinazolin-7-yl}-diethyl-amine (213) $^1$H NMR (400 MHz, DMSO-d6): δ=7.55 (d, J=15.2 Hz, 1H), 6.98-6.89 (m, 5H), 3.81 (s, 3H), 3.74-3.70 (m, 4H), 3.40-3.35 (m, 4H), 3.15-3.11 (m, 4H), 2.05-2.02 (m, 1H), 1.14 (t, J=7.2 Hz, 6H), 1.02-1.00 (m, 2H), 0.94-0.90 (m, 2H), MS: m/z 450.3 (M+H[+]).

Scheme 19:

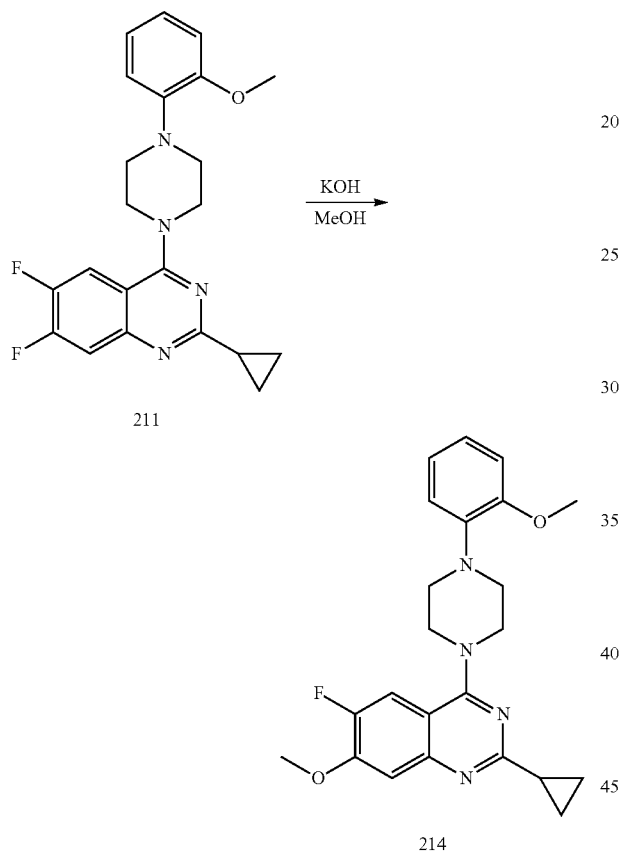

Example 151: 2-cyclopropyl-6-fluoro-7-methoxy-4-[4-(2-methoxy-phenyl)-piperazin-1-yl]-quinazoline (214)

A solution of compound (211) (200 mg, 0.51 mmol) and KOH (28.6 mg, 0.51 mmol) in MeOH (10 mL) was stirred at reflux overnight. The mixture was concentrated under reduced pressure and the residue was acidified with 1N HCl to pH=6. The aqueous phase was extracted with EtOAc (50 mL×2) and the extracts were washed with brine (10 mL). The solution was dried over Na2SO4 and concentrated under reduced pressure to give a crude product. It was triturated with DMF to give compound (214), (25 mg, yield: 12%) as white solid.

$^1$H NMR (400 MHz, CDCl3): δ=7.50 (d, J=12.0 Hz, 1H), 7.25 (s, 1H), 6.97-6.91 (m, 4H), 4.00 (s, 3H), 3.90 (s, H), 3.86-3.82 (m, 4H), 3.25-3.20 (m, 4H), 2.19-2.15 (m, 1H), 1.18-1.14 (m, 2H), 1.02-0.98 (m, 2H). MS: m/z 409.2 (M+H[+]).

Scheme 20:

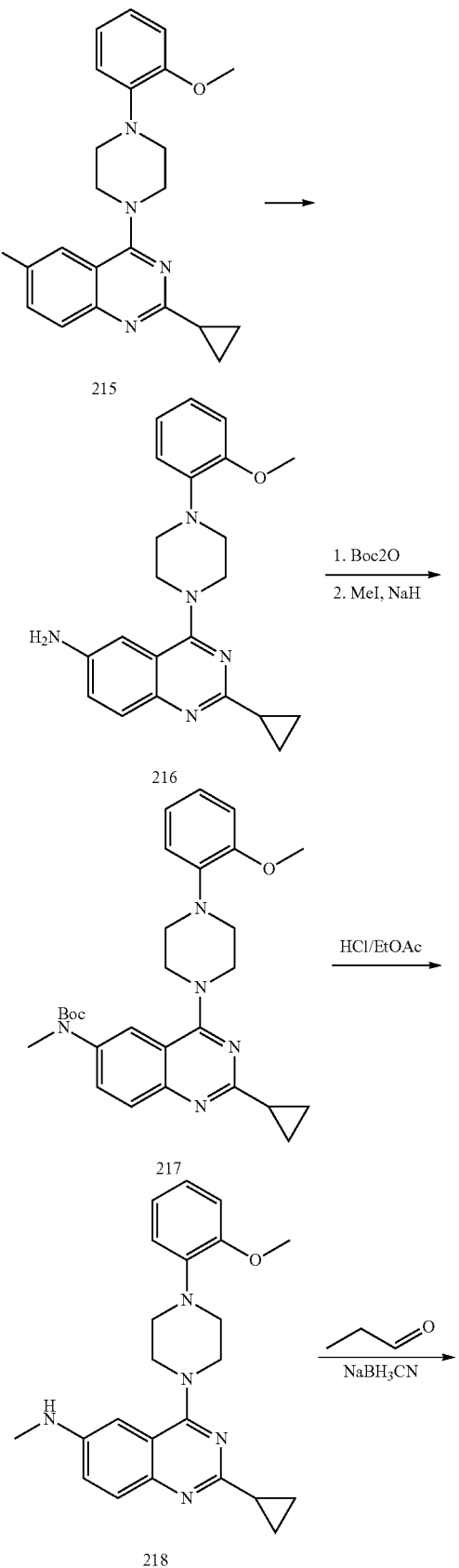

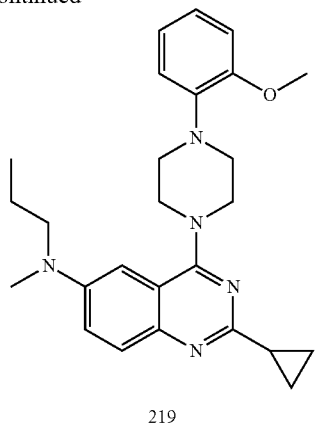

219

Example 152: {2-cyclopropyl-4-[4-(2-methoxy-phenyl)-piperazin-1-yl]-quinazolin-6-yl}-methyl-propyl-amine (219)

Starting material (215) was prepared as similar as compound (6).

$^1$H NMR (400 MHz, CDCl$_3$): δ=8.32 (d, J=2.8 Hz, 1H), 7.25 (dd, J=9.2, 2.8 Hz, 1H), 7.84 (d, J=9.2 Hz, 1H), 7.08-7.04 (m, 1H), 6.99-6.90 (m, 3H), 4.10-4.05 (m, 4H), 3.92 (s, H), 3.30-3.24 (m, 4H), 2.25-2.20 (m, 1H), 1.26-1.20 (m, 2H), 1.12-1.06 (m, 2H).

A mixture of compound (215) (1.60 g, 3.95 mmol), active iron powder (1.10 mg, 19.8 mmol), NH$_4$Cl (423 mg, 7.90 mmol) in EtOH/H$_2$O (16 mL/2 mL) was heated to reflux for 3 h. After cooled to room temperature, the mixture was filtered through celite. The filtrate was concentrated to dryness and the residue was purified by silica gel column chromatography (from DCM to MeOH/DCM=1/30) to afforded compound (216) (1.0 g, yield: 68%) as a yellow solid.

$^1$H NMR (400 MHz, CDCl$_3$): δ=7.67 (d, J=8.8 Hz, 1H), 7.13 (dd, J=8.2, 2.4 Hz, 1H), 7.08-6.88 (m, 5H), 3.88 (s, 3H), 3.87-3.78 (m, 4H), 3.25-3.20 (m, 4H), 2.20-2.14 (m, 1H), 1.16-1.10 (m, 2H), 0.98-0.93 (m, 2H).

To a stirred solution of compound (216) (800 mg, 2.13 mmol), TEA (430 mg, 4.26 mmol) and Boc$_2$O (558 mg, 2.56 mmol) in DCM (10 mL) was added DMAP (71 mg, 0.64 mmol). The mixture was stirred at 30° C. for 5 h. The mixture was diluted with DCM (80 mL) and washed with water (30 mL×2), brine (30 mL×2) and dried over Na$_2$SO$_4$. The solution was evaporated to dryness and the residue was purified by silica gel column chromatography (from PE/EtOAc=10/1 to PE/EtOAc=3/1) to give Boc protected product (810 mg, yield: 81%) as yellow solid.

$^1$H NMR (400 MHz, CDCl$_3$): δ=7.78-7.73 (m, 2H), 7.52 (dd, J=9.2, 2.0 Hz, 1H), 7.06-7.00 (m, 1H), 6.97-6.85 (m, 3H), 3.87-3.78 (m, 7H), 3.21-3.16 (m, 4H), 2.21-2.16 (m, 1H), 1.43 (s, 9H), 1.19-1.14 (m, 2H), 1.03-0.98 (m, 2H).

A solution of Boc protected product (500 mg, 1.05 mmol) was dissolved in dry THF (5 mL) and cooled to 0° C., NaH (60% in mineral oil, 63 mg, 1.57 mmol) was added and stirred at 0° C. for 1.5 h. CH$_3$I (298 mg, 2.1 mmol) was then added and the mixture was stirred at room temperature overnight. The reaction was quenched with saturated NH$_4$Cl solution (10 mL) and water (10 mL). The aqueous phase was extracted with EtOAc (10 mL×2). The combined organic layer was washed with water (10 mL) and brine (10 mL) and dried over Na$_2$SO$_4$. The solution was concentrated in vacuum and purified by silica gel column chromatography (EtOAc/PE=1/5) to give product (217) (240 mg, yield: 47%) as a yellow oil.

$^1$H NMR (400 MHz, CDCl$_3$): δ=7.74 (d, J=8.8 Hz, 1H), 7.67 (d, J=2.0 Hz, 1H), 7.06-6.87 (m, 4H), 3.90 (s, 3H), 3.90-3.86 (m, 4H), 3.32 (s, 3H), 3.25-3.20 (m, 4H), 2.23-2.15 (m, 1H), 1.18-1.14 (m, 2H), 1.02-0.98 (m, 2H).

Compound (217) (90 mg, 0.18 mmol) was dissolved in EtOAc (1.5 mL) and HCl/EtOAc (1M, 5 mL) and the mixture was stirred at room temperature for 2 hours. The reaction solution was concentrated to give HCl salt of (218) (80 mg, quantitative) as a yellow solid.

A solution of compound (218) (80 mg, 0.18 mmol) was dissolved in MeOH (3 mL), propionaldehyde (21 mg, 0.36 mmol) was added and the mixture was stirred for 1 h. NaBH$_3$CN was then added and the mixture was stirred overnight. 15 mL of water was added and the mixture was extracted with EtOAc (15 mL×2). The organic layer was washed with water (10 mL) and brine (10 mL) and dried over Na$_2$SO$_4$. The solution was concentrated in vacuum and the crude product was purified by prep-HPLC to give HCl salt of compound (219), (45 mg, yield: 58%) as a yellow solid.

$^1$HNMR (400 MHz, CD$_3$OD): δ=8.04 (d, J=9.2 Hz, 1H), 7.96-7.94 (m, 1H), 7.90 (d, J=9.2 Hz, 1H), 7.79 (d, J=7.6 Hz, 1H), 7.58 (t, J=8.4 Hz, 1H), 7.35 (d, J=8.4 Hz, 1H), 7.19 (t, J=8.4 Hz 1H), 4.03 (s, 4H), 4.08 (s, 3H), 4.04-4.02 (m, 4H), 3.60 (t, J=7.8 Hz, 2H), 3.27 (s, 3H), 2.32-2.28 (m, 1H), 1.72-1.66 (m, 2H), 1.50-1.38 (m, 4H), 0.99 (t, J=7.4 Hz, 3H). MS: m/z 432.3 (M+H$^+$).

Scheme 21:

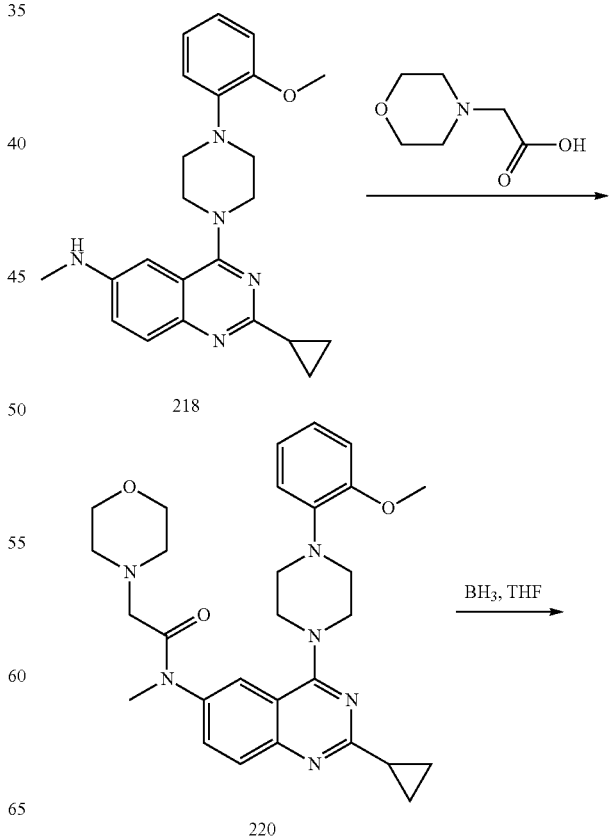

-continued

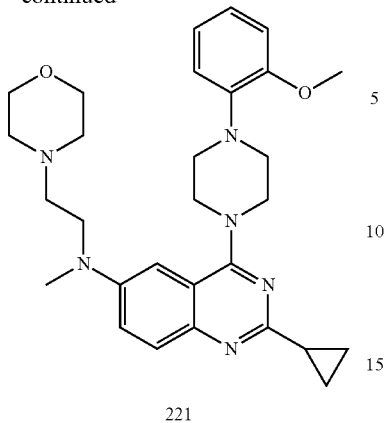

221

Example 153: {2-cyclopropyl-4-[4-(2-methoxy-phenyl)-piperazin-1-yl]-quinazolin-6-yl}-methyl-(2-morpholin-4-yl-ethyl)-amine (220)

Morpholin-4-yl-acetic acid (45 mg, 0.3 mmol) was suspended in oxalyl chloride (5 mL), a drop of DMF was added and the mixture was stirred at room temperature for 2 h. The solution was concentrated to afford morpholin-4-yl-acetyl chloride. The above acyl chloride was dissolved in DCM (1 mL) and a solution of compound 219 (60 mg) and TEA (0.5 mL) in DCM (4 mL) was added in the solution in an ice-cooling bath. The reaction mixture was stirred at room temperature overnight. The reaction was quenched with saturated NaHCO$_3$ solution (10 mL). The organic layer was separated and dried over Na$_2$SO$_4$. The solution was concentrated and purified by prep-TLC (EtOAc) to give compound (220), (50 mg, yield: 64%) as a white solid.

$^1$HNMR (400 MHz, DMSO-d$_6$): δ=7.87 (s, 1H), 7.71 (s, 2H), 6.98-6.89 (m, 4H), 3.83-3.81 (m, 7H), 3.47-3.42 (m, 4H), 3.30-3.12 (m, 6H), 2.91-2.89 (m, 1H), 2.54-2.50 (m, 2H), 2.33-2.27 (m, 4H), 2.13-2.09 (m, 1H), 1.07-1.06 (m, 2H), 1.00-0.96 (m, 2H). MS: m/z 517.3 (M+H$^+$).

Example 154: 2-cyclopropyl-4-(4-(2-methoxyphenyl)piperazin-1-yl)-N-methyl-N-(2-morpholinoethyl)quinazolin-6-amine (221)

BH$_3$ (Me$_2$S complex 10M, 0.09 mL, 0.9 mmol) was added to the solution of (220) (45 mg, 0.09 mmol) in THF (3 mL) at 0° C. The reaction was stirred at 55° C. overnight. The reaction was quenched with MeOH (1 mL). Then 6N HCl (10 mL) was added and the mixture was stirred at 60° C. for 3 h. The resulting solution was treated with sat. NaHCO$_3$ solution till pH=8 and the aqueous phase was extracted with EtOAc (10 mL×3). The organic layer was washed with water (10 mL) and brine (10 mL) and dried over Na$_2$SO$_4$. The solution was concentrated and the residue was purified by prep-HPLC to give HCl salt of compound (221), (8 mg, yield: 18%) as a yellow solid.

$^1$H NMR (400 MHz, CD$_3$OD): δ=7.83-7.78 (m, 3H), 7.59 (t, J=7.6 Hz, 1H), 7.35 (d, J=8.0 Hz, 1H), 7.27 (s, 1H), 7.20 (s, 1H), 4.68-4.69 (m, 4H), 4.08-3.96 (m, 12H), 3.58-3.55 (m, 2H), 3.45-3.43 (m, 2H), 3.19 (s, 3H), 2.29-2.27 (m, 1H), 1.44-1.40 (m, 2H), 1.37-1.27 (m, 5H). MS: m/z 503.3 (M+H$^+$).

Scheme 22:

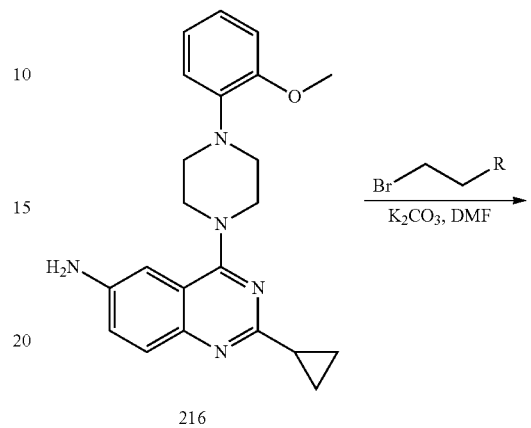

216

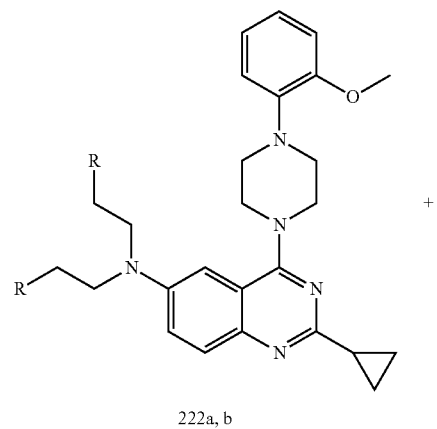

222a, b

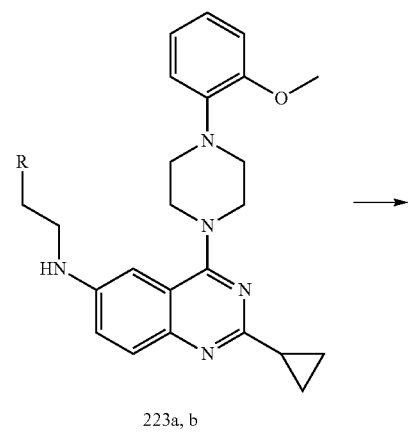

223a, b

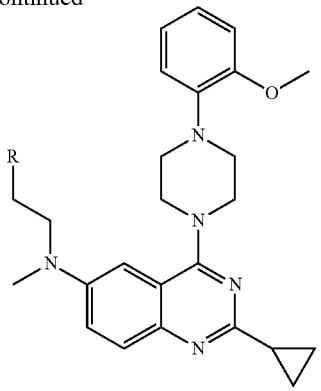

224, 225

224, R = OH
225, R = OMe

Example 155: 2,2'-((2-cyclopropyl-4-(4-(2-methoxyphenyl)piperazin-1-yl)quinazolin-6-yl)azanediyl)diethanol (222a)

2-cyclopropyl-4-[4-(2-methoxy-phenyl)-piperazin-1-yl]-quinazolin-6-ylamine (216) (150 mg, 0.4 mmol), 2-bromo-ethanol (400 mg, 3.2 mmol), potassium carbonate (166 mg, 1.2 mmol) and DMF (4 mL) was mixed and heated to 120° C. overnight. The reaction mixture was poured into water (15 mL) and extracted with EtOAc (10 mL). The organic layer was washed with water (10 mL) and brine (10 mL) and dried over $Na_2SO_4$. The solution was concentrated in vacuum to give a mixture of (222a) and (223a), which was purified by prep-HPLC to give compound (222a) (15 mg, 8%) as a yellow solid.

$^1$H NMR (400 MHz, $CDCl_3$): δ=7.83 (d, J=9.2 Hz, 1H), 7.31 (dd, J=9.2, 8.8 Hz, 1H), 7.07-6.90 (m, 5H), 4.02-4.00 (m, 4H), 3.91-3.89 (m, 7H), 3.64 (t, J=4.8 Hz, 4H), 3.22 (t, J=4.4 Hz, 4H), 2.40-2.39 (m, 1H), 1.21-1.18 (m, 2H), 1.12-1.10 (m, 2H). MS: m/z 464.3 (M+H$^+$).

Example 156: 2-({2-cyclopropyl-4-[4-(2-methoxy-phenyl)-piperazin-1-yl]-quinazolin-6-yl}-methyl-amino)-ethanol (224)

A solution of 223a (250 mg, 0.4 mmol, with minor 222a), $NaBH_3CN$ (63 mg, 1 mmol) and HCHO (40% in $H_2O$, 0.5 mL) in 5 mL of MeOH was stirred at room temperature overnight. The reaction mixture was poured into water (20 mL) and extracted with EtOAc (15 mL). The organic layer was washed with water (10 mL) and brine (10 mL) and dried over $Na_2SO_4$. The solution was concentrated to dryness and the residue was purified by prep-HPLC to give (224), (11 mg, 7% over 2 steps) as a yellow solid.

$^1$H NMR (400 MHz, $CDCl_3$): δ=7.75-7.73 (m, 1H), 7.37 (dd, J=9.2, 8.2 Hz, 1H), 7.06-6.90 (m, 5H), 3.90-3.81 (m, 9H), 3.55 (t, J=5.6 Hz, 2H), 3.24 (t, J=5.2 Hz, 4H), 3.05 (s, 3H), 2.22-2.08 (m, 1H), 1.16-1.13 (m, 2H), 0.99-0.94 (m, 2H). MS: m/z 434.3 (M+H$^+$).

Example 157: {2-cyclopropyl-4-[4-(2-methoxy-phenyl)-piperazin-1-yl]-quinazolin-6-yl}-(2-methoxy-ethyl)-methyl-amine (225)

A solution of (223b) (250 mg, 0.4 mmol, with minor 222a), $NaBH_3CN$ (63 mg, 1 mmol) and HCHO (40% in $H_2O$, 0.5 mL) in 5 mL of MeOH was stirred at room temperature overnight. The reaction mixture was poured into water (20 mL) and extracted with EtOAc (15 mL). The organic layer was washed with water (10 mL) and brine (10 mL) and dried over $Na_2SO_4$. The solution was concentrated to dryness and the residue was purified by prep-HPLC to give compound (225), (25 mg, 19% over 2 steps) as a yellow solid.

$^1$H NMR (400 MHz, $CD_3OD$): δ=7.91 (d, J=9.2 Hz, 1H), 7.84-7.79 (m, 2H), 7.66 (s, 1H), 7.59 (t, J=7.8 Hz, 1H), 7.36 (d, J=8.4, 1H), 7.19 (t, J=7.4 Hz, 1H), 3.90-3.81 (m, 9H), 3.55 (t, J=5.6 Hz, 2H), 3.24 (t, J=5.2 Hz, 4H), 3.05 (s, 3H), 2.22-2.08 (m, 1H), 1.16-1.13 (m, 2H), 0.99-0.94 (m, 2H). MS: m/z 448.3 (M+H$^+$).

Example 158: 2-({2-cyclopropyl-4-[4-(2-methoxy-phenyl)-piperidin-1-yl]-quinazolin-6-yl}-methyl-amino)-ethanol (226)

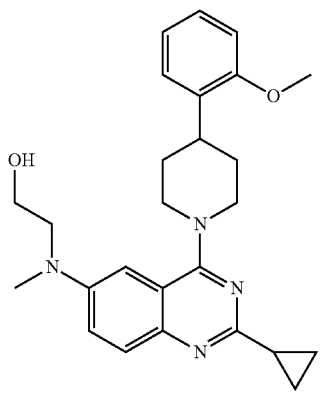

226

The title compound was prepared as described for compound (224), using the similar route and procedure.

$^1$H NMR (400 MHz, $CDCl_3$): δ=8.09-8.06 (m, 1H), 7.39-7.35 (m, 1H), 7.25-7.17 (m, 2H), 6.97-6.88 (m, 3H), 4.69-4.66 (m, 2H), 3.88-3.85 (m, 5H), 3.57 (t, J=5.4 Hz, 2H), 3.36-3.27 (m, 3H), 3.05 (s, 3H), 2.60 (m, 1H), 1.91-1.87 (m, 2H), 1.85-1.80 (m, 2H), 1.21-1.12 (m, 4H). MS: m/z 433.3 (M+H$^+$).

Example 159: {2-cyclopropyl-4-[4-(2-methoxy-phenyl)-piperidin-1-yl]-quinazolin-6-yl}-(2-methoxy-ethyl)-methyl-amine (227)

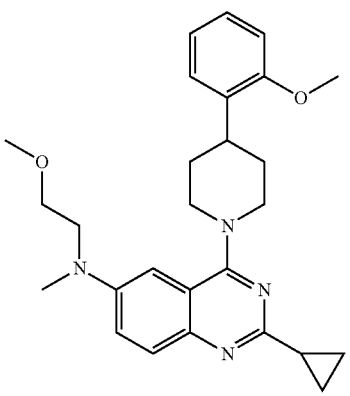

227

The title compound was prepared as described for compound (225), using the similar route and procedure.

$^1$H NMR (400 MHz, CD$_3$OD): δ=7.90-7.79 (m, 3H), 7.22-7.18 (m, 2H), 6.96 (dd, J=8.0, 4.4 Hz, 1H), 6.91 (t, J=7.2 Hz, 3H), 4.98-4.89 (m, 2H), 3.85 (s, 3H), 3.84-3.74 (m, 1H), 3.59-3.47 (m, 5H), 3.30-3.24 (m, 3H), 2.20-1.89 (m, 5H), 1.38-1.30 (m, 4H). MS: m/z 447.3 (M+H$^+$).

Example 160: {2-cyclopropyl-4-[4-(2-methoxy-phenyl)-piperidin-1-yl]-quinazolin-6-yl}-methyl-propyl-amine (228)

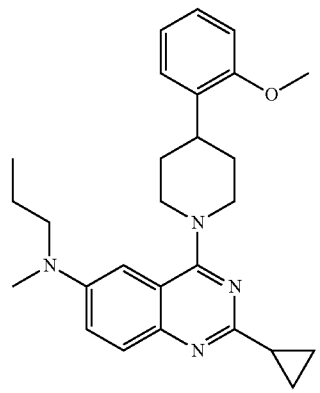

228

The title compound was prepared as described for compound (222), using the similar route and procedure.

$^1$H NMR (400 MHz, CD$_3$OD): δ=7.89-7.86 (m, 1H), 7.76-7.67 (m, 2H), 7.90 (d, J=9.2 Hz, 1H), 7.22-7.18 (m, 2H), 6.97-6.89 (m, 2H), 4.97 (d, J=13.6 Hz, 2H), 3.85 (s, 3H), 3.62-3.45 (m, 5H), 3.21 (t, J=1.6 Hz, 3H), 2.19-2.15 (m, 1H), 2.10 (d, J=12.0 Hz, 2H), 1.68-1.63 (m, 2H), 1.40-1.30 (m, 4H), 0.97 (t, J=7.4 Hz, 3H). MS: m/z 431.3 (M+H$^+$).

Example 161: {2-cyclopropyl-4-[4-(2-methoxy-phenyl)-piperidin-1-yl]-quinazolin-6-yl}-methyl-(2-morpholin-4-yl-ethyl)-amine (229)

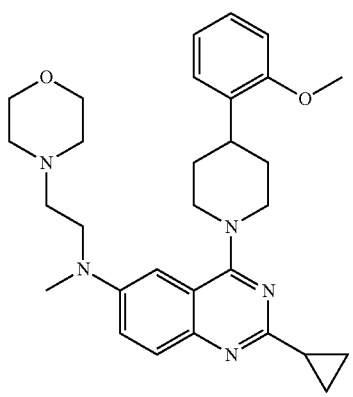

229

The title compound was prepared as described for compound (222), using the similar route and procedure.

$^1$H NMR (400 MHz, CD$_3$OD): δ=7.74-7.65 (m, 2H), 7.21-7.18 (m, 3H), 6.97-6.88 (m, 2H), 4.97 (d, J=13.6 Hz, 2H), 4.06-3.92 (m, 6H), 3.85 (s, 3H), 3.65-3.38 (m, 7H), 3.28-3.4 (m, 2H), 3.13 (s, 3H), 2.16-2.15 (m, 1H), 2.28 (d, J=12.4 Hz, 2H), 1.92-1.82 (m, 2H), 1.35-1.28 (m, 4H). MS: m/z 502.2 (M+H$^+$).

Scheme 23

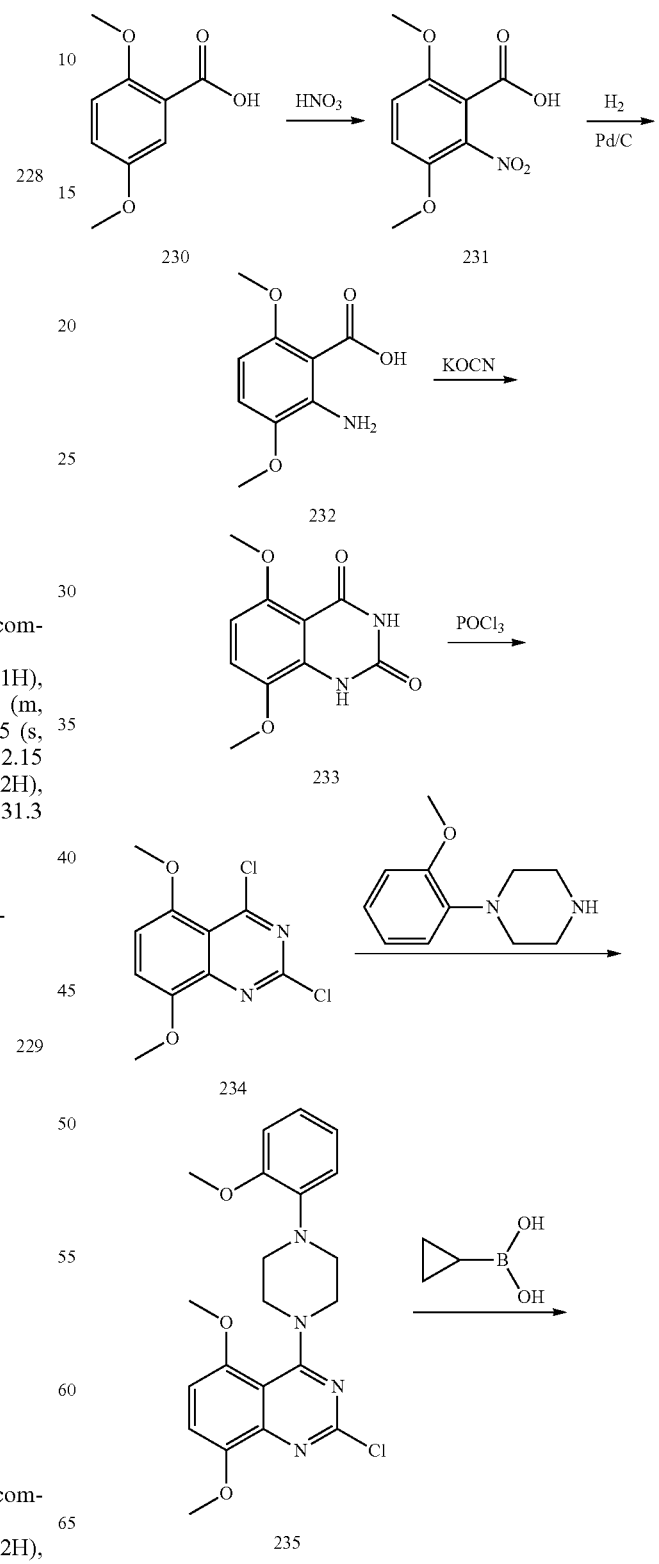

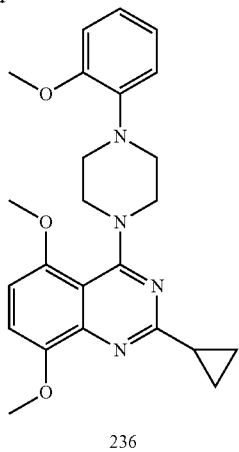

236

Example 162: 2-cyclopropyl-5,8-dimethoxy-4-[4-(2-methoxy-phenyl)-piperazin-1-yl]-quinazoline (236)

Finely powdered 2,5-dimethoxy-benzoic acid (230) (500 mg, 2.75 mmol) was added in portions over 3 min to concentrated HNO₃ (2 mL) at 0-2° C. After the addition, the mixture was kept stirring at 0-2° C. for a further 30 min, and then poured into ice-water (25 mL). The yellow resulting solid was filtered off, washed with cold water, and purified by Combi-Flash to give compound (231) (551 mg, yield: 88%) as a yellow solid.

¹H NMR (400 MHz, DMSO-d₆): δ=13.73 (brs, 1H), 7.42-7.35 (m, 2H), 3.84 (s, 3H), 3.82 (s, 3H).

Compound (231) (551 mg, 2.43 mmol) and 10% Pd/C (55 mg, 551 mg) in EtOH (11 mL) was hydrogenated at 50 psi for 4 h. The catalyst was removed by filtration and the solvent was evaporated under reduced pressure to give a crude product, which was purified by silica gel column chromatography (from DCM to DCM/MeOH=400/1) to give compound (232) (282 mg, yield: 58%) as a white solid.

¹H NMR (400 HMz, CDCl₃): δ=11.46 (brs, 1H), 6.74 (d, J=9.2 Hz, 1H), 6.66 (brs, 2H), 6.11 (d, J=8.4 Hz, 4H), 3.96 (s, 3H), 3.84 (s, 3H).

A solution of 2-amino-3,6-dimethoxy-benzoic acid (280 mg, 1.42 mmol) in water (13 mL) and acetic acid (0.5 mL) was stirred at 35° C. for 15 min. KOCN (288 mg, 3.6 mmol) was dissolved in water and added slowly to the suspension. The mixture was stirred at 35° C. for 30 min and NaOH (2.6 g, 63.9 mmol) was added slowly. The mixture was stirred at room temperature overnight. The reaction solution was acidified with 6 M HCl to pH=4. The resulting solid was collected by filtration and dried to give compound 233 (306 mg, yield: 97%) as a white solid.

¹H NMR (300 HMz, DMSO-d₆): δ=10.95 (brs, 1H), 10.18 (brs, 1H), 7.22 (d, J=9.0 Hz, 1H), 6.64 (d, J=9.0 Hz, 1H), 3.80 (s, 3H), 3.79 (s, 3H).

A solution of 5,8-dimethoxy-1H-quinazoline-2,4-dione (233) (300 mg, 1.35 mmol) in POCl₃ (2 mL) was stirred at 110° C. for 5 h. The reaction mixture was cooled to room temperature and added to ice-water (20 mL) dropwise. The mixture was extracted with DCM (30 mL×2) and the extracts were dried over Na₂SO₄. The solution was concentrated in vacuum and the residue was purified by silica gel column chromatography (DCM) to give compound (234) (181 mg, yield: 52%) as a yellow solid.

¹H NMR (300 HMz, CDCl₃): δ=7.26 (d, J=9.0 Hz, 1H), 6.97 (d, J=9.0 Hz, 1H), 3.96 (s, 3H), 3.84 (s, 3H).

To a solution of 2,4-dichloro-5,8-dimethoxy-quinazoline (234) (192 mg, 0.74 mmol) and DIPEA (106 mg, 0.82 mmol) in EtOAc (10 mL) was added 1-(2-methoxy-phenyl)-piperazine (1.4 g, 7.4 mmol), and the reaction mixture was stirred at room temperature for 1 h. Water was added and the mixture was extracted with EtOAc (50 mL×2). The organic layer was washed with brine (50 mL), dried over Na₂SO₄, concentrated, and purified by silica gel column chromatography (PE/EtOAc=5/1) to give an impure compound, which was further purified by prep-TLC (PE/EtOAc=1/1) to afford compound (235) (200 mg, yield: 65%) as pale solid.

¹H NMR (400 HMz, CDCl₃): δ=7.06-7.02 (m, 2H), 6.96-6.87 (m, 3H), 6.73 (d, J=8.8 Hz, 1H), 3.97 (s, 3H), 3.93 (s, 3H), 3.90 (s, 3H), 3.90-3.84 (m, 4H), 3.22-3.16 (m, 4H).

A solution of compound (235) (230 mg, 0.55 mmol), cyclopropylbronic acid (143 mg, 1.7 mmol), t-BuOK (123 mg, 1.1 mmol), and Pd(PPh₃)₄ (64 mg, 0.06 mmol) in toluene (20 mL) was purged with N₂ for 15 min. Then the mixture was stirred at reflux overnight under N₂. The mixture was concentrated to dryness under reduced pressure. The residue was diluted with water (40 mL). The mixture was extracted with DCM (40 mL×2). The extracts were washed with brine (40 mL) and dried over Na₂SO₄. The solution was concentrated in vacuum and the residue was purified by silica gel column chromatography (DCM/MeOH=50/1), further by prep-HPLC to give compound (236), (67.6 mg, yield: 29%) as a yellow solid.

¹H NMR (400 HMz, CDCl₃): δ=7.03-7.01 (m, 1H), 6.98-6.94 (m, 3H), 6.90-6.88 (m, 1H), 6.64 (d, J=8.8 Hz, 1H), 3.99 (s, 3H), 3.89 (s, 6H), 3.75-3.71 (m, 4H), 3.18-3.14 (m, 4H), 2.32 (m, 1H), 1.16-1.12 (m, 2H), 0.97-0.95 (m, 2H). MS: m/z 421.2 (M+H⁺).

Example 163: 2-cyclopropyl-4-[4-(2-methoxy-phenyl)-piperazin-1-yl]-quinazoline (237)

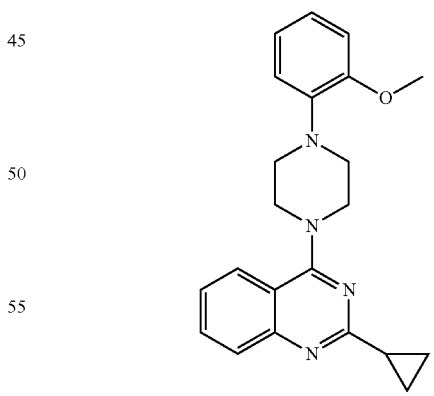

237

The title compound was prepared as described for compound (236), using the similar route and procedure.

¹H NMR (300 HMz, CDCl₃): δ=7.88 (d, J=8.1 Hz, 1H), 7.82 (d, J=8.4 Hz, 1H), 7.69-7.65 (m, 1H), 3.95-3.93 (m, 4H), 3.92 (s, 3H), 3.27-3.23 (m, 4H), 2.27-2.18 (m, 1H), 1.23-1.18 (m, 2H), 1.05-0.98 (m, 2H). MS: m/z 361.2 (M+H⁺).

Example 164: 2-cyclopropyl-5,6-dimethoxy-4-[4-(2-methoxy-phenyl)-piperazin-1-yl]-quinazoline (238)

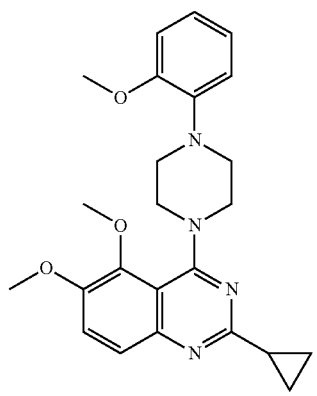

238

The title compound was prepared as described for compound (236), using the similar route and procedure.

$^1$H NMR (400 MHz, DMSO-d$_6$): δ=7.66 (d, J=8.8 Hz, 1H) 7.47 (d, J=9.2 Hz, 1H), 7.00-6.95 (m, 3H), 6.92-6.88 (m, 1H), 3.89 (s, 3H), 3.80 (s, 3H), 3.70 (s, 3H), 3.55-3.51 (m, 4H), 3.15-3.11 (m, 4H), 2.09-2.02 (m, 1H), 1.06-1.02 (m, 2H), 0.93-0.83 (m, 2H). MS: m/z 421.2 (M+H$^+$).

Example 165: 2-cyclopropyl-5-methoxy-4-[4-(2-methoxy-phenyl)-piperazin-1-yl]-quinazoline (239)

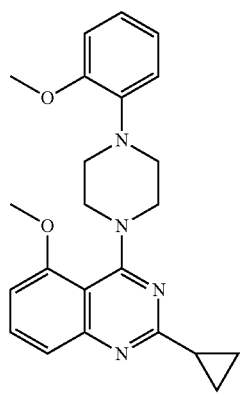

239

The title compound was prepared as described for compound (236), using the similar route and procedure.

$^1$H NMR (400 MHz, DMSO-d$_6$): δ=7.62 (t, J=8.0 Hz, 1H) 7.20 (d, J=8.4 Hz, 1H), 7.00-6.87 (m, 5H), 3.93 (s, 3H), 3.80 (s, 3H), 3.62-3.58 (m, 4H), 3.11-3.07 (m, 4H), 2.06-2.01 (m, 1H), 1.05-1.02 (m, 2H), 0.95-0.92 (m, 2H). MS: m/z 391.3 (M+H$^+$).

Example 166: 2-cyclopropyl-8-methoxy-4-[4-(2-methoxy-phenyl)-piperazin-1-yl]-quinazoline (240)

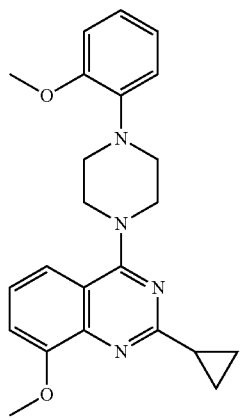

240

The title compound was prepared as described for compound (236), using the similar route and procedure.

$^1$H NMR (400 MHz, DMSO-d$_6$): δ=7.50 (d, J=8.4 Hz, 1H), 7.34 (t, J=8.0 Hz, 1H) 7.22 (d, J=7.6 Hz, 1H), 6.99-6.89 (m, 4H), 3.92 (s, 3H), 3.81 (s, 3H), 3.76-3.74 (m, 4H), 3.16-3.13 (m, 4H), 2.15-2.11 (m, 1H), 1.07-1.02 (m, 2H), 0.98-0.93 (m, 2H). MS: m/z 391.1 (M+H$^+$).

Scheme 24:

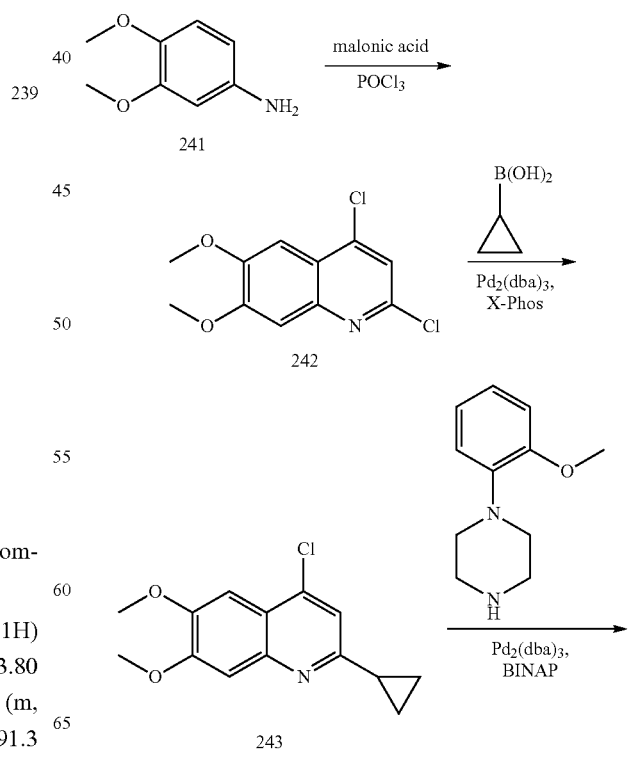

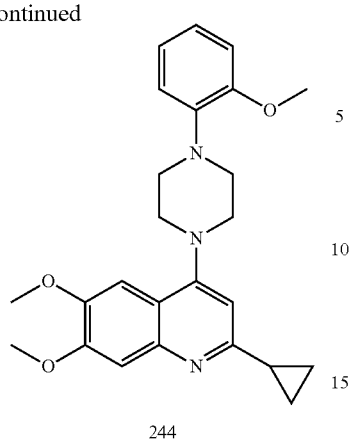

244

Example 167: 2-cyclopropyl-6,7-dimethoxy-4-[4-(2-methoxy-phenyl)-piperazin-1-yl]-quinoline (244)

To a solution of compound (241) (5 g, 31 mmol) in POCl$_3$ (20 mL) was added malonic acid (4.1 g, 39 mmol), it was then heated to 90° C. and stirred overnight. The resultant was poured into cold aqueous NaOH solution and the precipitate was filtered to afford crude compound (242) (6.4 g, yield: 76%), which was used for next step without further purification.

To a solution of compound (242) (500 mg, 1.94 mmol) in toluene (20 mL) was added cyclopropylboronicacid (325 mg, 3.77 mmol), Pd$_2$(dba)$_3$ (40 mg, 0.038 mmol), x-Phos (37 mg, 0.078 mmol) and K$_3$PO$_4$ (822 mg, 3.88 mmol), it was then refluxed overnight under N$_2$ atmosphere. The resultant was concentrated in vacuum and the residue was purified by Combi flash (from PE to EA/PE=3/7) to afford compound (243) (230 mg, yield: 45%) as a white solid.

To a solution of compound (243) (100 mg, 0.38 mmol) in toluene was added Pd$_2$(dba)$_3$ (6.8 mg, 0.008 mmol), BINAP (9.5 mg, 0.018 mmol) and t-BuOK (85 mg, 0.75 mmol), and the mixture was refluxed overnight. The reaction solution was concentrated to dryness in vacuum and the residue was purified by pre-HPLC to afford compound (244), (10 mg, yield: 6.3%) as white solid.

$^1$H NMR (400 MHz, CDCl$_3$): δ=7.30-7.25 (m, 2H), 7.07-7.04 (m, 2H), 6.97-6.93 (m, 2H), 6.66 (s, 1H), 4.01 (s, 3H), 3.98 (s, 3H), 3.91 (s, 3H), 3.46-3.36 (m, 8H), 2.17-2.13 (m, 1H), 1.08-1.03 (m, 4H). MS: m/z 420.2 (M+H$^+$).

Scheme 25:

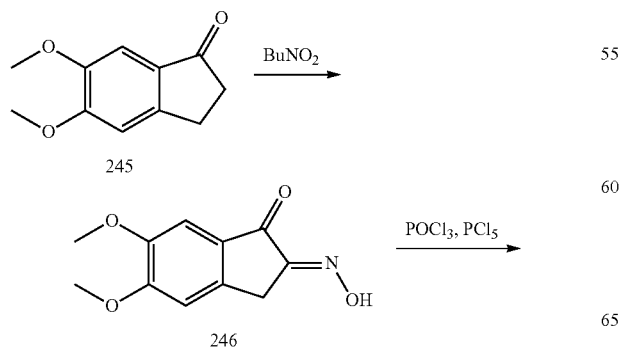

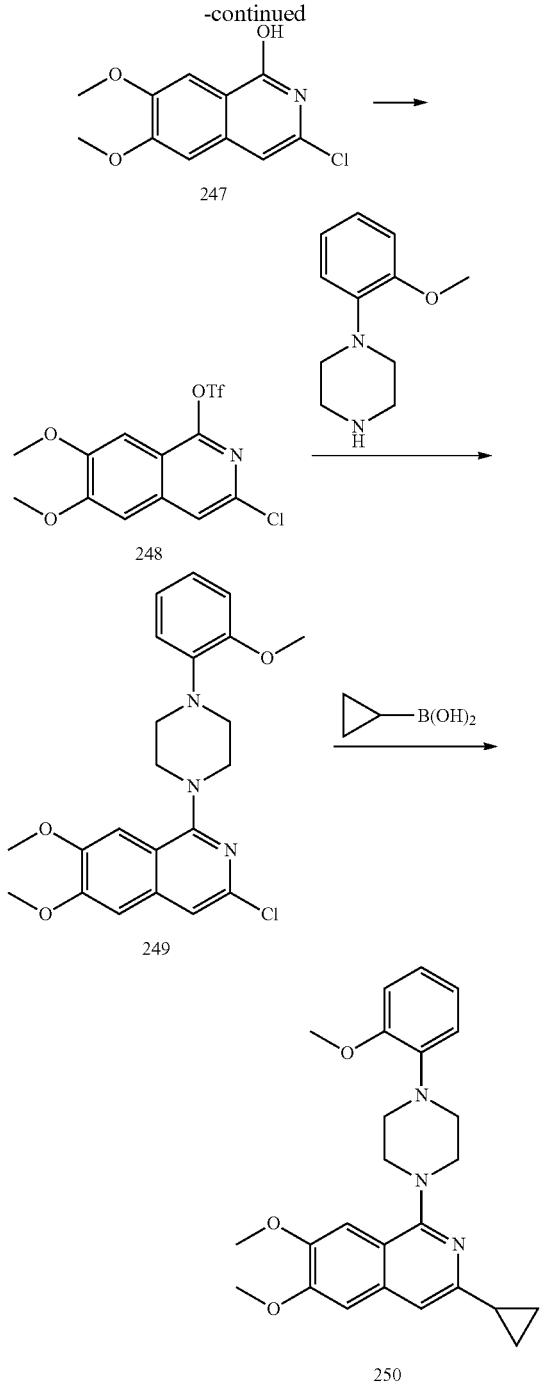

Example 168: 3-cyclopropyl-6,7-dimethoxy-1-[4-(2-methoxy-phenyl)-piperazin-1-yl]-isoquinoline (250)

To a solution of compound (245) (6.55 g, 0.034 mol) in MeOH (50 mL) was added HCl (3.5 mL), 1-nitro-butane (4.68 g, 0.04 mol) in MeOH (10 mL) and the mixture was stirred at 40° C. for 3 hours. The mixture was cooled to room temperature and filtered to give compound (246) (3.65 g, 49%) as yellow solid.

To a solution of compound (246) (885 mg, 4.00 mmol) in POCl$_3$ (15 mL) was added PCl$_5$ (1.30 g, 6.40 mmol) at 0° C. dropwise. Large amount of HCl gas was given out until the solution was stan. The reaction mixture was stirred at 30° C. for 2 h and the mixture was concentrated to remove most of POCl₃ under reduced pressure. 10 mL of ice water was added and the resulting solid was filtered. The solid was washed with water to give compound (247)(480 mg, yield: 50%) as brown solid.

To an ice-cooled solution of compound (247) (360 mg, 1.51 mmol) in DCM (5 mL) and pyridine (5 mL) was added trifluoromethanesulfonic anhydride (0.5 mL) at 0° C. dropwise. The reaction mixture was stirred at room temperature overnight. The mixture was concentrated to dryness under reduced pressure. The reaction mixture was diluted with EtOAc (60 mL) and the mixture was washed with brine (30 mL×2), dried over anhydrous Na₂SO₄ and filtered. The solution was concentrated in vacuum to give crude compound (248) (400 mg, yield: 71%) as black oil ¹H NMR (400 MHz, CDCl₃): δ=7.60 (s, 1H), 7.25 (s, 1H), 7.06 (s, 1H), 4.05 (s, 6H).

To a solution of compound (248) (400 mg, 1.08 mmol) in DMF (10 mL) was added 1-(2-methoxy-phenyl)-piperazine (4.14 g, 21.6 mmol). Then the mixture was stirred at 70° C. overnight. The reaction mixture was extracted with EtOAc (30 mL×2) and the extracts were washed with brine (30 mL×2), dried over anhydrous Na₂SO₄ and filtered. The solution was concentrated under reduced pressure and the residue was purified by silica gel column chromatography (from PE to PE/EtOc=5/1) to give compound (249) (260 mg, yield: 58%) as yellow oil.

¹H NMR (400 MHz, CDCl₃): δ=7.39 (s, H), 7.31 (s, 1H), 7.29 (s, 1H), 7.02-6.89 (m, 4H), 3.94 (s, 3H), 3.89 (s, 3H), 3.83 (s, 3H), 3.49-3.46 (m, 4H), 3.26-3.23 (m, 4H).

A solution of compound (249) (200 mg, 0.48 mmol), cyclopropyl boronic acid (125 mg, 1.45 mmol), t-BuOK (108 mg, 0.97 mmol) and Pd(PPh₃)₄ (56 mg, 0.05 mmol) in toluene (10 mL) was degassed and purged with N₂ for 15 min. The mixture was stirred at 110° C. overnight. The reaction mixture was diluted with EA (60 mL) and washed with brine (30 mL×2), dried over anhydrous Na₂SO₄ and filtered. The solution was concentrated under reduced pressure. The crude was purified by Prep-TLC (PE/EtOAc=5/1) to give compound (250) (20 mg, yield: 10%) as white solid.

¹H NMR (400 MHz, DMSO-d₆): δ=7.25 (s, 1H), 7.13-7.11 (m, 2H), 7.01-6.90 (m, 4H), 3.89 (s, 3H), 3.88 (s, 3H), 3.81 (s, 3H), 3.37-3.30 (m, 4H), 3.22-3.18 (m, 4H), 2.05-2.02 (m, 1H), 0.99-0.95 (m, 2H) 0.89-0.85 (m, 2H), MS: m/z 420.3 (M+H⁺).

Scheme 26:

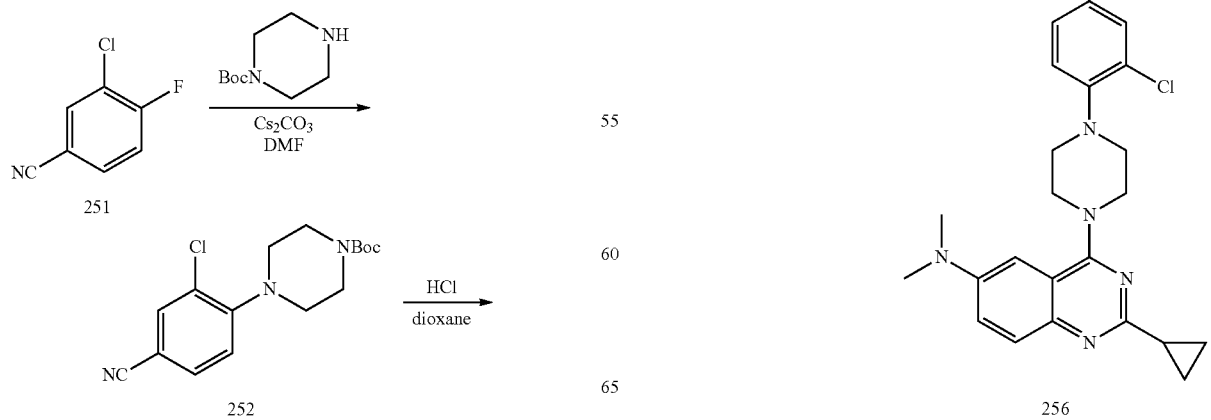

Example 169: 3-chloro-4-(4-(2-cyclopropyl-6-(dimethylamino)quinazolin-4-yl)piperazin-1-yl)benzonitrile (255)

A mixture of compound (251) (1.00 g, 6.40 mmol), piperazine-1-carboxylic acid tert-butyl ester (1.43 g, 7.70 mmol) and $Cs_2CO_3$ (2.45 g, 7.70 mmol) in DMF (10 mL) was stirred at 100° C. for 3 h. After cooled to room temperature, the reaction mixture was diluted with EtOAc (80 mL). The mixture was washed with water (50 mL), brine (30 mL×3), dried over anhydrous $Na_2SO_4$ and filtered. The filtrate was evaporated in vacuum to residue, which was purified by silica gel column chromatography (from PE to PE/EA=10/1) to give compound (252) (1.2 g, yield: 57%) as white solid.

$^1$H NMR (400 MHz, $CDCl_3$): δ=7.64 (s, 1H), 7.51 (d, J=8.4 Hz, 1H), 7.02 (d, J=8.8 Hz, 1H), 3.61-3.60 (m, 4H), 3.14-3.06 (m, 4H), 1.48 (s, 9H).

To a stirred solution of compound (252) (1.20 g, 3.70 mmol) in 1,4-dioxane (5 mL) was added HCl/dioxane (4M, 5 mL) dropwise. The mixture was stirred at room temperature for 2 h and evaporated in vacuum to dryness. The residue was suspended in ethyl ether (10 mL) and the resulting solid was filtered to give HCl salt of compound (253) (945 mg, yield: 100%) as white solid.

$^1$H NMR (300 MHz, DMSO-$d_6$): δ=9.28 (brs, 2H), 8.01 (d, J=1.8 Hz, 1H), 7.78 (dd, J=8.4, 1.8 Hz, 1H), 7.33 (d, J=8.4 Hz, 1H), 3.37-3.30 (m, 4H), 3.30-3.21 (m, 4H).

A mixture of compound (253) (940 mg, 3.70 mmol), 6-bromo-2-cyclopropyl-quinazolin-4-ol (966 mg, 3.70 mmol), DBU (3.20 g, 7.30 mmol) and BOP (834 mg, 5.50 mmol) in MeCN (20 mL) was stirred at room temperature for 16 h. The suspension was filtered and the cake was washed with MeCN (10 mL×2) and evaporated in vacuum to dryness to give compound (254) (570 mg, yield: 34%) as yellow solid.

$^1$H NMR (400 MHz, $CDCl_3$): δ=7.97 (d, J=2.0 Hz, 1H), 7.77-7.72 (m, 1H), 7.71-7.65 (m, 2H), 7.55-7.53 (m, 1H), 7.09 (d, J=8.4 Hz, 1H), 3.96-3.82 (m, 4H), 3.39-3.26 (m, 4H), 2.26-2.13 (m, 1H), 1.21-1.13 (m, 2H), 1.11-0.99 (m, 2H).

To a mixture of compound (254) (570 mg, 1.20 mmol), t-BuONa (351 mg, 3.70 mmol) and a solution of $Me_2NH$ in THF (3 mL, 2M) in anhydrous toluene (10 mL) was added BINAP (37 mg, 0.06 mmol) and $Pd_2(dba)_3$ (34 mg, 0.06 mmol). The mixture was stirred at 116° C. under $N_2$ for 16 h. After cooled to room temperature, the reaction solution was filtered. The filtrate was evaporated in vacuum to residue, which was purified by silica gel column chromatography (from DCM to DCM/MeOH=50/1), then further by prep-HPLC to afford compound (255), (82 mg, yield: 16%) as yellow solid.

$^1$H NMR (400 MHz, $CDCl_3$): δ=7.74 (d, J=9.2 Hz, 1H), 7.65 (d, J=2.0 Hz, 1H), 7.53 (dd, J=8.4, 2.0 Hz, 1H), 7.36 (dd, J=9.2, 2.8 Hz, 1H), 7.09 (d, J=8.4 Hz, 1H), 6.83 (d, J=2.8 Hz, 1H), 3.88-3.80 (m, 4H), 3.38-3.29 (m, 4H), 3.04 (s, 6H), 2.24-2.15 (m, 1H), 1.17-1.09 (m, 2H), 1.01-0.94 (m, 2H). MS: m/z 433.2 (M+H$^+$).

Example 170: 3-chloro-4-[4-(2-cyclopropyl-6-dimethylamino-quinazolin-4-yl)-piperazin-1-yl]-benzamide (256)

To a stirred concentrated $H_2SO_4$ (2 mL) at 0° C. was added compound (255) (60 mg, 0.14 mmol). The mixture was stirred at room temperature for 16 h and poured into ice water (50 mL) dropwise. The aqueous mixture was neutralized with sat. $NaHCO_3$ to pH=7 and extracted with EtOAc (30 mL×2). The combined organic layers were washed with brine (30 mL×2), dried over anhydrous $Na_2SO_4$ and filtered.

The filtrate was evaporated in vacuum to residue, which was purified by prep-HPLC to give compound (256), (20 mg, yield: 32%) as yellow solid.

$^1$H NMR (400 MHz, $CDCl_3$): δ=7.86 (d, J=2.0 Hz, 1H), 7.75 (d, J=8.8 Hz, 1H), 7.70 (dd, J=8.4, 2.4 Hz, 1H), 7.35 (dd, J=9.2, 2.8 Hz, 1H), 7.10 (d, J=8.0 Hz, 1H), 6.85 (d, J=2.4 Hz, 1H), 3.88-3.80 (m, 4H), 3.36-3.27 (m, 4H), 3.05 (s, 6H), 2.23-2.16 (m, 1H), 1.18-1.10 (m, 2H), 1.01-0.94 (m, 2H). MS: m/z 451.1 (M+H$^+$).

Scheme 27:

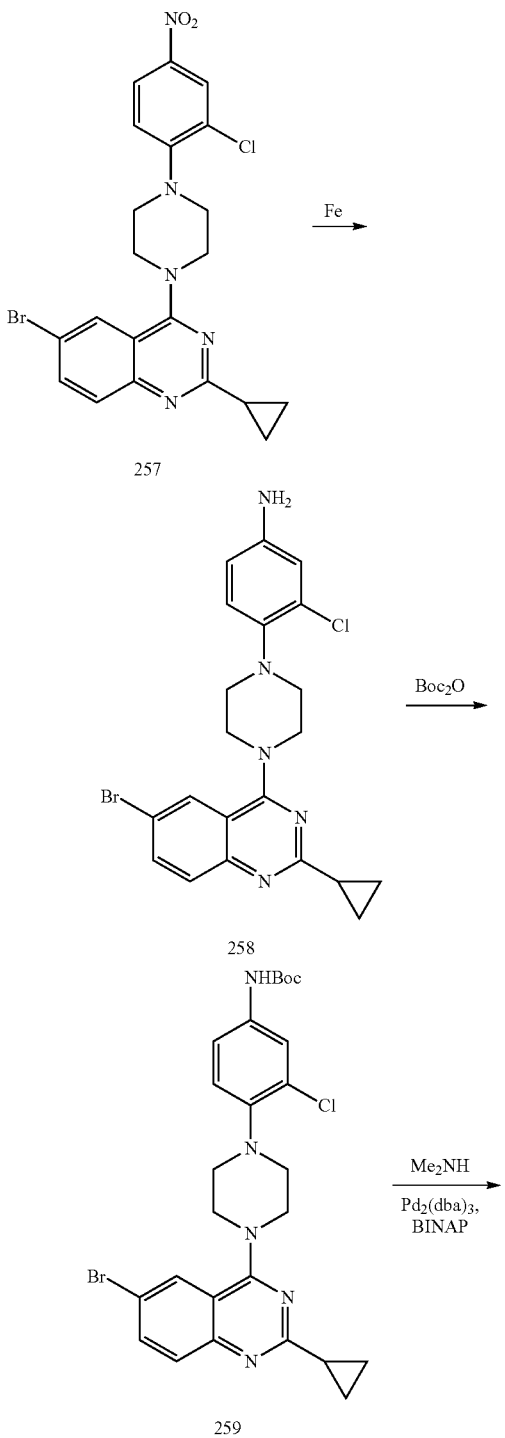

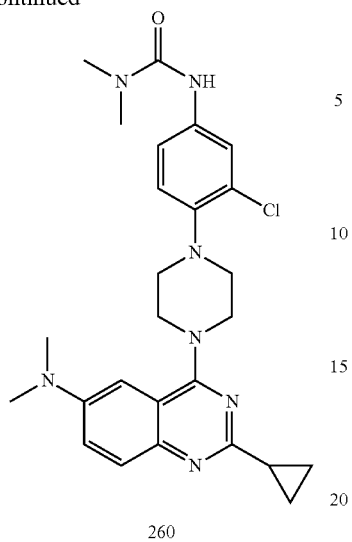

260

Example 171: 3-{3-chloro-4-[4-(2-cyclopropyl-6-dimethylamino-quinazolin-4-yl)-piperazin-1-yl]-phenyl}-1,1-dimethyl-urea (260)

A mixture of compound (257) (560 mg, 1.20 mmol), active Fe powder (322 mg, 5.80 mmol), NH₄Cl (123 mg, 2.30 mmol) and water (3 mL) in EtOH (15 mL) was refluxed for 2 h. The reaction mixture was cooled to room temperature, filtered and the filtrate was evaporated in vacuum to residue, which was diluted with EtOAc (50 mL), suspended with anhydrous Na₂SO₄ and filtered. The filtrate was evaporated in vacuum to dryness to afford compound (258) (320 mg, yield: 61%) as yellow solid.

¹H NMR (400 MHz, CDCl₃): δ=7.99-7.98 (m, 1H), 7.83-7.71 (m, 2H), 6.91 (d, J=8.4 Hz, 1H), 6.77 (d, J=2.8 Hz, 1H), 6.57 (dd, J=8.4, 2.8 Hz, 1H), 3.99-3.88 (m, 4H), 3.55 (brs, 2H), 3.18-3.05 (m, 4H), 2.33-2.22 (m, 1H), 1.24-1.13 (m, 2H), 1.10-1.01 (m, 2H).

To a stirred solution of compound (258) (320 mg, 0.70 mmol) in DCM (10 mL) was added Boc₂O (305 mg, 1.40 mmol) and DMAP (34 mg, 0.30 mmol) at 0° C. The mixture was stirred at room temperature for 2 hours and diluted with DCM (60 mL). The solution was washed with water (30 mL) and brine (30 mL×2), dried over anhydrous Na₂SO₄ and filtered. The filtrate was evaporated in vacuum to residue, which was purified by silica gel column chromatography (from DCM to DCM/MeOH=100/1) to afford compound (259) (230 mg, yield: 59%) as white solid.

¹H NMR (400 MHz, CDCl₃): δ=8.00-7.98 (m, 1H), 7.75-7.67 (m, 2H), 7.33 (d, J=2.4 Hz, 1H), 7.17 (dd, J=8.4, 2.4 Hz, 1H), 7.05 (d, J=8.8 Hz, 1H), 3.96-3.85 (m, 4H), 3.27-3.19 (m, 4H), 2.25-2.18 (m, 1H), 1.47 (s, 9H), 1.20-1.13 (m, 2H), 1.05-0.98 (m, 2H).

To a mixture of compound (259) (230 mg, 0.41 mmol), t-BuONa (118 mg, 1.2 mmol) and BINAP (12 mg, 0.02 mmol) in anhydrous toluene (10 mL) was added a solution of Me₂NH in THF (1 mL, 2M) and Pd₂(dba)₃ (11 mg, 0.02 mmol). The mixture was stirred at 116° C. under N₂ for 16 h. After cooled to room temperature filtered. The filtrate was evaporated in vacuum to residue, which was purified by silica gel chromatography (from DCM to DCM/MeOH=100/1) and then prep-HPLC to afford compound (260), (21 mg, yield: 10%) as yellow solid.

¹H NMR (300 MHz, CDCl₃): δ=7.73 (d, J=9.0 Hz, 1H), 7.48 (d, J=2.7 Hz, 1H), 7.33 (dd, J=9.3, 3.0 Hz, 1H), 7.29-7.23 (m, 1H), 7.02 (d, J=8.7 Hz, 1H), 6.86 (d, J=2.7 Hz, 1H), 6.21 (brs, 1H), 3.86-3.77 (m, 4H), 3.23-3.17 (m, 4H), 3.03 (s, 6H), 3.02 (s, 6H), 2.25-2.16 (m, 1H), 1.19-1.10 (m, 2H), 1.00-0.92 (m, 2H). MS: m/z 494.2 (M+H⁺).

Example 172: 6-bromo-2-cyclopropyl-4-[4-(2,5-dimethoxy-phenyl)-piperazin-1-yl]-quinazoline (261)

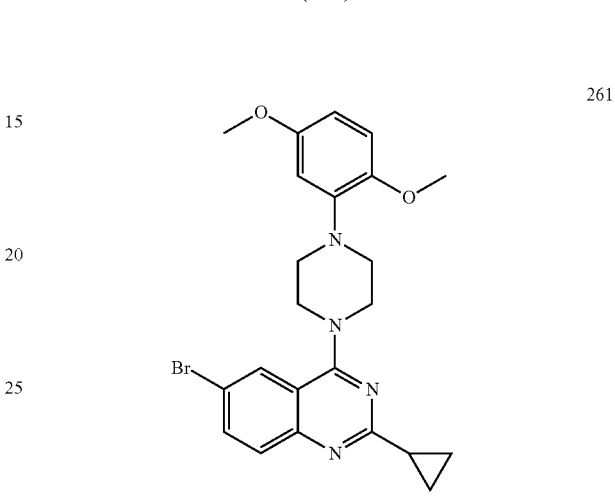

261

The title compound was prepared as described for compound (255), using the similar route and procedure.

¹H NMR (400 MHz, CDCl₃): δ=7.98 (s, 1H), 7.74-7.68 (m, 2H), 6.80 (d, J=8.4 Hz, 1H), 6.56 (d, J=2.8 Hz, 1H), 6.52 (dd, J=8.4, 2.8 Hz, 1H), 3.97-3.86 (m, 4H), 3.85 (s, 3H), 3.77 (s, 3H), 3.24-3.21 (m, 4H), 2.23-2.19 (m, 1H), 1.19-1.15 (m, 2H), 1.04-0.99 (m, 2H). MS: m/z 471.2 (M+H⁺).

Example 173: {2-cyclopropyl-4-[4-(2,5-dimethoxy-phenyl)-piperazin-1-yl]-quinazolin-6-yl}-dimethyl-amine (262)

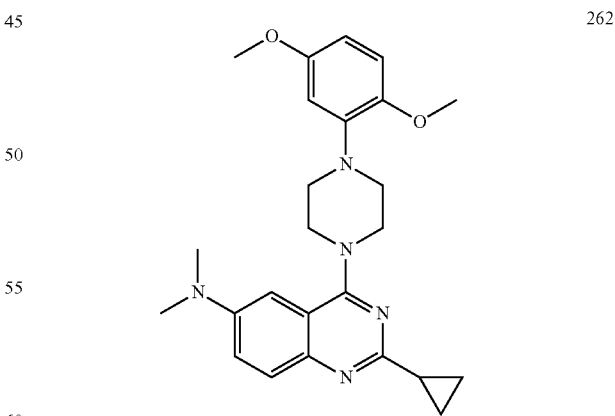

262

The title compound was prepared as described for compound (255), using the similar route and procedure.

¹H NMR (400 MHz, CDCl₃): δ=7.73 (d, J=12.0 Hz, 1H), 7.33 (dd, J=12.4, 4.0 Hz, 1H), 6.86 (d, J=3.6 Hz, 1H), 6.80 (d, J=11.6 Hz, 1H), 6.59 (d, J=4.0 Hz, 1H), 6.51 (dd, J=11.6, 3.6 Hz, 1H), 3.85 (s, 3H), 3.83-3.80 (m, 4H), 3.77 (s, 3H), 3.26-3.23 (m, 4H), 3.03 (s, 6H), 2.21-2.16 (m, 1H), 1.17-1.12 (m, 2H), 0.99-0.93 (m, 2H). MS: m/z 434.3 (M+H⁺).

Example 174: 6-bromo-2-cyclopropyl-4-[4-(2-methoxy-5-methyl-phenyl)-piperazin-1-yl]-quinazoline (263)

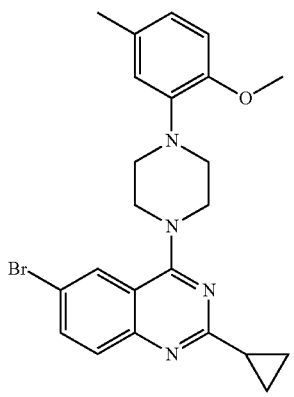

The title compound was prepared as described for compound (255), using the similar route and procedure.

¹H NMR (400 MHz, CDCl₃): δ=7.99 (s, 1H), 7.74-7.66 (m, 2H), 6.84-6.78 (m, 3H), 3.91-3.88 (m, 4H), 3.87 (s, 3H), 3.23-3.21 (m, 4H), 2.30 (s, 3H), 2.21-2.17 (m, 1H), 1.20-1.16 (m, 2H), 1.04-1.00 (m, 2H). MS: m/z 455.2 (M+H⁺).

Example 175: {2-cyclopropyl-4-[4-(2-methoxy-5-methyl-phenyl)-piperazin-1-yl]-quinazolin-6-yl}-dimethyl-amine (264)

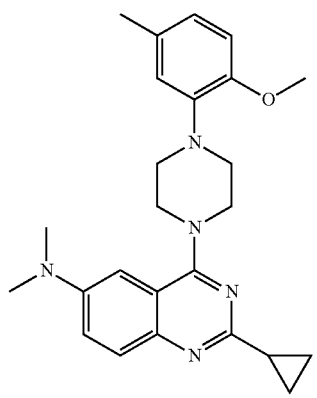

The title compound was prepared as described for compound (255), using the similar route and procedure.

¹H NMR (300 MHz, CDCl₃): δ=7.73 (d, J=9.3 Hz, 1H), 7.33 (dd, J=9.3, 3.0 Hz, 1H), 6.88 (d, J=2.7 Hz, 1H), 6.83-6.77 (m, 3H), 3.87 (s, 3H), 3.84-3.80 (m, 4H), 3.25-3.22 (m, 4H), 3.03 (s, 6H), 2.30 (s, 3H), 2.23-2.16 (m, 1H), 1.17-1.13 (m, 2H), 0.99-0.93 (m, 2H). MS: m/z 418.3 (M+H⁺).

Example 176: 6-bromo-2-cyclopropyl-4-[4-(4-fluoro-2-methoxy-phenyl)-piperazin-1-yl]-quinazoline (265)

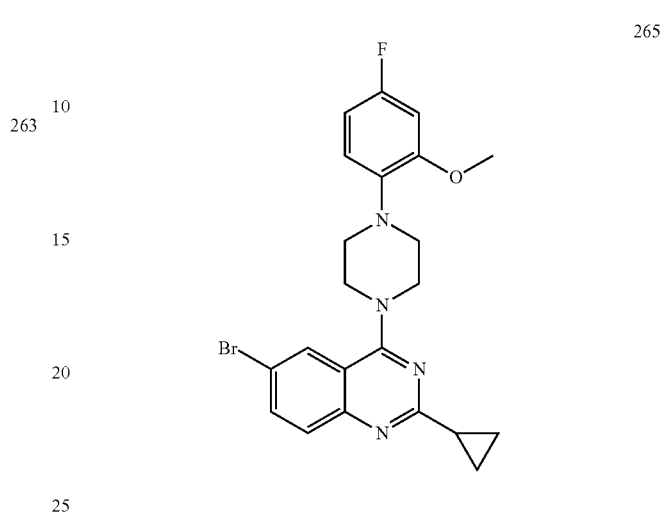

The title compound was prepared as described for compound (255), using the similar route and procedure.

¹H NMR (300 MHz, CDCl₃): δ=7.97 (s, 1H), 7.74-7.70 (m, 2H), 6.88 (t, J=9.1 Hz, 1H), 6.67-6.60 (m, 2H), 4.00-3.90 (m, 4H), 3.88 (s, 3H), 3.18-3.15 (m, 4H), 2.26-2.20 (m, 1H), 1.20-1.15 (m, 2H), 1.06-1.00 (m, 2H). MS: m/z 457.2 (M+H⁺).

Example 177: {2-cyclopropyl-4-[4-(4-fluoro-2-methoxy-phenyl)-piperazin-1-yl]-quinazolin-6-yl}-dimethyl-amine (266)

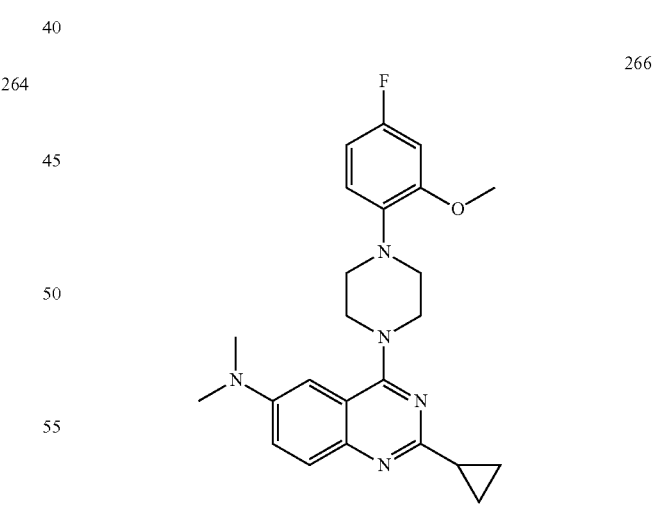

The title compound was prepared as described for compound (255), using the similar route and procedure.

¹H NMR (300 MHz, CDCl₃): δ=7.74 (d, J=9.0 Hz, 1H), 7.34 (dd, J=9.3, 2.7 Hz, 1H), 6.94-6.85 (m, 2H), 6.68-6.58 (m, 3H), 3.88 (s, 3H), 3.86-3.78 (m, 4H), 3.23-3.16 (m, 4H), 3.03 (s, 6H), 2.24-2.08 (m, 1H), 1.19-1.10 (m, 2H), 1.06-0.90 (m, 2H). MS: m/z 422.3 (M+H⁺).

Example 178: 4-[4-(6-bromo-2-cyclopropyl-quinazolin-4-yl)-piperazin-1-yl]-3-methoxy-benzonitrile (267)

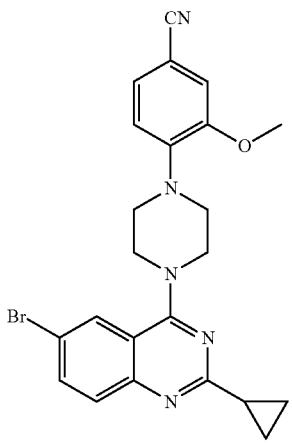

The title compound was prepared as described for compound (255), using the similar route and procedure.

$^1$H NMR (300 MHz, CDCl$_3$): δ=7.96 (s, 1H), 7.76-7.68 (m, 2H), 7.26-7.24 (m, 1H), 7.07 (d, J=1.5 Hz, 1H), 6.92 (d, J=8.4 Hz, 1H), 3.98-3.84 (m, 7H), 3.38-3.26 (m, 4H), 2.26-2.16 (m, 1H), 1.22-1.13 (m, 2H), 1.09-0.96 (m, 2H). MS: m/z 464.2 (M+H$^+$).

Example 179: 4-[4-(2-cyclopropyl-6-dimethyl-amino-quinazolin-4-yl)-piperazin-1-yl]-3-methoxy-benzonitrile (268)

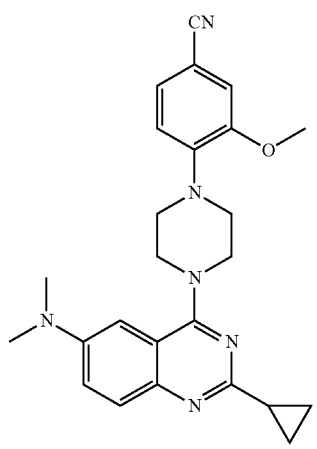

The title compound was prepared as described for compound (255), using the similar route and procedure.

$^1$H NMR (400 MHz, CDCl$_3$): δ=7.74 (d, J=9.2 Hz, 1H), 7.35 (dd, J=9.6, 2.4 Hz, 1H), 7.27 (d, J=4.0 Hz, 1H), 7.08 (s, 1H), 6.95 (d, J=8.0 Hz, 1H), 6.85 (d, J=2.0 Hz, 1H), 3.92 (s, 3H), 3.82-3.80 (m, 4H), 3.35-3.32 (m, 4H), 3.04 (s, 6H), 2.22-2.18 (m, 1H), 1.15-1.13 (m, 2H), 1.00-0.95 (m, 2H). MS: m/z 429.3 (M+H$^+$).

Example 180: 6-bromo-2-cyclopropyl-4-[4-(2-methoxy-4-trifluoromethoxy-phenyl)-piperazin-1-yl]-quinazoline (269)

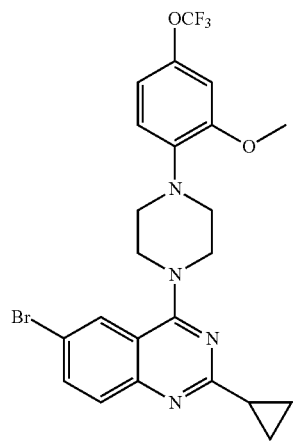

The title compound was prepared as described for compound (255), using the similar route and procedure.

$^1$H NMR (400 MHz, CDCl$_3$): δ=7.97 (d, J=1.2 Hz, 1H), 7.75-7.69 (m, 2H), 6.91 (d, J=8.4 Hz, 1H), 6.80 (d, J=8.4 Hz, 1H), 6.75 (s, 1H), 3.90 (s, 3H), 3.88-3.84 (m, 4H), 3.22-3.20 (m, 4H), 2.24-2.20 (m, 1H), 1.20-1.16 (m, 2H), 1.05-1.01 (m, 2H). MS: m/z 525.1 (M+H$^+$).

Example 181: {2-cyclopropyl-4-[4-(2-methoxy-4-trifluoromethoxy-phenyl)-piperazin-1-yl]-quinazolin-6-yl}-dimethyl-amine (270)

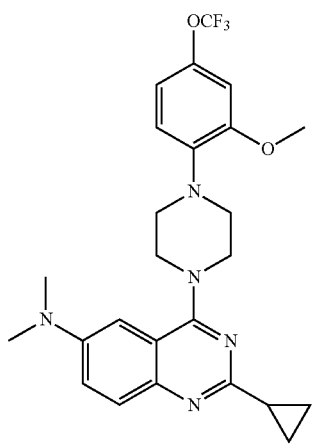

The title compound was prepared as described for compound (255), using the similar route and procedure.

$^1$H NMR (400 MHz, CDCl$_3$): δ=7.74 (d, J=9.6 Hz, 1H), 7.34 (dd, J=9.2, 2.8 Hz, 1H), 6.93 (d, J=8.8 Hz, 1H), 6.86 (d, J=2.8 Hz, 1H), 6.80 (dd, J=8.8, 2.4 Hz, 1H), 6.74 (d, J=2.4 Hz, 1H), 3.90 (s, 3H), 3.83-3.80 (m, 4H), 3.23-3.21 (m, 4H), 3.03 (s, 6H), 2.22-2.17 (m, 1H), 1.16-1.12 (m, 2H), 1.00-0.94 (m, 2H). MS: m/z 488.3 (M+H$^+$).

Example 182: 6-bromo-4-[4-(2-chloro-4-fluoro-phenyl)-piperazin-1-yl]-2-cyclopropyl-quinazoline (271)

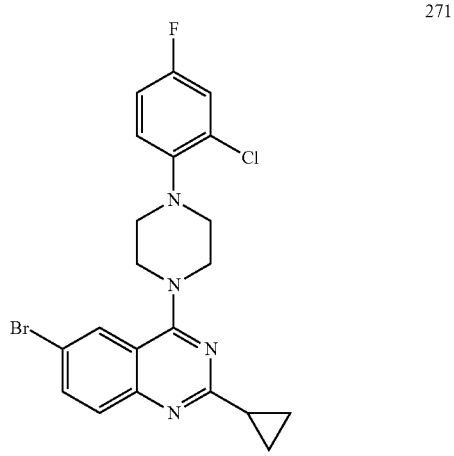 [SMILES: Fc1ccc(N2CCN(c3nc(C4CC4)nc4ccc(Br)cc34)CC2)c(Cl)c1]

The title compound was prepared as described for compound (255), using the similar route and procedure.

¹H NMR (400 MHz, CDCl₃): δ=7.96 (d, J=2.0 Hz, 1H), 7.74-7.70 (m, 2H), 7.15 (dd, J=8.4, 2.8 Hz, 1H), 7.04-6.93 (m, 2H), 3.88-3.86 (m, 4H), 3.15-3.13 (m, 4H), 2.23-2.19 (m, 1H), 1.19-1.15 (m, 2H), 1.04-1.00 (m, 2H). MS: m/z 463.1 (M+H⁺).

Example 183: {4-[4-(2-chloro-4-fluoro-phenyl)-piperazin-1-yl]-2-cyclopropyl-quinazolin-6-yl}-dimethyl-amine (272)

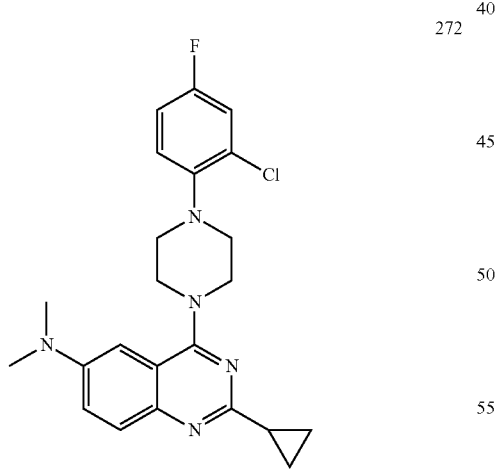

The title compound was prepared as described for compound (255), using the similar route and procedure.

¹H NMR (400 MHz, CDCl₃): δ=7.74 (d, J=9.6 Hz, 1H), 7.34 (dd, J=9.2, 2.4 Hz, 1H), 7.16 (dd, J=8.0, 2.8 Hz, 1H), 7.09-7.02 (m, 1H), 6.99-6.94 (m, 1H), 6.85 (d, J=2.8 Hz, 1H), 3.84-3.82 (m, 4H), 3.17-3.15 (m, 4H), 3.04 (s, 6H), 2.22-2.18 (m, 1H), 1.15-1.12 (m, 2H), 0.99-0.95 (m, 2H). MS: m/z 426.3 (M+H⁺).

Example 184: 6-bromo-4-[4-(2-chloro-4-methyl-phenyl)-piperazin-1-yl]-2-cyclopropyl-quinazoline (273)

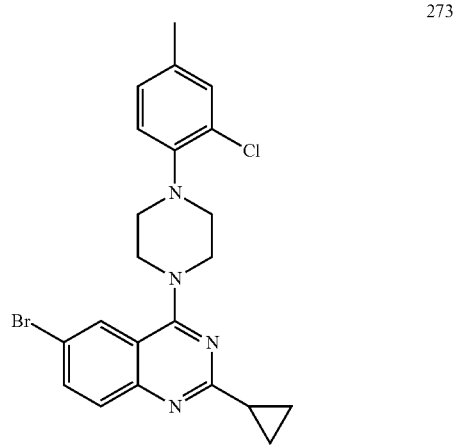 [SMILES: Cc1ccc(N2CCN(c3nc(C4CC4)nc4ccc(Br)cc34)CC2)c(Cl)c1]

The title compound was prepared as described for compound (255), using the similar route and procedure.

¹H NMR (400 MHz, CDCl₃): δ=7.98 (d, J=1.6 Hz, 1H), 7.75-7.69 (m, 2H), 7.22 (s, 1H), 7.04 (dd, J=8.0, 0.8 Hz, 1H), 6.96 (d, J=8.0 Hz, 1H), 3.90-3.88 (m, 4H), 3.18-3.16 (m, 4H), 2.29 (s, 3H), 2.28-2.20 (m, 1H), 1.20-1.17 (m, 2H), 1.05-1.01 (m, 2H). MS: m/z 459.1 (M+H⁺).

Example 185: {4-[4-(2-chloro-4-methyl-phenyl)-piperazin-1-yl]-2-cyclopropyl-quinazolin-6-yl}-dimethyl-amine (274)

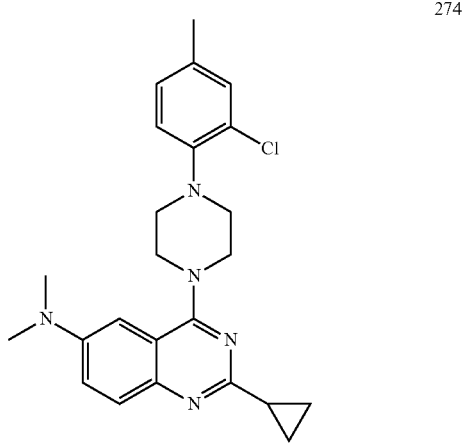 [SMILES: Cc1ccc(N2CCN(c3nc(C4CC4)nc4ccc(N(C)C)cc34)CC2)c(Cl)c1]

The title compound was prepared as described for compound (255), using the similar route and procedure.

¹H NMR (400 MHz, CDCl₃): δ=7.77 (d, J=4.4 Hz, 1H), 7.34 (dd, J=9.2, 2.8 Hz, 1H), 7.22 (d, J=1.2 Hz, 1H), 7.05 (d, J=1.2 Hz, 1H), 6.98 (d, J=8.0 Hz, 1H), 6.86 (d, J=2.4 Hz, 1H), 3.86-3.78 (m, 4H), 3.19-3.17 (m, 4H), 3.04 (s, 6H), 2.29 (s, 3H), 2.24-2.23 (m, 1H), 1.17-1.14 (m, 2H), 1.00-0.98 (m, 2H). MS: m/z 422.3 (M+H⁺).

Example 186: 6-bromo-4-[4-(4-chloro-2-methoxy-phenyl)-piperazin-1-yl]-2-cyclopropyl-quinazoline (275)

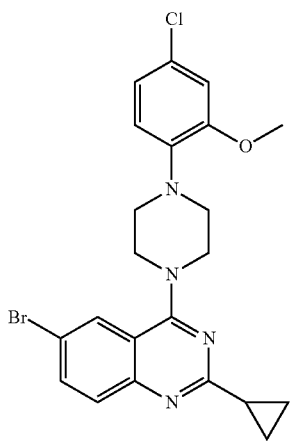

The title compound was prepared as described for compound (255), using the similar route and procedure.

¹H NMR (400 MHz, CDCl₃): δ=7.95 (d, J=1.6 Hz, 1H), 7.72-7.67 (m, 2H), 6.90-6.82 (m, 3H), 3.93-3.86 (m, 7H), 3.18-3.16 (m, 4H), 2.22-2.18 (m, 1H), 1.18-1.14 (m, 2H), 1.03-0.98 (m, 2H). MS: m/z 475.1 (M+H⁺).

Example 187: {4-[4-(4-chloro-2-methoxy-phenyl)-piperazin-1-yl]-2-cyclopropyl-quinazolin-6-yl}-dimethyl-amine (276)

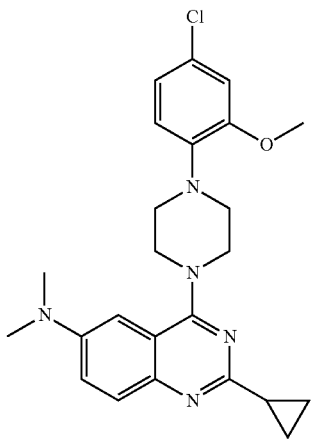

The title compound was prepared as described for compound (255), using the similar route and procedure.

¹H NMR (400 MHz, CDCl₃): δ=7.74 (d, J=12.0 Hz, 1H), 7.34 (dd, J=12.3, 3.6 Hz, 1H), 6.94-6.85 (m, 4H), 3.90 (s, 3H), 3.83-3.79 (m, 4H), 3.22-3.19 (m, 4H), 3.03 (s, 6H), 2.22-2.15 (m, 1H), 1.16-1.10 (m, 2H), 0.99-0.93 (m, 2H). MS: m/z 438.3 (M+H⁺).

Example 188: 6-bromo-2-cyclopropyl-4-[4-(4-methoxy-phenyl)-piperazin-1-yl]-quinazoline (277)

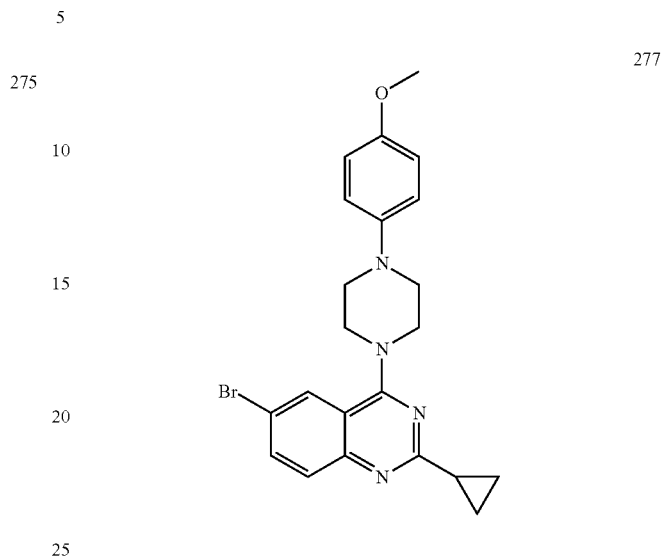

The title compound was prepared as described for compound (255), using the similar route and procedure.

¹H NMR (300 HMz, CDCl₃): δ=8.00 (d, J=1.8 Hz, 4H), 7.77-7.68 (m, 2H), 6.99-6.87 (m, 4H), 3.89-3.85 (m, 4H), 3.80 (s, 3H), 3.28-3.24 (m, 4H), 2.23-2.18 (m, 1H), 1.22-1.16 (m, 2H), 1.06-1.02 (m, 2H). MS: m/z 441.2 (M+H⁺).

Example 189: {2-cyclopropyl-4-[4-(4-methoxy-phenyl)-piperazin-1-yl]-quinazolin-6-yl}-dimethyl-amine (278)

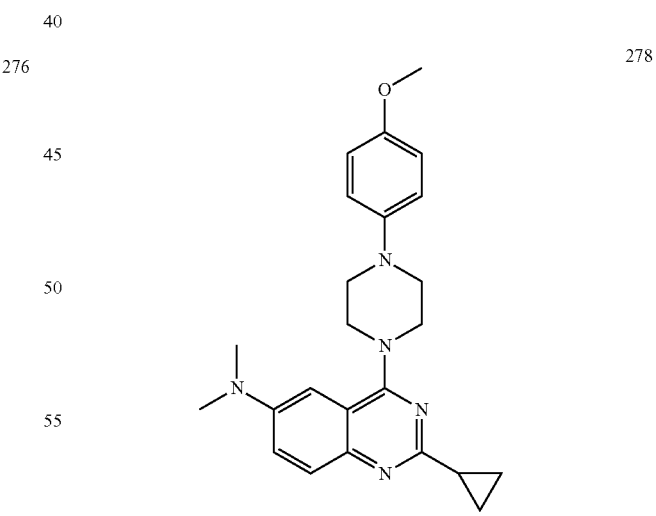

The title compound was prepared as described for compound (255), using the similar route and procedure.

¹H NMR (300 HMz, CDCl₃): δ=7.75 (d, J=9.0 Hz, 1H), 7.38-7.34 (m, 1H), 6.99-6.87 (m, 5H), 3.82-3.78 (m, 7H), 3.29-3.26 (m, 4H), 3.05 (s, 6H), 2.21-2.19 (m, 1H), 1.17-1.13 (m, 2H), 1.01-0.96 (m, 2H). MS: m/z 404.3 (M+H⁺).

Example 190: 6-bromo-2-cyclopropyl-4-[4-(3-methoxy-phenyl)-piperazin-1-yl]-quinazoline (279)

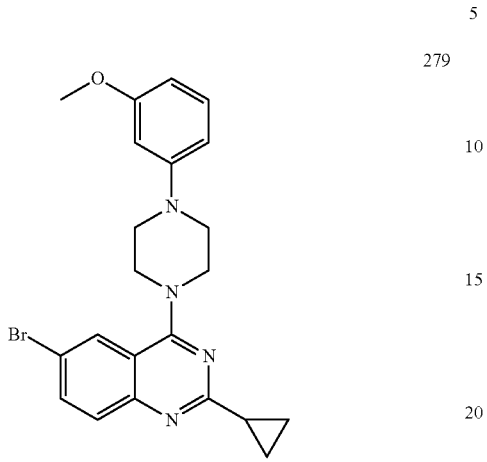

The title compound was prepared as described for compound (255), using the similar route and procedure.

¹H NMR (400 HMz, CDCl₃): δ=8.02 (d, J=2.0 Hz, 1H), 7.79-7.71 (m, 2H), 7.30-7.23 (m, 1H), 6.63-6.61 (m, 1H), 6.55-6.49 (m, 2H), 3.90-3.88 (m, 4H), 3.85 (s, 3H), 3.42-3.39 (m, 4H), 2.24-2.22 (m, 1H), 1.23-1.19 (m, 2H), 1.08-1.05 (m, 2H). MS: m/z 441.2 (M+H⁺).

Example 191: {2-cyclopropyl-4-[4-(3-methoxy-phenyl)-piperazin-1-yl]-quinazolin-6-yl}-dimethyl-amine (280)

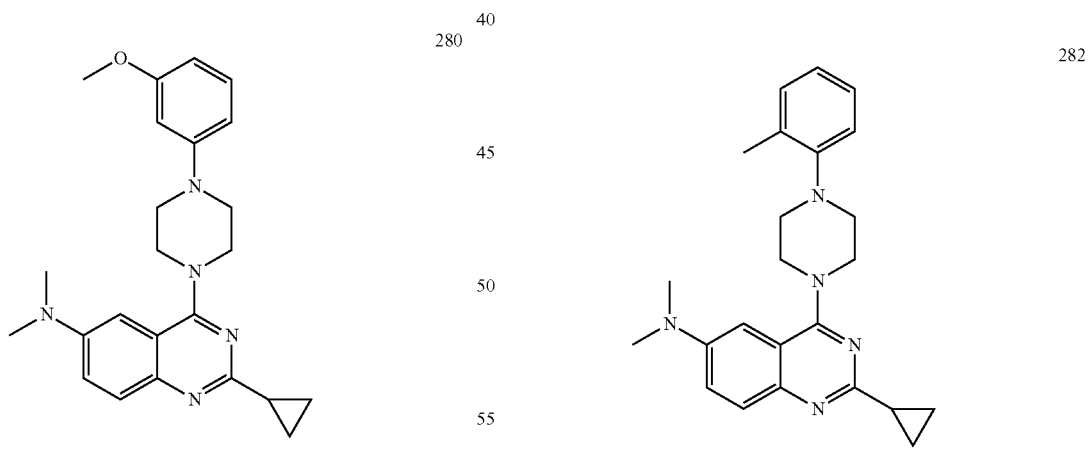

The title compound was prepared as described for compound (255), using the similar route and procedure.

¹H NMR (300 HMz, CDCl₃): δ=7.80-7.76 (m, 1H), 7.39-7.35 (m, 1H), 7.25-7.20 (m, 1H), 6.87-6.86 (m, 1H), 6.63-6.60 (m, 1H), 6.54-6.49 (m, 1H), 6.49-6.46 (m, 1H), 3.83-3.80 (m, 7H), 3.41-3.37 (m, 4H), 3.06 (s, 6H), 2.07-2.05 (m, 1H), 1.17-1.15 (m, 2H), 1.02-0.98 (m, 2H). MS: m/z 404.3 (M+H⁺).

Example 192: 6-bromo-2-cyclopropyl-4-(4-o-tolyl-piperazin-1-yl)-quinazoline (281)

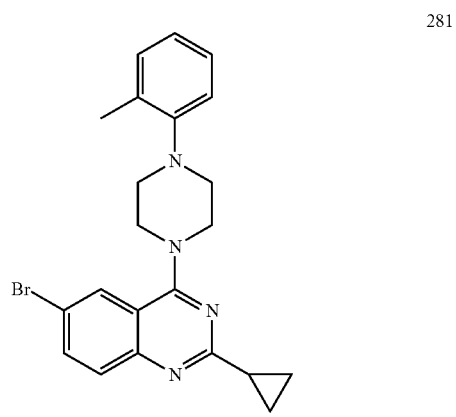 [SMILES: Fc1ccccc1N1CCN(c2nc(C3CC3)nc3ccc(Br)cc23)CC1]

The title compound was prepared as described for compound (255), using the similar route and procedure.

¹H NMR (400 HMz, CDCl₃): δ=8.00 (d, J=1.6 Hz, 1H), 7.75-7.67 (m, 2H), 7.23-7.18 (m, 2H), 7.08-7.01 (m, 2H), 3.87-3.84 (m, 4H), 3.10-3.07 (m, 4H), 2.37 (s, 3H), 2.21-2.19 (m, 1H), 1.19-1.16 (m, 2H), 1.05-1.01 (m, 2H). MS: m/z 423.1 (M+H⁺).

Example 193: [2-cyclopropyl-4-(4-o-tolyl-piperazin-1-yl)-quinazolin-6-yl]-dimethyl-amine (282)

The title compound was prepared as described for compound (255), using the similar route and procedure.

¹H NMR (400 HMz, CDCl₃): δ=7.74 (d, J=9.2 Hz, 1H), 7.36-7.33 (m, 1H), 7.22-7.18 (m, 2H), 7.09-6.99 (m, 2H), 6.89-6.88 (m, 1H), 3.80-3.76 (m, 4H), 3.11-3.09 (m, 4H), 3.04 (s, 6H), 2.37 (s, 3H), 2.21-2.18 (m, 1H), 1.17-1.13 (m, 2H), 0.99-0.95 (m, 2H). MS: m/z 388.2 (M+H⁺).

Example 194: 6-bromo-2-cyclopropyl-4-[4-(2-fluoro-phenyl)-piperazin-1-yl]-quinazoline (283)

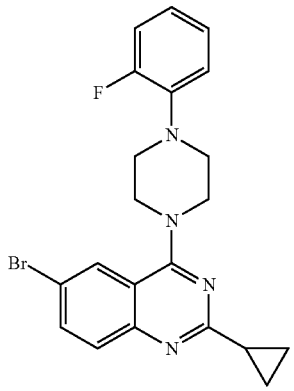

The title compound was prepared as described for compound (255), using the similar route and procedure.

$^1$H NMR (400 HMz, CDCl$_3$): δ=7.98 (s, 1H), 7.80-7.76 (m, 2H), 7.10-7.07 (m, 2H), 7.01-6.99 (m, 2H), 3.95-3.92 (m, 4H), 3.28-3.25 (m, 4H), 2.25-2.21 (m, 1H), 1.19-1.18 (m, 2H), 1.06-1.04 (m, 2H). MS: m/z 427.1 (M+H$^+$).

Example 195: 6-bromo-4-[4-(2-chloro-phenyl)-piperazin-1-yl]-2-cyclopropyl-quinazoline (284)

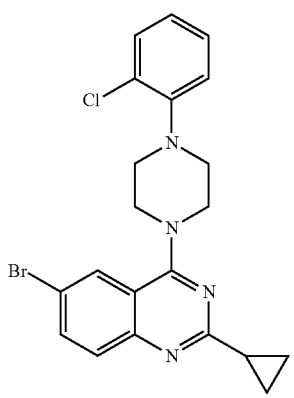

The title compound was prepared as described for compound (255), using the similar route and procedure.

$^1$H NMR (400 HMz, CDCl$_3$): δ=7.99 (s, 1H), 7.76-7.68 (m, 2H), 7.41-7.39 (m, 1H), 7.28-7.24 (m, 1H), 7.09-7.00 (m, 2H), 3.91-3.90 (m, 4H), 3.24-3.21 (m, 4H), 2.23-2.19 (m, 1H), 1.20-1.16 (m, 2H), 1.05-1.01 (m, 2H). MS: m/z 445.1 (M+H$^+$).

Example 196: {2-cyclopropyl-4-[4-(2-fluoro-phenyl)-piperazin-1-yl]-quinazolin-6-yl}-dimethyl-amine (285)

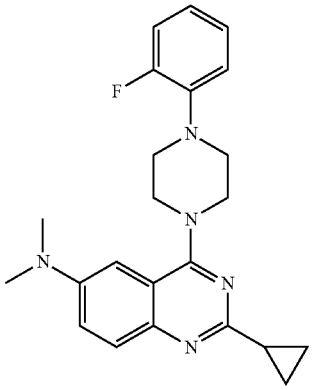

The title compound was prepared as described for compound (255), using the similar route and procedure.

$^1$H NMR (400 HMz, CDCl$_3$): δ=7.77-7.75 (m, 1H), 7.37-7.34 (m, 1H), 7.11-6.86 (m, 4H), 6.85 (s, 1H), 3.84-3.81 (m, 4H), 3.28-3.26 (m, 4H), 3.07 (s, 6H), 2.23-2.20 (m, 1H), 1.17-1.13 (m, 2H), 0.99-0.96 (m, 2H). MS: m/z 392.3 (M+H$^+$).

Example 197: {4-[4-(2-chloro-phenyl)-piperazin-1-yl]-2-cyclopropyl-quinazolin-6-yl}-dimethyl-amine (286)

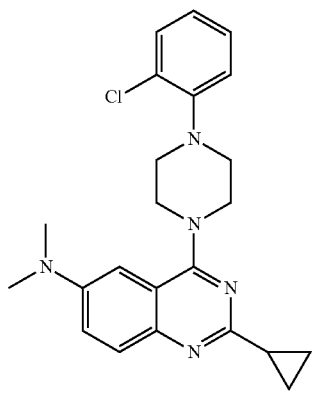

The title compound was prepared as described for compound (255), using the similar route and procedure.

$^1$H NMR (300 HMz, CDCl$_3$): δ=7.85 (d, J=9.0 Hz, 1H), 7.42-7.34 (m, 2H), 7.29-7.24 (m, 1H), 7.12-7.00 (m, 2H), 6.87-6.86 (m, 1H), 3.91-3.89 (m, 4H), 3.26-3.23 (m, 4H), 3.06 (s, 6H), 2.31-2.28 (m, 1H), 1.20-1.17 (m, 2H), 1.05-0.99 (m, 2H). MS: m/z 408.3 (M+H$^+$).

Example 198: 2-[4-(6-Bromo-2-cyclopropyl-quinazolin-4-yl)-piperazin-1-yl]-benzonitrile (287)

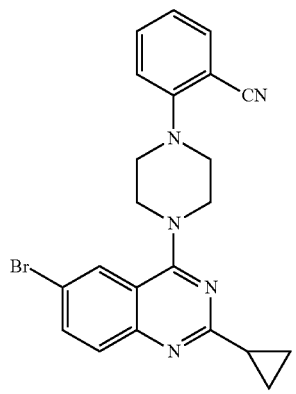

The title compound was prepared as described for compound (255), using the similar route and procedure.

$^1$H NMR (400 MHz, DMSO-d$_6$): δ=8.11 (s, 1H), 7.88 (d, J=8.4 Hz, 1H), 7.74 (d, J=7.6 Hz, 1H), 7.66-7.61 (m, 2H), 7.23 (d, J=8.4 Hz, 1H), 7.13 (t, J=7.2 Hz, 1H), 3.92-3.87 (m, 4H), 3.35-3.33 (m, 4H), 2.15-2.09 (m, 1H), 1.10-1.06 (m, 2H), 1.05-0.98 (m, 2H). MS: m/z 434.1 (M+H$^+$).

Example 199: 2-[4-(2-cyclopropyl-6-dimethylamino-quinazolin-4-yl)-piperazin-1-yl]-benzonitrile (288)

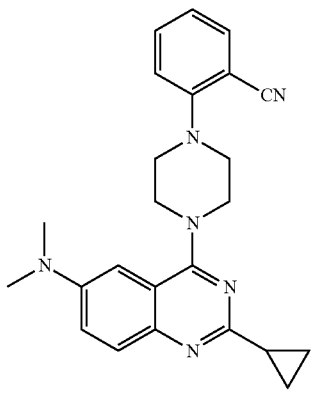

The title compound was prepared as described for compound (255), using the similar route and procedure.

$^1$H NMR (300 MHz, DMSO-d$_6$): δ=7.76-7.72 (m, 1H), 7.67-7.60 (m, 2H), 7.53-7.49 (m, 1H,) 7.23 (d, J=8.4 Hz, 1H), 7.16-7.12 (m, 1H), 6.89 (s, 1H), 3.98-3.94 (m, 4H), 3.42-3.37 (m, 4H), 3.00 (s, 6H), 2.15-2.12 (m, 1H), 1.07-1.01 (m, 4H) MS: m/z 399.2 (M+H$^+$).

Example 200: 2-[4-(2-cyclopropyl-6-dimethylamino-quinazolin-4-yl)-piperazin-1-yl]-benzamide (289)

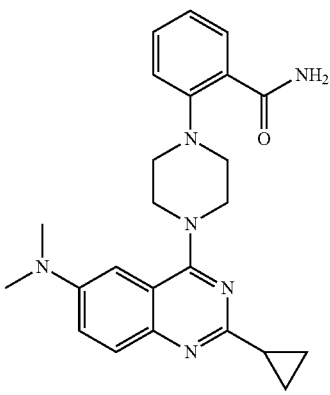

The title compound was prepared as described for compound (255), using the similar route and procedure.

$^1$H NMR (400 MHz, DMSO-d$_6$): δ=8.47 (brs, 1H), 7.72 (d, J=7.6 Hz, 1H), 7.60 (d, J=9.2 Hz, 1H), 7.51 (brs, 1H), 7.47-7.43 (m, 2H), 7.27 (d, J=7.6 Hz, 1H), 7.15 (t, J=8.0 Hz, 1H), 6.81 (s, 1H), 3.76-3.72 (m, 4H), 3.19-3.13 (m, 4H), 3.01 (s, 6H), 2.10-2.06 (m, 1H), 1.04-1.00 (m, 2H), 0.94-0.91 (m, 2H). MS: m/z 468.2 (M+H$^+$).

Scheme 28:

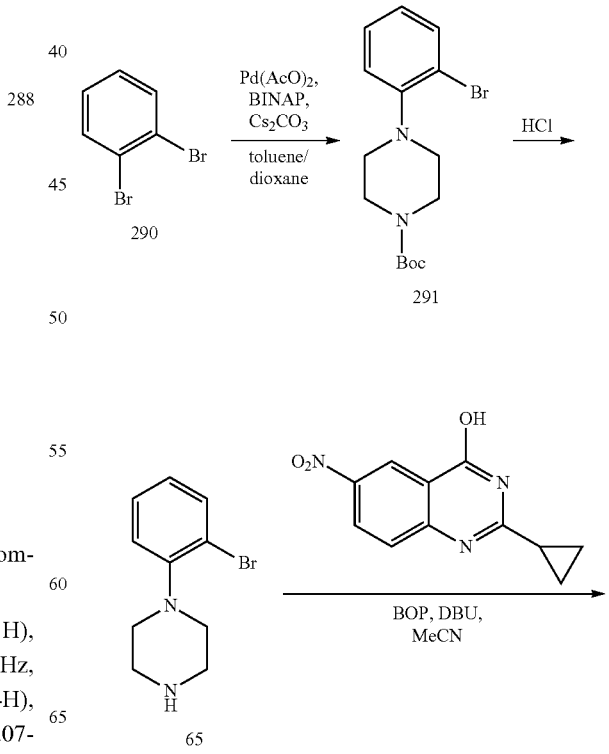

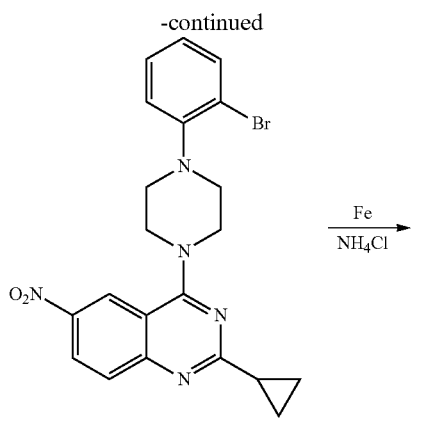

292

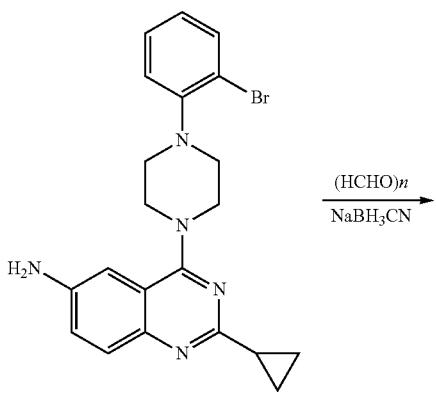

293

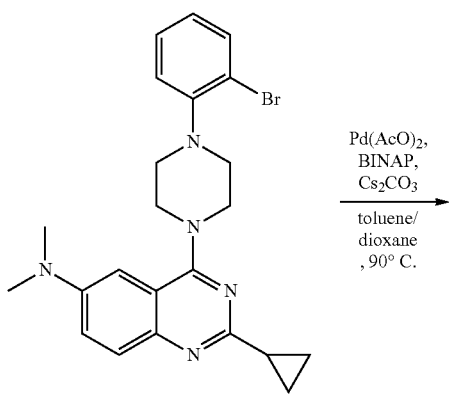

294

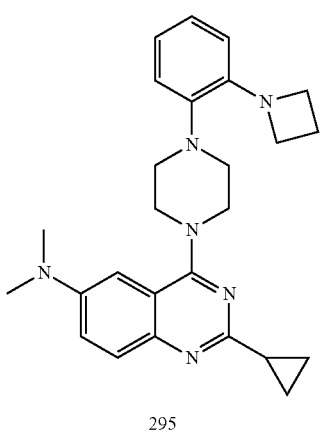

295

Example 201: {4-[4-(2-azetidin-1-yl-phenyl)-piperazin-1-yl]-2-cyclopropyl-quinazolin-6-yl}-dimethylamine (295)

A mixture of compound (290) (2.36 g, 10 mmol), piperazine-1-carboxylic acid tert-butyl ester (1.86 g, 10 mmol), Pd(OAc)$_2$ (224.5 mg, 1.0 mmol), BINAP (1.2 g, 2.0 mmol), Cs$_2$CO$_3$ (6.5 g, 20 mmol) and toluene/1,4-dioxane (15 mL/15 mL) was heated to 90° C. overnight. The reaction mixture was filtered and the filtrate was concentrated to dryness. The residue was purified by silica gel column chromatography (PE/EtOAc=1/50) to afford compound (291) (1.8 g, 53%) as a colorless oil. A mixture of compound (291) (1.5 g, 4.4 mmol) and HCl/EtOAc (2M, 20 mL) was stirred for 1 hour at room temperature. The reaction mixture was filtered and the solid was dried to afford compound (65) (1.0 g, 85%) as a white solid.

A mixture of 2-cyclopropyl-6-nitro-quinazolin-4-ol (700 mg, 3.0 mmol), compound (65) (924 mg, 3.33 mmol), BOP (2.0 g, 4.54 mmol) and DBU (921 mg, 6.06 mmol) in MeCN (20 mL) was stirred at room temperature overnight. The reaction mixture was filtered and the filtrate was concentrated to dryness in vacuum. The residue was purified by silica gel column chromatography (PE/EtOAc=1/50) to afford compound (292) (550 mg, yield: 40%) as a yellow semi-solid.

A mixture of compound (292) (550 mg, 1.21 mmol), active iron powder (340 mg, 6.05 mmol), saturated aqueous NH$_4$Cl solution (10 mL) in MeOH (20 mL) was heated to 85° C. for 2 h. After cooled to room temperature, the mixture was filtered through celite. The filtrate was concentrated to remove most of the organic solvent. The aqueous phase was extracted with DCM (10 mL×2). The combined organic layers were dried over Na$_2$SO$_4$ and concentrated to give crude product. The crude product was purified by silica gel column chromatography (MeOH/DCM=1/20) to afford compound (293) (350 mg, yield: 68%) as a yellow semi-solid.

A solution of compound (293) (300 mg, 0.71 mmol), NaBH$_3$CN (447.3 mg, 7.1 mmol), HCHO (40% in H$_2$O, 0.5 mL) in MeOH (5 mL) was stirred at room temperature overnight. 15 mL of water was added and the mixture was extracted with EtOAc (15 mL×3). The organic layer was washed with water (15 mL) and brine (15 mL) and dried over Na$_2$SO$_4$. The solution was concentrated to give a residue, which was purified by prep-TLC to afford compound (294) (250 mg, yield: 78%) as a yellow semi-solid.

A mixture of compound (294) (150 mg, 0.33 mmol), azetidine (38 mg, 0.66 mmol), Pd(OAc)$_2$ (7.4 mg, 0.033 mmol), BINAP (41 mg, 0.066 mmol), Cs$_2$CO$_3$ (324 mg, 0.99 mmol) and toluene/1,4-dioxane (5 mL/5 mL) was heated to 90° C. overnight. The reaction mixture was filtered and the filtrate was concentrated to dryness. The residue was purified by silica gel column chromatography (PE/EtOAc=3/7) then by prep-HPLC to afford compound (295), (33 mg, yield: 21%) as a yellow solid.

$^1$H NMR (400 MHz, DMSO-d$_6$): δ=7.59 (d, J=12.4 Hz, 1H), 7.46-7.43 (m, 1H), 7.02-6.91 (m, 2H), 6.81-6.73 (m, 2H), 6.48-6.46 (m, 1H), 3.89-3.84 (m, 4H), 3.74-3.67 (m, 4H), 3.07-3.00 (m, 10H), 2.21-2.07 (m, 3H), 1.02-0.99 (m, 2H), 0.94-0.89 (m, 2H). LC-MS: 429.3 (M+H$^+$)

Example 202: {4-[4-(2-azetidin-1-yl-phenyl)-piperazin-1-yl]-2-cyclopropyl-quinazolin-6-yl}-ethyl-methyl-amine (296)
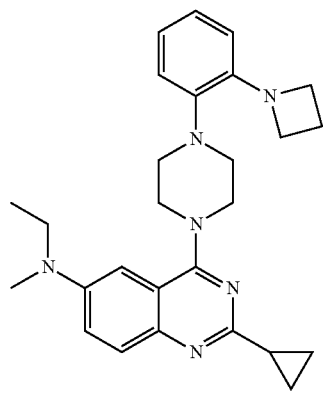
296
The title compound was prepared as described for compound (295), except that formaldehyde was substituted for acetaldehyde.
$^1$H NMR (400 MHz, CDCl$_3$): δ=7.74 (d, J=7.6 Hz, 1H), 7.32 (d, J=10.4 Hz, 1H), 7.05-7.00 (m, 2H), 6.83-6.79 (m, 2H), 6.53 (d, J=8.4 Hz, 1H), 3.97-3.93 (m, 4H), 3.78-3.70 (m, 4H), 3.50-3.44 (m, 2H), 3.15 (m, 4H), 2.98 (s, 3H), 2.26-2.19 (m, 3H), 1.17-1.14 (m, 5H), 0.98-0.96 (m, 2H). LC-MS: 443.3 (M+H$^+$)
Scheme 29:
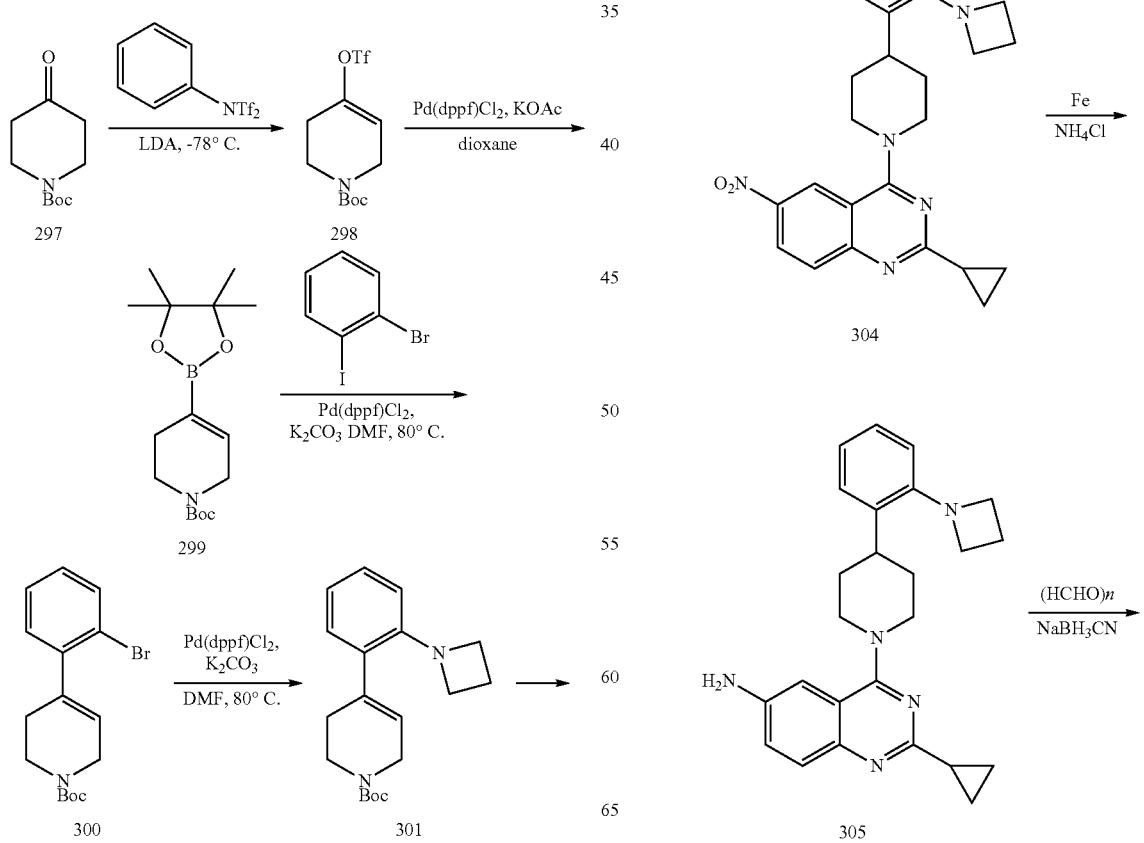
-continued
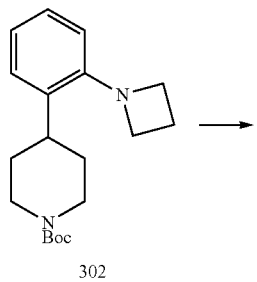
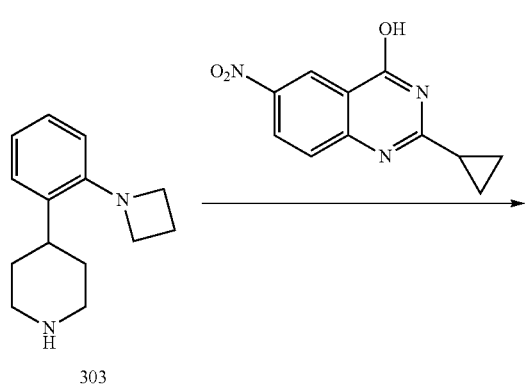

-continued

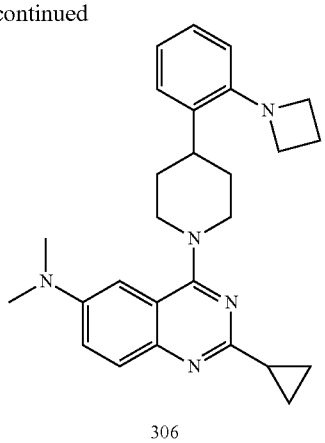

306

Example 203: {4-[4-(2-azetidin-1-yl-phenyl)-piperidin-1-yl]-2-cyclopropyl-quinazolin-6-yl}-dimethylamine (306)

LDA (2M, 65 mL) was added to a solution of 4-oxo-piperidine-1-carboxylic acid tert-butyl ester (20 g, 100 mmol) in 300 mL of dry THF at −78° C. and the mixture was stirred for 30 min. A solution of N,N-bis-(trifluoromethanesulfonyl)aniline in dry THF (100 mL) was added slowly at −78° C. and the mixture was allowed to warm to room temperature and stirred overnight. The reaction was quenched with sat. $NH_4Cl$ solution (50 mL) and water (400 mL). The mixture was extracted with EtOAc (200 mL). The organic layer was washed with water (50 mL) and brine (50 mL), and dried over $Na_2SO_4$. The solution was concentrated to dryness and the residue was purified by silica gel column chromatography (PE/EA=50/1) to give compound (298) (24.5 g, yield: 74%) as a yellow oil.

$^1$H NMR (300 MHz, $CDCl_3$): δ=5.76 (s, 1H), 4.04 (d, J=1.8 Hz, 2H), 3.62 (t, J=5.6 Hz, 2H), 2.43 (s, 2H), 1.47 (s, 9H).

A mixture of compound (298) (24.5 g, 74 mmol), bis(pinacolato)diboron (21.6 g, 85 mmol), KOAc (25.4 g, 259 mmol), Pd(dppf)$Cl_2$ (1.6 g, 2.22 mmol), dppf (1.23 g, 2.22 mmol) and 250 mL of 1,4-dioxane was stirred at 80° C. overnight. The reaction mixture was poured into water (500 mL) and extracted with EtOAc (200 mL). The organic layer was washed with water (100 mL) and brine (100 mL), dried over $Na_2SO_4$, concentrated and purified by silica gel column (PE/EA=20/1) to give compound (299) (28 g, quantitative) as a white solid.

$^1$H NMR (300 MHz, $CDCl_3$): δ=6.45 (s, 1H), 3.94 (d, J=2.7 Hz, 2H), 3.62 (t, J=5.6 Hz, 2H), 2.22 (s, 2H), 1.45 (s, 9H), 1.25 (s, 12H).

A mixture of compound (299) (16.1 g, 52 mmol), 1-bromo-2-iodo-benzene (9.8 g, 35 mmol), $K_2CO_3$ (19.3 g, 140 mmol), Pd(dppf)$Cl_2$ (1.25 g, 1.75 mmol), 225 mL of 1,4-dioxane and 75 mL of water was stirred at 70° C. overnight. The reaction mixture was poured into water (500 mL) and extracted with EtOAc (300 mL). The organic layer was washed with water and brine, dried over $Na_2SO_4$, concentrated and purified by silica gel column (PE/EA=60/1) to give compound (300) (8 g, yield: 67%) as a white solid.

$^1$H NMR (300 MHz, $CDCl_3$): δ=7.55 (d, J=7.8 Hz, 1H), 7.29-7.24 (m, 1H), 7.1-7.09 (m, 2H), 5.62 (s, 1H), 4.04 (d, J=2.1 Hz, 2H), 3.64 (t, J=5.6 Hz, 2H), 2.42 (s, 2H), 1.50 (s, 9H).

A mixture of compound (300) (7.1 g, 20.11 mmol), azetidine (1.4 g, 24.1 mmol), Pd(AcO)$_2$ (451 mg, 2.01 mmol), BINAP (2.5 g, 4.02 mmol), $Cs_2CO_3$ (13.07 g, 40.22 mmol) and toluene/1,4-dioxane (40 mL/40 mL) was stirred at 90° C. Filtration and concentration resulted in a brown residue which was purified by silica gel column (PE/EA=60/1) to give compound (301) (5.0 g, 79%) as a yellow oil.

$^1$H NMR (300 MHz, $CDCl_3$): δ=7.16-7.12 (m, 1H), 6.96 (dd, J=7.8, 7.5 Hz, 1H), 6.76 (t, J=7.4 Hz, 1H), 6.48 (d, J=8.1 Hz, 1H), 5.63-5.61 (m, 1H), 4.01 (d, J=2.1 Hz, 2H), 3.78 (t, J=7.2 Hz, 4H), 3.61 (t, J=5.6 Hz, 2H), 2.40 (s, 2H), 2.26-2.16 (m, 2H), 1.49 (s, 9H).

A mixture of to give compound (301) (5.0 g, 15.9 mmol), wet 10% Pd/C (1 g) and MeOH (200 mL) was stirred at 40° C. under 50 psi of $H_2$ overnight. The reaction mixture was filtered and concentrated to give compound (302) (5.0 g, quantitative) as a colorless oil.

A mixture of compound (302) (5.0 g, 15.9 mmol) was dissolved in DCM (80 mL), $CF_3CO_2H$ (80 mL) was added and stirred at room temperature for 2 h. The reaction solution was concentrated and the residue was treated with sat. $NaHCO_3$ solution (100 mL) and extracted with EtOAc (100 mL×5). The organic layer was combined and washed with brine, dried over $Na_2SO_4$ and concentrated to give compound (303) (2.5 g, yield: 74%) as a white solid.

The title compound (306) was prepared as described for compound (295), using the similar route and procedure.

$^1$HNMR (300 MHz, $CDCl_3$): δ=7.78-7.76 (m, 1H), 7.35 (dd, J=9.3 Hz, 1H), 7.24-7.15 (m, 2H), 6.93-6.87 (m, 2H), 6.64-6.61 (m, 1H), 4.41-4.37 (m, 2H), 3.96 (t, J=7.1 Hz, 4H), 3.814-3.04 (m, 8H), 2.35-2.23 (m, 3H), 2.04-1.91 (m, 5H), 1.18-1.15 (m, 2H), 1.00-0.97 (m, 2H). LC-MS: 428.2 (M+H$^+$).

Scheme 30:

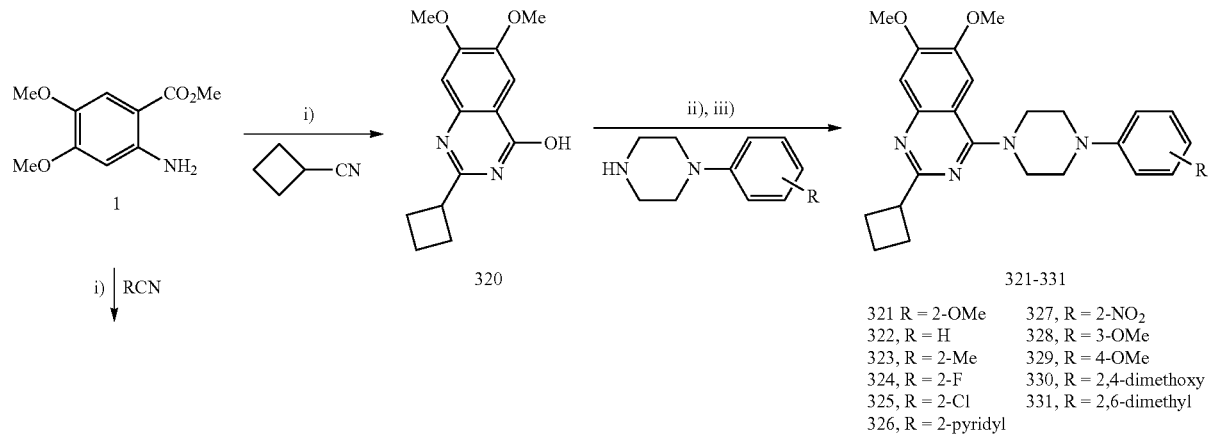

321 R = 2-OMe
322, R = H
323, R = 2-Me
324, R = 2-F
325, R = 2-Cl
326, R = 2-pyridyl
327, R = 2-NO$_2$
328, R = 3-OMe
329, R = 4-OMe
330, R = 2,4-dimethoxy
331, R = 2,6-dimethyl

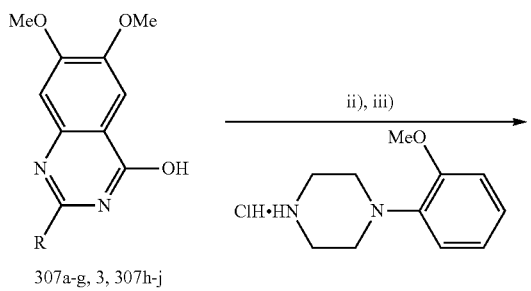
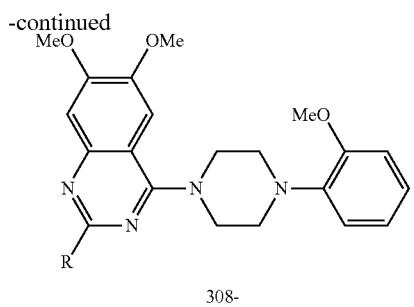

307a-g, 3, 307h-j

308-

308, R = Me
309, R = benzyl
310, R = ethyl
311, R = n-propyl
312, R = i-propyl
313, R = i-butyl
314, R = vinyl
315, R = cyclopropyl
316, R = cyclopentyl
317, R = methylcyclopropyl
318, R = 2-(N, N-dimethyl-
        amino)ethyl
319, R = 2-(4-(2-methoxyphenyl-
        piperazin-1-yl)ethyl Example 204: 2-cyclopropyl-6,7-dimethoxy-4-(4-(2-methoxyphenyl)piperazin-1-yl)quinazoline (315)

Methyl 2-amino-4,5-dimethoxy benzoate (1) (1.0 g, 4.73 mmol) and cyclopropyl carbonitrile (0.95 g, 14.2 mmol) were weighed into a reaction flask and 15 mL of 4M HCl in 1,4-dioxane was added and the resulting heterogenous mixture heated to 100° C. for 15 h. The reaction mixture was cooled and poured carefully into cold saturated NaHCO$_3$ solution (100 mL). The precipitate formed was collected by filtration, washed extensively with water and air-dried to afford the product 2-cyclopropyl-6,7-dimethoxyquinazolin-4-ol (3) as a white solid (0.76 g, 65%) which was used without purification. $^1$H NMR (500 MHz, DMSO-d$_6$) δ 12.3 (broad s, 1H), 7.37 (s, 1H), 7.0 (s, 1H), 3.86 (s, 3H), 3.83 (s, 3H), 1.95-1.88 (m, 1H), 1.08-1.01 (m, 2H), 1.01-0.95 (m, 2H); MS (ESI+ve): Calculated for C$_{13}$H$_{14}$N$_2$O$_3$, [M+H]= 247.11, observed [M+H]=247.13.

Compound (3) (0.3 g, 1.22 mmol) was suspended in phosphorus(V) oxychloride (10 mL) in a 40 mL vial and the mixture was heated at 110° C. for 15 h during which the suspension turned into a reddish brown solution. The mixture was allowed to cool to 23° C. and phosphorus(V) oxychloride was removed on a rotary evaporator. The residue was dissolved in 20 mL of dichloromethane and washed with saturated NaHCO$_3$ solution (3×, 10 mL). The organic layer was collected, dried over anhydrous Na$_2$SO$_4$ and the solvent was evaporated to afford the intermediate 4-chloro-2-cyclopropyl-6,7-dimethoxyquinazoline which was used in the next step without purification. MS (ESI+ve): Calculated for C$_{13}$H$_{13}$ClN$_2$O$_2$, [M+H]=265.07, observed [M+H]= 265.08.

1-(2-methoxyphenyl)piperazine hydrochloride (0.35 g, 1.53 mmol) and K$_2$CO$_3$ (0.7 g, 5.1 mmol) were weighed into a 35 mL microwave reaction tube. 4-chloro-2-cyclopropyl-6,7-dimethoxyquinazoline (0.27 g, 1.02 mmol) solution in 1,4-dioxane (10 mL) was added and the mixture was heated in the microwave at 80° C. for 1.5 h, when LCMS analysis showed that all the chloroquinazoline was consumed. The mixture was diluted with 50 mL water and then extracted with ethyl acetate (3×25 mL). The organic layer was dried over anhydrous Na$_2$SO$_4$ and the solvent was evaporated to afford a dark brown residue. The residue was subjected to silica gel flash chromatography (1:3 ethyl acetate/hexanes) to afford compound (315) (0.105 g, 14% over 3 steps) as a pale yellow foamy solid. $^1$H NMR (500 MHz, CDCl$_3$) δ 7.25 (s, 1H), 7.12 (s, 1H), 7.08-7.03 (m, 1H), 7.02-6.95 (m, 2H), 6.92 (d, J=8.0 Hz, 1H), 4.03 (s, 3H), 3.98 (s, 3H), 3.92 (s, 3H), 3.89-3.81 (m, 4H), 3.33-3.20 (m, 4H), 2.28-2.16 (m, 1H), 1.25-1.10 (m, 2H), 1.06-0.96 (m, 2H); $^{13}$C NMR (125 MHz, CDCl$_3$) δ 165.58, 163.99, 154.50, 152.28, 147.47, 140.98, 123.32, 121.05, 118.39, 111.37, 109.26, 106.69, 103.34, 56.19, 56.01, 55.42, 50.56, 49.82, 17.93, 9.54; HRMS (ESI+ve): Calculated for C$_{24}$H$_{28}$N$_4$O$_3$, [M+H]= 421.2234, observed [M+H]=421.2215.

Example 205: 6,7-dimethoxy-4-(4-(2-methoxyphenyl)piperazin-1-yl)-2-methylquinazoline (308)

As described for compound (315) using methyl 2-amino-4,5-dimethoxy benzoate (1.00 g, 4.73 mmol), 5 mL acetonitrile, and 10 mL of 4 M HCl/dioxane, the crude 6,7-dimethoxy-2-methylquinazolin-4-ol (307a), an off-white solid (0.81 g, 78%), was obtained and used without purification. $^1$H NMR (500 MHz, CDCl$_3$) δ 7.57 (d, J=3.5 Hz, 1H), 7.35 (d, J=3.7 Hz, 1H), 7.09 (d, J=3.6 Hz, 1H), 4.09-3.96 (m, 6H), 3.24 (s, 3H); MS (ESI+ve): Calculated for C$_{11}$H$_{12}$N$_2$O$_3$, [M+H]=221.09, observed [M+H]=221.03.

Compound (307a) (150 mg, 0.68 mmol) and 5 mL of phosphorus(V) oxychloride afforded 4-chloro-6,7-dimethoxy-2-methylquinazoline which was used without purification. MS (ESI+ve): Calculated for C$_{11}$H$_{11}$ClN$_2$O$_2$, [M+ H]=239.06, observed [M+H]=239.01. 4-chloro-6,7-dimethoxy-2-methylquinazoline (160 mg, 0.67 mmol), 1-(2-methoxyphenyl)piperazine hydrochloride (223 mg, 1.01 mmol), potassium carbonate (463 mg, 3.35 mmol), and 1,4-dioxane (5 mL) resulted in a brown residue which was purified by silica gel flash chromatography eluting with 0 to 80% ethyl acetate/hexanes. The product (308) was obtained as a white solid, (46 mg, 13% over 3 steps). $^1$H NMR (500 MHz, CDCl$_3$) δ 7.22 (s, 1H), 7.16 (s, 1H), 7.09-7.01 (m, 2H), 7.00-6.95 (m, 1H), 6.95-6.90 (m, 1H), 4.03 (s, 3H), 4.00 (s, 3H), 3.92 (s, 3H), 3.89-3.84 (m, 4H), 3.34-3.29 (m, 4H), 2.69 (s, 3H); HRMS (ESI+ve): Calculated for C$_{22}$H$_{26}$N$_4$O$_3$, [M+H]=395.2078, observed [M+H]= 395.2059.

Example 206: 2-benzyl-6,7-dimethoxy-4-(4-(2-methoxyphenyl)piperazin-1-yl)quinazoline (309)

As described for compound (315), starting from methyl 2-amino-4,5-dimethoxy benzoate (1.00 g, 4.73 mmol), 2-phenylacetonitrile (0.55 g, 4.73 mmol), and 10 mL of 4 M HCl/dioxane the 2-benzyl-6,7-dimethoxyquinazolin-4-ol (307b) was obtained as an off-white solid (0.86 g, 61%) and was used without purification. $^1$H NMR (500 MHz, CDCl$_3$) δ 9.44 (s, 1H), 7.57 (s, 1H), 7.39 (d, J=4.6 Hz, 4H), 7.34 (tt, J=9.4, 3.7 Hz, 1H), 7.18 (s, 1H), 4.10 (s, 2H), 4.04 (s, 3H), 4.01 (s, 3H); MS (ESI+ve): Calculated for C$_{17}$H$_{16}$N$_2$O$_3$, [M+H]=297.12, observed [M+H]=297.09.

Compound (307b) (200 mg, 0.67 mmol) and 10 mL of phosphorus(V) oxychloride afforded the 2-benzyl-4-chloro-6,7-dimethoxyquinazoline which was used without purification. MS (ESI+ve): Calculated for C$_{17}$H$_{15}$ClN$_2$O$_2$, [M+H]= 315.09, observed [M+H]=315.0. The crude 2-benzyl-4-chloro-6,7-dimethoxyquinazoline (210 mg, 0.67 mmol), 1-(2-methoxyphenyl)piperazine hydrochloride (229 mg, 1.0 mmol), potassium carbonate (461 mg, 3.34 mmol), and 1,4-dioxane (5 mL) resulted in a brown residue which was purified by silica gel flash chromatography eluting with 0 to 50% ethyl acetate/hexanes. The product (309) was obtained as a yellow solid, (89 mg, 17% over 3 steps). $^1$H NMR (500 MHz, CDCl$_3$) δ 7.55-7.45 (m, 2H), 7.35-7.26 (m, 3H), 7.25-7.20 (m, 1H), 7.20 (s, 1H), 7.15-7.07 (m, 1H), 7.0-6.9 (m, 2H), 6.9-6.84 (m, 1H), 4.25 (s, 2H), 4.03 (s, 3H), 4.0 (s, 3H), 3.94 (s, 3H), 3.9-3.85 (m, 4H), 3.4-3.28 (m, 4H); HRMS (ESI+ve): Calculated for C$_{28}$H$_{30}$N$_4$O$_3$, [M+H]= 471.2391, observed [M+H]=471.2373.

Example 207: 2-ethyl-6,7-dimethoxy-4-(4-(2-methoxyphenyl)piperazin-1-yl)quinazoline (310)

As described for compound (315), starting from methyl 2-amino-4,5-dimethoxy benzoate (1.0 g, 4.73 mmol), propionitrile (8 mL, 115 mmol) and 4M HCl in 1,4-dioxane (10 mL), the product 2-ethyl-6,7-dimethoxyquinazolin-4-ol (307c) was obtained as a gray solid (1.08 g, 97%) and used without any further purification. $^1$H NMR (500 MHz, DMSO-d$_6$) δ 12.0 (broad, 1H), 7.41 (s, 1H), 7.08 (s, 1H), 3.89 (s, 3H), 3.86 (s, 3H), 2.59 (q, J=7.5 Hz, 2H), 1.24 (t, J=7.5 Hz, 3H). MS (ESI+ve): Calculated for C$_{12}$H$_{14}$N$_2$O$_3$, [M+H]=235.10, observed [M+H]=235.39.

Compound (307c) (0.3 g, 1.28 mmol) in thionyl chloride (10 mL) was treated with dimethylformamide (0.1 mL) and then was stirred at reflux for two hours. The reaction was allowed to cool before being diluted with hexanes (20 mL). The liquor was decanted and the resulting residue was dried via an azeotrope with toluene (15 mL). The crude 4-chloro-2-ethyl-6,7-dimethoxyquinazoline (0.36 g) was used without further purification. MS (ESI+ve): Calculated for C$_{12}$H$_{13}$ClN$_2$O$_2$, [M+H]=253.07, observed [M+H]=253.29.

4-chloro-2-ethyl-6,7-dimethoxyquinazoline (0.13 g, 0.51 mmol), diisopropylethylamine (0.45 mL, 2.57 mmol), and 1-(2-methoxyphenyl)piperazine hydrochloride (0.12 g, 0.51 mmol) resulted in a brown residue which was purified by silica gel flash chromatography eluting with 70% ethyl acetate/hexanes. The product, (310) (31 mg, 15%) was obtained as a tan solid. $^1$H NMR (500 MHz, CDCl$_3$) δ 7.29 (broad s, 1H), 7.17 (s, 1H), 7.09-6.98 (m, 2H), 6.98-6.95 (m, 1H), 6.93 (dd, J=8.0, 1.1 Hz, 1H), 4.04 (s, 3H), 4.00 (s, 3H), 3.93 (s, 3H), 3.92-3.88 (m, 4H), 3.33-3.28 (m, 4H), 2.95 (q, J=7.6 Hz, 2H), 1.41 (t, J=7.6 Hz, 3H). HRMS (ESI+ve): Calculated for C$_{23}$H$_{28}$N$_4$O$_3$, [M+H]=409.2234, observed [M+H]=409.2218.

Example 208: 6,7-dimethoxy-4-(4-(2-methoxyphenyl)piperazin-1-yl)-2-propylquinazoline (311)

As described for compound (315), starting from methyl 2-amino-4,5-dimethoxy benzoate (1.00 g, 4.73 mmol), n-butyronitrile (0.33 g, 4.73 mmol), and 10 mL of 4 M HCl/dioxane, 6,7-dimethoxy-2-propylquinazolin-4-ol (307d)) was obtained as an off-white solid (1.81 g, 155%) and used without purification. $^1$H NMR (500 MHz, DMSO-d$_6$) δ 7.40 (s, 1H), 7.06 (s, 1H), 3.88 (s, 3H), 3.84 (s, 3H), 2.63-2.51 (m, 2H), 1.80-1.62 (m, 2H), 0.91 (t, J=7.3 Hz, 3H); MS (ESI+ve): Calculated for C$_{13}$H$_{17}$N$_2$O$_3$, [M+H]=249.12, observed [M+H]=249.10.

Compound (307d) (1.2 g, 4.83 mmol) and 20 mL of phosphorus(V) oxychloride afforded 4-chloro-6,7-dimethoxy-2-propylquinazoline (0.319 g) which was used without purification. MS (ESI+ve): Calculated for C$_{13}$H$_{16}$ClN$_2$O$_2$, [M+H]=267.08, observed [M+H]=267.13. 4-chloro-6,7-dimethoxy-2-propylquinazoline (700 mg, 2.6 mmol), 2-methoxyphenylpiperazine (901 mg, 3.9 mmol), potassium carbonate (1.82 g, 13.1 mmol), and 1,4-dioxane (10 mL) resulted in a crude brown residue which was purified by silica gel flash chromatography eluting with 50% to 75% ethyl acetate/hexanes. The product (311) was a yellow solid, (244.6 mg, 12% over 3 steps). $^1$H NMR (400 MHz, CDCl$_3$) δ 7.50-7.30 (br m, 1H), 7.16 (s, 1H), 7.10-6.9 (m, 4H), 4.05 (s, 3H), 4.00 (s, 3H), 4.00-3.85 (m, 4H), 3.93 (s, 3H), 3.33-3.28 (m, 4H), 2.98-2.86 (m, 2H), 1.91 (h, J=7.5 Hz, 2H), 1.04 (t, J=7.5 Hz, 3H); HRMS (ESI+ve): Calculated for C$_{24}$H$_{31}$N$_4$O$_3$, [M+H]=423.2391, observed [M+H]= 423.2372.

Example 209: 2-isopropyl-6,7-dimethoxy-4-(4-(2-methoxyphenyl)piperazin-1-yl)quinazoline (312)

As described for compound (315), starting from methyl 2-amino-4,5-dimethoxy benzoate (1.00 g, 4.73 mmol), isobutyronitrile (0.98 g, 14.2 mmol), and 10 mL of 4 M HCl/dioxane, 2-isopropyl-6,7-dimethoxyquinazolin-4-ol (307e) was obtained as an off-white solid (0.187 g, 16%) and used without purification. $^1$H NMR (400 MHz, DMSO-d$_6$) δ 11.98 (s, 1H), 7.41 (s, 1H), 7.08 (d, J=2.6 Hz, 1H), 3.90 (s, 3H), 3.85 (s, 3H), 2.85 (m, 1H), 1.25 (d, J=4.5 Hz, 6H). MS (ESI+ve): Calculated for C$_{13}$H$_{17}$N$_2$O$_3$, [M+H]=249.12, observed [M+H]=249.11.

Compound (307e) (0.187 g, 0.753 mmol) and 10 mL of phosphorus(V) oxychloride afforded 4-chloro-2-isopropyl-6,7-dimethoxyquinazoline (0.319 g) which was used without purification. MS (ESI+ve): Calculated for C$_{13}$H$_{16}$ClN$_2$O$_2$, [M+H]=267.08, observed [M+H]=267.12. 4-chloro-2-isopropyl-6,7-dimethoxyquinazoline (318 mg, 1.19 mmol), 2-methoxyphenylpiperazine (409 mg, 1.79 mmol), potassium carbonate (0.825 g, 5.97 mmol), and 1,4-dioxane (8 mL) resulted in a crude brown oil which was purified by silica gel flash chromatography eluting with 50% to 75% ethyl acetate/hexanes. The product (312) was a yellow solid (180.8 mg, 9% over 3 steps). $^1$H NMR (400 MHz, CDCl$_3$) δ 7.50-7.25 (br m, 1H), 7.16 (s, 1H), 7.11-6.9 (m, 4H), 4.1-3.9 (m, 4H), 4.05 (s, 3H), 4.00 (s, 3H), 3.93 (s, 3H), 3.35-3.10 (m, 5H), 1.40 (d, J=6.8 Hz, 6H); HRMS (ESI+ve): Calculated for C$_{24}$H$_{31}$N$_4$O$_3$, [M+H]=423.2391, observed [M+H]=423.2371.

Example 210: 2-isobutyl-6,7-dimethoxy-4-(4-(2-methoxyphenyl)piperazin-1-yl)quinazoline (313)

As described for compound (315), starting from methyl 2-amino-4,5-dimethoxy benzoate (1.00 g, 4.73 mmol), isovaleronitrile (1.18 g, 14.2 mmol), and 20 mL of 4 M HCl/dioxane, 2-isobutyl-6,7-dimethoxyquinazolin-4-ol (307f) was obtained as an off-white solid (0.9 g, 73%) and used without purification. $^1$H NMR (500 MHz, DMSO-d$_6$)

δ 7.40 (s, 1H), 7.07 (s, 1H), 3.88 (s, 3H), 3.85 (s, 3H), 2.43 (d, J=7.3 Hz, 2H), 2.17-2.13 (m, 1H), 0.91 (d, J=6.9 Hz, 6H). MS (ESI+ve): Calculated for $C_{14}H_{18}N_2O_3$, [M+H]=263.14, observed [M+H]=263.18.

Compound (3070 (300 mg, 1.14 mmol) and 10 mL of phosphorus(V) oxychloride afforded 4-chloro-2-isobutyl-6,7-dimethoxyquinazoline (320 mg) which was used without purification. MS (ESI+ve): Calculated for $C_{14}H_{17}ClN_2O_2$, [M+H]=281.11, observed [M+H]=281.15.

4-chloro-2-isobutyl-6,7-dimethoxyquinazoline (320 mg, 1.14 mmol), 1-(2-methoxyphenyl)piperazine hydrochloride (391 mg, 1.71 mmol), potassium carbonate (788 mg, 5.7 mmol), and 1,4-dioxane (5 mL) resulted in a brown residue which was purified by silica gel flash chromatography eluting with 0 to 40% ethyl acetate/hexanes. The product (313) was obtained as a yellow solid, (0.26 mg, 38% over 3 steps). $^1$H NMR (500 MHz, CDCl$_3$) δ 7.29 (s, 1H), 7.16 (s, 1H), 7.08-6.94 (m, 3H), 6.92 (dd, J=8.0, 1.4 Hz, 1H), 4.03 (s, 3H), 4.00 (s, 3H), 3.92 (s, 3H), 3.90-3.86 (m, 4H), 3.31-3.26 (m, 4H), 2.79 (d, J=7.3 Hz, 2H), 2.43-2.3 (m, 1H), 1.00 (d, J=6.6 Hz, 6H); HRMS (ESI+ve): Calculated for $C_{26}H_{32}N_4O_3$, [M+H]=437.2547, observed [M+H]=437.2530.

Example 211 and 212

6,7-dimethoxy-4-(4-(2-methoxyphenyl)piperazin-1-yl)-2-vinylquinazoline (314) and 6,7-dimethoxy-4-(4-(2-methoxyphenyl)piperazin-1-yl)-2-(2-(4-(2-methoxyphenyl)piperazin-1-yl)ethyl)quinazoline (319)

As described for compound (315), starting from methyl 2-amino-4,5-dimethoxy benzoate (0.50 g, 2.4 mmol), 3-methoxypropionitrile (0.19 g, 2.4 mmol), and 5 mL of 4 M HCl/dioxane, 2-(2-chloroethyl)-6,7-dimethoxyquinazolin-4-ol (307g) was obtained as tan solid (0.653 g, 101%) and used without purification.

Compound (307g) (219 mg, 0.815 mmol) and 10 mL of phosphorus(V) oxychloride afforded 4-chloro-2-(2-chloroethyl)-6,7-dimethoxyquinazoline (0.12 g) which was used without purification. MS (ESI+ve): Calculated for $C_{12}H_{13}Cl_2N_2O_2$, [M+H]=287.03, observed [M+H]=287.01.

4-chloro-2-(2-chloroethyl)-6,7-dimethoxyquinazoline (0.12 g, 0.42 mmol), 2-methoxyphenylpiperazine (239 mg, 1.05 mmol), potassium carbonate (0.40 g, 2.9 mmol), and 1,4-dioxane (6 mL) resulted in a crude brown oil which was purified by silica gel flash chromatography eluting with 30% to 75% ethyl acetate/hexanes, and then with 10% methanol/ethyl acetate. 10.9 mg of the partially pure (314) was obtained, and was repurified by reverse phase prep HPLC using a water/acetonitrile/0.1% formic acid gradient (95:5 to 2:98) to deliver 8 mg of (314) as a white solid (1% over 3 steps). $^1$H NMR (500 MHz, CDCl$_3$) δ 7.28 (broad m, 1H), 7.18 (s, 1H), 7.1-6.9 (m, 5H), 6.71 (br d, J=17.1 Hz, 1H), 5.75 (br m, 1H), 4.1-3.8 (m, 4H), 4.06 (s, 3H), 4.02 (s, 3H), 3.94 (s, 3H), 3.32-3.27 (m, 4H); HRMS (ESI+ve): Calculated for $C_{23}H_{27}N_4O_3$, [M+H]=407.2078, observed [M+H]=407.2064.

Additionally, the flash chromatography also afforded partially pure compound (319) as a tan solid, 85.6 mg. This product was repurified by reverse phase prep HPLC using a water/acetonitrile/0.1% formic acid gradient (95:5 to 2:98) to deliver 48 mg of the desired (319) as a white solid (3% over 3 steps). $^1$H NMR (500 MHz, CDCl$_3$) δ 7.27 (s, 1H), 7.16 (s, 1H), 7.10-6.88 (m, 8H), 4.07 (s, 3H), 4.01 (s, 3H), 3.95-3.88 (m, 4H), 3.94 (s, 3H), 3.89 (s, 3H), 3.8-3.2 (m, 12H), 3.1-2.85 (m, 4H); HRMS (ESI+ve): Calculated for $C_{34}H_{43}N_6O_4$, [M+H]=599.3340, observed [M+H]=599.3334.

Example 213: 2-cyclopentyl-6,7-dimethoxy-4-(4-(2-methoxyphenyl)piperazin-1-yl)quinazoline (316)

As described for compound (315), starting from methyl 2-amino-4,5-dimethoxy benzoate (1.00 g, 4.73 mmol), cyclopentanecarbonitrile (0.45 g, 4.73 mmol), and 10 mL of 4 M HCl/dioxane, 2-cyclopentyl-6,7-dimethoxyquinazolin-4-ol (307h) was obtained as an off-white solid (0.9 g, 69%) and was used without purification. $^1$H NMR (500 MHz, DMSO-d$_6$) δ 11.97 (s, 1H), 7.39 (s, 1H), 7.03 (s, 1H), 3.89 (s, 3H), 3.84 (s, 3H), 2.99 (p, J=8.2 Hz, 1H), 2.02-1.92 (m, 2H), 1.91-1.82 (m, 2H), 1.78-1.68 (m, 2H), 1.65-1.55 (m, 2H). MS (ESI+ve): Calculated for $C_{15}H_{18}N_2O_3$, [M+H]=275.14, observed [M+H]=275.11.

Compound (307h) (150 mg, 0.44 mmol) and 5 mL of phosphorus(V) oxychloride afforded 4-chloro-2-cyclopentyl-6,7-dimethoxyquinazoline which was used without purification. MS (ESI+ve): Calculated for $C_{15}H_{17Cl}N_2O_2$, [M+H]=293.11, observed [M+H]=293.02.

4-chloro-2-cyclopentyl-6,7-dimethoxyquinazoline (128 mg, 0.44 mmol), 1-(2-methoxyphenyl)piperazine hydrochloride (150 mg, 0.66 mmol), potassium carbonate (302 mg, 2.19 mmol), and 1,4-dioxane (5 mL) resulted in a brown residue which was purified by silica gel flash chromatography eluting with 0 to 25% ethyl acetate/hexanes. The product (316) was obtained as a yellow solid, (62 mg, 18% over 3 steps). $^1$H NMR (500 MHz, CDCl$_3$) δ 7.25 (s, 1H), 7.16 (s, 1H), 7.08-6.9 (m, 4H), 4.03 (s, 3H), 4.00 (s, 3H), 3.93 (s, 3H), 3.92-3.86 (m, 4H), 3.36-3.24 (m, 5H), 2.15-2.05 (m, 2H), 2.05-1.95 (m, 2H), 1.93-1.84 (m, 2H), 1.78-1.68 (m, 2H); HRMS (ESI+ve): Calculated for $C_{26}H_{32}N_4O_3$, [M+H]=449.2547, observed [M+H]=449.2530.

Example 214: 2-(cyclopropylmethyl)-6,7-dimethoxy-4-(4-(2-methoxyphenyl)piperazin-1-yl)quinazoline (317)

As described for compound (315), starting from methyl 2-amino-4,5-dimethoxy benzoate (1.00 g, 4.73 mmol), 2-cyclopropylacetonitrile (0.38 g, 4.73 mmol), and 10 mL of 4 M HCl/dioxane, 2-(cyclopropylmethyl)-6,7-dimethoxyquinazolin-4-ol (307i) was obtained as an off-white solid (1.04 g, 85%) and used without purification. $^1$H NMR (400 MHz, DMSO-d$_6$) δ 7.48-7.32 (m, 1H), 7.16-6.98 (m, 1H), 3.90-3.88 (m, 3H), 3.86-3.84 (m, 3H), 2.45 (d, J=8.5 Hz, 2H), 1.17 (s, 1H), 0.47 (d, J=8.0 Hz, 2H), 0.27-0.24 (m, 2H). MS (ESI+ve): Calculated for $C_{14}H_{16}N_2O_3$, [M+H]=261.12, observed [M+H]=247.11.

Compound (307i) (250 mg, 0.96 mmol) and 10 mL of phosphorus(V) oxychloride afforded 4-chloro-2-(cyclopropylmethyl)-6,7-dimethoxyquinazoline (245 mg) which was used without purification. MS (ESI+ve): Calculated for $C_{14}H_{16}ClN_2O_2$, [M+H]=279.09, observed [M+H]=279.13.

4-chloro-2-(cyclopropylmethyl)-6,7-dimethoxyquinazoline (245 mg, 0.88 mmol), 1-(2-methoxyphenyl)piperazine hydrochloride (302 mg, 1.32 mmol), potassium carbonate (607 mg, 4.39 mmol), and 1,4-dioxane (5 mL) resulted in a brown residue which was purified by silica gel flash chromatography eluting with 0 to 40% ethyl acetate/hexanes. The product (317) was obtained as a yellow solid, (188 mg, 38% over 3 steps). $^1$H NMR (400 MHz, CDCl$_3$) δ 7.29 (s, 1H), 7.17 (s, 1H), 7.1-6.9 (m, 4H), 4.03 (s, 3H), 4.00 (s, 3H), 3.94-3.88 (m, 4H), 3.92 (s, 3H), 3.31-3.26 (m, 4H), 2.81 (d, J=7.0 Hz, 2H), 1.40-1.25 (m, 1H), 0.57-0.46 (m, 2H), 0.39-0.30 (m, 2H); HRMS (ESI+ve): Calculated for $C_{25}H_{30}N_4O_3$, [M+H]=435.2391, observed [M+H]=435.2372.

Example 215: 2-(6,7-dimethoxy-4-(4-(2-methoxyphenyl)piperazin-1-yl)quinazolin-2-yl)-N,N-dimethylethanamine (318)

As described for compound (315), starting from methyl 2-amino-4,5-dimethoxy benzoate (0.50 g, 2.4 mmol), 3-(dimethylamino)propionitrile (0.23 g, 2.4 mmol), and 5 mL of 4 M HCl/dioxane, 2-(2-(dimethylamino)ethyl)-6,7-dimethoxyquinazolin-4-ol (307j) was obtained as a tan solid (0.137 g, 21%). (307j) contained some of the chloroethyl side product, but was used without purification. $^1$H NMR (500 MHz, DMSO-$d_6$) δ 12.07 (s, 1H), 7.41 (s, 1H), 7.08 (s, 1H), 3.90 (s, 3H), 3.86 (s, 3H), 2.75-2.64 (m, 4H), 2.19 (s, 6H); MS (ESI+ve): Calculated for $C_{14}H_{20}N_3O_3$, [M+H]=278.14, observed [M+H]=278.14.

Compound (307j) (135 mg, 0.487 mmol) and 10 mL of phosphorus(V) oxychloride afforded 2-(4-chloro-6,7-dimethoxyquinazolin-2-yl)-N,N-dimethylethanamine (0.15 g) which was used without purification. MS (ESI+ve): Calculated for $C_{14}H_{19}ClN_3O_2$, [M+H]=296.11, observed [M+H]=296.13.

2-(4-chloro-6,7-dimethoxyquinazolin-2-yl)-N,N-dimethylethanamine (0.15 g, 0.51 mmol), 2-methoxyphenylpiperazine (286 mg, 1.25 mmol), potassium carbonate (0.483 g, 3.5 mmol), and 1,4-dioxane (6 mL) resulted in a crude brown oil product, which was purified by silica gel flash chromatography eluting with 30% to 75% ethyl acetate/hexanes, and then with 10% methanol/ethyl acetate. The partially pure product was recovered as a tan solid, 78.5 mg. This product was repurified by reverse phase prep HPLC using a water/acetonitrile/0.1% formic acid gradient (95:5 to 2:98) to deliver 6 mg of the desired (318) as a tan solid (0.6% over 3 steps). $^1$H NMR (500 MHz, CDCl$_3$) δ 7.28 (s, 1H), 7.27 (s, 1H), 7.07-7.0 (m, 1H), 6.99-6.90 (m, 2H), 6.90-6.85 (m, 1H), 4.04 (s, 3H), 3.99 (s, 3H), 3.89 (s, 3H), 3.34 (s, 6H), 3.21 (m, 8H), 2.96 (m, 4H); HRMS (ESI+ve): Calculated for $C_{25}H_{34}N_5O_3$, [M+H]=452.2656, observed [M+H]=452.2653.

Example 216: 2-cyclobutyl-6,7-dimethoxy-4-(4-(2-methoxyphenyl)piperazin-1-yl)quinazoline (321)

As described for compound (315), starting from methyl 2-amino-4,5-dimethoxy benzoate (1.00 g, 4.73 mmol), cyclobutanecarbonitrile (0.38 g, 4.73 mmol), and 10 mL of 4 M HCl/dioxane, 2-cyclobutyl-6,7-dimethoxyquinazolin-4-ol (320) was obtained as a pinkish white solid (0.98 g, 80%) and was used without purification. $^1$H NMR (500 MHz, DMSO-$d_6$) δ 11.92 (s, 1H), 7.40 (s, 1H), 7.11 (s, 1H), 3.90 (s, 3H), 3.85 (s, 3H), 3.50-3.41 (m, 1H), 2.42-2.33 (m, 2H), 2.27-2.17 (m, 2H), 2.02-1.91 (m, 1H), 1.87-1.77 (m, 1H); MS (ESI+ve): Calculated for $C_{14}H_{16}N_2O_3$, [M+H]=261.12, observed [M+H]=261.07.

Compound (320) (0.4 g, 1.54 mmol) and 20 mL of phosphorus(V) oxychloride afforded the 4-chloro-2-cyclobutyl-6,7-dimethoxyquinazoline (0.3 g) which was used without purification. MS (ESI+ve): Calculated for $C_{14}H_{15}ClN_2O_2$, [M+H]=279.09, observed [M+H]=279.01.

The crude 4-chloro-2-cyclobutyl-6,7-dimethoxyquinazoline (250 mg, 0.90 mmol), 1-(2-methoxyphenyl)piperazine hydrochloride (308 mg, 1.35 mmol), potassium carbonate (620 mg, 4.48 mmol), and 1,4-dioxane (4 mL) resulted in a brown residue which was purified by silica gel flash chromatography eluting with 0 to 50% ethyl acetate/hexanes. The product (321) was obtained as a pale yellow solid, (155 mg, 9% over 3 steps). $^1$H NMR (500 MHz, CDCl$_3$) δ 7.25 (s, 1H), 7.16 (s, 1H), 7.10-7.05 (m, 1H), 7.09-7.01 (m, 2H), 7.0-6.95 (m, 1H), 6.93 (d, J=8.0 Hz, 1H), 4.03 (s, 3H), 4.00 (s, 3H), 3.96-3.89 (m, 7H), 3.76 (p, J=8.9 Hz, 1H), 3.35-3.25 (m, 4H), 2.59-2.48 (m, 2H), 2.42-2.34 (m, 2H), 2.15-2.03 (m, 1H), 2.04-1.93 (m, 1H); HRMS (ESI+ve): Calculated for $C_{25}H_{30}N_4O_3$, [M+H]=435.2391, observed [M+H]=435.2380.

Example 217: 2-cyclobutyl-6,7-dimethoxy-4-(4-phenylpiperazin-1-yl)quinazoline (322)

As described for Compound (315), the crude 4-chloro-2-cyclobutyl-6,7-dimethoxyquinazoline resulting from (320) (75 mg, 0.27 mmol) 1-phenylpiperazine (66 mg, 0.4 mmol), potassium carbonate (186 mg, 1.35 mmol), and 1,4-dioxane (3 mL) resulted in a brown residue which was purified by silica gel flash chromatography eluting with 0 to 35% ethyl acetate/hexanes. The product (322) was obtained as a white solid, (65 mg, 14% over 3 steps). $^1$H NMR (500 MHz, CDCl$_3$) δ 7.33 (dd, J=8.7, 7.2 Hz, 2H), 7.26 (s, 1H), 7.16 (s, 1H), 7.05-7.01 (d, J=7.5 Hz, 2H), 6.93 (t, J=7.3 Hz, 1H), 4.03 (s, 3H), 4.00 (s, 3H), 3.90-3.85 (m, 4H), 3.76 (p, J=8.5 Hz, 1H), 3.47-3.41 (m, 4H), 2.61-2.47 (m, 2H), 2.44-2.34 (m, 2H), 2.15-2.04 (m, 1H), 2.03-1.93 (m, 1H); HRMS (ESI+ve): Calculated for $C_{24}H_{28}N_4O_2$, [M+H]=405.2285, observed [M+H]=405.2272.

Example 218: 2-cyclobutyl-6,7-dimethoxy-4-(4-(o-tolyl)piperazin-1-yl)quinazoline (323)

As described for compound (315), the crude 4-chloro-2-cyclobutyl-6,7-dimethoxyquinazoline resulting from (320) (75 mg, 0.27 mmol), 1-(o-tolyl)piperazine hydrochloride (86 mg, 0.4 mmol), potassium carbonate (186 mg, 1.35 mmol), and 1,4-dioxane (3 mL) resulted in a brown residue which was purified by silica gel flash chromatography eluting with 0 to 35% ethyl acetate/hexanes. The product (323) was obtained as a white solid, (66 mg, 13% over 3 steps). $^1$H NMR (500 MHz, CDCl$_3$) δ 7.25 (s, 1H), 7.25-7.20 (m, 2H), 7.18 (s, 1H), 7.12 (d, J=8.0 Hz, 1H), 7.08-7.02 (m, 1H), 4.03 (s, 3H), 4.01 (s, 3H), 3.89-3.82 (m, 4H), 3.82-3.73 (m, 1H), 3.19-3.13 (m, 4H), 2.61-2.50 (m, 2H), 2.4 (s, 3H), 2.45-2.34 (m, 2H), 2.16-2.04 (m, 1H), 2.03-1.94 (m, 1H); HRMS (ESI+ve): Calculated for $C_{23}H_{25}FN_3O_2S$, [M+H]=419.2442, observed [M+H]=419.2429.

Example 219: 2-cyclobutyl-4-(4-(2-fluorophenyl)piperazin-1-yl)-6,7-dimethoxyquinazoline (324)

As described for compound (315), the crude 4-chloro-2-cyclobutyl-6,7-dimethoxyquinazoline resulting from (320) (75 mg, 0.27 mmol), 1-(2-fluorophenyl)piperazine (88 mg, 0.4 mmol), potassium carbonate (186 mg, 1.35 mmol), and 1,4-dioxane (3 mL) resulted in a brown residue which was purified by silica gel flash chromatography eluting with 0 to 35% ethyl acetate/hexanes. The product (324) was obtained as a white solid, (62 mg, 13% over 3 steps). $^1$H NMR (500 MHz, CDCl$_3$) δ 7.26 (s, 1H), 7.15 (s, 1H), 7.14-6.96 (m, 4H), 4.03 (s, 3H), 4.00 (s, 3H), 3.93-3.87 (m, 4H), 3.80-3.70 (m, 1H), 3.36-3.31 (m, 4H), 2.59-2.48 (m, 2H), 2.43-2.34 (m, 2H), 2.14-2.04 (m, 1H), 2.04-1.94 (m, 1H); HRMS (ESI+ve): Calculated for $C_{24}H_{27}FN_4O_2$, [M+H]=423.2191, observed [M+H]=423.2174.

Example 220: 4-(4-(2-chlorophenyl)piperazin-1-yl)-2-cyclobutyl-6,7-dimethoxyquinazoline (325)

As described for compound (315), the crude 4-chloro-2-cyclobutyl-6,7-dimethoxyquinazoline resulting from (320) (75 mg, 0.27 mmol), 1-(2-chlorophenyl)piperazine (79 mg, 0.4 mmol), potassium carbonate (186 mg, 1.35 mmol), and 1,4-dioxane (3 mL) resulted in a brown residue which was purified by silica gel flash chromatography eluting with 0 to 35% ethyl acetate/hexanes. The product (325) was obtained as a white solid, (70 mg, 14% over 3 steps). $^1$H NMR (500 MHz, CDCl$_3$) δ 7.42 (dd, J=8.0, 1.5 Hz, 1H), 7.30-7.28 (m, 1H), 7.26 (s, 1H), 7.16 (s, 1H), 7.13 (dd, J=8.0, 1.5 Hz, 1H), 7.03 (td, J=8.0, 1.5 Hz, 1H), 4.03 (s, 3H), 4.00 (s, 3H), 3.95-3.88 (m, 4H), 3.81-3.72 (m, 1H), 3.32-3.26 (m, 4H), 2.60-2.48 (m, 2H), 2.44-2.34 (m, 2H), 2.16-2.04 (m, 1H), 2.03-1.94 (m, 1H); HRMS (ESI+ve): Calculated for C$_{23}$H$_{25}$FN$_3$O$_2$S, [M+H]=439.1895, observed [M+H]=439.1882.

Example 221: 2-cyclobutyl-6,7-dimethoxy-4-(4-(pyridin-2-yl)piperazin-1-yl)quinazoline (326)

As described for compound (315), the crude 4-chloro-2-cyclobutyl-6,7-dimethoxyquinazoline resulting from (320) (150 mg, 0.54 mmol), 1-(2-pyridyl)piperazine (132 mg, 0.81 mmol), potassium carbonate (372 mg, 2.69 mmol), and 1,4-dioxane (5 mL) resulted in a brown residue which was purified by silica gel flash chromatography eluting with 0 to 25% ethyl acetate/hexanes. The product (326) was obtained as a yellow solid, (120 mg, 44% over 3 steps). $^1$H NMR (500 MHz, CDCl$_3$) δ 8.25 (dd, J=4.9, 2.0, 1H), 7.56 (ddd, J=8.5, 7.1, 2.0 Hz, 1H), 7.26 (broad s, 1H), 7.17 (s, 1H), 6.75 (d, J=8.5 Hz, 1H), 6.71 (dd, J=7.1, 5.0 Hz, 1H), 4.04 (s, 3H), 4.00 (s, 3H), 3.93-3.72 (m, 9H), 2.59-2.47 (m, 2H), 2.44-2.34 (m, 2H), 2.15-2.04 (m, 1H), 2.03-1.93 (m, 1H); HRMS (ESI+ve): Calculated for C$_{21}$H$_{23}$N$_4$O$_2$, [M+H]=406.2238, observed [M+H]=406.2221.

Example 222: 2-cyclobutyl-6,7-dimethoxy-4-(4-(2-nitrophenyl)piperazin-1-yl)quinazoline (327)

As described for compound (315), the crude 4-chloro-2-cyclobutyl-6,7-dimethoxyquinazoline resulting from (320) (150 mg, 0.54 mmol), 1-(2-nitrophenyl)piperazine (167 mg, 0.81 mmol), potassium carbonate (372 mg, 2.69 mmol), and 1,4-dioxane (5 mL) resulted in a brown residue which was purified by silica gel flash chromatography eluting with 0 to 25% ethyl acetate/hexanes. The product (327) was obtained as a orange solid, (149 mg, 46% over 3 steps). $^1$H NMR (500 MHz, CDCl$_3$) δ 7.84 (dd, J=8.2, 1.6 Hz, 1H), 7.54 (ddd, J=8.2, 7.4, 1.6 Hz, 1H), 7.4-7.25 (m, 1H), 7.23 (d, J=8.2, 1H), 7.16-7.10 (m, 2H), 4.04 (s, 3H), 4.00 (s, 3H), 3.98-3.92 (m, 4H), 3.84 (broad s, 1H), 3.4-3.26 (m, 4H), 2.58-2.47 (m, 2H), 2.45-2.35 (m, 2H), 2.17-2.04 (m, 1H), 2.03-1.92 (m, 1H); HRMS (ESI+ve): Calculated for C$_{24}$H$_{27}$N$_5$O$_4$, [M+H]=450.2136, observed [M+H]=450.2120.

Example 223: 2-cyclobutyl-6,7-dimethoxy-4-(4-(3-methoxyphenyl)piperazin-1-yl)quinazoline (328)

As described for compound (315), the crude 4-chloro-2-cyclobutyl-6,7-dimethoxyquinazoline resulting from (320) (100 mg, 0.36 mmol), 1-(2-methoxyphenyl)piperazine hydrochloride (143 mg, 0.54 mmol), potassium carbonate (248 mg, 1.79 mmol), and 1,4-dioxane (3 mL) resulted in a brown residue which was purified by silica gel flash chromatography eluting with 0 to 35% ethyl acetate/hexanes. The product (328) was obtained as a pale yellow solid, (100 mg, 15% over 3 steps). $^1$H NMR (500 MHz, CDCl$_3$) δ 7.27-7.20 (m, 2H), 7.15 (s, 1H), 6.63 (dd, J=8.0, 2.3 Hz, 1H), 6.55 (t, J=2.3 Hz, 1H), 6.48 (dd, J=8.0, 2.3 Hz, 1H), 4.03 (s, 3H), 4.00 (s, 3H), 3.88-3.84 (m, 4H), 3.83 (s, 3H), 3.78-3.72 (m, 1H), 3.47-3.40 (m, 4H), 2.58-2.47 (m, 2H), 2.43-2.33 (m, 2H), 2.14-2.05 (m, 1H), 2.03-1.93 (m, 1H); HRMS (ESI+ve): Calculated for C$_{25}$H$_{30}$N$_4$O$_3$, [M+H]=435.2391, observed [M+H]=435.2375.

Example 224: 2-cyclobutyl-6,7-dimethoxy-4-(4-(4-methoxyphenyl)piperazin-1-yl)quinazoline (329)

As described for compound (315), the crude 4-chloro-2-cyclobutyl-6,7-dimethoxyquinazoline resulting from (320) (100 mg, 0.36 mmol), 1-(4-methoxyphenyl)piperazine hydrochloride (143 mg, 0.54 mmol), potassium carbonate (248 mg, 1.79 mmol), and 1,4-dioxane (3 mL) resulted in a brown residue which was purified by silica gel flash chromatography eluting with 0 to 35% ethyl acetate/hexanes. The product (329) was obtained as a yellow solid, (106 mg, 15% over 3 steps). $^1$H NMR (500 MHz, DMSO-d$_6$) δ 7.20 (s, 1H), 7.16 (broad s, 1H), 6.97 (d, J=9.0 Hz, 2H), 6.86 (d, J=9.0 Hz, 2H), 3.93 (s, 3H), 3.91 (s, 3H), 3.76 (broad s, 4H), 3.70 (s, 3H), 3.67-3.61 (m, 1H), 3.26-3.24 (m, 4H), 2.46-2.36 (m, 2H), 2.31-2.21 (m, 2H), 2.06-1.95 (m, 1H), 1.92-1.84 (m, 1H); HRMS (ESI+ve): Calculated for C$_{25}$H$_{30}$N$_4$O$_3$, [M+H]=435.2391, observed [M+H]=435.2374.

Example 225: 2-cyclobutyl-4-(4-(2,4-dimethoxyphenyl)piperazin-1-yl)-6,7-dimethoxyquinazoline (330)

As described for compound (315) the crude 4-chloro-2-cyclobutyl-6,7-dimethoxyquinazoline resulting from (320) (150 mg, 0.54 mmol), 1-(2,4-dimethoxyphenyl)piperazine (179 mg, 0.81 mmol), potassium carbonate (372 mg, 2.69 mmol), and 1,4-dioxane (5 mL) resulted in a brown residue which was purified by silica gel flash chromatography eluting with 0 to 25% ethyl acetate/hexanes. The product (330) was obtained as a yellow solid, (150 mg, 45% over 3 steps). $^1$H NMR (500 MHz, CDCl$_3$) δ ca. 7.3 (broad s, 1H), 7.16 (s, 1H), 6.94 (d, J=8.6 Hz, 1H), 6.54 (d, J=2.7 Hz, 1H), 6.48 (dd, J=8.6, 2.7 Hz, 1H), 4.03 (s, 3H), 4.00 (s, 3H), 3.98-3.92 (m, 4H), 3.90 (s, 3H), 3.82 (s, 3H), 3.85-3.75 (s, 1H), 3.26-3.20 (m, 4H), 2.60-2.47 (m, 2H), 2.45-2.34 (m, 2H), 2.15-2.04 (m, 1H), 2.03-1.93 (m, 1H); HRMS (ESI+ve): Calculated for C$_{26}$H$_{32}$N$_4$O$_4$, [M+H]=465.2496, observed [M+H]=465.2477.

Example 226: 2-cyclobutyl-4-(4-(2,6-dimethylphenyl)piperazin-1-yl)-6,7-dimethoxyquinazoline (331)

As described for compound (315), the crude 4-chloro-2-cyclobutyl-6,7-dimethoxyquinazoline resulting from (320) (150 mg, 0.54 mmol), 1-(2,6-dimethyphenyl)piperazine (179 mg, 0.81 mmol), potassium carbonate (372 mg, 2.69 mmol), and 1,4-dioxane (5 mL) resulted in a brown residue which was purified by silica gel flash chromatography eluting with 0 to 30% ethyl acetate/hexanes. The product (331) was obtained as a yellow solid, (140 mg, 45% over 3 steps). $^1$H NMR (500 MHz, CDCl$_3$) δ 7.28 (s, overlapped by solvent, 1H), 7.19 (s, 1H), 7.1-6.95 (m, 3H), 4.05 (s, 3H), 4.01 (s, 3H), 3.95-3.74 (m, 5H), 3.38-3.31 (m, 4H), 2.60-2.49 (m, 2H), 2.46-2.36 (m, 2H), 2.41 (s, 6H), 2.16-2.05 (m, 1H), 2.03-1.94 (m, 1H); HRMS (ESI+ve): Calculated for C$_{26}$H$_{32}$N$_4$O$_2$, [M+H]=433.2598, observed [M+H]= 433.2581.

Scheme 31:

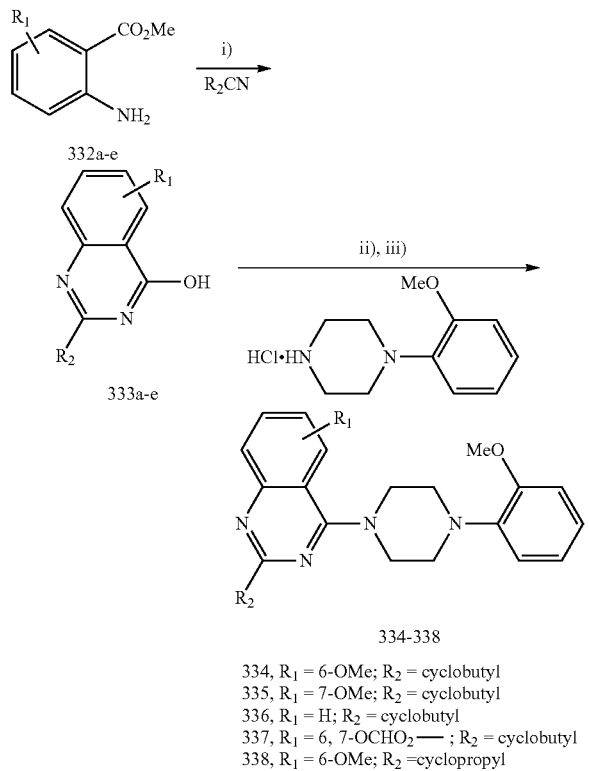

334, R$_1$ = 6-OMe; R$_2$ = cyclobutyl
335, R$_1$ = 7-OMe; R$_2$ = cyclobutyl
336, R$_1$ = H; R$_2$ = cyclobutyl
337, R$_1$ = 6, 7-OCHO$_2$—; R$_2$ = cyclobutyl
338, R$_1$ = 6-OMe; R$_2$ = cyclopropyl Example 227: 2-cyclobutyl-6-methoxy-4-(4-(2-methoxyphenyl)piperazin-1-yl)quinazoline (334)

As described for compound (315), starting from methyl 2-amino-4-methoxy benzoate (332a) (190 mg, 1.05 mmol), cyclobutanecarbonitrile (170 mg, 2.1 mmol), and 2 mL of 4 M HCl/dioxane, 2-cyclobutyl-6-methoxyquinazolin-4-ol (333a) was obtained as an off-white solid (190 mg, 79%) and used without purification. $^1$H NMR (500 MHz, CDCl$_3$) δ 9.81 (s, 1H), 8.17 (d, J=8.8 Hz, 1H), 7.13 (d, J=2.5 Hz, 1H), 7.04 (dd, J=8.8, 2.5 Hz, 1H), 3.95 (s, 3H), 3.56 (p, J=8.8 Hz, 1H), 2.58-2.39 (m, 4H), 2.22-2.10 (m, 1H), 2.05-1.95 (m, 1H); MS (ESI+ve): Calculated for C$_{13}$H$_{14}$N$_2$O$_2$, [M+H]=231.11, observed [M+H]=231.07.

Compound (333a) (150 mg, 0.65 mmol) and 3 mL of phosphorus(V) oxychloride afforded 4-chloro-2-cyclobutyl-6-methoxyquinazoline which was used without purification. MS (ESI+ve): Calculated for C$_{13}$H$_{13}$ClN$_2$O, [M+H]= 249.08, observed [M+H]=249.01.

4-chloro-2-cyclobutyl-6-methoxyquinazoline (140 mg, 0.56 mmol), 1-(2-methoxyphenyl)piperazine hydrochloride (193 mg, 0.84 mmol), potassium carbonate (389 mg, 2.81 mmol), and 1,4-dioxane (5 mL) resulted in a brown residue which was purified by silica gel flash chromatography eluting with 0 to 10% ethyl acetate/hexanes. The product (334) was obtained as a pale yellow solid, (80 mg, 30% over 3 steps). $^1$H NMR (500 MHz, CDCl$_3$) δ 7.84 (d, J=9.1 Hz, 1H), 7.39 (dd, J=9.2, 2.8 Hz, 1H), 7.22 (d, J=2.8 Hz, 1H), 7.09-6.95 (m, 3H), 6.93 (dd, J=8.0, 1.4 Hz, 1H), 3.99-3.95 (m, 4H), 3.93 (s, 3H), 3.93 (s, 3H), 3.83-3.73 (m, 1H), 3.35-3.28 (m, 4H), 2.60-2.48 (m, 2H), 2.44-2.33 (m, 2H), 2.14-2.04 (m, 1H), 2.04-1.95 (m, 1H); HRMS (ESI+ve): Calculated for C$_{24}$H$_{28}$N$_4$O$_2$ [M+H]=405.2285, observed [M+H]=405.2269.

Example 228: 2-cyclobutyl-7-methoxy-4-(4-(2-methoxyphenyl)piperazin-1-yl)quinazoline (335)

As described for compound (315), starting from methyl 2-amino-5-methoxy benzoate (332b) (120 mg, 0.66 mmol), cyclobutanecarbonitrile (54 mg, 0.66 mmol), and 2 mL of 4 M HCl/dioxane, 2-cyclobutyl-7-methoxyquinazolin-4-ol (333b) (150 mg, 98%) was obtained as an off-white solid and used without purification. $^1$H NMR (500 MHz, CDCl$_3$) δ 9.59 (s, 1H), 7.67 (d, J=8.9 Hz, 1H), 7.64 (d, J=3.0 Hz, 1H), 7.38 (dd, J=8.9, 3.0 Hz, 1H), 3.94 (s, 3H), 3.61-3.50 (m, 1H), 2.57-2.47 (m, 2H), 2.47-2.39 (m, 2H), 2.20-2.10 (m, 1H), 2.05-1.96 (m, 1H); MS (ESI+ve): Calculated for C$_{13}$H$_{14}$N$_2$O$_2$, [M+H]=231.11, observed [M+H]=231.06.

Compound (333b) (190 mg, 0.83 mmol) and 10 mL of phosphorus(V) oxychloride afforded 4-chloro-2-cyclobutyl-7-methoxyquinazoline which was used without purification. MS (ESI+ve): Calculated for C$_{13}$H$_{13}$ClN$_2$O, [M+H]= 249.08, observed [M+H]=249.0.

4-chloro-2-cyclobutyl-7-methoxyquinazoline (205 mg, 0.83 mmol), 1-(2-methoxyphenyl)piperazine hydrochloride (283 mg, 1.24 mmol), potassium carbonate (570 mg, 4.12 mmol), and 1,4-dioxane (5 mL) resulted in a brown residue which was purified by silica gel flash chromatography eluting with 0 to 20% ethyl acetate/hexanes. The product (335) was obtained as a yellow solid, (180 mg, 42% over 3 steps). $^1$H NMR (400 MHz, CDCl$_3$) δ 7.82 (d, J=9.1 Hz, 1H), 7.21 (s, 1H), 7.10-6.95 (m, 4H), 6.93 (d, J=8.0 Hz, 1H), 4.03-3.96 (m, 4H), 3.94 (s, 3H), 3.93 (s, 3H), 3.80-3.69 (m, 1H), 3.33-3.23 (m, 4H), 2.61-2.47 (m, 2H), 2.43-2.32 (m, 2H), 2.08 (q, J=9.3 Hz, 1H), 2.04-1.94 (m, 1H); HRMS (ESI+ve): Calculated for C$_{24}$H$_{28}$N$_4$O$_2$ [M+H]=405.2285, observed [M+H]=405.2269.

Example 229: 2-cyclobutyl-4-(4-(2-methoxyphenyl)piperazin-1-yl)quinazoline (336)

As described for compound (315), starting from methyl 2-aminobenzoate (332c) (1.00 g, 6.62 mmol), cyclobutanecarbonitrile (0.54 g, 6.62 mmol), and 10 mL of 4 M HCl/dioxane, 2-cyclobutylquinazolin-4-ol (333c) was obtained as an off-white solid (0.97 g, 73%) and used without purification. $^1$H NMR (500 MHz, DMSO-d$_6$) δ 9.91 (s, 1H), 8.28 (dd, J=7.9, 1.5 Hz, 1H), 7.87-7.68 (m, 2H), 7.48 (ddd, J=8.1, 6.8, 1.5 Hz, 1H), 3.59 (p, J=8.8 Hz, 1H), 2.54 (dq, J=11.8, 9.3 Hz, 2H), 2.48-2.40 (m, 2H), 2.21-2.10 (m, 1H), 2.05-1.97 (m, 1H). MS (ESI+ve): Calculated for C$_{12}$H$_{12}$N$_2$O, [M+H]=201.11, observed [M+H]=201.05.

Compound (333c) (150 mg, 0.75 mmol) and 5 mL of phosphorus(V) oxychloride afforded the 4-chloro-2-cyclobutylquinazoline which was used without purification. MS (ESI+ve): Calculated for C$_{12}$H$_{11}$ClN$_2$, [M+H]=219.07, observed [M+H]=219.01.

4-chloro-2-cyclobutylquinazoline (164 mg, 0.75 mmol), 1-(2-methoxyphenyl)piperazine hydrochloride (189 mg, 0.83 mmol), potassium carbonate (518 mg, 3.75 mmol), and 1,4-dioxane (5 mL) resulted in a brown residue which was purified by silica gel flash chromatography eluting with 0 to 25% ethyl acetate/hexanes. The product (336) was obtained as a yellow solid, (15 mg, 4% over 3 steps). $^1$H NMR (500 MHz, CDCl$_3$) δ 7.93 (dd, J=8.3, 1.3 Hz, 1H), 7.88 (broad s, 1H), 7.71 (t, J=7.6 Hz, 1H), 7.41 (t, J=7.7 Hz, 1H), 7.09-6.95 (m, 1H), 6.93 (dd, J=8.0, 1.4 Hz, 1H), 4.04 (broad s, 4H), 3.93 (s, 3H), 3.86-3.74 (m, 1H), 3.35-3.25 (m, 4H), 2.60-2.49 (m, 2H), 2.44-2.34 (m, 2H), 2.15-2.04 (m, 1H), 2.04-1.95 (m, 1H); HRMS (ESI+ve): Calculated for $C_{23}H_{22}N_4O$, [M+H]=375.2179, observed [M+H]=375.2165.

Example 230: 6-cyclobutyl-8-(4-(2-methoxyphenyl)piperazin-1-yl)-[1,3]dioxolo[4,5-g]quinazoline (337)

As described for compound (315), starting from methyl 6-aminobenzo[d][1,3]dioxole-5-carboxylate (332d) (135 mg, 0.69 mmol), cyclobutanecarbonitrile (56 mg, 0.69 mmol), and 2 mL of 4 M HCl/dioxane, 6-cyclobutyl-[1,3]dioxolo[4,5-g]quinazolin-8-ol (333d) (120 mg, 71%) was obtained as an off-white solid and used without purification. $^1$H NMR (400 MHz, CDCl$_3$) δ 10.58 (s, 1H), 7.59 (s, 1H), 7.11 (s, 1H), 6.13 (s, 2H), 3.58 (t, J=8.7 Hz, 1H), 2.59-2.36 (m, 4H), 2.22-2.08 (m, 1H), 2.06-1.94 (m, 1H); MS (ESI+ve): Calculated for $C_{13}H_{12}N_2O_3$, [M+H]=245.09, observed [M+H]=245.06.

Compound (333d) (130 mg, 0.53 mmol) and 5 mL of phosphorus(V) oxychloride afforded the 8-chloro-6-cyclobutyl-[1,3]dioxolo[4,5-g]quinazoline which was used without purification. MS (ESI+ve): Calculated for $C_{13}H_{12}ClN_2O_2$, [M+H]=263.06, observed [M+H]=262.99.

8-chloro-6-cyclobutyl-[1,3]dioxolo[4,5-g]quinazoline (140 mg, 0.53 mmol), 1-(2-methoxyphenyl)piperazine hydrochloride (183 mg, 0.8 mmol), potassium carbonate (368 mg, 2.66 mmol), and 1,4-dioxane (5 mL) resulted in a brown residue which was purified by silica gel flash chromatography eluting with 0 to 30% ethyl acetate/hexanes. The product (337) was obtained as a white solid, (100 mg, 35% over 3 steps). $^1$H NMR (500 MHz, CDCl$_3$) δ 7.35 (s, 1H), 7.29 (broad s, 1H), 7.16-7.02 (m, 3H), 7.00 (dd, J=8.0, 1.4 Hz, 1H), 6.17 (s, 2H), 4.00 (s, 3H), 3.96-3.90 (m, 4H), 3.87-3.76 (m, 1H), 3.41-3.31 (t, 4H), 2.65-2.55 (m, 2H), 2.49-2.39 (m, 2H), 2.21-2.09 (m, 1H), 2.10-2.01 (m, 1H); HRMS (ESI+ve): Calculated for $C_{24}H_{26}N_4O_3$, [M+H]=419.2078, observed [M+H]=419.2057.

Example 231: 2-cyclopropyl-6-methoxy-4-(4-(2-methoxyphenyl)piperazin-1-yl)quinazoline (338)

As described for compound (315), starting from (332e) (300 mg, 1.05 mmol), cyclopropanecarbonitrile (333 mg, 4.97 mmol), and 4 mL of 4 M HCl/dioxane, 2-cyclopropyl-6-methoxyquinazolin-4-ol (333e) (200 mg, 56%) was obtained as an off-white solid and used without purification. $^1$H NMR (500 MHz, DMSO-d$_6$) δ 7.55 (d, J=8.9 Hz, 1H), 7.37 (dd, J=8.8, 3.0 Hz, 1H), 7.33 (dd, J=9.0, 2.9 Hz, 1H), 3.85 (s, 3H), 1.96-1.89 (m, 1H), 1.08-1.02 (m, 2H), 1.02-0.96 (m, 2H); MS (ESI+ve): Calculated for $C_{12}H_{12}N_2O_2$, [M+H]=217.10, observed [M+H]=217.11. Compound (333e) (200 mg, 0.93 mmol) and 10 mL of phosphorus(V) oxychloride afforded the 4-chloro-2-cyclopropyl-6-methoxyquinazoline, which was used without purification. MS (ESI+ve): Calculated for $C_{12}H_{12}ClN_2O$, [M+H]=235.06, observed [M+H]=235.09.

4-chloro-2-cyclopropyl-6-methoxyquinazoline (217 mg, 0.93 mmol), 1-(2-methoxyphenyl)piperazine hydrochloride (317 mg, 1.39 mmol), potassium carbonate (639 mg, 4.62 mmol), and 1,4-dioxane (5 mL) resulted in a brown residue which was purified by silica gel flash chromatography eluting with 0 to 40% ethyl acetate/hexanes. The product (338) was obtained as a yellow solid, (30 mg, 5% over 3 steps). $^1$H NMR (500 MHz, CDCl$_3$) δ 7.81 (s, 1H), 7.39 (d, J=9.1 Hz, 1H), 7.19 (d, J=2.8 Hz, 1H), 7.10-7.03 (m, 1H), 7.03-6.95 (m, 2H), 6.93 (dd, J=8.0, 1.3 Hz, 1H), 4.02-3.76 (m, 10H), 3.30-3.19 (m, 4H), 2.25 (broad s, 1H), 1.24-1.15 (m, 2H), 1.04 (s, 2H); HRMS (ESI+ve): Calculated for $C_{23}H_{26}N_4O_2$, [M+H]=391.2129, observed [M+H]=391.2116.

Scheme 32:

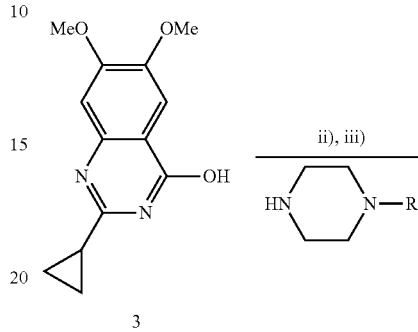

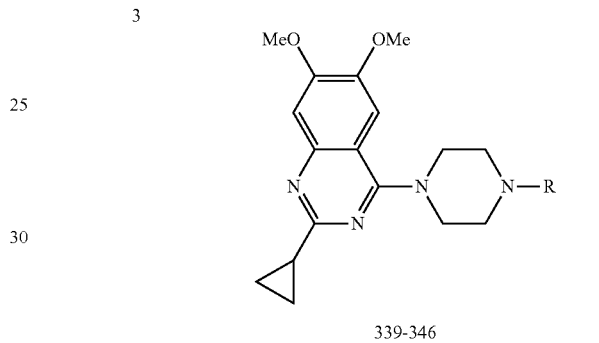

339-346

339, R = 2-ethoxyphenyl
340, R = 2-chlorophenyl
341, R = ―SO$_2$Ph
342, R = 4-methylbenzyl
343, R = 2-methoxybenzyl
344, R = benzoyl
345, R = 2-methoxybenzoyl
346, R = H Example 232: 2-cyclopropyl-4-(4-(2-ethoxyphenyl)piperazin-1-yl)-6,7-dimethoxyquinazoline (339)

As described for compound (315), the crude chloroquinazoline resulting from (3) (250 mg, 0.94 mmol), 1-(2-ethoxyphenyl)piperazine hydrochloride (344 mg, 1.42 mmol), potassium carbonate (653 mg, 4.72 mmol), and 1,4-dioxane (5 mL) resulted in a brown residue which was purified by silica gel flash chromatography eluting with 0 to 30% ethyl acetate/hexanes. The product (339) was obtained as a yellow solid, (112 mg, 17% over 3 steps). $^1$H NMR (500 MHz, CDCl$_3$) δ 7.32 (broad s, 1H), 7.13 (s, 1H), 7.05-7.00 (m, 1H), 7.00-6.93 (m, 2H), 6.91 (d, J=8.0 Hz, 1H), 4.13 (q, J=7.0 Hz, 2H), 4.04 (s, 3H), 3.99 (s, 3H), 3.92-3.82 (m, 4H), 3.35-3.21 (m, 4H), 2.32-2.22 (m, 1H), 1.50 (t, J=7.0 Hz, 3H), 1.23-1.16 (m, 2H), 1.09-0.99 (m, 2H); HRMS (ESI+ve): Calculated for $C_{25}H_{30}N_4O_3$, [M+H]=435.2391, observed [M+H]=435.2373.

Example 233: 4-(4-(2-chlorophenyl)piperazin-1-yl)-2-cyclopropyl-6,7-dimethoxyquinazoline (340)

As described for compound (315), the crude chloroquinazoline resulting from (3) (260 mg, 0.98 mmol), 1-(2-chlorophenyl)piperazine (290 mg, 1.47 mmol), potassium carbonate (679 mg, 4.91 mmol), and 1,4-dioxane (5 mL) resulted in a brown residue which was purified by silica gel flash chromatography eluting with 0 to 40% ethyl acetate/hexanes. The product (340) was obtained as a yellow solid, (116 mg, 18% over 3 steps). $^1$H NMR (500 MHz, CDCl$_3$) δ 7.42 (dd, J=8.0, 1.5 Hz, 1H), 7.28-7.25 (m, 2H), 7.13-7.09 (m, 2H), 7.04 (td, J=7.7, 1.5 Hz, 1H), 4.04 (s, 3H), 3.99 (s, 3H), 3.87 (broad s, 4H), 3.28-3.14 (m, 4H), 2.24 (s, 1H), 1.22-1.16 (m, 2H), 1.04 (s, 2H); HRMS (ESI+ve): Calculated for C$_{23}$H$_{25}$ClN$_4$O$_2$, [M+H]=425.1739, observed [M+H]=425.1726.

Example 234: 2-cyclopropyl-6,7-dimethoxy-4-(4-(phenylsulfonyl)piperazin-1-yl)quinazoline (341)

As described for compound (315), the crude chloroquinazoline resulting from (3) (250 mg, 0.94 mmol), 1-(phenylsulfonyl)piperazine (321 mg, 1.42 mmol), potassium carbonate (653 mg, 4.72 mmol), and 1,4-dioxane (5 mL) resulted in a brown residue which was purified by silica gel flash chromatography eluting with 0 to 60% ethyl acetate/hexanes. The product (341) was obtained as an off-white solid, (135 mg, 19% over 3 steps). $^1$H NMR (500 MHz, CDCl$_3$) δ 7.83-7.78 (m, 2H), 7.68-7.62 (m, 1H), 7.61-7.56 (m, 2H), 7.28 (broad s, 1H), 6.93 (s, 1H), 4.01 (s, 3H), 3.94 (s, 3H), 3.75 (s, 4H), 3.25-3.15 (m, 4H), 2.27-2.11 (m, 1H), 1.05-0.95 (m, 4H); HRMS (ESI+ve): Calculated for C$_{23}$H$_{26}$N$_4$O$_4$S, [M+H]=455.1748, observed [M+H]=455.1728.

Example 235: 2-cyclopropyl-6,7-dimethoxy-4-(4-(4-methylbenzyl)piperazin-1-yl)quinazoline (342)

As described for compound (315), the crude chloroquinazoline resulting from (3) (250 mg, 0.94 mmol), 1-(4-methylbenzyl)piperazine (270 mg, 1.42 mmol), potassium carbonate (653 mg, 4.72 mmol), and 1,4-dioxane (5 mL) resulted in a brown residue which was purified by silica gel flash chromatography eluting with 0 to 60% ethyl acetate/hexanes. The product (342) was obtained as a yellow solid, (65 mg, 11% over 3 steps). $^1$H NMR (500 MHz, CDCl$_3$) δ 7.29-7.23 (m, 3H), 7.17 (d, J=7.7 Hz, 2H), 7.05 (s, 1H), 4.02 (s, 3H), 3.95 (s, 3H), 3.70 (s, 4H), 3.57 (s, 2H), 2.70-2.55 (m, 4H), 2.37 (s, 3H), 2.24 (broad s, 1H), 1.17-1.13 (m, 2H), 1.01 (t, J=9.0 Hz, 2H); HRMS (ESI+ve): Calculated for C$_{25}$H$_{30}$N$_4$O$_2$, [M+H]=419.2442, observed [M+H]=419.2424.

Example 236: 2-cyclopropyl-6,7-dimethoxy-4-(4-(2-methoxybenzyl)piperazin-1-yl)quinazoline (343)

As described for compound (315), the crude chloroquinazoline resulting from (3) (260 mg, 0.98 mmol), 1-(2-methoxybenzyl)piperazine (304 mg, 1.47 mmol), potassium carbonate (679 mg, 4.91 mmol), and 1,4-dioxane (5 mL) resulted in a brown residue which was purified by silica gel flash chromatography eluting with 0 to 40% ethyl acetate/hexanes. The product (343) was obtained as a yellow solid, (110 mg, 17% over 3 steps). $^1$H NMR (500 MHz, CDCl$_3$) δ 7.45-7.40 (m, 1H), 7.30-7.20 (m, 2H), 7.07 (s, 1H), 6.98 (td, J=7.4, 1.1 Hz, 1H), 6.93-6.89 (m, 1H), 4.01 (s, 3H), 3.96 (s, 3H), 3.85 (s, 3H), 3.74-3.65 (m, 6H), 2.75-2.67 (m, 4H), 2.21 (s, 1H), 1.17-1.11 (m, 2H), 1.00 (m, 2H); HRMS (ESI+ve): Calculated for C$_{25}$H$_{30}$N$_4$O$_3$, [M+H]=435.2391, observed [M+H]=435.2372.

Example 237: (4-(2-cyclopropyl-6,7-dimethoxyquinazolin-4-yl)piperazin-1-yl)(phenyl)methanone (344)

As described for compound (315), the crude chloroquinazoline resulting from (3) (240 mg, 0.91 mmol), phenyl (piperazin-1-yl)methanone (242 mg, 1.27 mmol), potassium carbonate (627 mg, 4.53 mmol), and 1,4-dioxane (5 mL) resulted in a brown residue which was purified by silica gel flash chromatography eluting with 0 to 60% ethyl acetate/hexanes. The product (344) was obtained as a pale yellow solid, (67 mg, 12%). $^1$H NMR (500 MHz, CDCl$_3$) δ 7.47 (s, 5H), ca. 7.28 (s, overlap with 1H), 7.04 (s, 1H), 4.05 (s, 3H), 3.97 (m, 4H), 3.76 (m, 7H), 2.36 (broad s, 1H), 1.19-1.12 (m, J=3.8, 3.2 Hz, 2H), 1.09 (s, 2H); HRMS (ESI+ve): Calculated for C$_{24}$H$_{26}$N$_4$O$_3$, [M+H]=419.2078, observed [M+H]=419.2061.

Example 238: (4-(2-cyclopropyl-6,7-dimethoxyquinazolin-4-yl)piperazin-1-yl)(2-methoxyphenyl)methanone (345)

As described for compound (315), the crude chloroquinazoline resulting from (3) (240 mg, 0.91 mmol), (2-methoxyphenyl)(piperazin-1-yl)methanone trifluoroacetate (302 mg, 0.95 mmol), potassium carbonate (627 mg, 4.53 mmol), and 1,4-dioxane (5 mL) resulted in a brown residue which was purified by silica gel flash chromatography eluting with 0 to 60% ethyl acetate/hexanes. The product (345) was obtained as a pale yellow solid, (110 mg, 16% over 3 steps). $^1$H NMR (500 MHz, CDCl$_3$) δ 7.40 (ddd, J=8.5, 7.5, 1.8 Hz, 1H), 7.30 (dd, J=7.5, 1.8 Hz, 2H), 7.08-7.01 (m, 1H), 7.04 (s, 1H), 6.96 (d, J=8.5 Hz, 1H), 4.09-4.01 (m, 4H), 3.99-3.91 (m, 4H), 3.88 (s, 3H), 3.83-3.73 (m, 2H), 3.67-3.56 (m, 2H), 3.54-3.41 (m, 2H), 2.34-2.19 (m, 1H), 1.18-1.10 (m, 2H), 1.04 (s, 2H); HRMS (ESI+ve): Calculated for C$_{25}$H$_{28}$N$_4$O$_4$, [M+H]=449.2183, observed [M+H]=449.2166.

Example 239: 2-cyclopropyl-6,7-dimethoxy-4-(piperazin-1-yl)quinazoline trifluoroacetate (346)

As described for compound (315), the crude chloroquinazoline resulting from (3) (530 mg, 2.0 mmol), t-butyl piperazine-1-carboxylate (559 mg, 3.0 mmol), potassium carbonate (1.38 g, 10.01 mmol), and 1,4-dioxane (10 mL) resulted in a brown residue which was purified by silica gel flash chromatography eluting with 0 to 30% ethyl acetate/hexanes. The product tert-butyl 4-(2-cyclopropyl-6,7-dimethoxyquinazolin-4-yl)piperazine-1-carboxylate was obtained as a yellow solid, (85 mg, 13% over 3 steps). $^1$H NMR (500 MHz, CDCl$_3$) δ 7.28 (s, 2H), 7.05 (s, 1H), 4.03 (s, 3H), 3.97 (s, 3H), 3.63 (s, 7H), 2.31 (s, 1H), 1.51 (s, 9H), 1.20-1.11 (m, 2H), 1.08-0.98 (m, 2H); MS (ESI+ve): Calculated for C$_{22}$H$_{30}$N$_4$O$_4$, [M+H]=415.23, observed [M+H]=415.30.

To a solution of tert-butyl 4-(2-cyclopropyl-6,7-dimethoxyquinazolin-4-yl)piperazine-1-carboxylate (80 mg, 0.193 mmol) in dry dichloromethane (2 mL), trifluoroacetic acid (2 mL) was added dropwise at room temperature and the mixture was stirred at room temperature for 2h. The solvent was evaporated and the residue dissolved in water (10 mL) and extracted with dichloromethane (3×, 2 mL). The aqueous layer was freeze-dried to afford the product (346) as off-white solid (60 mg, 5% over 4 steps). $^1$H NMR (500 MHz, Methanol-d$_4$) δ 7.30 (s, 1H), 7.19 (s, 1H), 4.38-4.23 (m, 4H), 4.05 (s, 3H), 4.00 (s, 3H), 3.48-3.35 (m, 4H), 2.29-2.16 (m, 1H), 1.44-1.26 (m, 4H); HRMS (ESI+ve): Calculated for C$_{23}$H$_{25}$FN$_3$O$_2$S, [M+H]=315.1816, observed [M+H]=315.1807.

Pharmaceutical Composition Examples

Example A1: Parenteral Composition

To prepare a parenteral pharmaceutical composition suitable for administration by injection, 100 mg of a watersoluble salt of a compound of Formula I, or pharmaceutically acceptable salt, N-oxide, racemate or stereoisomer thereof, is dissolved in 2% HPMC, 1% Tween 80 in DI water, pH 2.2 with MSA, q.s. to at least 20 mg/mL. The mixture is incorporated into a dosage unit form suitable for administration by injection.

Example A2: Oral Composition

To prepare a pharmaceutical composition for oral delivery, 100 mg of a compound of Formula I, or pharmaceutically acceptable salt, N-oxide, racemate or stereoisomer thereof, is mixed with 750 mg of starch. The mixture is incorporated into an oral dosage unit for, such as a hard gelatin capsule, which is suitable for oral administration.

Biology Examples

The cell lines utilized in the high-content imaging assays, which include the NTR1-, NTR2-, and GPR35-U2OS osteosarcomas, were obtained from the laboratory of Dr. Lawrence Barak at the Duke University Medical Center. The media used in the culture of the cell lines, as well as the assays themselves, consisted of Minimum Essential Medium (15-010-CM) and L-glutamine (25-005-CL) from Cellgro/Mediatech (Manassas, Va.), fetal bovine serum (SH30396.03) from Hyclone (Logan, Utah), penicillin-streptomycin solution (PS-20) from Omega Scientific in Tarzana, Calif., G418 (ant-gn-1) from Invivogen (San Diego, Calif.), and zeocin (R250-01) from Invitrogen (Carlsbad, Calif.). Cell lines were cultured in T225 tissue culture flasks (431082) supplied by Corning (Corning, N.Y.). Additional reagents employed include Dulbecco's Phosphate-Buffered Saline (DPBS) (21-031CV) from Cellgro/Mediatech, Trypsin-EDTA 0.05% (25300) from Invitrogen, paraformaldehyde (30528954) from Acros Organics (Geel, Belgium), Hoechst 33342 (H3570) from Invitrogen. The high-content assays were run in 1536-well plates (29326) supplied by Aurora Biotechnology (Poway, Calif.) and utilized aluminum plate seals (T592100) from E&K Scientific (Santa Clara, Calif.).

The neurotensin 1 peptide (N6383) from Sigma-Aldrich (St. Louis, Mo.) was used as a positive control in the NTR1 primary HCS assay. For the NTR2 selectivity assay, the non-specific, small molecule 3-(4-fluorophenyl)-7,8-dimethoxy-5-(4-methylbenzyl)-5H-pyrazolo[4,3-c]quinolone which was synthesized internally was used as a positive control. The GPR35 selectivity screen utilized zaprinast (ALX430-020-M010) from Alexis Biochemicals (Farmingdale, N.Y.) as a control.

The NTR1 β-Arrestin assays were performed using a PathHunter™ eXpress kit (93-0446E2) which contained the NTSR1 (NTR1) CHO cell line, OCC2 media (30-409), as well as the PathHunter Detection Reagents (93-0446E2). The kit was obtained from DiscoveRx (Fremont, Calif.). The assay employed the same neurotensin 1 peptide as a control as was used in the NTR1 primary assay. The assay was run in 1536-well, white, solid-bottom tissue culture plates (3727) from Corning.

The NTR1 $Ca^{2+}$ Flux assay was performed by ChanTest (Rockville, Md.). The assay used a CHO cell line, provided by ChanTest, which stably expressed the NTR1 receptor. The cells were grown and plated in Ham's F12 (11765) that was supplemented with fetal bovine serum (10437). Both were supplied by Gibco/Life Technologies (Carlsbad, Calif.). The DPBS (21-031CV) used in the assay was obtained from Cellgro/Mediatech and the G418 (ant-gn-1) was supplied by Invivogen. The Fluo-4 NW Dye (Invitrogen F36206) used to detect calcium mobilization was sourced by Invitrogen. The assay utilized 384-well, black, optical bottom assay plates (3683) and 384-well clear, non-binding plates (3640) as a compound source plate, both from Corning. The neurotensin 1 agonist control (1909) was obtained from Tocris (Bristol, U.K.).

NTR1 HTS
Primary Screen

The high-content imaging based NTR1 primary screen in 1536-well format was utilized to assay the MLSMR library of chemical entities in the following manner. On day one, 4 uL of a cell suspension containing 350,000 NTR1-U2OS cells per mL is added to each well of a 1536-well assay plate. Cells are plated in MEM medium containing 2.5% Fetal Bovine Serum, 1% Penicillin/Streptomycin solution, 1% L-Glutamine, 400 ug/mL G418, and 200 ug/mL Zeocin. The assay plates are then incubated overnight at 37° C., under 5% $CO_2$. Following the overnight incubation, a volume of 60 nL of the compounds at 2 mM in DMSO (final 20 µM, 1% DMSO) was transferred to columns 5-48 of the assay plates using a LabCyte Echo Liquid Handler. Next, 60 nL of DMSO were dispensed to columns 1-4, which served as the positive and neutral control wells. A volume of 2 µL of 300 nM neurotensin 1 (FAC=100 nM) peptide dissolved in DPBS was added to the positive control wells of columns 1 and 2, and 2 uL of DPBS only was transferred to the neutral control wells of columns 3 and 4 using a Kalypsys liquid handler (Kalypsys Systems). The assay plates were centrifuged on an Eppendorf 5810 centrifuge at 1000 rpm for 1 min to ensure even liquid levels in the wells of the assay plates. The assay plates were then returned to the incubator for 1 hour. Following the hour-long incubation at 37° C., the cells in each well were fixed with 4 uL of 6% paraformaldehyde added with a Multidrop Combi. The assay plates were centrifuged as before and incubated at room temperature for 1 hour. On the Kalypsys, plates were then aspirated down to 2.5 uL per well and washed twice with 11 uL per well of DPBS, followed by a final aspiration to 2.5 uL per well. On the Combi dispenser, 5 uL of 5 ug/mL Hoechst 33342 diluted in DPBS was added to each well of assay plates. The plates were again centrifuged as previously described, sealed, and incubated for at least 1 hour prior to being loaded on a PerkinElmer Opera QEHS.

Image acquisition was performed with a 45 plate capacity loader/stacker and the following settings: 40×0.6 NA air objective, acquisition camera set to 2-by-2 binning for an image size of 688 by 512 pixels, beta-arrestin-GFP acquired using 488 nm laser excitation and 540/75 nm emission filters, DAPI (nuclei) using 365 nm Xenon lamp excitation and 450/50 nm emission filters, 3 fields per well. Image analysis was performed using the Acapella Spot Detection Algorithm. For analysis settings and the metrics employed in the data analyses, please refer to supplemental information.

Compounds were selected as hits if they exhibited a percent activity of greater than or equal to 40 when compared to the neurotensin 1 control in the "Ratio of Spot Intensity to Cytoplasmic Intensity" metric. Compounds were excluded from the hit set if the "CellCount" was less than or equal to 20 which was indicative of cellular toxicity.

NTR1 Single Concentration Hit Confirmation

Hits from the primary screen were ordered and received from the MLSMR as 10 mM solutions in DMSO. The hit confirmation assays were performed in an identical manner as the primary screen with the exception of the source plate compound concentration, and therefore the volume transferred to the assay plate to achieve the same concentration as in the primary screen. A volume of 12.5 nL of test compounds at 10 mM in DMSO (final 20 µM, 0.2% DMSO) was delivered. Compounds were screened in quadruplicate and those with an average activity with regards to the "Ratio of Spot Intensity to Cytoplasmic Intensity" metric of greater than or equal to 40% were identified as being "confirmed".

NTR1 Dose Response

Compounds that were successfully confirmed in quadruplicate at 20 uM were then run in dose response in the primary assay. As with the single concentration hit confirmation, the assay was performed in an identical manner as the primary screen with the following modifications. For the initial hit confirmation in dose response, 40, 20, 10, 5, and 2.5 nL of 6 mM and 188 uM test compound in DMSO were transferred from source well to assay wells to achieve the final assay concentrations ranging from 40 to 0.078 uM. Test compound wells and control wells were backfilled with DMSO to achieve a final volume of DMSO of 40 nL or a final assay concentration of 0.5%. $EC_{50}$ values for this assay and the following dose response assays were calculated in the CBIS database (Cheminnovation) using the same analysis parameters and metrics as in the primary assay. All subsequent dose response assays followed the same basic protocol.

NTR2 Dose Response

The operating procedure used for the NTR1 dose response assay was adapted to the development of the NTR2 assay which was used to assess receptor selectivity. The protocol put to use for the NTR2 dose response assays was identical to that used in the NTR1 dose response experiments with a few deviations. Firstly, the NTR2-U2OS cell line was used for the assay, but cell densities as well as cell media in the assay remained the same. Secondly, because the response of the NTR2 cell line to the neurotensin 1 peptide was low relative to the primary NTR1 cell line, a non-specific, small molecule 3-(4-fluorophenyl)-7,8-dimethoxy-5-(4-methylbenzyl)-5H-pyrazolo[4,3-c]quinoline was used at a saturating concentration of 10 uM to generate a more robust signal window.

GPR35 Dose Response

The GPR35 dose response assay was used to assess selectivity against an unrelated GPCR. It utilized a very similar protocol to the NTR1 and NTR2 dose response assays with a few modifications. The GPR35-U2OS cells were plated at the same density and in the same media as the other two assays. Zaprinast was added to control wells in the same volume and in the same manner as the NTR1 primary assay to yield a final concentration of 40 uM.

NTR1 β-Arrestin Dose Response

On day one of the assay, 5 uL of a cell suspension containing 120,000 NTSR1 (NTR1) CHO-K1 cells per mL in OCC2 media is added to each well of a 1536-well assay plate using a Multidrop Combi. The assay plates are then incubated for 48 hours at 37° C., under 5% $CO_2$. Following the two day incubation, a volume of 20, 10, and 5 nL of 10 and 1.2 mM test compounds in DMSO were transferred from source wells to test compound wells in assay plates with a LabCyte Echo to achieve final assay concentrations ranging from 33 to 1.03 uM for each test sample. Test compound wells and control wells were backfilled with DMSO to achieve a final volume of DMSO of 20 nL or a final assay concentration of 0.33%. Next, 1 uL of 120 nM neurotensin 1 peptide (FAC=20 nM) control diluted in assay media is dispensed with a Multidrop Combi to the positive control wells followed by 1 uL of assay media only to the neutral control and test compound wells. The assay plates were centrifuged on an Eppendorf 5810 centrifuge at 1000 rpm for 1 minute. The assay plates were then incubated in the dark at room temperature for 90 minutes. During the incubation, the detection reagent was prepared according to manufacturer's instructions. After 90 minutes, 3 uL of the detection reagent is delivered to all wells of each assay plate. Plates are again centrifuged as previously described then incubated at room temperature for 1 hour before being read on the PerkinElmer using a luminescent protocol.

NTR1 $Ca^{2+}$ Flux Dose Response

NTSR1 (NTR1) CHO cells are plated in 20 uL of assay media containing Ham's F12 supplemented with 10% fetal bovine serum and 0.4 mg/mL G418 at a concentration of $1.0 \times 10^6$ cells per mL into black, 384-well assay plates with clear bottoms using a Multidrop liquid handler. Assay plates are incubated at 37° C. in 5% $CO_2$. The next day, the assay plates are aspirated to remove growth media and washed once with 20 uL of DPBS. The DPBS is then aspirated from the assay plate and replaced with 25 uL of Fluo-4 NW calcium dye prepared according to the manufacturer's recommendations then the plates are incubated for 1 hour at 37° C. Following the incubation in the presence of dye, the assay is run on a Molecular Devices FlexStation-III using 494 excitation and 516 emission wavelengths set to read for 90 seconds with the addition at 18 seconds of 5 uL of 6× final concentration of test compounds and peptide control diluted in assay media containing 0.1% BSA and no more than 9% DMSO to yield a maximum final DMSO concentration of 1.5%. Percent activation is calculated based on the maximum response minus the minimum value over the time course relative to the neurotensin 1 control peptide at 100 pM. $EC_{50}$ values were calculated for those compounds tested in 8-point dose dependent response.

Representative biological data is presented below.

TABLE 1

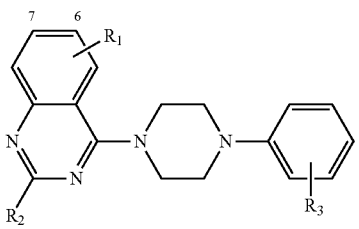

| $R_1$ | $R_2$ | $R_3$ | $EC_{50}$ (µM) | Emax (%) |
|---|---|---|---|---|
| 6,7-di-OMe | cyclobutyl | 2-OMe | 5.9 ± 0.5 (10) | 85.3 |
| 6,7-di-OMe | phenyl | 2-OMe | 20.0 ± 10.7 (5) | 78.0 |
| 6,7-di-OMe | phenyl | —H | >80 | — |
| 6,7-di-OMe | phenyl | 2-F | >80 | — |
| 6,7-di-OMe | phenyl | 4-F | >80 | — |
| 6,7-di-OMe | phenyl | 2-Cl | >80 | — |
| 6-OEt, 7-OMe | phenyl | 2-OMe | >80 | — |
| 6-OEt, 7-OMe | phenyl | —H | >80 | — |
| 6-OEt, 7-OMe | phenyl | 2-F | >80 | — |

HCS NTR1 Potency Ave. ± S.E.M. (n = 4 unless otherwise noted)

TABLE 2

SAR of Quinazoline-based Agonists of NTR1

Core structure: 6,7-dimethoxy-2-cyclobutyl-quinazoline with piperazine linked to phenyl bearing substituent R.

| R | EC$_{50}$ (μM) | Emax (%) |
|---|---|---|
| 2-OMe | 5.9 ± 0.5 (10) | 85.3 |
| —H | 12.1 ± 1.4 | 77.0 |
| 2-Me | 14.9 ± 3.2 | 916 |
| 2-F | 17.7 ± 1.0 (3) | 97.2 |
| 2-Cl | 12.2 ± 2.5 | 70.5 |
| 2-pyridyl | 25.5 ± 1.7 (6) | 91.4 |
| 2-nitro | 75.4 ± 1.1 (2) | 100.0 |
| 3-OMe | 17.2 ± 1.0 (2) | 74.9 |
| 4-OMe | 46.4 ± 17.6 (3) | 100.0 |
| 2,4-di-OMe | 22.8 ± 0.4 (6) | 103.3 |
| 2,6-di-Me | 61.2 ± 5.2 | 100.0 |

HCS NTR1 Potency Ave. ± S.E.M. (n = 4 unless otherwise noted)

TABLE 3

SAR of Quinazoline-based Agonists of NTR1

Core structure: 6,7-dimethoxy-quinazoline with 2-R substituent, piperazine linked to 2-methoxyphenyl.

| R | EC$_{50}$ (μM) | Emax (%) |
|---|---|---|
| -cyclobutyl | 5.9 ± 0.5 (10) | 85.3 |
| —H | >80 | — |
| —Me | >80 | — |
| —CH$_2$Ph | 13.8 ± 3.4 | 81.9 |
| -ethyl | 42.6 ± 4.4 | 100.0 |
| n-propyl | 16.6 ± 1.7 | 100.0 |
| i-propyl | 7.7 ± 1.0 | 100.0 |
| i-butyl | 15.1 ± 1.5 | 96.3 |
| -vinyl | 7.0 ± 1.0 | 100.0 |
| -cyclopropyl | 2.0 ± 0.1 (8) | 104.7 |
| -cyclopentyl | 5.8 ± 1.5 | 92.8 |
| methylcyclopropyl | 14.2 ± 1.2 | 96.9 |
| —CH$_2$CH$_2$NMe$_2$ | >80 | — |
| *-CH$_2$CH$_2$-piperazine-(2-MeO-phenyl) | 25.9 ± 13.7 (2) | 74.3 |

HCS NTR1 Potency Ave. ± S.E.M. (n = 4 unless otherwise noted)

TABLE 4

SAR of Quinazoline-based Agonists of NTR1

Core structure: quinazoline with R1 on benzo ring (positions 6,7), 2-R2 substituent, piperazine linked to 2-methoxyphenyl.

| R2 | R1 | EC$_{50}$ (μM) | Emax (%) |
|---|---|---|---|
| -cyclobutyl | 6,7-di-OMe | 5.9 ± 0.5 (10) | 85.3 |
| -cyclobutyl | 6-OMe | 10.0 ± 1.57 | 101.9 |
| -cyclobutyl | 7-OMe | 30.0 ± 0.0 (3) | 111.5 |
| -cyclobutyl | H | 22.6 ± 3.9 | 100.0 |
| -cyclobutyl | 6,7-OCH$_2$O-dioxolane | 33.7 ± 16.7 (3) | 87.0 |
| -cyclopropyl | 6-OMe | 4.1 ± 0.5 | 95.7 |

HCS NTR1 Potency Ave. ± S.E.M. (n = 4 unless otherwise noted)

TABLE 5

SAR of Quinazoline-based Agonists of NTR1

Core structure: 6,7-dimethoxy-2-cyclopropyl-quinazoline with piperazine bearing N-R substituent.

| R | EC$_{50}$ (μM) | Emax (%) |
|---|---|---|
| 2-MeO-phenyl | 2.0 ± 0.1 (8) | 104.7 |
| 2-EtO-phenyl | 6.1 ± 0.4 | 98.4 |
| 2-Cl-phenyl | 19.8 ± 2.2 | 100.0 |
| phenylsulfonyl (—S(O)$_2$Ph) | >80 | — |
| 4-methylbenzyl | 25.0 ± 3.2 | 100.0 |

HCS NTR1 Potency Ave. ± S.E.M. (n = 4 unless otherwise noted)

TABLE 5-continued

SAR of Quinazoline-based Agonists of NTR1

Scaffold: 2-cyclopropyl-6,7-dimethoxy-4-(piperazin-1-yl)quinazoline with N-R substitution on the distal piperazine nitrogen.

| R | HCS NTR1 Potency Ave. ± S.E.M. (n = 4 unless otherwise noted) | |
|---|---|---|
|  | EC₅₀ (μM) | Emax (%) |
| 2-methoxybenzyl (*-CH₂-C₆H₄-2-OMe) | 34.9 ± 4.4 | 100.0 |
| benzoyl (*-C(O)-C₆H₅) | 45.3 (1) | 100.0 |
| 2-methoxybenzoyl (*-C(O)-C₆H₄-2-OMe) | 67.7 ± 5.5 (3) | 100.0 |
| —H | >80 | — |

All quinazolines including in Tables 1 to 5 were >40 fold selective for NTR1 over NTR2 and GPR35. The agonist activity of compound 315 in the primary NTR1 HCS assay was further confirmed in the DiscoveRx β-arrestin assay (EC$_{50}$=3.41 μM) and was profiled by ChanTest in an NTR1 Ca$^{2+}$ Flux assay (not active). Compound 315 appears to be a biased agonist operating via the β-arrestin pathway rather than the traditional G$_q$ coupled pathway.

TABLE 6

| Cpd. No. | Name | HCS NTR1 Agonist (EC$_{50}$) |
|---|---|---|
| 6 | 2-cyclopropyl-4-[4-(4-fluoro-2-methoxy-phenyl)-piperazin-1-yl]-6,7-dimethoxy-quinazoline | C |
| 7 | 2-cyclopropyl-6,7-dimethoxy-4-[4-(2-methoxy-4-trifluoromethoxy-phenyl)-piperazin-1-yl]-quinazoline | C |
| 8 | 4-[4-(4-chloro-2-methoxy-phenyl)-piperazin-1-yl]-2-cyclopropyl-6,7-dimethoxy-quinazoline | C |
| 9 | 2-cyclopropyl-6,7-dimethoxy-4-[4-(2-methoxy-4-nitro-phenyl)-piperazin-1-yl]-quinazoline | C |
| 10 | 4-[4-(2-cyclopropyl-6,7-dimethoxy-quinazolin-4-yl)-piperazin-1-yl]-3-methoxy-phenylamine | C |
| 11 | 4-[4-(2-cyclopropyl-6,7-dimethoxy-quinazolin-4-yl)-piperazin-1-yl]-3-methoxy-benzonitrile | C |
| 12 | 4-[4-(2-cyclopropyl-6,7-dimethoxy-quinazolin-4-yl)-piperazin-1-yl]-3-methoxy-benzoic acid | C |
| 13 | 4-[4-(2-cyclopropyl-6,7-dimethoxy-quinazolin-4-yl)-piperazin-1-yl]-3-methoxy-benzamide | C |
| 14 | {4-[4-(2-cyclopropyl-6,7-dimethoxy-quinazolin-4-yl)-piperazin-1-yl]-3-methoxy-phenyl}-dimethyl-amine | C |
| 15 | 2-cyclopropyl-6,7-dimethoxy-4-[4-(2-methoxy-4-trifluoromethyl-phenyl)-piperazin-1-yl]-quinazoline | C |
| 16 | 2-cyclopropyl-4-[4-(2,4-dimethoxy-phenyl)-piperazin-1-yl]-6,7-dimethoxy-quinazoline | C |
| 17 | 2-cyclopropyl-6,7-dimethoxy-4-[4-(2-methoxy-5-methyl-phenyl)-piperazin-1-yl]-quinazoline | C |
| 18 | 2-[4-(2-cyclopropyl-6,7-dimethoxy-quinazolin-4-yl)-piperazin-1-yl]-benzonitrile | C |
| 19 | 2-cyclopropyl-6,7-dimethoxy-4-[4-(2-methoxy-5-nitro-phenyl)-piperazin-1-yl]-quinazoline | C |
| 20 | 3-[4-(2-cyclopropyl-6,7-dimethoxy-quinazolin-4-yl)-piperazin-1-yl]-4-methoxy-phenylamine | C |
| 21 | N-{3-[4-(2-cyclopropyl-6,7-dimethoxy-quinazolin-1-yl]-4-methoxy-phenyl}-acetamide | C |
| 22 | N-{3-[4-(2-cyclopropyl-6,7-dimethoxy-quinazolin-4-yl)-piperazin-1-yl]-4-methoxy-phenyl}-methanesulfonamide | C |
| 23 | {3-[4-(2-cyclopropyl-6,7-dimethoxy-quinazolin-4-yl)-piperazin-1-yl]-4-methoxy-phenyl}-dimethyl-amine | C |

TABLE 6-continued

| Cpd. No. | Name | HCS NTR1 Agonist (EC$_{50}$) |
|---|---|---|
| 24 | {3-[4-(2-cyclopropyl-6,7-dimethoxy-quinazolin-4-yl)-piperazin-1-yl]-4-methoxy-phenyl}-methyl-amine | C |
| 26 | 2-cyclopropyl-4-[4-(2,3-dichloro-phenyl)-piperazin-1-yl]-6,7-dimethoxy-quinazoline | C |
| 27 | 2-cyclopropyl-4-[4-(2,4-dichloro-phenyl)-piperazin-1-yl]-6,7-dimethoxy-quinazoline | C |
| 28 | 3-chloro-4-[4-(2-cyclopropyl-6,7-dimethoxy-quinazolin-4-yl)-piperazin-1-yl]-benzonitrile | C |
| 29 | 4-[4-(2-chloro-4-nitro-phenyl)-piperazin-1-yl]-2-cyclopropyl-6,7-dimethoxy-quinazoline | C |
| 30 | 3-chloro-4-[4-(2-cyclopropyl-6,7-dimethoxy-quinazolin-4-yl)-piperazin-1-yl]-benzoic acid | C |
| 31 | 3-chloro-4-[4-(2-cyclopropyl-6,7-dimethoxy-quinazolin-4-yl)-piperazin-1-yl]-benzamide | C |
| 32 | 3-chloro-4-[4-(2-cyclopropyl-6,7-dimethoxy-quinazolin-4-yl)-piperazin-1-yl]-phenylamine | C |
| 33 | N-{3-chloro-4-[4-(2-cyclopropyl-6,7-dimethoxy-quinazolin-4-yl)-piperazin-1-yl]-phenyl}-acetamide | C |
| 34 | N-{3-chloro-4-[4-(2-cyclopropyl-6,7-dimethoxy-quinazolin-4-yl)-piperazin-1-yl]-phenyl}-methanesulfonamide | C |
| 35 | 3-chloro-4-[4-(2-cyclopropyl-6,7-dimethoxy-quinazolin-4-yl)-piperazin-1-yl]-benzoic acid | C |
| 36 | 4-[4-(2-chloro-4-fluoro-phenyl)-piperazin-1-yl]-2-cyclopropyl-6,7-dimethoxy-quinazoline | C |
| 37 | 4-[4-(2-chloro-4-trifluoromethyl-phenyl)-piperazin-1-yl]-2-cyclopropyl-6,7-dimethoxy-quinazoline) | C |
| 38 | 4-[4-(2-chloro-4-methyl-phenyl)-piperazin-1-yl]-2-cyclopropyl-6,7-dimethoxy-quinazoline | C |
| 39 | 4-[4-(2-chloro-4-methoxy-phenyl)-piperazin-1-yl]-2-cyclopropyl-6,7-dimethoxy-quinazoline | C |
| 41 | 2-[4-(2-cyclopropyl-6,7-dimethoxy-quinazolin-4-yl)-piperazin-1-yl]-benzonitrile | C |
| 42 | 2-[4-(2-cyclopropyl-6,7-dimethoxy-quinazolin-4-yl)-piperazin-1-yl]-5-methoxy-benzonitrile | C |
| 43 | 5-chloro-2-[4-(2-cyclopropyl-6,7-dimethoxy-quinazolin-4-yl)-piperazin-1-yl]-benzonitrile | C |
| 44 | 2-[4-(2-cyclopropyl-6,7-dimethoxy-quinazolin-4-yl)-piperazin-1-yl]-5-nitro-benzonitrile | C |
| 45 | 5-amino-2-[4-(2-cyclopropyl-6,7-dimethoxy-quinazolin-4-yl)-piperazin-1-yl]-benzonitrile | C |
| 47 | 2-cyclopropyl-6,7-dimethoxy-4-[4-(2-nitro-phenyl)-piperazin-1-yl]-quinazoline | C |
| 48 | 2-[4-(2-cyclopropyl-6,7-dimethoxy-quinazolin-4-yl)-piperazin-1-yl]-phenylamine | C |
| 49 | 2-(4-(2-cyclopropyl-6,7-dimethoxyquinazolin-4-yl)piperazin-1-yl)-N-ethylaniline | C |
| 50 | {2-[4-(2-cyclopropyl-6,7-dimethoxy-quinazolin-4-yl)-piperazin-1-yl]-phenyl}-dimethyl-amine | B |
| 51 | {2-[4-(2-cyclopropyl-6,7-dimethoxy-quinazolin-4-yl)-piperazin-1-yl]-phenyl}-diethyl-amine | C |
| 52 | 4-[4-(2-aziridin-1-yl-phenyl)-piperazin-1-yl]-2-cyclopropyl-6,7-dimethoxy-quinazoline | C |
| 54 | 4-[4-(4-benzyloxy-2-nitro-phenyl)-piperazin-1-yl]-2-cyclopropyl-6,7-dimethoxy-quinazoline | C |
| 55 | 3-amino-4-[4-(2-cyclopropyl-6,7-dimethoxy-quinazolin-4-yl)-piperazin-1-yl]-phenol | C |
| 57d | 2-cyclopropyl-6,7-dimethoxy-4-[4-(4-methoxy-2-nitro-phenyl)-piperazin-1-yl]-quinazoline | — |
| 58b | 2-[4-(2-cyclopropyl-6,7-dimethoxy-quinazolin-4-yl)-piperazin-1-yl]-5-fluoro-phenylamine | C |
| 58d | 2-[4-(2-cyclopropyl-6,7-dimethoxy-quinazolin-4-yl)-piperazin-1-yl]-5-methoxy-phenylamine | C |
| 59 | {5-bromo-2-[4-(2-cyclopropyl-6,7-dimethoxy-quinazolin-4-yl)-piperazin-1-yl]-phenyl}-dimethyl-amine | C |
| 60 | {2-[4-(2-cyclopropyl-6,7-dimethoxy-quinazolin-4-yl)-piperazin-1-yl]-5-fluoro-phenyl}-dimethyl-amine | C |
| 61 | {5-chloro-2-[4-(2-cyclopropyl-6,7-dimethoxy-quinazolin-4-yl)-piperazin-1-yl]-phenyl}-dimethyl-amine | C |
| 62 | {2-[4-(2-cyclopropyl-6,7-dimethoxy-quinazolin-4-yl)-piperazin-1-yl]-5-methoxy-phenyl}-dimethyl-amine | C |
| 64 | 4-[4-(2-cyclopropyl-6,7-dimethoxy-quinazolin-4-yl)-piperazin-1-yl]-3-dimethylamino-benzoic acid | C |
| 67 | {2-[4-(2-cyclopropyl-6,7-dimethoxy-quinazolin-4-yl)-piperazin-1-yl]-phenyl}-phenyl-amine | C |
| 68 | 2-cyclopropyl-6,7-dimethoxy-4-[4-(2-morpholin-4-yl-phenyl)-piperazin-1-yl]-quinazoline | C |

TABLE 6-continued

| Cpd. No. | Name | HCS NTR1 Agonist ($EC_{50}$) |
|---|---|---|
| 69 | 2-cyclopropyl-6,7-dimethoxy-4-[4-(2-pyrrolidin-1-yl-phenyl)-piperazin-1-yl]-quinazoline | C |
| 70 | 4-[4-(2-azetidin-1-yl-phenyl)-piperazin-1-yl]-2-cyclopropyl-6,7-dimethoxy-quinazoline | B |
| 72 | 2-cyclopropyl-6,7-dimethoxy-4-[4-(2-piperidin-1-yl-phenyl)-piperazin-1-yl]-quinazoline | C |
| 75 | 2-Cyclopropyl-6,7-dimethoxy-4-{4-[2-(4-methyl-piperazin-1-yl)-phenyl]-piperazin-1-yl}-quinazoline | C |
| 79 | 5-amino-2-[4-(2-cyclopropyl-6,7-dimethoxy-quinazolin-4-yl)-piperazin-1-yl]-phenol | C |
| 82 | 4-(4-(2-cyclopropyl-6,7-dimethoxyquinazolin-4-yl)piperazin-1-yl)-N,N-dimethylaniline | C |
| 83 | {4-[4-(2-cyclopropyl-6,7-dimethoxy-quinazolin-4-yl)-piperazin-1-yl]-phenyl}-diethyl-amine | C |
| 84 | 3-(4-(2-cyclopropyl-6,7-dimethoxyquinazolin-4-yl)piperazin-1-yl)-N,N-dimethylaniline | C |
| 85 | {3-[4-(2-cyclopropyl-6,7-dimethoxy-quinazolin-4-yl)-piperazin-1-yl]-phenyl}-diethyl-amine | C |
| 89 | N-(2-cyclopropyl-6,7-dimethoxy-quinazolin-5-yl)-N'-(2-methoxy-phenyl)-ethane-1,2-diamine | C |
| 90 | N'-(2-cyclopropyl-6,7-dimethoxy-quinazolin-5-yl)-N-(2-methoxy-phenyl)-N-methyl-ethane-1,2-diamine | C |
| 94 | 2-cyclopropyl-6,7-dimethoxy-4-[4-(2-methoxy-phenyl)-2-methyl-piperazin-1-yl]-quinazoline | C |
| 97 | N-(2-cyclopropyl-6,7-dimethoxy-quinazolin-4-yl)-N'-phenyl-ethane-1,2-diamine | C |
| 98 | N-(2-cyclopropyl-6,7-dimethoxy-quinazolin-4-yl)-N'-(2-methoxy-phenyl)-propane-1,3-diamine | C |
| 99 | N-(2-cyclopropyl-6,7-dimethoxy-quinazolin-4-yl)-N'-(2-methoxy-phenyl)-N,N'-dimethyl-ethane-1,2-diamine | C |
| 100 | 2-cyclopropyl-6,7-dimethoxy-4-[4-(2-methoxy-phenyl)-[1,4]diazepan-1-yl]-quinazoline | C |
| 101 | [1-(2-cyclopropyl-6,7-dimethoxy-quinazolin-4-yl)-piperidin-4-yl]-(2-methoxy-phenyl)-amine | C |
| 102 | 2-(2-cyclopropyl-6,7-dimethoxy-quinazolin-4-ylamino)-N-(2-methoxy-phenyl)-acetamide | C |
| 108 | 2-Cyclopropyl-6,7-dimethoxy-4-[4-(2-methoxy-phenyl)-piperidin-1-yl]-quinazoline | B |
| 109 | {2-[1-(2-Cyclopropyl-6,7-dimethoxy-quinazolin-4-yl)-piperidin-4-yl]-phenyl}-dimethyl-amine | C |
| 110 | 2-cyclopropyl-6,7-dimethoxy-4-[4-(2-methoxy-phenyl)-3,6-dihydro-2H-pyridin-1-yl]-quinazoline | C |
| 115 | 2-cyclopropyl-6,7-dimethoxy-4-(3-phenyl-pyrrolidin-1-yl)-quinazoline | C |
| 116 | 2-cyclopropyl-6,7-dimethoxy-4-[3-(2-methoxy-phenyl)-pyrrolidin-1-yl]-quinazolin | C |
| 117 | {2-[1-(2-cyclopropyl-6,7-dimethoxy-quinazolin-4-yl)-pyrrolidin-3-yl]-phenyl}-dimethyl-amine | C |
| 118 | 2-cyclopropyl-6,7-dimethoxy-4-[3-(3-methoxy-phenyl)-cyclopentyl]-quinazoline | C |
| 119 | {3-[1-(2-cyclopropyl-6,7-dimethoxy-quinazolin-4-yl)-pyrrolidin-3-yl]-phenyl}-dimethyl-amine | C |
| 121 | 1-(2-cyclopropyl-6,7-dimethoxy-quinazolin-4-yl)-3-phenyl-pyrrolidin-3-ol | C |
| 122 | 1-(2-cyclopropyl-6,7-dimethoxy-quinazolin-4-yl)-3-(2-dimethylamino-phenyl)-pyrrolidin-3-ol | C |
| 123 | 1-(2-cyclopropyl-6,7-dimethoxy-quinazolin-4-yl)-3-(3-methoxy-phenyl)-pyrrolidin-3-ol | C |
| 125 | 2-cyclopropyl-4-(3-fluoro-3-phenyl-pyrrolidin-1-yl)-6,7-dimethoxy-quinazoline | C |
| 126 | {2-[1-(2-cyclopropyl-6,7-dimethoxy-quinazolin-4-yl)-3-fluoro-pyrrolidin-3-yl]-phenyl}-dimethyl-amine | C |
| 127 | 2-cyclopropyl-4-[3-fluoro-3-(3-methoxy-phenyl)-pyrrolidin-1-yl]-6,7-dimethoxy-quinazoline | C |
| 130 | 2-cyclopropyl-6,7-dimethoxy-4-(3-methyl-4-phenyl-piperazin-1-yl)-quinazoline | C |
| 135 | 2-cyclopropyl-6,7-dimethoxy-4-[1-(2-methoxy-phenyl)-piperidin-4-yl]-quinazoline | C |
| 140 | 6,7-dimethoxy-4-[4-(2-methoxy-phenyl)-piperazin-1-yl]-2-piperidin-4-yl-quinazoline | C |
| 141 | 6,7-dimethoxy-4-[4-(2-methoxy-phenyl)-piperazin-1-yl]-2-(1-methyl-piperidin-4-yl)-quinazoline | C |
| 144 | 6,7-dimethoxy-4-[4-(2-methoxy-phenyl)-piperazin-1-yl]-2-(4-methyl-cyclohexyl)-quinazoline | C |
| 145 | 4-{6,7-dimethoxy-4-[4-(2-methoxy-phenyl)-piperazin-1-yl]-quinazolin-2-yl}-piperidine-1-carboxylic acid benzyl ester | C |

TABLE 6-continued

| Cpd. No. | Name | HCS NTR1 Agonist (EC$_{50}$) |
|---|---|---|
| 146 | 6,7-dimethoxy-4-[4-(2-methoxy-phenyl)-piperazin-1-yl]-2-(tetrahydro-pyran-4-yl)-quinazoline | C |
| 147 | 6,7-dimethoxy-4-[4-(2-methoxy-phenyl)-piperazin-1-yl]-2-(tetrahydro-furan-3-yl)-quinazoline | C |
| 148 | 6,7-dimethoxy-4-[4-(2-methoxy-phenyl)-piperazin-1-yl]-2-(2-methyl-cyclopropyl)-quinazoline | C |
| 150 | cis-6,7-dimethoxy-2-(4-methoxy-cyclohexyl)-4-[4-(2-methoxy-phenyl)-piperazin-1-yl]-quinazoline | C |
| 151 | trans-6,7-dimethoxy-2-(4-methoxy-cyclohexyl)-4-[4-(2-methoxy-phenyl)-piperazin-1-yl]-quinazoline | C |
| 152 | 6,7-dimethoxy-4-[4-(2-methoxy-phenyl)-piperazin-1-yl]-2-(4-methyl-pyrrolidin-3-yl)-quinazoline | C |
| 153 | 2-(1,4-dimethyl-pyrrolidin-3-yl)-6,7-dimethoxy-4-[4-(2-methoxy-phenyl)-piperazin-1-yl]-quinazoline | C |
| 154 | 6,7-dimethoxy-4-[4-(2-methoxy-phenyl)-piperazin-1-yl]-2-pyrrolidin-3-yl-quinazoline | C |
| 155 | 6,7-dimethoxy-4-[4-(2-methoxy-phenyl)-piperazin-1-yl]-2-(1-methyl-pyrrolidin-3-yl)-quinazoline | C |
| 158 | 2-((1R,3R)-3-chloro-3-methylcyclobutyl)-6,7-dimethoxy-4-(4-(2-methoxyphenyl)piperazin-1-yl)quinazoline | C |
| 159 | 2-((1S,3S)-3-chloro-3-methylcyclobutyl)-6,7-dimethoxy-4-(4-(2-methoxyphenyl)piperazin-1-yl)quinazoline | C |
| 160 | 6,7-dimethoxy-4-[4-(2-methoxy-phenyl)-piperazin-1-yl]-2-(3-methyl-cyclobutyl)-quinazoline | C |
| 161 | 2-cyclohexyl-6,7-dimethoxy-4-[4-(2-methoxy-phenyl)-piperazin-1-yl]-quinazoline | C |
| 162 | 2-tert-Butyl-6,7-dimethoxy-4-[4-(2-methoxy-phenyl)-piperazin-1-yl]-quinazoline | C |
| 163 | 2-tert-Butyl-6,7-dimethoxy-4-[4-(2-methoxy-phenyl)-piperidin-1-yl]-quinazoline | C |
| 164 | 6,7-dimethoxy-4-[4-(2-methoxy-phenyl)-piperazin-1-yl]-2-(1-methyl-cyclopropyl)-quinazoline | B |
| 165 | 6,7-dimethoxy-4-[4-(2-methoxy-phenyl)-piperidin-1-yl]-2-(1-methyl-cyclopropyl)-quinazoline | B |
| 168 | 6,7-dimethoxy-4-[4-(2-methoxy-phenyl)-piperazin-1-yl]-2-(1-trifluoromethyl-cyclopropyl)-quinazoline | C |
| 169 | Example 113: 6,7-dimethoxy-4-[4-(2-methoxy-phenyl)-piperidin-1-yl]-2-(1-trifluoromethyl-cyclopropyl)-quinazoline | — |
| 172 | [4-[4-(2-Methoxy-phenyl)-piperidin-1-yl]-2-(1-methyl-cyclopropyl)-quinazolin-6-yl]-methyl-(2-morpholin-4-yl-ethyl)-amine | — |
| 178 | 7-chloro-2-cyclopropyl-6-methoxy-4-[4-(2-methoxy-phenyl)-piperazin-1-yl]-quinazoline | C |
| 179 | 2-cyclopropyl-4-[4-(2-methoxy-phenyl)-piperazin-1-yl]-pyrido[2,3-d]pyrimidine | C |
| 180 | 2-cyclopropyl-6,8-dimethoxy-4-[4-(2-methoxy-phenyl)-piperazin-1-yl]-quinazoline | C |
| 181 | 2-cyclopropyl-6-methoxy-4-[4-(2-methoxy-phenyl)-piperazin-1-yl]-7-methyl-quinazoline | B |
| 182 | 2-cyclopropyl-7-fluoro-6-methoxy-4-[4-(2-methoxy-phenyl)-piperazin-1-yl]-quinazoline | C |
| 183 | 6-bromo-2-cyclopropyl-4-[4-(2-methoxy-phenyl)-piperazin-1-yl]-quinazoline | C |
| 184 | 2-cyclopropyl-4-[4-(2-methoxy-phenyl)-piperazin-1-yl]-quinazolin-6-yl}-dimethylamine | B |
| 185 | 6-bromo-2-cyclopropyl-7-fluoro-4-[4-(2-methoxy-phenyl)-piperazin-1-yl]-quinazoline | C |
| 186 | {2-cyclopropyl-7-fluoro-4-[4-(2-methoxy-phenyl)-piperazin-1-yl]-quinazolin-6-yl}-dimethyl-amine | C |
| 187 | {2-cyclopropyl-7-fluoro-4-[4-(2-methoxy-phenyl)-piperazin-1-yl]-quinazolin-6-yl}-diethyl-amine | C |
| 188 | 6-bromo-7-chloro-2-cyclopropyl-4-[4-(2-methoxy-phenyl)-piperazin-1-yl]-quinazoline | C |
| 189 | {7-chloro-2-cyclopropyl-4-[4-(2-methoxy-phenyl)-piperazin-1-yl]-quinazolin-6-yl}-dimethyl-amine | C |
| 190 | {7-chloro-2-cyclopropyl-4-[4-(2-methoxy-phenyl)-piperazin-1-yl]-quinazolin-6-yl}-diethyl-amine | C |
| 191 | 6-bromo-2-cyclopropyl-4-[4-(2-methoxy-phenyl)-piperazin-1-yl]-7-methyl-quinazoline | C |
| 192 | {2-cyclopropyl-4-[4-(2-methoxy-phenyl)-piperazin-1-yl]-7-methyl-quinazolin-6-yl}-dimethyl-amine | B |
| 193 | {2-cyclopropyl-4-[4-(2-methoxy-phenyl)-piperazin-1-yl]-7-methyl-quinazolin-6-yl}-ethyl-methyl-amine | C |
| 194 | 6-bromo-2-cyclopropyl-4-[4-(2-methoxy-phenyl)-piperidin-1-yl]-7-methyl-quinazoline | C |
| 195 | {2-cyclopropyl-4-[4-(2-methoxy-phenyl)-piperidin-1-yl]-7-methyl-quinazolin-6-yl}-diethyl-amine | C |

TABLE 6-continued

| Cpd. No. | Name | HCS NTR1 Agonist (EC$_{50}$) |
|---|---|---|
| 196 | 2-cyclopropyl-6-methoxy-4-[4-(2-methoxy-phenyl)-piperazin-1-yl]-pyrido[3,4-d]pyrimidine | C |
| 197 | 6-bromo-2-cyclopropyl-4-[4-(2-methoxy-phenyl)-piperidin-1-yl]-7-methyl-quinazoline | B |
| 198 | {2-cyclopropyl-4-[4-(2-methoxy-phenyl)-piperidin-1-yl]-7-methyl-quinazolin-6-yl}-diethyl-amine | C |
| 199 | {2-cyclopropyl-4-[4-(2-methoxy-phenyl)-piperazin-1-yl]-quinazolin-7-yl}-dimethyl-amine | C |
| 200 | {2-cyclopropyl-4-[4-(2,5-dimethoxy-phenyl)-piperazin-1-yl]-quinazolin-6-yl}-dimethyl-amine | C |
| 201 | 2-cyclopropyl-4-[4-(2-methoxy-phenyl)-piperazin-1-yl]-6-piperidin-1-yl-quinazoline | C |
| 202 | {2-cyclopropyl-4-[4-(2-methoxy-phenyl)-piperazin-1-yl]-quinazolin-6-yl}-diethyl-amine | A |
| 203 | 2-cyclopropyl-4-[4-(2-methoxy-phenyl)-piperazin-1-yl]-6-morpholin-4-yl-quinazoline | C |
| 204 | 2-cyclopropyl-4-[4-(2-methoxy-phenyl)-piperazin-1-yl]-6-pyrrolidin-1-yl-quinazoline | B |
| 205 | {2-cyclopropyl-4-[4-(2-methoxy-phenyl)-piperazin-1-yl]-quinazolin-6-yl}-phenyl-amine | C |
| 206 | {2-cyclopropyl-4-[4-(2-methoxy-phenyl)-piperidin-1-yl]-quinazolin-6-yl}-dimethyl-amine | A |
| 207 | {2-cyclopropyl-4-[4-(2-methoxy-phenyl)-piperidin-1-yl]-quinazolin-6-yl}-ethyl-methyl-amine | A |
| 208 | {7-chloro-2-cyclopropyl-4-[4-(2-methoxyphenyl)piperidyl]quinazolin-6-yl}dimethylamine | B |
| 209 | 2-cyclopropyl-4-[4-(2-methoxy-phenyl)-piperazin-1-yl]-6-piperazin-1-yl-quinazoline | C |
| 210 | 2-cyclopropyl-4-[4-(2-methoxy-phenyl)-piperazin-1-yl]-6-(4-methyl-piperazin-1-yl)-quinazoline | C |
| 211 | 2-cyclopropyl-6,7-difluoro-4-[4-(2-methoxy-phenyl)-piperazin-1-yl]-quinazoline | C |
| 212 | {2-cyclopropyl-6-fluoro-4-[4-(2-methoxy-phenyl)-piperazin-1-yl]-quinazolin-7-yl}-dimethyl-amine | C |
| 213 | {2-cyclopropyl-6-fluoro-4-[4-(2-methoxy-phenyl)-piperazin-1-yl]-quinazolin-7-yl}-diethyl-amine | C |
| 214 | 2-cyclopropyl-6-fluoro-7-methoxy-4-[4-(2-methoxy-phenyl)-piperazin-1-yl]-quinazoline | C |
| 219 | {2-ycyclopropyl-4-[4-(2-methoxy-phenyl)-piperazin-1-yl]-quinazolin-6-yl}-methyl-propyl-amine | B |
| 220 | {2-cyclopropyl-4-[4-(2-methoxy-phenyl)-piperazin-1-yl]-quinazolin-6-yl}-methyl-(2-morpholin-4-yl-ethyl)-amine | C |
| 221 | 2-cyclopropyl-4-(4-(2-methoxyphenyl)piperazin-1-yl)-N-methyl-N-(2-morpholinoethyl)quinazolin-6-amine | C |
| 222a | 2,2'-((2-cyclopropyl-4-(4-(2-methoxyphenyl)piperazin-1-yl)quinazolin-6-yl)azanediyl)diethanol | C |
| 224 | 2-({2-yclopropyl-4-[4-(2-methoxy-phenyl)-piperazin-1-yl]-quinazolin-6-yl}-methyl-amino)-ethanol | B |
| 225 | {2-cyclopropyl-4-[4-(2-methoxy-phenyl)-piperazin-1-yl]-quinazolin-6-yl}-(2-methoxy-ethyl)-methyl-amine | B |
| 226 | 2-({2-cyclopropyl-4-[4-(2-methoxy-phenyl)-piperidin-1-yl]-quinazolin-6-yl}-methyl-amino)-ethanol | A |
| 227 | {2-cyclopropyl-4-[4-(2-methoxy-phenyl)-piperidin-1-yl]-quinazolin-6-yl}-(2-methoxy-ethyl)-methyl-amine | B |
| 228 | {2-cyclopropyl-4-[4-(2-methoxy-phenyl)-piperidin-1-yl]-quinazolin-6-yl}-methyl-propyl-amine | A |
| 229 | {2-cyclopropyl-4-[4-(2-methoxy-phenyl)-piperidin-1-yl]-quinazolin-6-yl}-methyl-(2-morpholin-4-yl-ethyl)-amine | A |
| 236 | 2-cyclopropyl-5,8-dimethoxy-4-[4-(2-methoxy-phenyl)-piperazin-1-yl]-quinazoline | C |
| 237 | 2-cyclopropyl-4-[4-(2-methoxy-phenyl)-piperazin-1-yl]-quinazoline | C |
| 238 | 2-cyclopropyl-5,6-dimethoxy-4-[4-(2-methoxy-phenyl)-piperazin-1-yl]-quinazoline | C |
| 239 | 2-cyclopropyl-5-methoxy-4-[4-(2-methoxy-phenyl)-piperazin-1-yl]-quinazoline | C |
| 240 | 2-cyclopropyl-8-methoxy-4-[4-(2-methoxy-phenyl)-piperazin-1-yl]-quinazoline | C |
| 244 | 2-cyclopropyl-6,7-dimethoxy-4-[4-(2-methoxy-phenyl)-piperazin-1-yl]-quinoline | C |
| 250 | 3-cyclopropyl-6,7-dimethoxy-1-[4-(2-methoxy-phenyl)-piperazin-1-yl]-isoquinoline | C |
| 255 | 3-chloro-4-(4-(2-cyclopropyl-6-(dimethylamino)quinazolin-4-yl)piperazin-1-yl)benzonitrile | C |
| 256 | 3-chloro-4-[4-(2-cyclopropyl-6-dimethylamino-quinazolin-4-yl)-piperazin-1-yl]-benzamide | C |

TABLE 6-continued

| Cpd. No. | Name | HCS NTR1 Agonist (EC$_{50}$) |
|---|---|---|
| 260 | 3-{3-chloro-4-[4-(2-cyclopropyl-6-dimethylamino-quinazolin-4-yl)-piperazin-1-yl]-phenyl}-1,1-dimethyl-urea | C |
| 261 | 6-bromo-2-cyclopropyl-4-[4-(2,5-dimethoxy-phenyl)-piperazin-1-yl]-quinazoline | C |
| 262 | {2-cyclopropyl-4-[4-(2,5-dimethoxy-phenyl)-piperazin-1-yl]-quinazolin-6-yl}-dimethyl-amine | C |
| 263 | 6-bromo-2-cyclopropyl-4-[4-(2-methoxy-5-methyl-phenyl)-piperazin-1-yl]-quinazoline | C |
| 264 | {2-cyclopropyl-4-[4-(2-methoxy-5-methyl-phenyl)-piperazin-1-yl]-quinazolin-6-yl}-dimethyl-amine | C |
| 265 | 6-bromo-2-cyclopropyl-4-[4-(4-fluoro-2-methoxy-phenyl)-piperazin-1-yl]-quinazoline | C |
| 266 | {2-cyclopropyl-4-[4-(4-fluoro-2-methoxy-phenyl)-piperazin-1-yl]-quinazolin-6-yl}-dimethyl-amine | C |
| 267 | 4-[4-(6-bromo-2-cyclopropyl-quinazolin-4-yl)-piperazin-1-yl]-3-methoxy-benzonitrile | C |
| 268 | 4-[4-(2-cyclopropyl-6-dimethylamino-quinazolin-4-yl)-piperazin-1-yl]-3-methoxy-benzonitrile | C |
| 269 | 6-bromo-2-cyclopropyl-4-[4-(2-methoxy-4-trifluoromethoxy-phenyl)-piperazin-1-yl]-quinazoline | C |
| 270 | {2-cyclopropyl-4-[4-(2-methoxy-4-trifluoromethoxy-phenyl)-piperazin-1-yl]-quinazolin-6-yl}-dimethyl-amine | C |
| 271 | 6-bromo-4-[4-(2-chloro-4-fluoro-phenyl)-piperazin-1-yl]-2-cyclopropyl-quinazoline | C |
| 272 | {4-[4-(2-chloro-4-fluoro-phenyl)-piperazin-1-yl]-2-cyclopropyl-quinazolin-6-yl}-dimethyl-amine | C |
| 273 | 6-bromo-4-[4-(2-chloro-4-methyl-phenyl)-piperazin-1-yl]-2-cyclopropyl-quinazoline | C |
| 274 | {4-[4-(2-chloro-4-methyl-phenyl)-piperazin-1-yl]-2-cyclopropyl-quinazolin-6-yl}-dimethyl-amine | C |
| 275 | 6-bromo-4-[4-(4-chloro-2-methoxy-phenyl)-piperazin-1-yl]-2-cyclopropyl-quinazoline | C |
| 276 | {4-[4-(4-chloro-2-methoxy-phenyl)-piperazin-1-yl]-2-cyclopropyl-quinazolin-6-yl}-dimethyl-amine | C |
| 277 | 6-bromo-2-cyclopropyl-4-[4-(4-methoxy-phenyl)-piperazin-1-yl]-quinazoline | C |
| 278 | {2-cyclopropyl-4-[4-(4-methoxy-phenyl)-piperazin-1-yl]-quinazolin-6-yl}-dimethyl-amine | C |
| 279 | 6-bromo-2-cyclopropyl-4-[4-(3-methoxy-phenyl)-piperazin-1-yl]-quinazoline | C |
| 280 | {2-cyclopropyl-4-[4-(3-methoxy-phenyl)-piperazin-1-yl]-quinazolin-6-yl}-dimethyl-amine | C |
| 281 | 6-bromo-2-cyclopropyl-4-(4-o-tolyl-piperazin-1-yl)-quinazoline | C |
| 282 | [2-cyclopropyl-4-(4-o-tolyl-piperazin-1-yl)-quinazolin-6-yl]-dimethyl-amine | C |
| 283 | 6-bromo-2-cyclopropyl-4-[4-(2-fluoro-phenyl)-piperazin-1-yl]-quinazoline | C |
| 284 | 6-bromo-4-[4-(2-chloro-phenyl)-piperazin-1-yl]-2-cyclopropyl-quinazoline | C |
| 285 | {2-cyclopropyl-4-[4-(2-fluoro-phenyl)-piperazin-1-yl]-quinazolin-6-yl}-dimethyl-amine | C |
| 286 | {4-[4-(2-chloro-phenyl)-piperazin-1-yl]-2-cyclopropyl-quinazolin-6-yl}-dimethyl-amine | C |
| 287 | 2-[4-(6-Bromo-2-cyclopropyl-quinazolin-4-yl)-piperazin-1-yl]-benzonitrile | C |
| 288 | 2-[4-(2-cyclopropyl-6-dimethylamino-quinazolin-4-yl)-piperazin-1-yl]-benzonitrile | C |
| 289 | 2-[4-(2-cyclopropyl-6-dimethylamino-quinazolin-4-yl)-piperazin-1-yl]-benzamide | C |
| 295 | {4-[4-(2-azetidin-1-yl-phenyl)-piperazin-1-yl]-2-cyclopropyl-quinazolin-6-yl}-dimethyl-amine | — |
| 296 | {4-[4-(2-azetidin-1-yl-phenyl)-piperazin-1-yl]-2-cyclopropyl-quinazolin-6-yl}-ethyl-methyl-amine | — |
| 306 | {4-[4-(2-azetidin-1-yl-phenyl)-piperidin-1-yl]-2-cyclopropyl-quinazolin-6-yl}-dimethyl-amine | — |
| | 2-cyclopropyl-6-methoxy-4-(4-(2-methoxyphenyl)piperazin-1-yl)-7-(trifluoromethyl)quinazoline | C |

Pharmacology.

Instruments:

All liquid dispense and transfer steps were performed with the Freedom Evo automated liquid handler (Tecan US). LC/MS/MS (Applied Biosystems, Sciex API4000 Q-Trap). Standard compounds obtained from Sigma and MP Biomedicals.

Solubility:

The aqueous solubility of the compound was determined using a direct UV kinetic solubility method (Avdeef, A. 2001. Physicochemical profiling (solubility, permeability and charge state). *Curr Top Med Chem* 1:277-351) in a 96-well format at pH 5.0, 6.2 and 7.4. Compounds (250 µM) were incubated for 18.0h at room temperature to achieve equilibrium, and then filtered to remove any precipitate. The concentration of the compound in solution was measured by UV absorbance (250-498 nm) and compared to the spectra of precipitation-free reference solutions. Spectroscopically pure 1-Propanol (Sigma, St Louis, Mo.) was used as a cosolvent to suppress precipitation in the reference solutions. The solubility of each compound was determined using μSOL Evolution Plus software v3.2 (pION Inc) and is expressed as the concentration (μg/mL) of a solute in a saturated solution Metabolic Stability in Hepatic Microsomes:

Hepatic metabolic stability was determined using established protocols (Di, L., Kerns, E. H., Hong, Y., Kleintop, T. A., McConnell, O. J., and Huryn, D. M. 2003. Optimization of a higher throughput microsomal stability screening assay for profiling drug discovery candidates. J Biomol Screen 8:453-462). Briefly, the compound (1.0 and 10.0 μM) was preincubated for 10 min at 37° C. in potassium phosphate buffer (pH 7.4) together with 0.5 mg/mL mouse or human hepatic microsomes (Xenotech, Kansas City). The cofactor mixture comprising NADP, G6P, and G6P-DH (BD Biosciences) was added, and aliquots were taken after 0 and 60 min. Samples were analyzed on an Acquity UPLC, coupled with a sample organizer, and interfaced with a triple quadrupole ABI 4000 LC/MS/MS using the methodology described above. The percentage of the compound remaining after a 60 min incubation period was calculated according the following equation: [(area at time 60 min)/(area at time 0 min)]×100%.

Parallel Artificial Membrane Permeability Assay (PAMPA):

The PAMPA in a 96-well sandwich plate format was used to determine the capacity of compounds to cross a model of cell membrane by passive diffusion (Avdeef, A., Nielsen, P. E., and Tsinman, O. 2004. PAMPA—a drug absorption in vitro model 11. Matching the in vivo unstirred water layer thickness by individual-well stirring in microtitre plates. Eur J Pharm Sci 22:365-374). The effective permeability of the compound was measured at an initial concentration of 50 μM. The permeability measurements were performed using a cosolvent buffer system (20% ACN/aqueous buffer) solution (pION Inc, Woburn Mass.) prepared according to the manufacturer's instructions. The compound was dissolved in buffer solution and ACN (20%, cosolvent) to the desired concentration (50 μM). The PAMPA sandwich plate consisting of a donor bottom plate and an acceptor filter plate was used. The donor wells contained the compounds in 190 μl system solution, and magnetic stir bars. The filter on the bottom of each acceptor well was coated with GIT-0 phospholipid solution (pION Inc) and filled with 200 μl of Acceptor Sink Buffer, pH 7.4 (pION Inc) containing surfactant. The permeation time was 30 min and moderate stirring (equivalent to 40 μm Aqueous Boundary Layer thickness) was applied using the Gut-Box™ (pION, Inc). After the permeation time, the sandwich was disassembled and the amount of compound present in both the donor and acceptor wells was measured by UV absorbance (250-498 nm) and compared to spectra obtained reference standards. Mass balance was used to determine the amount of material embedded in the membrane filter. The effective permeability, Pe, was calculated using the software PAMPA Evolution Plus, version 3.2 (pION Inc).

Cell Viability with ATP-Lite:

Hepatic toxicity of compounds was determined with Fa2N-4 immortalized human hepatocytes using the ATP-lite 1-step assay (Perkin Elmer). assay according to the manufacturer's instructions. Fa2N-4 cells (XenoTech, Kansas City, Kans.) were seeded at 50,000 cells/well, and incubated with a range of concentrations of the test compound (0.01 μM-50 μM) in MFE support, media for 24 hrs at 37° C., 5% $CO_2$. At the end of the experiment, cell viability was determined by cellular ATP levels using the ATP-lite kit according to the manufacturer's instructions Luminescence was measured on the Infinite M200 plate reader (Tecan US). The concentration of each compound that killed 50% of the cells (LC50) was calculated by non-linear regression analysis using a log(inhibitor) vs response equation with a variable slope, using the statistic software package Prism4 (GraphPad, San Diego, Calif.).

Plasma Protein Binding:

The extent of compound bound to plasma proteins was measured using the Rapid Equilibrium Device (Pierce Thermo Scientific, Rockford Ill.). The base plate was rinsed with 20% followed by 2× washes with ultrapure water and allowed to dry. Human and mouse plasma (BioChemed Services, Winchester Va.) collected in EDTA was allowed to thaw at room temperature and then warmed to 37° C., and diluted 1:1 (v:v) with 1×PBS, pH 7.4, prior to the assay. The compound (1.0 and 10.0 μM final) was added to the chamber containing 300 μl plasma:PBS. Next, 500 μl of dialysis buffer (1×PBS, pH7.4) was added to the buffer chambers of the inserts. The chambers were covered with sealing tape and incubated at 37° C. on an orbital shaker at 300× rpm for 4 hours. After the incubation time, a sample volume of 50 μl from the buffer side, representing the free concentration, and an equivalent sample volume from the plasma side, representing the total concentration, i.e. the free concentration+ the concentration of drug bound to protein, were transferred from the dialysis cells to a 96 deep well plate for LCMS analysis. Results reported are the mean of each reaction duplicate, normalized to the internal standard, and expressed as a percent compound bound after the incubation time. The amount of compound in the supernatant was determined by LC/MS/MS and the percent of free and bound compounds were calculated with the following formulas: Percent of free parent compound=(amount of compound in receiver chamber/amount of compound in donor chamber)*100.

Plasma Stability:

Plasma stability was determined using previously published methods (Kerns, E. H., and Di, L. 2008. Drug-like Properties: Concepts, Structure Design and Methods. Oxford UK: Elsevier). Compound (1.0 μM) was incubated at 37° C. in human or mouse plasma (from blood of healthy donors collected on EDTA) diluted to 50% (v/v) with pH 7.4 isotonic phosphate buffer. At time 0 min and 180 min, aliquots were collected, added to acetonitrile to quench the reaction and precipitate plasma proteins. These samples were centrifuged and the supernatant analyzed by the LC/MS/MS method described above for the presence of the parental compound.

In Vitro ADME/T Profiling and Chemical Stability:

In vitro pharmacology screening was also conducted for compound 315. Consistent with its aqueous solubility data, 315 exhibited high permeability in the PAMPA assay with increasing pH of the donor compartment. When incubated with an artificial membrane that models the blood-brain-barrier (BBB), 315 was found to be highly permeable. Compound 315 was highly plasma protein bound and exhibited very high plasma stability. However, compound 315 was metabolized rapidly when incubated in vitro with human and mouse liver homogenates. This result is not completely surprising because of the presence of several unsubstituted aryl and alkyl positions and Ar—OMe ethers which are prone to oxidation, hydrolysis, conjugation and other metabolic reactions. Lastly, 315 showed a >15-fold window for toxicity (LC$_{50}$=30 μM) towards human hepatocytes.

TABLE 6

Summary of in vitro ADME/T Properties of NTR1 agonist 315

| | |
|---|---|
| Aqueous Solubility in pION's buffer (μg/mL) [μM]$^a$ pH 5.0/6.2/7.4 | >125/9.0/0.52 [>297/21.4/1.2] |
| Aqueous Solubility in 1x PBS, pH 7.4 (μg/mL) [μM]$^a$ | 0.45 [1.1] |
| PAMPA Permeability, P$_e$ (×10$^{-6}$ cm/s) Donor pH: 5.0/6.2/7.4 Acceptor pH: 7.4 | 1163/2145/2093 |
| BBB-PAMPA Permeability, Pe (×10$^{-6}$ cm/s) Donor pH: 7.4 Acceptor pH: 7.4 | 399 |
| Plasma Protein Binding    Human 1 μM/10 μM (% Bound)                  Mouse 1 μM/10 μM | 99.45/99.22 99.67/98.84 |
| Plasma Stability (% Remaining at 3 hrs) Human/Mouse | 100/99.55 |
| Hepatic Microsome Stability (% Remaining at 1 hr) Human/Mouse | 1.36/0.16 |
| Toxicity Towards Fa2N-4 Immortalized Human Hepatocytes LC$_{50}$ (μM) | 29.6 |

$^a$Solubility also expressed in molar units (μM) as indicated in italicized [bracketed values], in addition to more traditional μg/mL units Cross Reactivity:

Compound 315 was also submitted to the Psychoactive Drug Screening Program (PDSP) at the University of North Carolina (Bryan Roth, PI) for testing in a GPCR binding assay panel (~40 receptors tested), and was found to be moderately promiscuous at 10 μM, with K$_i$s<10 μM on 7 receptors. However, these activities in in vitro binding assays may not translate into functional modulation of these receptors. A follow up study at Panlabs/Ricerca in their lead profiling panel confirmed activity in two of those receptors (MOR, 86% @ 10 μM and signal 69% @ 10 μM), In addition, compound 315 showed activity across a range of adrenergic receptors ($\alpha_{1a}$, $\alpha_{1B}$, $\alpha_{1D}$, $\alpha_{2A}$ 63-100% @ 10 μM) in the Panlabs panel.

In Vivo PO and Brain Levels

Compound 315 had modest PK properties in mouse (Cl=81 mL/mg/kg, V$_{dss}$=6.22 L/kg, t$_{1/2}$=1.93 hr after a 2 mg/kg iv dose, C$_{max}$=763 ng/mL, t$_{1/2}$=2.58 hr, AUC=1223 ng hr/mL after a 10 mg/kg ip dose). However, compound 315 displayed excellent brain penetration after ip dosing, with brain levels of 924 ng/mL and 1506 ng/mL at 1 hr after a 10 mg/kg or 30 mg/kg ip dose (brain/plasma=1.3 or 1.6, respectively).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A compound of Formula I, or a pharmaceutically acceptable salt, solvate, or tautomer thereof:

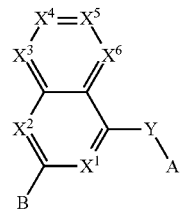

Formula I wherein:
A is A$^1$, —O-A$^1$, —NH-A$^1$, —C(=O)-A$^1$, or —S(=O)$_2$-A$^1$; A$^1$ is selected from the group consisting of optionally substituted phenyl, optionally substituted naphthyl, optionally substituted 5-membered heteroaryl, optionally substituted 6-membered heteroaryl, optionally substituted 9-membered heteroaryl and optionally substituted 10-membered heteroaryl; wherein optional substituents for A are selected from the group consisting of hydrogen, halogen, —CN, —OH, —NO$_2$, —N(R$^{13}$)—R$^{14}$, C(=O)—N(R$^{13}$)—R$^{14}$ NR$^{13}$C(=O)R$^{15}$, —C(=O)—O—R$^{13}$, —O—C(=O)—R$^{15}$, —SR$^{13}$, —S(=O)R$^{15}$, —S(=O)$_2$R$^{15}$, —N(R$^3$)S(=O)$_2$R$^{15}$, —S(=O)$_2$—N(R$^{13}$)—R$^{14}$, —C(=O)R$^{13}$, optionally substituted alkyl, optionally substituted cycloalkyl, optionally substituted heterocycloalkyl, optionally substituted alkoxy, optionally substituted haloalkyl, optionally substituted haloalkoxy, optionally substituted phenyl, and optionally substituted 5- or 6-membered heteroaryl;
B is selected from the group consisting of optionally substituted alkyl, and optionally substituted cycloalkyl;
Y is selected from optionally substituted heterocyloalkyl, optionally substituted spiroheterocyloalkyl, and —NR$^2$ (CH$_2$)NR$^3$—;
n is 2, 3, 4, 5, or 6;
R$^2$ is H or alkyl;
R$^3$ is H or alkyl;
X$^1$ is N or C(R$^1$);
X$^2$ is N or C(R$^1$);
X$^3$ is N or C(R$^4$);
X$^4$ is N or C(R$^5$);
X$^5$ is N or C(R$^6$);
X$^6$ is N or C(R$^7$);
each R$^1$ is independently selected from the group consisting of hydrogen, halogen, —CN, —OH, —NO$_2$, optionally substituted alkyl, optionally substituted alkoxy, optionally substituted haloalkyl, and optionally substituted haloalkoxy;
each of R$^4$, R$^5$, R$^6$, and R$^7$ is independently selected from the group consisting of hydrogen, halogen, —CN, —OH, —NO$_2$, —N(R$^{13}$)—R$^{14}$, —C(=O)—N(R$^{13}$)—R$^{14}$, —NR$^{13}$C(=O)R$^{15}$, —C(=O)—O—R$^{13}$, —O—C(=O)—R$^{15}$, —SR$^{13}$, —S(=O)R$^{15}$, —S(=O)$_2$R$^{15}$, —N(R$^{13}$)S(=O)$_2$R$^{15}$, —S(=O)$_2$—N (R$^{13}$)—R$^{14}$, —C(=O)R$^{13}$, optionally substituted alkyl, optionally substituted cycloalkyl, optionally substituted heterocycloalkyl, optionally substituted alkoxy, optionally substituted haloalkyl, optionally substituted haloalkoxy, optionally substituted phenyl, and optionally substituted 5- or 6-membered heteroaryl;
or R$^5$ and R$^6$ are taken together with the atoms connecting R$^5$ and R$^6$ to form an optionally substituted heterocyloalkyl;

each of $R^{13}$ and $R^{14}$ is independently selected from the group consisting of hydrogen, optionally substituted alkyl, optionally substituted cycloalkyl, optionally substituted heterocycloalkyl, optionally substituted alkoxy, optionally substituted haloalkyl, optionally substituted haloalkoxy, optionally substituted phenyl, and optionally substituted 5- or 6-membered heteroaryl;

or $R^{13}$ and $R^{14}$, when on the same nitrogen atom, are taken together with the nitrogen atom to which they are attached to form an optionally substituted heterocycloalkyl;

$R^{15}$ is selected from the group consisting of optionally substituted alkyl, optionally substituted cycloalkyl, optionally substituted heterocycloalkyl, optionally substituted alkoxy, optionally substituted haloalkyl, optionally substituted haloalkoxy, optionally substituted phenyl, and optionally substituted 5- or 6-membered heteroaryl;

wherein a heteroaryl comprises one to six heteroatoms selected from the group consisting of nitrogen, oxygen, and sulfur;

wherein a heterocycloalkyl comprises from 2 to 10 carbons in the ring and one to 6 heteroatoms selected from the group consisting of nitrogen, oxygen, and sulfur.

2. The compound of claim 1, or a pharmaceutically acceptable salt, solvate, or tautomer thereof, wherein:
$X^1$ is $C(R^1)$; and $X^2$ is $C(R^1)$; or
$X^1$ is N; and $X^2$ is $C(R^1)$; or
$X^1$ is $C(R^1)$; and $X^2$ is N; or
$X^1$ is N; and $X^2$ is N; or
$X^3$ is N; $X^4$ is $C(R^5)$; $X^5$ is $C(R^6)$; and $X^6$ is N or $C(R^7)$; or
$X^3$ is $C(R^4)$; $X^4$ is N; $X^5$ is $C(R^6)$; and $X^6$ is $C(R^7)$; or
$X^3$ is $C(R^4)$; $X^4$ is $C(R^5)$; $X^5$ is N; and $X^6$ is $C(R^7)$; or
$X^3$ is N or $C(R^4)$; $X^4$ is $C(R^5)$; $X^5$ is $C(R^6)$; and $X^6$ is N; or
$X^3$ is $C(R^4)$; $X^4$ is $C(R^5)$; $X^5$ is $C(R^6)$; and $X^6$ is $C(R^7)$.

3. The compound of claim 1, wherein the compound of Formula I has the following structure of Formula II, or a pharmaceutically acceptable salt, solvate, or tautomer thereof:

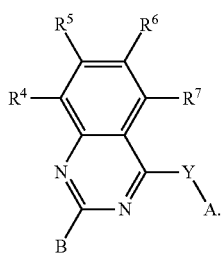

Formula II

4. The compound of claim 3, or a pharmaceutically acceptable salt, solvate, or tautomer thereof, wherein:
Y is selected from optionally substituted 5-, 6-, 7-, or 8-membered heterocyloalkyl, optionally substituted spiroheterocyloalkyl, and —$NR^2(CH_2)_nNR^3$—.

5. The compound of claim 4, or a pharmaceutically acceptable salt, solvate, or tautomer thereof, wherein:
Y is an optionally substituted 6-membered heterocyloalkyl that is an optionally substituted piperidinyl or optionally substituted piperazinyl.

6. The compound of claim 1, or a pharmaceutically acceptable salt, solvate, or tautomer thereof, wherein:

Y is 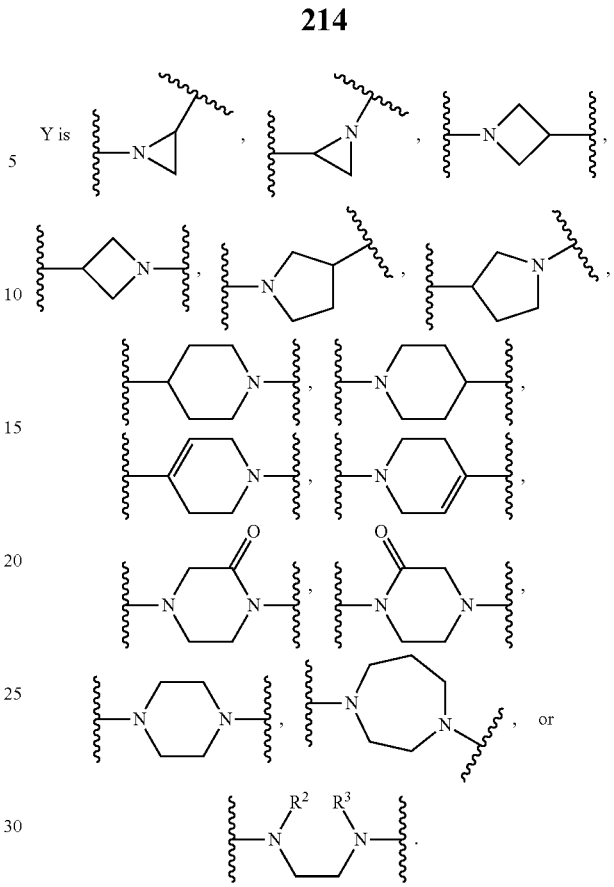

7. The compound of claim 3, wherein the compound has the following structure of Formula III or Formula V, or a pharmaceutically acceptable salt, solvate, or tautomer thereof:

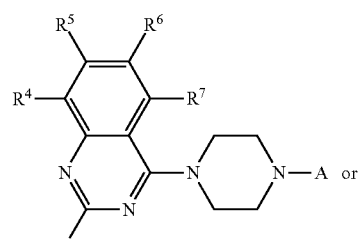

Formula III

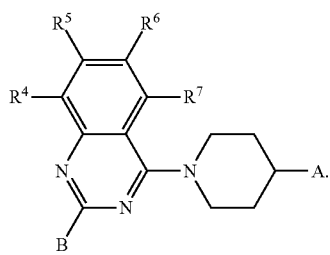

Formula V

8. The compound of claim 7, or a pharmaceutically acceptable salt, solvate, or tautomer thereof, wherein:
A is selected from the group consisting of optionally substituted phenyl, optionally substituted naphthyl, optionally substituted furanyl, optionally substituted pyrrolyl, optionally substituted oxazolyl, optionally substituted thiazolyl, optionally substituted imidazolyl, optionally substituted pyrazolyl, optionally substituted triazolyl, optionally substituted tetrazolyl, optionally substituted isoxazolyl, optionally substituted isothiazolyl, optionally substituted oxadiazolyl, optionally substituted thiadiazolyl, optionally substituted pyridinyl, optionally substituted pyrimidinyl, optionally substituted pyrazinyl, optionally substituted pyridazinyl, optionally substituted triazinyl, optionally substituted quinolinyl, optionally substituted isoquinolinyl, optionally substituted quinazolinyl, optionally substituted quinoxalinyl, optionally substituted naphthyridinyl, optionally substituted indolyl, optionally substituted indazolyl, optionally substituted benzoxazolyl, optionally substituted benzisoxazolyl, optionally substituted benzofuranyl, benzothienyl, optionally substituted benzothiazolyl, optionally substituted benzimidazolyl, optionally substituted purinyl, optionally substituted cinnolinyl, optionally substituted phthalazinyl, and optionally substituted pteridinylene.

9. The compound of claim 8, wherein the compound has the following structure of Formula VII or Formula IX, or a pharmaceutically acceptable salt, solvate, or tautomer thereof:

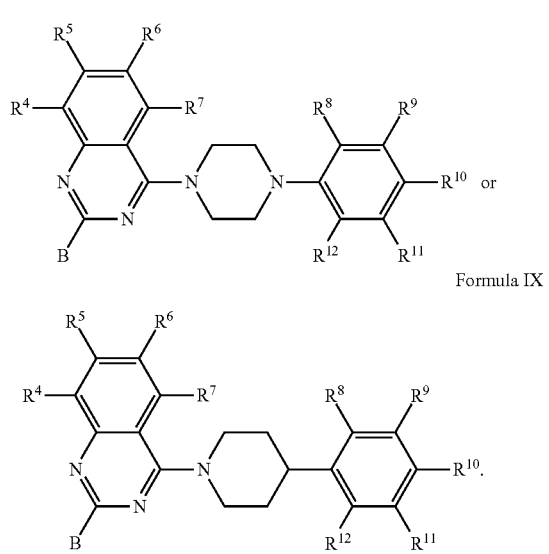

Formula VII

Formula IX wherein:
each of $R^8$, $R^9$, $R^{10}$, $R^{11}$, and $R^{12}$ is independently selected from the group consisting of hydrogen, halogen, —CN, —OH, —NO$_2$, —N($R^{13}$)—$R^{14}$, —C(=O)—N($R^{13}$)—$R^{14}$, —N$R^{13}$C(=O)$R^{15}$, —C(=O)—O—$R^{13}$, —O—C(=O)—$R^{15}$, —S$R^{13}$, —S(=O)$R^{15}$, —S(=O)$_2R^{15}$, —N($R^{13}$)S(=O)$_2R^{15}$, —S(=O)$_2$—N($R^{13}$)—$R^{14}$, —C(=O)$R^{13}$, optionally substituted alkyl, optionally substituted cycloalkyl, optionally substituted heterocycloalkyl, optionally substituted alkoxy, optionally substituted haloalkyl, optionally substituted haloalkoxy, optionally substituted phenyl, and optionally substituted 5- or 6-membered heteroaryl.

10. The compound of claim 7, or a pharmaceutically acceptable salt, solvate, or tautomer thereof, wherein:
B is an optionally substituted cycloalkyl.

11. The compound of claim 10, wherein the compound has the following structure of Formula XI or Formula XIII, or a pharmaceutically acceptable salt, solvate, or tautomer thereof:

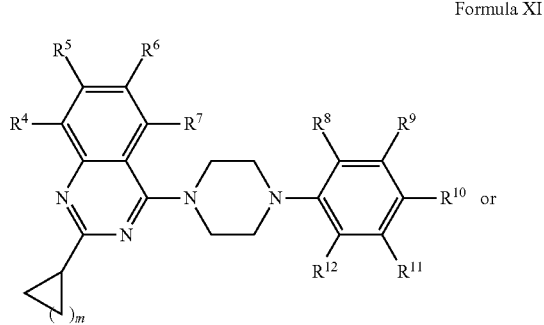

Formula XI

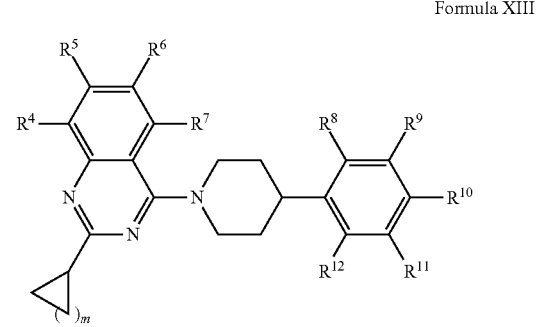

Formula XIII wherein:
m is 1, 2, 3, 4, 5, 6, or 7.

12. The compound of claim 11, or a pharmaceutically acceptable salt, solvate, or tautomer thereof, wherein:
m is 1 or 2;
$R^4$ is hydrogen;
$R^7$ is hydrogen; and
at least two of $R^8$, $R^9$, $R^{10}$, $R^{11}$, and $R^{12}$ is hydrogen.

13. The compound of claim 1, wherein the compound is
2-cyclobutyl-6,7-dimethoxy-4-(4-(2-methoxyphenyl)piperazin-1-yl)quinazoline;
2-phenyl-6,7-dimethoxy-4-(4-(2-methoxyphenyl)piperazin-1-yl)quinazoline;
2-phenyl-6,7-dimethoxy-4-(4-(phenyl)piperazin-1-yl)quinazoline;
2-phenyl-6,7-dimethoxy-4-(4-(2-fluorophenyl)piperazin-1-yl)quinazoline;
2-phenyl-6,7-dimethoxy-4-(4-(4-fluorophenyl)piperazin-1-yl)quinazoline;
2-phenyl-6,7-dimethoxy-4-(4-(2-chlorophenyl)piperazin-1-yl)quinazoline;
2-phenyl-6-ethoxy-7-methoxy-4-(4-(2-methoxyphenyl)piperazin-1-yl)quinazoline;
2-phenyl-6-ethoxy-7-methoxy-4-(4-(phenyl)piperazin-1-yl)quinazoline;
2-phenyl-6-ethoxy-7-methoxy-4-(4-(2-fluorophenyl)piperazin-1-yl)quinazoline;
or a pharmaceutically acceptable salt, solvate, or tautomer thereof.

14. The compound of claim 1, wherein the compound has the following structure, or a pharmaceutically acceptable salt, solvate, or tautomer thereof:

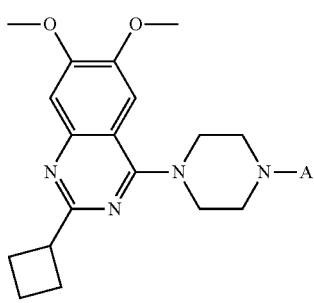

wherein,
A is phenyl, 2-methoxyphenyl, 3-methoxyphenyl, 4-methoxyphenyl, 2,4-dimethoxyphenyl, 2-methylphenyl, 2,6-dimethylphenyl, 2-fluorophenyl, 2-chlorophenyl, pyridin-2-yl, or 2-nitrophenyl.

15. The compound of claim 1, wherein the compound is
2-cyclobutyl-6,7-dimethoxy-4-(4-(2-methoxyphenyl)piperazin-1-yl)quinazoline;
2-cyclobutyl-6-methoxy-4-(4-(2-methoxyphenyl)piperazin-1-yl)quinazoline;
2-cyclobutyl-7-methoxy-4-(4-(2-methoxyphenyl)piperazin-1-yl)quinazoline;
2-cyclobutyl-4-(4-(2-methoxyphenyl)piperazin-1-yl)quinazoline;
6-cyclobutyl-8-(4-(2-methoxyphenyl)piperazin-1-yl)-[1,3]dioxolo[4,5-g]quinazoline;
2-cyclopropyl-6-methoxy-4-(4-(2-methoxyphenyl)piperazin-1-yl)quinazoline;
or a pharmaceutically acceptable salt, solvate, or tautomer thereof.

16. The compound of claim 1, wherein the compound has the following structure, or a pharmaceutically acceptable salt, solvate, or tautomer thereof:

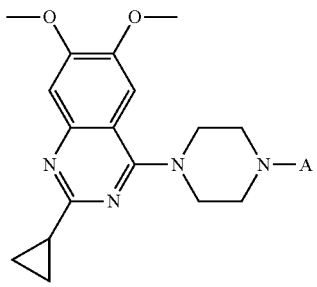

wherein,
A is 2-methoxyphenyl, 2-ethoxyphenyl, 2-chlorophenyl, —SO$_2$-phenyl, 4-methylbenzyl, 2-methoxybenzyl, benzoyl, or 2-methoxybenzoyl.

17. A compound that is:
2-cyclopropyl-4-[4-(4-fluoro-2-methoxy-phenyl)-piperazin-1-yl]-6,7-dimethoxy-quinazoline;
2-cyclopropyl-6,7-dimethoxy-4-[4-(2-methoxy-4-trifluoromethoxy-phenyl)-piperazin-1-yl]-quinazoline;
4-[4-(4-chloro-2-methoxy-phenyl)-piperazin-1-yl]-2-cyclopropyl-6,7-dimethoxy-quinazoline;
2-cyclopropyl-6,7-dimethoxy-4-[4-(2-methoxy-4-nitro-phenyl)-piperazin-1-yl]-quinazoline;
4-[4-(2-cyclopropyl-6,7-dimethoxy-quinazolin-4-yl)-piperazin-1-yl]-3-methoxy-phenylamine;
4-[4-(2-cyclopropyl-6,7-dimethoxy-quinazolin-4-yl)-piperazin-1-yl]-3-methoxy-benzonitrile;
4-[4-(2-cyclopropyl-6,7-dimethoxy-quinazolin-4-yl)-piperazin-1-yl]-3-methoxy-benzoic acid;
4-[4-(2-cyclopropyl-6,7-dimethoxy-quinazolin-4-yl)-piperazin-1-yl]-3-methoxy-benzamide;
{4-[4-(2-cyclopropyl-6,7-dimethoxy-quinazolin-4-yl)-piperazin-1-yl]-3-methoxy-phenyl}-dimethyl-amine;
2-cyclopropyl-6,7-dimethoxy-4-[4-(2-methoxy-4-trifluoromethyl-phenyl)-piperazin-1-yl]-quinazoline;
2-cyclopropyl-4-[4-(2,4-dimethoxy-phenyl)-piperazin-1-yl]-6,7-dimethoxy-quinazoline;
2-cyclopropyl-6,7-dimethoxy-4-[4-(2-methoxy-5-methyl-phenyl)-piperazin-1-yl]-quinazoline;
2-[4-(2-cyclopropyl-6,7-dimethoxy-quinazolin-4-yl)-piperazin-1-yl]-benzonitrile;
2-cyclopropyl-6,7-dimethoxy-4-[4-(2-methoxy-5-nitro-phenyl)-piperazin-1-yl]-quinazoline;
3-[4-(2-cyclopropyl-6,7-dimethoxy-quinazolin-4-yl)-piperazin-1-yl]-4-methoxy-phenylamine;
N-{3-[4-(2-cyclopropyl-6,7-dimethoxy-quinazolin-4-yl)-piperazin-1-yl]-4-methoxy-phenyl}-acetamide;
N-{3-[4-(2-cyclopropyl-6,7-dimethoxy-quinazolin-4-yl)-piperazin-1-yl]-4-methoxy-phenyl}-methanesulfonamide;
{3-[4-(2-cyclopropyl-6,7-dimethoxy-quinazolin-4-yl)-piperazin-1-yl]-4-methoxy-phenyl}-dimethyl-amine;
{3-[4-(2-cyclopropyl-6,7-dimethoxy-quinazolin-4-yl)-piperazin-1-yl]-4-methoxy-phenyl}-methyl-amine;
2-cyclopropyl-4-[4-(2,3-dichloro-phenyl)-piperazin-1-yl]-6,7-dimethoxy-quinazoline;
2-cyclopropyl-4-[4-(2,4-dichloro-phenyl)-piperazin-1-yl]-6,7-dimethoxy-quinazoline;
3-chloro-4-[4-(2-cyclopropyl-6,7-dimethoxy-quinazolin-4-yl)-piperazin-1-yl]-benzonitrile;
4-[4-(2-chloro-4-nitro-phenyl)-piperazin-1-yl]-2-cyclopropyl-6,7-dimethoxy-quinazoline;
3-chloro-4-[4-(2-cyclopropyl-6,7-dimethoxy-quinazolin-4-yl)-piperazin-1-yl]-benzoic acid;
3-chloro-4-[4-(2-cyclopropyl-6,7-dimethoxy-quinazolin-4-yl)-piperazin-1-yl]-benzamide;
3-chloro-4-[4-(2-cyclopropyl-6,7-dimethoxy-quinazolin-4-yl)-piperazin-1-yl]-phenylamine;
N-{3-chloro-4-[4-(2-cyclopropyl-6,7-dimethoxy-quinazolin-4-yl)-piperazin-1-yl]-phenyl}-acetamide;
N-{3-chloro-4-[4-(2-cyclopropyl-6,7-dimethoxy-quinazolin-4-yl)-piperazin-1-yl]-phenyl}-methanesulfonamide;
3-chloro-4-[4-(2-cyclopropyl-6,7-dimethoxy-quinazolin-4-yl)-piperazin-1-yl]-benzoic acid;
4-[4-(2-chloro-4-fluoro-phenyl)-piperazin-1-yl]-2-cyclopropyl-6,7-dimethoxy-quinazoline;
4-[4-(2-chloro-4-trifluoromethyl-phenyl)-piperazin-1-yl]-2-cyclopropyl-6,7-dimethoxy-quinazoline;
4-[4-(2-chloro-4-methyl-phenyl)-piperazin-1-yl]-2-cyclopropyl-6,7-dimethoxy-quinazoline;
4-[4-(2-chloro-4-methoxy-phenyl)-piperazin-1-yl]-2-cyclopropyl-6,7-dimethoxy-quinazoline;
2-[4-(2-cyclopropyl-6,7-dimethoxy-quinazolin-4-yl)-piperazin-1-yl]-benzonitrile;
2-[4-(2-cyclopropyl-6,7-dimethoxy-quinazolin-4-yl)-piperazin-1-yl]-5-methoxy-benzonitrile;
5-chloro-2-[4-(2-cyclopropyl-6,7-dimethoxy-quinazolin-4-yl)-piperazin-1-yl]-benzonitrile;
2-[4-(2-cyclopropyl-6,7-dimethoxy-quinazolin-4-yl)-piperazin-1-yl]-5-nitro-benzonitrile;

5-amino-2-[4-(2-cyclopropyl-6,7-dimethoxy-quinazolin-4-yl)-piperazin-1-yl]-benzonitrile;
2-cyclopropyl-6,7-dimethoxy-4-[4-(2-nitro-phenyl)-piperazin-1-yl]-quinazoline;
2-[4-(2-cyclopropyl-6,7-dimethoxy-quinazolin-4-yl)-piperazin-1-yl]-phenylamine;
2-(4-(2-cyclopropyl-6,7-dimethoxyquinazolin-4-yl)piperazin-1-yl)-N-ethylaniline;
{2-[4-(2-cyclopropyl-6,7-dimethoxy-quinazolin-4-yl)-piperazin-1-yl]-phenyl}-dimethyl-amine;
{2-[4-(2-cyclopropyl-6,7-dimethoxy-quinazolin-4-yl)-piperazin-1-yl]-phenyl}-diethyl-amine;
4-[4-(2-aziridin-1-yl-phenyl)-piperazin-1-yl]-2-cyclopropyl-6,7-dimethoxy-quinazoline;
4-[4-(4-benzyloxy-2-nitro-phenyl)-piperazin-1-yl]-2-cyclopropyl-6,7-dimethoxy-quinazoline;
3-amino-4-[4-(2-cyclopropyl-6,7-dimethoxy-quinazolin-4-yl)-piperazin-1-yl]-phenol;
2-cyclopropyl-6,7-dimethoxy-4-[4-(4-methoxy-2-nitro-phenyl)-piperazin-1-yl]-quinazoline;
2-[4-(2-cyclopropyl-6,7-dimethoxy-quinazolin-4-yl)-piperazin-1-yl]-5-fluoro-phenylamine;
2-[4-(2-cyclopropyl-6,7-dimethoxy-quinazolin-4-yl)-piperazin-1-yl]-5-methoxy-phenylamine;
{5-bromo-2-[4-(2-cyclopropyl-6,7-dimethoxy-quinazolin-4-yl)-piperazin-1-yl]-phenyl}-dimethyl-amine;
{2-[4-(2-cyclopropyl-6,7-dimethoxy-quinazolin-4-yl)-piperazin-1-yl]-5-fluoro-phenyl}-dimethyl-amine;
{5-chloro-2-[4-(2-cyclopropyl-6,7-dimethoxy-quinazolin-4-yl)-piperazin-1-yl]-phenyl}-dimethyl-amine;
{2-[4-(2-cyclopropyl-6,7-dimethoxy-quinazolin-4-yl)-piperazin-1-yl]-5-methoxy-phenyl}-dimethyl-amine;
4-[4-(2-cyclopropyl-6,7-dimethoxy-quinazolin-4-yl)-piperazin-1-yl]-3-dimethylamino-benzoic acid;
{2-[4-(2-cyclopropyl-6,7-dimethoxy-quinazolin-4-yl)-piperazin-1-yl]-phenyl)}-phenyl-amine;
2-cyclopropyl-6,7-dimethoxy-4-[4-(2-morpholin-4-yl-phenyl)-piperazin-1-yl]-quinazoline;
2-cyclopropyl-6,7-dimethoxy-4-[4-(2-pyrrolidin-1-yl-phenyl)-piperazin-1-yl]-quinazoline;
4-[4-(2-azetidin-1-yl-phenyl)-piperazin-1-yl]-2-cyclopropyl-6,7-dimethoxy-quinazoline;
2-cyclopropyl-6,7-dimethoxy-4-[4-(2-piperidin-1-yl-phenyl)-piperazin-1-yl]-quinazoline;
2-Cyclopropyl-6,7-dimethoxy-4-{4-[2-(4-methyl-piperazin-1-yl)-phenyl]-piperazin-1-yl}-quinazoline;
5-amino-2-[4-(2-cyclopropyl-6,7-dimethoxy-quinazolin-4-yl)-piperazin-1-yl]-phenol;
4-(4-(2-cyclopropyl-6,7-dimethoxyquinazolin-4-yl)piperazin-1-yl)-N,N-dimethylaniline;
{4-[4-(2-cyclopropyl-6,7-dimethoxy-quinazolin-4-yl)-piperazin-1-yl]-phenyl}-diethyl-amine;
3-(4-(2-cyclopropyl-6,7-dimethoxyquinazolin-4-yl)piperazin-1-yl)-N,N-dimethylaniline;
{3-[4-(2-cyclopropyl-6,7-dimethoxy-quinazolin-4-yl)-piperazin-1-yl]-phenyl}-diethyl-amine;
N-(2-cyclopropyl-6,7-dimethoxy-quinazolin-5-yl)-N'-(2-methoxy-phenyl)-ethane-1,2-diamine;
N'-(2-cyclopropyl-6,7-dimethoxy-quinazolin-5-yl)-N-(2-methoxy-phenyl)-N-methyl-ethane-1,2-diamine;
2-cyclopropyl-6,7-dimethoxy-4-[4-(2-methoxy-phenyl)-2-methyl-piperazin-1-yl]-quinazoline;
N-(2-cyclopropyl-6,7-dimethoxy-quinazolin-4-yl)-N'-phenyl-ethane-1,2-diamine;
N-(2-cyclopropyl-6,7-dimethoxy-quinazolin-4-yl)-N'-(2-methoxy-phenyl)-propane-1,3-diamine;
N-(2-cyclopropyl-6,7-dimethoxy-quinazolin-4-yl)-N'-(2-methoxy-phenyl)-N,N'-dimethyl-ethane-1,2-diamine;
2-cyclopropyl-6,7-dimethoxy-4-[4-(2-methoxy-phenyl)-[1,4]diazepan-1-yl]-quinazoline;
[1-(2-cyclopropyl-6,7-dimethoxy-quinazolin-4-yl)-piperidin-4-yl]-(2-methoxy-phenyl)-amine;
2-(2-cyclopropyl-6,7-dimethoxy-quinazolin-4-ylamino)-N-(2-methoxy-phenyl)-acetamide;
2-Cyclopropyl-6,7-dimethoxy-4-[4-(2-methoxy-phenyl)-piperidin-1-yl]-quinazoline;
{2-[1-(2-Cyclopropyl-6,7-dimethoxy-quinazolin-4-yl)-piperidin-4-yl]-phenyl}-dimethyl-amine;
2-cyclopropyl-6,7-dimethoxy-4-[4-(2-methoxy-phenyl)-3,6-dihydro-2H-pyridin-1-yl]-quinazoline;
2-cyclopropyl-6,7-dimethoxy-4-(3-phenyl-pyrrolidin-1-yl)-quinazoline;
2-cyclopropyl-6,7-dimethoxy-4-[3-(2-methoxy-phenyl)-pyrrolidin-1-yl]-quinazoline;
{2-[1-(2-cyclopropyl-6,7-dimethoxy-quinazolin-4-yl)-pyrrolidin-3-yl]-phenyl}-dimethyl-amine;
2-cyclopropyl-6, 7-dimethoxy-4-[3-(3-methoxy-phenyl)-cyclopentyl]-quinazoline;
{3-[1-(2-cyclopropyl-6,7-dimethoxy-quinazolin-4-yl)-pyrrolidin-3-yl]-phenyl}-dimethyl-amine;
1-(2-cyclopropyl-6,7-dimethoxy-quinazolin-4-yl)-3-phenyl-pyrrolidin-3-ol;
1-(2-cyclopropyl-6,7-dimethoxy-quinazolin-4-yl)-3-(2-dimethylamino-phenyl)-pyrrolidin-3-ol;
1-(2-cyclopropyl-6,7-dimethoxy-quinazolin-4-yl)-3-(3-methoxy-phenyl)-pyrrolidin-3-ol;
2-cyclopropyl-4-(3-fluoro-3-phenyl-pyrrolidin-1-yl)-6,7-dimethoxy-quinazoline;
{2-[1-(2-cyclopropyl-6,7-dimethoxy-quinazolin-4-yl)-3-fluoro-pyrrolidin-3-yl]-phenyl}-dimethyl-amine;
2-cyclopropyl-4-[3-fluoro-3-(3-methoxy-phenyl)-pyrrolidin-1-yl]-6,7-dimethoxy-quinazoline;
2-cyclopropyl-6,7-dimethoxy-4-(3-methyl-4-phenyl-piperazin-1-yl)-quinazoline;
2-cyclopropyl-6,7-dimethoxy-4-[1-(2-methoxy-phenyl)-piperidin-4-yl]-quinazoline;
6,7-dimethoxy-4-[4-(2-methoxy-phenyl)-piperazin-1-yl]-2-piperidin-4-yl-quinazoline;
6,7-dimethoxy-4-[4-(2-methoxy-phenyl)-piperazin-1-yl]-2-(1-methyl-piperidin-4-yl)-quinazoline;
6,7-dimethoxy-4-[4-(2-methoxy-phenyl)-piperazin-1-yl]-2-(4-methyl-cyclohexyl)-quinazoline;
4-{6,7-dimethoxy-4-[4-(2-methoxy-phenyl)-piperazin-1-yl]-quinazolin-2-yl}-piperidine-1-carboxylic acid benzyl ester;
6,7-dimethoxy-4-[4-(2-methoxy-phenyl)-piperazin-1-yl]-2-(tetrahydro-pyran-4-yl)-quinazoline;
6,7-dimethoxy-4-[4-(2-methoxy-phenyl)-piperazin-1-yl]-2-(tetrahydro-furan-3-yl)-quinazoline;
6,7-dimethoxy-4-[4-(2-methoxy-phenyl)-piperazin-1-yl]-2-(2-methyl-cyclopropyl)-quinazoline;
cis-6,7-dimethoxy-2-(4-methoxy-cyclohexyl)-4-[4-(2-methoxy-phenyl)-piperazin-1-yl]-quinazoline;
trans-6,7-dimethoxy-2-(4-methoxy-cyclohexyl)-4-[4-(2-methoxy-phenyl)-piperazin-1-yl]-quinazoline;
6,7-dimethoxy-4-[4-(2-methoxy-phenyl)-piperazin-1-yl]-2-(4-methyl-pyrrolidin-3-yl)-quinazoline;
2-(1,4-dimethyl-pyrrolidin-3-yl)-6,7-dimethoxy-4-[4-(2-methoxy-phenyl)-piperazin-1-yl]-quinazoline;
6,7-dimethoxy-4-[4-(2-methoxy-phenyl)-piperazin-1-yl]-2-pyrrolidin-3-yl-quinazoline;
6,7-dimethoxy-4-[4-(2-methoxy-phenyl)-piperazin-1-yl]-2-(1-methyl-pyrrolidin-3-yl)-quinazoline;

2-((1R,3R)-3-chloro-3-methylcyclobutyl)-6,7-dimethoxy-4-(4-(2-methoxyphenyl)piperazin-1-yl)quinazoline;
2-((1S,3S)-3-chloro-3-methylcyclobutyl)-6,7-dimethoxy-4-(4-(2-methoxyphenyl)piperazin-1-yl)quinazoline;
6,7-dimethoxy-4-[4-(2-methoxy-phenyl)-piperazin-1-yl]-2-(3-methyl-cyclobutyl)-quinazoline;
2-cyclohexyl-6,7-dimethoxy-4-[4-(2-methoxy-phenyl)-piperazin-1-yl]-quinazoline;
2-tert-Butyl-6,7-dimethoxy-4-[4-(2-methoxy-phenyl)-piperazin-1-yl]-quinazoline;
2-tert-Butyl-6,7-dimethoxy-4-[4-(2-methoxy-phenyl)-piperidin-1-yl]-quinazoline;
6,7-dimethoxy-4-[4-(2-methoxy-phenyl)-piperazin-1-yl]-2-(1-methyl-cyclopropyl)-quinazoline;
6,7-dimethoxy-4-[4-(2-methoxy-phenyl)-piperidin-1-yl]-2-(1-methyl-cyclopropyl)-quinazoline;
6,7-dimethoxy-4-[4-(2-methoxy-phenyl)-piperazin-1-yl]-2-(1-trifluoromethyl-cyclopropyl)-quinazoline;
6,7-dimethoxy-4-[4-(2-methoxy-phenyl)-piperidin-1-yl]-2-(1-trifluoromethyl-cyclopropyl)-quinazoline;
[4-[4-(2-Methoxy-phenyl)-piperidin-1-yl]-2-(1-methyl-cyclopropyl)-quinazolin-6-yl]-methyl-(2-morpholin-4-yl-ethyl)-amine;
7-chloro-2-cyclopropyl-6-methoxy-4-[4-(2-methoxy-phenyl)-piperazin-1-yl]-quinazoline;
2-cyclopropyl-4-[4-(2-methoxy-phenyl)-piperazin-1-yl]-pyrido[2,3-d]pyrimidine;
2-cyclopropyl-6, 8-dimethoxy-4-[4-(2-methoxy-phenyl)-piperazin-1-yl]-quinazoline;
2-cyclopropyl-6-methoxy-4-[4-(2-methoxy-phenyl)-piperazin-1-yl]-7-methyl-quinazoline;
2-cyclopropyl-7-fluoro-6-methoxy-4-[4-(2-methoxy-phenyl)-piperazin-1-yl]-quinazoline;
6-bromo-2-cyclopropyl-4-[4-(2-methoxy-phenyl)-piperazin-1-yl]-quinazoline;
2-cyclopropyl-4-[4-(2-methoxy-phenyl)-piperazin-1-yl]-quinazolin-6-yl}-dimethylamine;
6-bromo-2-cyclopropyl-7-fluoro-4-[4-(2-methoxy-phenyl)-piperazin-1-yl]-quinazoline;
{2-cyclopropyl-7-fluoro-4-[4-(2-methoxy-phenyl)-piperazin-1-yl]-quinazolin-6-yl}-dimethyl-amine;
{2-cyclopropyl-7-fluoro-4-[4-(2-methoxy-phenyl)-piperazin-1-yl]-quinazolin-6-yl}-diethyl-amine;
6-bromo-7-chloro-2-cyclopropyl-4-[4-(2-methoxy-phenyl)-piperazin-1-yl]-quinazoline;
{7-chloro-2-cyclopropyl-4-[4-(2-methoxy-phenyl)-piperazin-1-yl]-quinazolin-6-yl}-dimethyl-amine;
{7-chloro-2-cyclopropyl-4-[4-(2-methoxy-phenyl)-piperazin-1-yl]-quinazolin-6-yl}-diethyl-amine;
6-bromo-2-cyclopropyl-4-[4-(2-methoxy-phenyl)-piperazin-1-yl]-7-methyl-quinazoline;
{2-cyclopropyl-4-[4-(2-methoxy-phenyl)-piperazin-1-yl]-7-methyl-quinazolin-6-yl}-dimethyl-amine;
{2-cyclopropyl-4-[4-(2-methoxy-phenyl)-piperazin-1-yl]-7-methyl-quinazolin-6-yl}-ethyl-methyl-amine;
6-bromo-2-cyclopropyl-4-[4-(2-methoxy-phenyl)-piperidin-1-yl]-7-methyl-quinazoline;
{2-cyclopropyl-4-[4-(2-methoxy-phenyl)-piperidin-1-yl]-7-methyl-quinazolin-6-yl}-diethyl-amine;
2-cyclopropyl-6-methoxy-4-[4-(2-methoxy-phenyl)-piperazin-1-yl]-pyrido [3,4-d]pyrimidine;
6-bromo-2-cyclopropyl-4-[4-(2-methoxy-phenyl)-piperidin-1-yl]-7-methyl-quinazoline;
{2-cyclopropyl-4-[4-(2-methoxy-phenyl)-piperidin-1-yl]-7-methyl-quinazolin-6-yl}-diethyl-amine;
{2-cyclopropyl-4-[4-(2-methoxy-phenyl)-piperazin-1-yl]-quinazolin-7-yl)}-dimethyl-amine;
{2-cyclopropyl-4-[4-(2, 5-dimethoxy-phenyl)-piperazin-1-yl]-quinazolin-6-yl}-dimethyl-amine;
2-cyclopropyl-4-[4-(2-methoxy-phenyl)-piperazin-1-yl]-6-piperidin-1-yl-quinazoline;
{2-cyclopropyl-4-[4-(2-methoxy-phenyl)-piperazin-1-yl]-quinazolin-6-yl)}-diethyl-amine;
2-cyclopropyl-4-[4-(2-methoxy-phenyl)-piperazin-1-yl]-6-morpholin-4-yl-quinazoline;
2-cyclopropyl-4-[4-(2-methoxy-phenyl)-piperazin-1-yl]-6-pyrrolidin-1-yl-quinazoline;
{2-cyclopropyl-4-[4-(2-methoxy-phenyl)-piperazin-1-yl]-quinazolin-6-yl)}-phenyl-amine;
{2-cyclopropyl-4-[4-(2-methoxy-phenyl)-piperidin-1-yl]-quinazolin-6-yl)}-dimethyl-amine;
{2-cyclopropyl-4-[4-(2-methoxy-phenyl)-piperidin-1-yl]-quinazolin-6-yl)}-ethyl-methyl-amine;
{7-chloro-2-cyclopropyl-4-[4-(2-methoxyphenyl)piperidyl]quinazolin-6-yl}dimethylamine;
2-cyclopropyl-4-[4-(2-methoxy-phenyl)-piperazin-1-yl]-6-piperazin-1-yl-quinazoline;
2-cyclopropyl-4-[4-(2-methoxy-phenyl)-piperazin-1-yl]-6-(4-methyl-piperazin-1-yl)-quinazoline;
2-cyclopropyl-6,7-difluoro-4-[4-(2-methoxy-phenyl)-piperazin-1-yl]-quinazoline;
{2-cyclopropyl-6-fluoro-4-[4-(2-methoxy-phenyl)-piperazin-1-yl]-quinazolin-7-yl}-dimethyl-amine;
{2-cyclopropyl-6-fluoro-4-[4-(2-methoxy-phenyl)-piperazin-1-yl]-quinazolin-7-yl}-diethyl-amine;
2-cyclopropyl-6-fluoro-7-methoxy-4-[4-(2-methoxy-phenyl)-piperazin-1-yl]-quinazoline;
{2-cyclopropyl-4-[4-(2-methoxy-phenyl)-piperazin-1-yl]-quinazolin-6-yl}-methyl-propyl-amine;
{2-cyclopropyl-4-[4-(2-methoxy-phenyl)-piperazin-1-yl]-quinazolin-6-yl)}-methyl-(2-morpholin-4-yl-ethyl)-amine;
2-cyclopropyl-4-(4-(2-methoxyphenyl)piperazin-1-yl)-N-methyl-N-(2-morpholinoethyl)quinazolin-6-amine;
2,2'-((2-cyclopropyl-4-(4-(2-methoxyphenyl)piperazin-1-yl)quinazolin-6-yl)azanediyl)diethanol;
2-({2-cyclopropyl-4-[4-(2-methoxy-phenyl)-piperazin-1-yl]-quinazolin-6-yl)}-methyl-amino)-ethanol;
{2-cyclopropyl-4-[4-(2-methoxy-phenyl)-piperazin-1-yl]-quinazolin-6-yl)}-(2-methoxy-ethyl)-methyl-amine;
2-({2-cyclopropyl-4-[4-(2-methoxy-phenyl)-piperidin-1-yl]-quinazolin-6-yl)}-methyl-amino)-ethanol;
{2-cyclopropyl-4-[4-(2-methoxy-phenyl)-piperidin-1-yl]-quinazolin-6-yl)}-(2-methoxy-ethyl)-methyl-amine;
{2-cyclopropyl-4-[4-(2-methoxy-phenyl)-piperidin-1-yl]-quinazolin-6-yl)}-methyl-propyl-amine;
{2-cyclopropyl-4-[4-(2-methoxy-phenyl)-piperidin-1-yl]-quinazolin-6-yl)}-methyl-(2-morpholin-4-yl-ethyl)-amine;
2-cyclopropyl-5, 8-dimethoxy-4-[4-(2-methoxy-phenyl)-piperazin-1-yl]-quinazoline;
2-cyclopropyl-4-[4-(2-methoxy-phenyl)-piperazin-1-yl]-quinazoline;
2-cyclopropyl-5,6-dimethoxy-4-[4-(2-methoxy-phenyl)-piperazin-1-yl]-quinazoline;
2-cyclopropyl-5-methoxy-4-[4-(2-methoxy-phenyl)-piperazin-1-yl]-quinazoline;
2-cyclopropyl-8-methoxy-4-[4-(2-methoxy-phenyl)-piperazin-1-yl]-quinazoline;

2-cyclopropyl-6,7-dimethoxy-4-[4-(2-methoxy-phenyl)-piperazin-1-yl]-quinoline;
3-cyclopropyl-6,7-dimethoxy-1-[4-(2-methoxy-phenyl)-piperazin-1-yl]-isoquinoline;
3-chloro-4-(4-(2-cyclopropyl-6-(dimethylamino)quinazolin-4-yl)piperazin-1-yl)benzonitrile;
3-chloro-4-[4-(2-cyclopropyl-6-dimethylamino-quinazolin-4-yl)-piperazin-1-yl]-benzamide;
3-{3-chloro-4-[4-(2-cyclopropyl-6-dimethylamino-quinazolin-4-yl)-piperazin-1-yl]-phenyl}-1,1-dimethyl-urea;
6-bromo-2-cyclopropyl-4-[4-(2, 5-dimethoxy-phenyl)-piperazin-1-yl]-quinazoline;
{2-cyclopropyl-4-[4-(2,5-dimethoxy-phenyl)-piperazin-1-yl]-quinazolin-6-yl}-dimethyl-amine;
6-bromo-2-cyclopropyl-4-[4-(2-methoxy-5-methyl-phenyl)-piperazin-1-yl]-quinazoline;
{2-cyclopropyl-4-[4-(2-methoxy-5-methyl-phenyl)-piperazin-1-yl]-quinazolin-6-yl}-dimethyl-amine;
6-bromo-2-cyclopropyl-4-[4-(4-fluoro-2-methoxy-phenyl)-piperazin-1-yl]-quinazoline;
{2-cyclopropyl-4-[4-(4-fluoro-2-methoxy-phenyl)-piperazin-1-yl]-quinazolin-6-yl}-dimethyl-amine;
4-[4-(6-bromo-2-cyclopropyl-quinazolin-4-yl)-piperazin-1-yl]-3-methoxy-benzonitrile;
4-[4-(2-cyclopropyl-6-dimethylamino-quinazolin-4-yl)-piperazin-1-yl]-3-methoxy-benzonitrile;
6-bromo-2-cyclopropyl-4-[4-(2-methoxy-4-trifluoromethoxy-phenyl)-piperazin-1-yl]-quinazoline;
{2-cyclopropyl-4-[4-(2-methoxy-4-trifluoromethoxy-phenyl)-piperazin-1-yl]-quinazolin-6-yl}-dimethyl-amine;
6-bromo-4-[4-(2-chloro-4-fluoro-phenyl)-piperazin-1-yl]-2-cyclopropyl-quinazoline;
{4-[4-(2-chloro-4-fluoro-phenyl)-piperazin-1-yl]-2-cyclopropyl-quinazolin-6-yl}-dimethyl-amine;
6-bromo-4-[4-(2-chloro-4-methyl-phenyl)-piperazin-1-yl]-2-cyclopropyl-quinazoline;
{4-[4-(2-chloro-4-methyl-phenyl)-piperazin-1-yl]-2-cyclopropyl-quinazolin-6-yl}-dimethyl-amine;
6-bromo-4-[4-(4-chloro-2-methoxy-phenyl)-piperazin-1-yl]-2-cyclopropyl-quinazoline;
{4-[4-(4-chloro-2-methoxy-phenyl)-piperazin-1-yl]-2-cyclopropyl-quinazolin-6-yl}-dimethyl-amine;
6-bromo-2-cyclopropyl-4-[4-(4-methoxy-phenyl)-piperazin-1-yl]-quinazoline;
{2-cyclopropyl-4-[4-(4-methoxy-phenyl)-piperazin-1-yl]-quinazolin-6-yl}-dimethyl-amine;
6-bromo-2-cyclopropyl-4-[4-(3-methoxy-phenyl)-piperazin-1-yl]-quinazoline;
{2-cyclopropyl-4-[4-(3-methoxy-phenyl)-piperazin-1-yl]-quinazolin-6-yl}-dimethyl-amine;
6-bromo-2-cyclopropyl-4-(4-o-tolyl-piperazin-1-yl)-quinazoline;
[2-cyclopropyl-4-(4-o-tolyl-piperazin-1-yl)-quinazolin-6-yl]-dimethyl-amine;
6-bromo-2-cyclopropyl-4-[4-(2-fluoro-phenyl)-piperazin-1-yl]-quinazoline;
6-bromo-4-[4-(2-chloro-phenyl)-piperazin-1-yl]-2-cyclopropyl-quinazoline;
{2-cyclopropyl-4-[4-(2-fluoro-phenyl)-piperazin-1-yl]-quinazolin-6-yl}-dimethyl-amine;
{4-[4-(2-chloro-phenyl)-piperazin-1-yl]-2-cyclopropyl-quinazolin-6-yl}-dimethyl-amine;
2-[4-(6-Bromo-2-cyclopropyl-quinazolin-4-yl)-piperazin-1-yl]-benzonitrile;
2-[4-(2-cyclopropyl-6-dimethylamino-quinazolin-4-yl)-piperazin-1-yl]-benzonitrile;
2-[4-(2-cyclopropyl-6-dimethylamino-quinazolin-4-yl)-piperazin-1-yl]-benzamide;
{4-[4-(2-azetidin-1-yl-phenyl)-piperazin-1-yl]-2-cyclopropyl-quinazolin-6-yl}-dimethyl-amine;
{4-[4-(2-azetidin-1-yl-phenyl)-piperazin-1-yl]-2-cyclopropyl-quinazolin-6-yl}-ethyl-methyl-amine;
{4-[4-(2-azetidin-1-yl-phenyl)-piperidin-1-yl]-2-cyclopropyl-quinazolin-6-yl}-dimethyl-amine;
2-cyclopropyl-6,7-dimethoxy-4-(4-(2-methoxyphenyl)piperazin-1-yl)quinazoline;
6,7-dimethoxy-4-(4-(2-methoxyphenyl)piperazin-1-yl)-2-methylquinazoline;
2-benzyl-6,7-dimethoxy-4-(4-(2-methoxyphenyl)piperazin-1-yl)quinazoline;
2-ethyl-6,7-dimethoxy-4-(4-(2-methoxyphenyl)piperazin-1-yl)quinazoline;
6,7-dimethoxy-4-(4-(2-methoxyphenyl)piperazin-1-yl)-2-propylquinazoline;
2-isopropyl-6,7-dimethoxy-4-(4-(2-methoxyphenyl)piperazin-1-yl)quinazoline;
2-isobutyl-6,7-dimethoxy-4-(4-(2-methoxyphenyl)piperazin-1-yl)quinazoline;
6,7-dimethoxy-4-(4-(2-methoxyphenyl)piperazin-1-yl)-2-vinylquinazoline;
6,7-dimethoxy-4-(4-(2-methoxyphenyl)piperazin-1-yl)-2-(2-(4-(2-methoxyphenyl)piperazin-1-yl)ethyl)quinazoline;
2-cyclopentyl-6,7-dimethoxy-4-(4-(2-methoxyphenyl)piperazin-1-yl)quinazoline;
2-(cyclopropylmethyl)-6,7-dimethoxy-4-(4-(2-methoxyphenyl)piperazin-1-yl)quinazoline;
2-(6,7-dimethoxy-4-(4-(2-methoxyphenyl)piperazin-1-yl)quinazolin-2-yl)-N,N-dimethylethanamine;
2-cyclobutyl-6,7-dimethoxy-4-(4-(2-methoxyphenyl)piperazin-1-yl)quinazoline;
2-cyclobutyl-6,7-dimethoxy-4-(4-phenylpiperazin-1-yl)quinazoline;
2-cyclobutyl-6,7-dimethoxy-4-(4-(o-tolyl)piperazin-1-yl)quinazoline;
2-cyclobutyl-4-(4-(2-fluorophenyl)piperazin-1-yl)-6,7-dimethoxyquinazoline;
4-(4-(2-chlorophenyl)piperazin-1-yl)-2-cyclobutyl-6,7-dimethoxyquinazoline;
2-cyclobutyl-6,7-dimethoxy-4-(4-(pyridin-2-yl)piperazin-1-yl)quinazoline;
2-cyclobutyl-6,7-dimethoxy-4-(4-(2-nitrophenyl)piperazin-1-yl)quinazoline;
2-cyclobutyl-6,7-dimethoxy-4-(4-(3-methoxyphenyl)piperazin-1-yl)quinazoline;
2-cyclobutyl-6,7-dimethoxy-4-(4-(4-methoxyphenyl)piperazin-1-yl)quinazoline;
2-cyclobutyl-4-(4-(2,4-dimethoxyphenyl)piperazin-1-yl)-6,7-dimethoxyquinazoline;
2-cyclobutyl-4-(4-(2, 6-dimethylphenyl)piperazin-1-yl)-6,7-dimethoxyquinazoline;
2-cyclobutyl-6-methoxy-4-(4-(2-methoxyphenyl)piperazin-1-yl)quinazoline;
2-cyclobutyl-7-methoxy-4-(4-(2-methoxyphenyl)piperazin-1-yl)quinazoline;
2-cyclobutyl-4-(4-(2-methoxyphenyl)piperazin-1-yl)quinazoline;
6-cyclobutyl-8-(4-(2-methoxyphenyl)piperazin-1-yl)-[1,3]dioxolo [4,5-g]quinazoline;
2-cyclopropyl-6-methoxy-4-(4-(2-methoxyphenyl)piperazin-1-yl)quinazoline;

2-cyclopropyl-4-(4-(2-ethoxyphenyl)piperazin-1-yl)-6,7-dimethoxyquinazoline;
4-(4-(2-chlorophenyl)piperazin-1-yl)-2-cyclopropyl-6,7-dimethoxyquinazoline;
2-cyclopropyl-6,7-dimethoxy-4-(4-(phenylsulfonyl)piperazin-1-yl)quinazoline;
2-cyclopropyl-6,7-dimethoxy-4-(4-(4-methylbenzyl)piperazin-1-yl)quinazoline;
2-cyclopropyl-6,7-dimethoxy-4-(4-(2-methoxybenzyl)piperazin-1-yl)quinazoline;
(4-(2-cyclopropyl-6,7-dimethoxyquinazolin-4-yl)piperazin-1-yl)(phenyl)methanone;
(4-(2-cyclopropyl-6,7-dimethoxyquinazolin-4-yl)piperazin-1-yl)(2-methoxyphenyl)methanone;
2-cyclopropyl-6,7-dimethoxy-4-(piperazin-1-yl)quinazoline trifluoroacetate;
2-cyclopropyl-6-methoxy-4-(4-(2-methoxyphenyl)piperazin-1-yl)-7-(trifluoromethyl)quinazoline;
or a pharmaceutically acceptable salt, solvate, or tautomer thereof.

18. A pharmaceutical composition comprising a compound of claim 1, or a pharmaceutically acceptable salt, solvate, or tautomer thereof, and a pharmaceutically acceptable excipient.

* * * * *

UNITED STATES PATENT AND TRADEMARK OFFICE
CERTIFICATE OF CORRECTION

PATENT NO. : 9,868,707 B2
APPLICATION NO. : 14/652705
DATED : January 16, 2018
INVENTOR(S) : Anthony B. Pinkerton et al.

It is certified that error appears in the above-identified patent and that said Letters Patent is hereby corrected as shown below:

In the Specification

Column 16, Line 41:
Delete "substituted with alkyl, and $-NR^2(CH_2)NR^3-$;" and replace with --substituted with alkyl, and $-NR^2(CH_2)_nNR^3-$;--

In the Claims

Column 212, Line 26:
In Claim 1, delete "$-N(R^3)S(=O)_2R^{15}$, $-S(=O)_2-N(R^{13})-R^{14}$," and replace with -- $-N(R^{13})S(=O)_2R^{15}$, $-S(=O)_2-N(R^{13})-R^{14}$,--

Column 212, Lines 36-37:
In Claim 1, delete "optionally substituted spiroheterocyloalkyl, and $-NR^2(CH_2)NR^3-$;" and replace with --optionally substituted spiroheterocyloalkyl, and $-NR^2(CH_2)_nNR^3-$;--

Signed and Sealed this
Twenty-fourth Day of July, 2018

Andrei Iancu
*Director of the United States Patent and Trademark Office*

UNITED STATES PATENT AND TRADEMARK OFFICE
CERTIFICATE OF CORRECTION

PATENT NO. : 9,868,707 B2
APPLICATION NO. : 14/652705
DATED : January 16, 2018
INVENTOR(S) : Pinkerton et al.

It is certified that error appears in the above-identified patent and that said Letters Patent is hereby corrected as shown below:

In the Claims

Column 212, Lines 23-24:
In Claim 1, delete "C(=O)-N($R^{13}$)-$R^{14}$ $NR^{13}$(C=O)$R^{15}$," and replace with -- -C(=O)-N($R^{13}$)-$R^{14}$, -$NR^{13}$(C=O)$R^{15}$,--.

Column 212, Lines 35-37:
In Claim 1, "Y is selected from optionally substituted heterocyloalkyl, optionally substituted spiroheterocyloalkyl, and –$NR^{2}(CH_{2})_{n}NR^{3}$-;" should read --Y is selected from optionally substituted heterocycloalkyl, optionally substituted spiroheterocycloalkyl, and -$NR^{2}(CH_{2})_{n}NR^{3}$-;--.

Column 213, Lines 59-60:
In Claim 4, "8-membered heterocyloalkyl, optionally substituted spiroheterocyloalkyl, and -$NR^{2}(CH_{2})_{n}NR^{3}$-." should read --8-membered heterocycloalkyl, optionally substituted spiroheterocycloalkyl, and -$NR^{2}(CH_{2})_{n}NR^{3}$-.--.

Column 213, Lines 63-65:
In Claim 5, "Y is an optionally substituted 6-membered heterocyloalkyl that is an optionally substituted piperidinyl or optionally substituted piperazinyl." should read --Y is an optionally substituted 6-membered heterocycloalkyl that is an optionally substituted piperidinyl or optionally substituted piperazinyl.--.

Column 219, Lines 36-37:
In Claim 17, delete "{2-[4-(2-cyclopropyl-6,7-dimethoxy-quinazolin-4-yl)-piperazin-1-yl]-phenyl)}-phenyl-amine;" and replace with --{2-[4-(2-cyclopropyl-6,7-dimethoxy-quinazolin-4-yl)-piperazin-1-yl]-phenyl}-phenyl-amine;--.

Signed and Sealed this
Twenty-third Day of April, 2019

Andrei Iancu
*Director of the United States Patent and Trademark Office*

CERTIFICATE OF CORRECTION (continued)
U.S. Pat. No. 9,868,707 B2

Column 221, Lines 38-39:
In Claim 17, "2-cyclopropyl-4-[4-(2-methoxy-phenyl)-piperazin-1-yl]-quinazolin-6-yl}-dimethylamine;" should read --{2-cyclopropyl-4-[4-(2-methoxy-phenyl)-piperazin-1-yl]-quinazolin-6-yl}-dimethylamine;--.

Column 222, Lines 1-2:
In Claim 17, delete "{2-cyclopropyl-4-[4-(2-methoxy-phenyl)-piperazin-1-yl]-quinazolin-7-yl)}-dimethyl-amine;" and replace with --{2-cyclopropyl-4-[4-(2-methoxy-phenyl)-piperazin-1-yl]-quinazolin-7-yl}-dimethyl-amine;--.

Column 222, Lines 7-8:
In Claim 17, delete "{2-cyclopropyl-4-[4-(2-methoxy-phenyl)-piperazin-1-yl]-quinazolin-6-yl)}-diethyl-amine;" and replace with --{2-cyclopropyl-4-[4-(2-methoxy-phenyl)-piperazin-1-yl]-quinazolin-6-yl}-diethyl-amine;--.

Column 222, Lines 14-15:
In Claim 17, delete "{2-cyclopropyl-4-[4-(2-methoxy-phenyl)-piperazin-1-yl]-quinazolin-6-yl)}-phenyl-amine;" and replace with --{2-cyclopropyl-4-[4-(2-methoxy-phenyl)-piperazin-1-yl]-quinazolin-6-yl}-phenyl-amine;--.

Column 222, Lines 16-17:
In Claim 17, delete "{2-cyclopropyl-4-[4-(2-methoxy-phenyl)-piperidin-1-yl]-quinazolin-6-yl)}-dimethyl-amine;" and replace with --{2-cyclopropyl-4-[4-(2-methoxy-phenyl)-piperidin-1-yl]-quinazolin-6-yl}-dimethyl-amine;--.

Column 222, Lines 18-19:
In Claim 17, delete "{2-cyclopropyl-4-[4-(2-methoxy-phenyl)-piperidin-1-yl]-quinazolin-6-yl)}-ethyl-methyl-amine;" and replace with --{2-cyclopropyl-4-[4-(2-methoxy-phenyl)-piperidin-1-yl]-quinazolin-6-yl}-ethyl-methyl-amine;--.

Column 222, Lines 36-38:
In Claim 17, delete "{2-cyclopropyl-4-[4-(2-methoxy-phenyl)-piperazin-1-yl]-quinazolin-6-yl)}-methyl-(2-morpholin-4-yl-ethyl)-amine;" and replace with --{2-cyclopropyl-4-[4-(2-methoxy-phenyl)-piperazin-1-yl]-quinazolin-6-yl}-methyl-(2-morpholin-4-yl-ethyl)-amine;--.

Column 222, Lines 43-44:
In Claim 17, delete "2-({2-cyclopropyl-4-[4-(2-methoxy-phenyl)-piperazin-1-yl]-quinazolin-6-yl)}-methyl-amino)-ethanol;" and replace with --2-({2-cyclopropyl-4-[4-(2-methoxy-phenyl)-piperazin-1-yl]-quinazolin-6-yl}-methyl-amino)-ethanol;--.

Column 222, Lines 45-47:
In Claim 17, delete "{2-cyclopropyl-4-[4-(2-methoxy-phenyl)-piperazin-1-yl]-quinazolin-6-yl)}-(2-methoxy-ethyl)-methyl-amine;" and replace with --{2-cyclopropyl-4-[4-(2-methoxy-phenyl)-piperazin-1-yl]-quinazolin-6-yl}-(2-methoxy-ethyl)-methyl-amine;--.

CERTIFICATE OF CORRECTION (continued)
U.S. Pat. No. 9,868,707 B2

Column 222, Lines 48-49:
In Claim 17, delete "2-({2-cyclopropyl-4-[4-(2-methoxy-phenyl)-piperidin-1-yl]-quinazolin-6-yl)}-methyl-amino)-ethanol;" and replace with --2-({2-cyclopropyl-4-[4-(2-methoxy-phenyl)-piperidin-1-yl]-quinazolin-6-yl}-methyl-amino)-ethanol;--.

Column 222, Lines 50-53:
In Claim 17, delete "{2-cyclopropyl-4-[4-(2-methoxy-phenyl)-piperidin-1-yl]-quinazolin-6-yl)}-(2-methoxy-ethyl)-methyl-amine;" and replace with --{2-cyclopropyl-4-[4-(2-methoxy-phenyl)-piperidin-1-yl]-quinazolin-6-yl}-(2-methoxy-ethyl)-methyl-amine;--.

Column 222, Lines 55-58:
In Claim 17, delete "{2-cyclopropyl-4-[4-(2-methoxy-phenyl)-piperidin-1-yl]-quinazolin-6-yl)}-methyl-(2-morpholin-4-yl-ethyl)-amine;" and replace with --{2-cyclopropyl-4-[4-(2-methoxy-phenyl)-piperidin-1-yl]-quinazolin-6-yl}-methyl-(2-morpholin-4-yl-ethyl)-amine;--.

UNITED STATES PATENT AND TRADEMARK OFFICE
CERTIFICATE OF CORRECTION

| | |
|---|---|
| PATENT NO. | : 9,868,707 B2 |
| APPLICATION NO. | : 14/652705 |
| DATED | : January 16, 2018 |
| INVENTOR(S) | : Anthony Pinkerton et al. |

Page 1 of 1

It is certified that error appears in the above-identified patent and that said Letters Patent is hereby corrected as shown below:

In Column 1, Lines 20 through 22, please replace:
"This invention was made with the support of the United States government under Grants number U54 HG005033-03, 1 R03 MH089653-01 and 5P30DA029925."

With:
"This invention was made with government support under U54 HG005033, R03 MH089653 and P30 DA029925 awarded by the National Institutes of Health. The government has certain rights in the invention."

Signed and Sealed this
Third Day of September, 2019

Andrei Iancu
*Director of the United States Patent and Trademark Office*

UNITED STATES PATENT AND TRADEMARK OFFICE
CERTIFICATE OF CORRECTION

PATENT NO. : 9,868,707 C1
APPLICATION NO. : 90/014321
DATED : November 6, 2019
INVENTOR(S) : Pinkerton et al.

It is certified that error appears in the above-identified patent and that said Letters Patent is hereby corrected as shown below:

In the Claims

Column 10, Lines 13-14:
In Claim 17, delete "6-cyclobutyl-8-(4-(2-methoxyphenyl)piperazin-1-yl)-[1,3]dioxolo[4,5-g]quinazoline" and replace with --6-cyclobutyl-8-(4-(2-methoxyphenyl)piperazin-1-yl)-[1,3]dioxolo[4,5-g]quinazoline--.

Signed and Sealed this
Fifth Day of May, 2020

Andrei Iancu
*Director of the United States Patent and Trademark Office*

(12) EX PARTE REEXAMINATION CERTIFICATE (11595th)
United States Patent
Pinkerton et al.

(10) Number: US 9,868,707 C1
(45) Certificate Issued: Nov. 6, 2019

(54) SMALL MOLECULE AGONISTS OF NEUROTENSIN RECEPTOR 1

(71) Applicants: SANFORD-BURNHAM MEDICAL RESEARCH INSTITUTE, La Jolla, CA (US); DUKE UNIVERSITY, Durham, NC (US)

(72) Inventors: Anthony Pinkerton, La Jolla, CA (US); Patrick Maloney, La Jolla, CA (US); Paul Hershberger, La Jolla, CA (US); Satyamaheshwar Peddibhotla, La Jolla, CA (US); Michael Hedrick, La Jolla, CA (US); Lawrence Barak, La Jolla, CA (US); Marc Caron, La Jolla, CA (US)

(73) Assignee: DUKE UNIVERSITY, Durham, NC (US)

Reexamination Request:
No. 90/014,321, Jun. 20, 2019

Reexamination Certificate for:
Patent No.: 9,868,707
Issued: Jan. 16, 2018
Appl. No.: 14/652,705
PCT Filed: Dec. 19, 2013
PCT No.: PCT/US2013/076735
§ 371 (c)(1),
(2) Date: Jun. 16, 2015
PCT Pub. No.: WO2014/100501
PCT Pub. Date: Jun. 26, 2014

Certificate of Correction issued Jul. 24, 2018
Certificate of Correction issued Apr. 23, 2019

Related U.S. Application Data

(60) Provisional application No. 61/740,362, filed on Dec. 20, 2012.

(51) Int. Cl.
| | | |
|---|---|---|
| C07D 239/94 | (2006.01) |
| C07D 471/04 | (2006.01) |
| C07D 405/04 | (2006.01) |
| C07D 401/12 | (2006.01) |
| C07D 401/04 | (2006.01) |
| C07D 217/22 | (2006.01) |
| C07D 215/42 | (2006.01) |
| C07D 401/14 | (2006.01) |
| A61K 31/517 | (2006.01) |
| A61K 31/519 | (2006.01) |
| C07D 403/04 | (2006.01) |
| A61K 45/06 | (2006.01) |
| A61K 31/5377 | (2006.01) |
| A61K 9/00 | (2006.01) |
| A61K 47/26 | (2006.01) |
| A61K 47/38 | (2006.01) |
| A61K 9/48 | (2006.01) |
| C07D 403/12 | (2006.01) |

(52) U.S. Cl.
CPC .......... *C07D 239/94* (2013.01); *A61K 9/0019* (2013.01); *A61K 9/4866* (2013.01); *A61K 31/517* (2013.01); *A61K 31/519* (2013.01); *A61K 31/5377* (2013.01); *A61K 47/26* (2013.01); *A61K 47/38* (2013.01); *C07D 215/42* (2013.01); *C07D 217/22* (2013.01); *C07D 401/04* (2013.01); *C07D 401/12* (2013.01); *C07D 401/14* (2013.01); *C07D 403/12* (2013.01); *C07D 405/04* (2013.01); *C07D 471/04* (2013.01)

(58) Field of Classification Search
None
See application file for complete search history.

(56) References Cited

To view the complete listing of prior art documents cited during the proceeding for Reexamination Control Number 90/014,321, please refer to the USPTO's public Patent Application Information Retrieval (PAIR) system under the Display References tab.

*Primary Examiner* — Dwayne C. Jones

(57) ABSTRACT

Provided herein are small molecule neurotensin receptor agonists, compositions comprising the compounds, and methods of using the compounds and compositions comprising the compounds.

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 10-16 are cancelled.

Claims 1 and 17 are determined to be patentable as amended.

Claims 2-9 and 18, dependent on an amended claim, are determined to be patentable.

1. A compound of Formula I, or a pharmaceutically acceptable salt, solvate, or tautomer thereof:

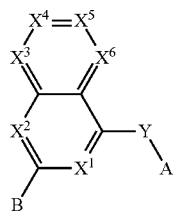

Formula I wherein:
A is $A^1$, —O-$A^1$, —NH-$A^1$, —C(=O)-$A^1$, or —(S=O)$_2$-$A^1$; $A^1$ is selected from the group consisting of optionally substituted phenyl, optionally substituted naphthyl, optionally substituted 5-membered heteroaryl, optionally substituted 6-membered heteroaryl, optionally substituted 9-membered heteroaryl and optionally substituted 10-membered heteroaryl; wherein optional substituents for A are selected from the group consisting of hydrogen, halogen, —CN, —OH, —NO$_2$, —N($R^{13}$)-$R^{14}$, —C(=O)-N($R^{13}$)-$R^{14}$, —N$R^{13}$C(=O)$R^{15}$, —C(=O)-O-$R^{13}$, —O-C(=O)-$R^{15}$, —S$R^{13}$, —S(=O)$R^{15}$, —S(=O)$_2$$R^{15}$, —N($R^{13}$)S(=O)$_2$$R^{15}$, —S(=O)$_2$-N($R^{13}$)-$R^{14}$, —C(=O)$R^{13}$, optionally substituted alkyl, optionally substituted cycloalkyl, optionally substituted heterocycloalkyl, optionally substituted alkoxy, optionally substituted haloalkyl, optionally substituted haloalkoxy, optionally substituted phenyl, and optionally substituted 5- or 6-membered heteroaryl;

B is [selected from the group consisting of optionally substituted alkyl, and optionally] *a* substituted cycloalkyl;

Y is selected from optionally substituted heterocycloalkyl, optionally substituted spiroheterocycloalkyl, and —N$R^2$(CH$_2$)$_n$N$R^3$—;
n is 2, 3, 4, 5, or 6;
$R^2$ is H or alkyl;
$R^3$ is H or alkyl;
$X^1$ is N or C($R^1$);
$X^2$ is N or C($R^1$);
$X^3$ is N or C($R^4$);
$X^4$ is N or C($R^5$);
$X^5$ is N or C($R^6$);
$X^6$ is N or C($R^7$);
each $R^1$ is independently selected from the group consisting of hydrogen, halogen, —CN, —OH, —NO$_2$, optionally substituted alkyl, optionally substituted alkoxy, optionally substituted haloalkyl, and optionally substituted haloalkoxy;
each of $R^4$, $R^5$, $R^6$, and $R^7$ is independently selected from the group consisting of hydrogen, halogen, —CN, —OH, —NO$_2$, —N($R^{13}$)-$R^{14}$, —C(=O)-N($R^{13}$)-$R^{14}$, —N$R^{13}$C(=O)$R^{15}$, —C(=O)-O-$R^{13}$, —O-C(=O)-$R^{15}$, —S$R^{13}$, —S(=O)$R^{15}$, —S(=O)$_2$$R^{15}$, —N($R^{13}$)S(=O)$_2$$R^{15}$, —S(=O)$_2$-N($R^{13}$)-$R^{14}$, —C(=O)$R^{13}$, optionally substituted alkyl, optionally substituted cycloalkyl, optionally substituted heterocycloalkyl, optionally substituted alkoxy, optionally substituted haloalkyl, optionally substituted haloalkoxy, optionally substituted phenyl, and optionally substituted 5- or 6-membered heteroaryl;
or $R^5$ and $R^6$ are taken together with the atoms connecting $R^5$ and $R^6$ to form an optionally substituted heterocycloalkyl;
each of $R^{13}$ and $R^{14}$ is independently selected from the group consisting of hydrogen, optionally substituted alkyl, optionally substituted cycloalkyl, optionally substituted heterocycloalkyl, optionally substituted alkoxy, optionally substituted haloalkyl, optionally substituted haloalkoxy, optionally substituted phenyl, and optionally substituted 5- or 6-membered heteroaryl;
or $R^{13}$ and $R^{14}$, when on the same nitrogen atom, are taken together with the nitrogen atom to which they are attached to form an optionally substituted heterocycloalkyl;
$R^{15}$ is selected from the group consisting of optionally substituted alkyl, optionally substituted cycloalkyl, optionally substituted heterocycloalkyl, optionally substituted alkoxy, optionally substituted haloalkyl, optionally substituted haloalkoxy, optionally substituted phenyl, and optionally substituted 5- or 6-membered heteroaryl;
wherein a heteroaryl comprises one to six heteroatoms selected from the group consisting of nitrogen, oxygen, and sulfur;
wherein a heterocycloalkyl comprises from 2 to 10 carbons in the ring and one to 6 heteroatoms selected from the group consisting of nitrogen, oxygen, and sulfur.

17. A compound that is:
2-cyclopropyl-4[4-(4-fluoro-2-methoxy-phenyl)-piperazin-1-yl]-6,7-dimethoxy-quinazoline;
2-cyclopropyl-6,7-dimethoxy-4-[4-(2-methoxy-4-trifluoromethoxy-phenyl)-piperazin-1-yl]-quinazoline;
4-[4-(4-chloro-2-methoxy-phenyl)-piperazin-1-yl]-2-cyclopropyl-6,7-dimethoxy-quinazoline;
2-cyclopropyl-6,7-dimethoxy-4-[4-(2-methoxy-4-nitrophenyl)-piperazin-1-yl]-quinazoline;
4-[4(2-cyclopropyl-6,7-dimethoxy-quinazolin-4-yl)-piperazin-1-yl]-3-methoxy-phenylamine;
4-[4-(2-cyclopropyl-6,7-dimethoxy-quinazolin-4-yl)-piperazin-1-yl]-3-methoxy-benzonitrile;
4-[4-(2-cyclopropyl-6,7-dimethoxy-quinazolin-4-yl)-piperazin-1-yl]-3-methoxy-benzoic acid;
4-[4-(2-cyclopropyl-6,7-dimethoxy-quinazolin-4-yl)-piperazin-1-yl]-3-methoxy-benzamide;
{4-[4-(2-cyclopropyl-6,7-dimethoxy-quinazolin-4-yl)-piperazin-1-yl]-3-methoxy-phenyl}-dimethyl-amine;
2-cyclopropyl-6,7-dimethoxy-4-[4-(2-methoxy-4-trifluoromethyl-phenyl)-piperazin-1-yl]-quinazoline;

2-cyclopropyl-4-[4-(2,4-dimethoxy-phenyl)-piperazin-1-yl]-6,7-dimethoxy-quinazoline;
2-cyclopropyl-6,7-dimethoxy-4-[4-(2-methoxy-5-methyl-phenyl)-piperazin-1-yl]-quinazoline;
2-[4-(2-cyclopropyl-6,7-dimethoxy-quinazolin-4-yl)-piperazin-1-yl]-benzonitrile;
2-cyclopropyl-6,7-dimethoxy-4-[4-(2-methoxy-5-nitro-phenyl)-piperazin-1-yl]-quinazoline;
3-[4-(2-cyclopropyl-6,7-dimethoxy-quinazolin-4-yl)-piperazin-1-yl]-4-methoxy-phenylamine;
N-{3-[4-(2-cyclopropyl-6,7-dimethoxy-quinazolin-4-yl)-piperazin-1-yl]-4-methoxy-phenyl}-acetamide;
N-{3-[4-(2-cyclopropyl-6,7-dimethoxy-quinazolin-4-yl)-piperazin-1-yl]-4-methoxy-phenyl}-methanesulfonamide;
{3-[4-(2-cyclopropyl-6,7-dimethoxy-quinazolin-4-yl)-piperazin-1-yl]-4-methoxy-phenyl}-dimethyl-amine;
{3-[4-(2-cyclopropyl-6,7-dimethoxy-quinazolin-4-yl)-piperazin-1-yl]-4-methoxy-phenyl}-methyl-amine;
2-cyclopropyl-4-[4-(2,3-dichloro-phenyl)-piperazin-1-yl]-6,7-dimethoxy-quinazoline;
2-cyclopropyl-4-[4-(2,4-dichloro-phenyl)-piperazin-1-yl]-6,7-dimethoxy-quinazoline;
3-chloro-4-[4-(2-cyclopropyl-6,7-dimethoxy-quinazolin-4-yl)-piperazin-1-yl]-benzonitrile;
4-[4-(2-chloro-4-nitro-phenyl)-piperazin-1-yl]-2-cyclopropyl-6,7-dimethoxy-quinazoline;
3-chloro-4-[4-(2-cyclopropyl-6,7-dimethoxy-quinazolin-4-yl)-piperazin-1-yl]-benzoic acid;
3-chloro-4-[4-(2-cyclopropyl-6,7-dimethoxy-quinazolin-4-yl)-piperazin-1-yl]-benzamide;
3-chloro-4-[4-(2-cyclopropyl-6,7-dimethoxy-quinazolin-4-yl)-piperazin-1-yl]-phenylamine;
N-{3-chloro-4-[4-(2-cyclopropyl-6,7-dimethoxy-quinazolin-4-yl)-piperazin-1-yl]-phenyl}-acetamide;
N-{3-chloro-4-[4-(2-cyclopropyl-6,7-dimethoxy-quinazolin-4-yl)-piperazin-1-yl]-phenyl}-methanesulfonamide;
3-chloro-4-[4-(2-cyclopropyl-6,7-dimethoxy-quinazolin-4-yl)-piperazin-1-yl]-benzoic acid;
4-[4-(2-chloro-4-fluoro-phenyl)-piperazin-1-yl]-2-cyclopropyl-6,7-dimethoxy-quinazoline;
4-[4-(2-chloro-4-trifluoromethyl-phenyl)-piperazin-1-yl]-2-cyclopropyl-6,7-dimethoxy-quinazoline;
4-[4-(2-chloro-4-methyl-phenyl)-piperazin-1-yl]-2-cyclopropyl-6,7-dimethoxy-quinazoline;
4-[4-(2-chloro-4-methoxy-phenyl)-piperazin-1-yl]-2-cyclopropyl-6,7-dimethoxy-quinazoline;
2-[4-(2-cyclopropyl-6,7-dimethoxy-quinazolin-4-yl)-piperazin-1-yl]-benzonitrile;
2-[4-(2-cyclopropyl-6,7-dimethoxy-quinazolin-4-yl)-piperazin-1-yl]-5-methoxy-benzonitrile;
5-chloro-2-[4-(2-cyclopropyl-6,7-dimethoxy-quinazolin-4-yl)-piperazin-1-yl]-benzonitrile;
2-[4-(2-cyclopropyl-6,7-dimethoxy-quinazolin-4-yl)-piperazin-1-yl]-5-nitro-benzonitrile;
5-amino-2-[4-(2-cyclopropyl-6,7-dimethoxy-quinazolin-4-yl)-piperazin-1-yl]-benzonitrile;
2-cyclopropyl-6,7-dimethoxy-4-[4-(2-nitro-phenyl)-piperazin-1-yl]-quinazoline;
2-[4-(2-cyclopropyl-6,7-dimethoxy-quinazolin-4-yl)-piperazin-1-yl]-phenylamine;
2-(4-(2-cyclopropyl-6,7-dimethoxyquinazolin-4-yl)piperazin-1-yl)-N-ethylaniline;
{2-[4-(2-cyclopropyl-6,7-dimethoxy-quinazolin-4-yl)-piperazin-1-yl]-phenyl}-dimethyl-amine;
{2-[4-(2-cyclopropyl-6,7-dimethoxy-quinazolin-4-yl)-piperazin-1-yl]-phenyl}-diethyl-amine;
4-[4-(2-aziridin-1-yl-phenyl)-piperazin-1-yl]--cyclopropyl-6,7-dimethoxy-quinazoline;
4-[4-(4-benzyloxy-2-nitro-phenyl)-piperazin-1-yl]-2-cyclopropyl-6,7-dimethoxy-quinazoline;
3-amino-4-[4-(2-cyclopropyl-6,7-dimethoxy-quinazolin-4-yl)-piperazin-1-yl]-phenol;
2-cyclopropyl-6,7-dimethoxy-4-[4-(4-methoxy-2-nitro-phenyl)-piperazin-1-yl]-quinazoline;
2-[4-(2-cyclopropyl-6,7-dimethoxy-quinazolin-4-yl)-piperazin-1-yl]-5-fluoro-phenylamine;
2-[4-(2-cyclopropyl-6,7-dimethoxy-quinazolin-4-yl)-piperazin-1-yl]-5-methoxy-phenylamine;
{5-bromo-2-[4-(2-cyclopropyl-6,7-dimethoxy-quinazolin-4-yl)-piperazin-1-yl]-phenyl}-dimethyl-amine ;
{2-[4-(2-cyclopropyl-6,7-dimethoxy-quinazolin-4-yl)-piperazin-1-yl]-5-fluoro-phenyl}-dimethyl-amine;
{5-chloro-2-[4-(2-cyclopropyl-6,7-dimethoxy-quinazolin-4-yl)-piperazin-1-yl]-phenyl}-dimethyl-amine;
{2-[4-(2-cyclopropyl-6,7-dimethoxy-quinazolin-4-yl)-piperazin-1-yl]-5-methoxy-phenyl}-dimethyl-amine;
4-[4-(2-cyclopropyl-6,7-dimethoxy-quinazolin-4-yl)-piperazin-1-yl]-3-dimethylamino-benzoic acid;
{2-[4-(2-cyclopropyl-6,7-dimethoxy-quinazolin-4-yl)-piperazin-1-yl]-phenyl}-phenyl-amine;
2-cyclopropyl-6,7-dimethoxy-4-[4-(2-morpholin-4-yl-phenyl)-piperazin-1-yl]-quinazoline;
2-cyclopropyl-6,7-dimethoxy-4-[4-(2-pyrrolidin-1-yl-phenyl)-piperazin-1-yl]-quinazoline;
4-[4-(2-azetidin-1-yl-phenyl)-piperazin-1-yl]-2-cyclopropyl-6,7-dimethoxy-quinazoline;
2-cyclopropyl-6,7-dimethoxy-4-[4-(2-piperidin-1-yl-phenyl)-piperazin-1-yl]-quinazoline;
2-Cyclopropyl-6,7-dimethoxy-4-{4-[2-(4-methyl-piperazin-1-yl)-phenyl]-piperazin-1-yl}-quinazoline;
5-amino-2-[4-(2-cyclopropyl-6,7-dimethoxy-quinazolin-4-yl)-piperazin-1-yl]-phenol;
4-(4-(2-cyclopropyl-6,7-dimethoxyquinazolin-4-yl)piperazin-1-yl)-N,N-dimethylaniline;
{4-[4-(2-cyclopropyl-6,7-dimethoxy-quinazolin-4-yl)-piperazin-1-yl]-phenyl}-diethyl-amine;
3-(4-(2-cyclopropyl-6,7-dimethoxyquinazolin-4-yl)piperazin-1-yl)-N,N-dimethylaniline;
{3-[4-(2-cyclopropyl-6,7-dimethoxy-quinazolin-4-yl)-piperazin-1-yl]-phenyl}-diethyl-amine;
N-(2-cyclopropyl-6,7-dimethoxy-quinazolin-5-yl)-N'-(2-methoxy-phenyl)-ethane-1,2-diamine;
N'-(2-cyclopropyl-6,7-dimethoxy-quinazolin-5-yl)-N-(2-methoxy-phenyl)-N-methyl-ethane-1,2-diamine;
2-cyclopropyl-6,7-dimethoxy-4[4-(2-methoxy-phenyl)-2-methyl-piperazin-1-yl]-quinazoline;
N-(2-cyclopropyl-6,7-dimethoxy-quinazolin-4-yl)-N'-phenyl-ethane-1,2-diamine;
N-(2-cyclopropyl-6,7-dimethoxy-quinazolin-4-yl)-N'-(2-methoxy-phenyl)-propane-1,3-diamine;
N-(2-cyclopropyl-6,7-dimethoxy-quinazolin-4-yl)-N'-(2-methoxy-phenyl)-N,N'-dimethyl-ethane-1,2-diamine;
2-cyclopropyl-6,7-dimethoxy-4-[4-(2-methoxy-phenyl)-[1,4]diazepan-1-yl]-quinazoline;
[1-(2-cyclopropyl-6,7-dimethoxy-quinazolin-4-yl)-piperidin-4-yl]-(2-methoxy-phenyl)-amine;
2-(2-cyclopropyl-6,7-dimethoxy-quinazolin-4-ylamino)-N-(2-methoxy-phenyl)-acetamide;
2-Cyclopropyl-6,7-dimethoxy-4-[4-(2-methoxy-phenyl)-piperidin-1-yl]-quinazoline;

{2-[1-(2-Cyclopropyl-6,7-dimethoxy-quinazolin-4-yl)-piperidin-4-yl]-phenyl}-dimethyl-amine;
2-cyclopropyl-6,7-dimethoxy-4-[4-(2-methoxy-phenyl)-3,6-dihydro-2H-pyridin-1-yl]-quinazoline;
2-cyclopropyl-6,7-dimethoxy-4-(3-phenyl-pyrrolidin-1-yl)-quinazoline;
2-cyclopropyl-6,7-dimethoxy-4-[3-(3-methoxy-phenyl)-pyrrolidin-1-yl]-quinazoline;
{2-[1-(2-cyclopropyl-6,7-dimethoxy-quinazolin-4-yl)-pyrrolidin-3-yl]-phenyl}-dimethyl-amine;
2-cyclopropyl-6,7-dimethoxy-4-[3-(3-methoxy-phenyl)-cyclopentyl]-quinazoline;
{3-[1-(2-cyclopropyl-6,7-dimethoxy-quinazolin-4-yl)-pyrrolidin-3-yl]-phenyl}-dimethyl-amine;
1-(2-cyclopropyl-6,7-dimethoxy-quinazolin-4-yl)-3-phenyl-pyrrolidin-3-ol;
1-(2-cyclopropyl-6,7-dimethoxy-quinazolin-4-yl)-3-(2-dimethylamino-phenyl)-pyrrolidin-3-ol;
1-(2-cyclopropyl-6,7-dimethoxy-quinazolin-4-yl)-3-(3-methoxy-phenyl)-pyrrolidin-3-ol;
2-cyclopropyl-4-(3-fluoro-3-phenyl-pyrrolidin-1-yl)-6,7-dimethoxy-quinazoline;
{2-[1-(2-cyclopropyl-6,7-dimethoxy-quinazolin-4-yl)-3-fluoro-pyrrolidin-3-yl]-phenyl}-dimethyl-amine;
2-cyclopropyl-4-[3-fluoro-3-(3-methoxy-phenyl)-pyrrolidin-1-yl]-6,7-dimethoxy-quinazoline;
2-cyclopropyl-6,7-dimethoxy-4-(3-methyl-4-phenyl-piperazin-1-yl)-quinazoline;
2-cyclopropyl-6,7-dimethoxy-4-[1-(2-methoxy-phenyl)-piperidin-4-yl]-quinazoline;
6,7-dimethoxy-4-[4-(2-methoxy-phenyl)-piperazin-1-yl]-2-piperidin-4-yl-quinazoline;
6,7-dimethoxy-4-[4-(2-methoxy-phenyl)-piperazin-1-yl]-2-(1-methyl-piperidin-4-yl)-quinazoline;
6,7-dimethoxy-4-[4-(2-methoxy-phenyl)-piperazin-1-yl]-2-(4-methyl-cyclohexyl)-quinazoline;
4-{6,7-dimethoxy-4-[4-(2-methoxy-phenyl)-piperazin-1-yl]-quinazolin-2-yl}-piperidine-1-carboxylic acid benzyl ester;
6,7-dimethoxy-4-[4-(2-methoxy-phenyl)-piperazin-1-yl]-2-(tetrahydro-pyran-4-yl)-quinazoline;
6,7-dimethoxy-4-[4-(2-methoxy-phenyl)-piperazin-1-yl]-2-(tetrahydro-furan-3-yl)-quinazoline;
6,7-dimethoxy-4-[4-(2-methoxy-phenyl)-piperazin-1-yl]-2-(2-methyl-cyclopropyl)-quinazoline;
cis-6,7-dimethoxy-2-(4-methoxy-cyclohexyl)-4[4-(2-methoxy-phenyl)-piperazin-1-yl]-quinazo line;
trans-6,7-dimethoxy-2-(4-methoxy-cyclohexyl)-4-[4-(2-methoxy-phenyl)-piperazin-1-yl]-quinazoline;
6,7-dimethoxy-4-[4-(2-methoxy-phenyl)-piperazin-1-yl]-2-(4-methyl-pyrrolidin-3-yl)-quinazoline;
2-(1,4-dimethyl-pyrrolidin-3-yl)-6,7-dimethoxy-4-[4-(2-methoxy-phenyl)-piperazin-1-yl]-quinazoline;
6,7-dimethoxy-4[4-(2-methoxy-phenyl)-piperazin-1-yl]-2-pyrrolidin-3-yl-quinazoline;
6,7-dimethoxy-4-[4-(2-methoxy-phenyl)-piperazin-1-yl]-2-(1-methyl-pyrrolidin-3-yl)-quinazoline;
2-((1R, 3R)-3-chloro-3-methylcyclobutyl)-6,7-dimethoxy-4-(4-(2-methoxyphenyl)piperazin-1-yl)quinazo line;
2-((1S,3S)-3-chloro-3-methykyclobutyl)-6,7-dimethoxy-4-(4-(2-methoxyphenyl)piperazin-1-yOquinazo line;
6,7-dimethoxy-4-[4-(2-methoxy-phenyl)-piperazin-1-yl]-2-(3-methyl-cyclobutyl)-quinazoline;
2-cyclohexyl-6,7-dimethoxy-4-[4-(2-methoxy-phenyl)-piperazin-1-yl]-quinazoline;
2-tert-Butyl-6,7-dimethoxy-4-[4-(2-methoxy-phenyl)-piperazin-1-yl]-quinazoline;
2-tert-Butyl-6,7-dimethoxy-4-[4-(2-methoxy-phenyl)-piperidin-1-yl]-quinazoline;
6,7-dimethoxy-4-[4-(2-methoxy-phenyl)-piperazin-1-yl]-2-(1-methyl-cyclopropyl)-quinazoline;
6,7-dimethoxy-4-[4-(2-methoxy-phenyl)-piperidin-1-yl]-2-(1-methyl-cyclopropyl)-quinazoline;
6,7-dimethoxy-4-[4-(2-methoxy-phenyl)-piperazin-1-yl]-2-(1-trifluoromethyl-cyclopropyl)-quinazoline;
6,7-dimethoxy-4-[4-(2-methoxy-phenyl)-piperidin-1-yl]-2-(1-trifluoromethyl-cyclopropyl)-quinazoline;
[4-[4-(2-Methoxy-phenyl)-piperidin-1-yl]-2-(1-methyl-cyclopropyl)-quinazolin-6-yl]-methyl-(2-morpholin-4-yl-ethyl)-amine;
7-chloro-2-cyclopropyl-6-methoxy-4-[4-(2-methoxy-phenyl)-piperazin-1-yl]-quinazoline;
2-cyclopropyl-[4-[4-(2-methoxy-phenyl)-piperazin-1-yl]-pyrido[2,3-d]pyrimidine;
2-cyclopropyl-6,8-dimethoxy-4-[4-(2-methoxy-phenyl)-piperazin-1-yl]-quinazoline;
2-cyclopropyl-6-methoxy-4-[4-(2-methoxy-phenyl)-piperazin-1-yl]-7-methyl-quinazoline;
2-cyclopropyl-7-fluoro-6-methoxy-4-[4-(2-methoxy-phenyl)-piperazin-1-yl]-quinazoline;
6-bromo-2-cyclopropyl-4-[4-(2-methoxy-phenyl)-piperazin-1-yl]-quinazoline;
{2-cyclopropyl-4-[4-(2-methoxy-phenyl)-piperazin-1-yl]-quinazolin-6-yl}-dimethylamine;
6-bromo-2-cyclopropyl-7-fluoro-4-[4-(2-methoxy-phenyl)-piperazin-1-yl]-quinazoline;
{2-cyclopropyl-7-fluoro-4-[4-(2-methoxy-phenyl)-piperazin-1-yl]-quinazolin-6-yl}-dimethyl-amine;
{2-cyclopropyl-7-fluoro-4-[4-(2-methoxy-phenyl)-piperazin-1-yl]-quinazolin-6-yl}-diethyl-amine;
6-bromo-7-chloro-2-cyclopropyl-4-4-(2-methoxy-phenyl)-piperazin-1-yl]-quinazoline;
{7-chloro-2-cyclopropyl-4-[4-(2-methoxy-phenyl)-piperazin-1-yl]-quinazolin-6-yl}-dimethyl-amine;
{7-chloro-2-cyclopropyl-4-[4-(2-methoxy-phenyl)-piperazin-1-yl]-quinazolin-6-yl}-diethyl-amine;
6-bromo-2-cyclopropyl-4-[4-(2-methoxy-phenyl)-piperazin-1-yl]-7-methyl-quinazoline;
{2-cyclopropyl-4-[4-(2-methoxy-phenyl)-piperazin-1-yl]-7-methyl-quinazolin-6-yl}-dimethyl-amine;
{2-cyclopropyl-4-[4-(2-methoxy-phenyl)-piperazin-1-yl]-7-methyl-quinazolin-6-yl}-ethyl-methyl-amine;
6-bromo-2-cyclopropyl-4-[4-(2-methoxy-phenyl)-piperidin-1-yl]-7-methyl-quinazoline;
{2-cyclopropyl-4-[4-(2-methoxy-phenyl)-piperidin-1-yl]-7-methyl-quinazolin-6-yl}-diethyl-amine;
2-cyclopropyl-6-methoxy-4-[4-(2-methoxy-phenyl)-piperazin-1-yl]-pyrido [3,4-d]pyrimidine;
6-bromo-2-cyclopropyl-4-[4-(2-methoxy-phenyl)-piperidin-1-yl]-7-methyl-quinazoline;
{2-cyclopropyl-4-[4-(2-methoxy-phenyl)-piperidin-1-yl]-7-methyl-quinazolin-6-yl}-diethyl-amine;
{2-cyclopropyl-4-[4-(2-methoxy-phenyl)-piperazin-1-yl]-quinazolin-7-yl}-dimethyl-amine;
{2-cyclopropyl-4-[4-(2,5-dimethoxy-phenyl)-piperazin-1-yl]-quinazolin-6-yl}dimethyl-amine;
2-cyclopropyl-4-[4-(2-methoxy-phenyl)-piperazin-1-yl]-6-piperidin-1-yl-quinazoline;
{2-cyclopropyl-4-[4-(2-methoxy-phenyl)-piperazin-1-yl]-quinazolin-6-yl}-diethyl-amine;
2-cyclopropyl-4-[4-(2-methoxy-phenyl)-piperazin-1-yl]-6-morpholin-4-yl-quinazoline;

2-cyclopropyl-4[4-(2-methoxy-phenyl)-piperazin-1-yl]-6-pyrrolidin-1-yl-quinazoline;
{2-cyclopropyl-4-[4-(2-methoxy-phenyl)-piperazin-1-yl]-quinazolin6yl}-phenyl-amine;
{2-cyclopropyl-4-[4-(2-methoxy-phenyl)-piperidin-1-yl]-quinazolin-6-yl}-dimethyl-amine;
{2-cyclopropyl-4-[4-(2-methoxy-phenyl)-piperidin-1-yl]-quinazolin-6-yl}-ethyl-methyl-amine;
{7-chloro-2-cyclopropyl-4-[4-(2-methoxyphenyl)piperidyl]quinazolin-6-yl}dimethylamine;
2-cyclopropyl-4-[4-(2-methoxy-phenyl)-piperazin-1-yl]-6-piperazin-1-yl-quinazoline;
2-cyclopropyl-4-[4-(2-methoxy-phenyl)-piperazin-1-yl]-6-(4-methyl-piperazin-1-yl)-quinazoline;
2-cyclopropyl-6,7-difluoro-4-[4-(2-methoxy-phenyl)-piperazin-1-yl]-quinazoline;
{2-cyclopropyl-6-fluoro-4-[4-(2-methoxy-phenyl)-piperazin-1-yl]-quinazolin-7-yl}-dimethyl-amine;
{2-cyclopropyl-6-fluoro-4-[4-(2-methoxy-phenyl)-piperazin-1-yl]-quinazolin-7-yl}-diethyl-amine;
2-cyclopropyl-6-fluoro-7-methoxy-4[4-(2-methoxy-phenyl)-piperazin-1-yl]-quinazoline;
{2-yclopropyl-4-[4-(2-methoxy-phenyl)-piperazin-1-yl]-quinazolin-6-yl}-methyl-propyl-amine;
{2-cyclopropyl-4-[4-(2-methoxy-phenyl)-piperazin-1-yl]-quinazolin-6-yl}-methyl-(2-morpholin-4-yl-ethyl)-amine;
2-cyclopropyl-4-(4-(2-methoxyphenyl)piperazin-1-yl)-N-methyl-N-(2-morpholinoethyl)quinazolin-6-amine;
2,2'-((2-cyclopropyl-4-(4-(2-methoxyphenyl)piperazin-1-yl)quinazolin-6-yl)azanediyl)diethanol;
2-({2-yclopropyl-4-[4-(2-methoxy-phenyl)-piperazin-1-yl]-quinazolin-6-yl}-methyl-amino)-ethanol;
{2-cyclopropyl-4-[4-(2-methoxy-phenyl)-piperazin-1-yl]-quinazolin-6-yl}-(2-methoxy-ethyl)-methyl-amine;
2-({2-cyclopropyl-4-[4-(2-methoxy-phenyl)-piperidin-1-yl]-quinazolin-6-yl}-methyl-amino)-ethanol;
{2-cyclopropyl-4-[4-(2-methoxy-phenyl)-piperidin-1-yl]-quinazolin-6-yl}-(2-methoxy-ethyl)-methyl-amine;
{2-cyclopropyl-4-[4-(2-methoxy-phenyl)-piperidin-1-yl]-quinazolin-6-yl}-methyl-propyl-amine;
{2-cyclopropyl-4-[4-(2-methoxy-phenyl)-piperidin-1-yl]-quinazolin-6-yl}-methyl-(2-morpholin-4-yl-ethyl)-amine;
2-cyclopropyl-5,8-dimethoxy-4-[4-(2-methoxy-phenyl)-piperazin-1-yl]-quinazoline;
2-cyclopropyl-4-[4-(2-methoxy-phenyl)-piperazin-1-yl]-quinazoline;
2-cyclopropyl-5,6-dimethoxy-4-[4-(2-methoxy-phenyl)-piperazin-1-yl]-quinazoline;
2-cyclopropyl-5-methoxy-4[4-(-methoxy-phenyl)-piperazin-1-yl]-quinazoline;
2-cyclopropyl-8-methoxy-4-[4-(2-methoxy-phenyl)-piperazin-1-yl]-quinazoline;
2-cyclopropyl-6,7-dimethoxy-4-[4-(2-methoxy-phenyl)-piperazin-1-yl]-quinoline;
3-cyclopropyl-6,7-dimethoxy-1-[4-(2-methoxy-phenyl)-piperazin-1-yl]-isoquinoline;
3-chloro-4-(4-(2-cyclopropyl-6-(dimethylamino)quinazolin-4-yl)piperazin-1-yl)benzonitrile;
3-chloro-4-[4-(2-cyclopropyl-6-dimethylamino-quinazolin-4-yl)-piperazin-1-yl]-benzamide;
3-{3-chloro-4-[4-(2-cyclopropyl-6-dimethylamino-quinazolin-4-yl)-piperazin-1-yl]-phenyl}-1,1-dimethyl-urea;
6-bromo-2-cyclopropyl-4-[4-(2,5-dimethoxy-phenyl)-piperazin-1-yl]-quinazoline;
{2-cyclopropyl-4-[4-(2,5-dimethoxy-phenyl)-piperazin-1-yl]-quinazo lin-6-yl}-dimethyl-amine;
6-bromo-2-cyclopropyl-4-[4-(2-methoxy-5-methyl-phenyl)-piperazin-1-yl]-quinazoline;
{2-cyclopropyl-4-[4-(2-methoxy-5-methyl-phenyl)-piperazin-1-yl]-quinazolin-6-yl}-dimethyl-amine;
6-bromo-2-cyclopropyl-4-[4-(4-fluoro-2-methoxy-phenyl)-piperazin-1-yl]-quinazoline;
{2-cyclopropyl-4-[4-(4-fluoro-2-methoxy-phenyl)-piperazin-1-yl]-quinazolin-6-yl}-dimethyl-amine;
4-[4-(6-bromo-2-cyclopropyl-quinazolin-4-yl)-piperazin-1-yl]-3-methoxy-benzonitrile;
4-[4-(2-cyclopropyl-6-dimethylamino-quinazolin-4-yl)-piperazin-1-yl]-3-methoxy-benzonitrile;
6-bromo-2-cyclopropyl-4-[4-(2-methoxy-4-trifluoromethoxy-phenyl)-piperazin-1-yl]-quinazoline;
{2-cyclopropyl-4-[4-(2-methoxy-4-trifluoromethoxy-phenyl)-piperazin-1-yl]-quinazolin-6-yl}-dimethyl-amine;
6-bromo-4-[4-(2-chloro-4-fluoro-phenyl)-piperazin-1-yl]-2-cyclopropyl-quinazoline;
{4-[4-(2-chloro-4-fluoro-phenyl)-piperazin-1-yl]-2-cyclopropyl-quinazolin-6-yl}-dimethyl-amine;
6-bromo-4-[4-(2-chloro-4-methyl-phenyl)-piperazin-1-yl]-2-cyclopropyl-quinazoline;
{4-[4-(2-chloro-4-methyl-phenyl)-piperazin-1-yl]-2-cyclopropyl-quinazolin-6-yl}-dimethyl-amine;
6-bromo-4-[4-(4-chloro-2-methoxy-phenyl)-piperazin-1-yl]-2-cyclopropyl-quinazoline;
{4-[4-(4-chloro-2-methoxy-phenyl)-piperazin-1-yl]-2-cyclopropyl-quinazolin-6-yl}-dimethyl-amine;
6-bromo-2-cyclopropyl-4-[4-(4-methoxy-phenyl)-piperazin-1-yl]-quinazoline;
{2-cyclopropyl-4-[4-(4-methoxy-phenyl)-piperazin-1-yl]-quinazolin-6-yl}-dimethyl-amine;
6-bromo-2-cyclopropyl-4-[4-(3-methoxy-phenyl)-piperazin-1-yl]-quinazoline;
{2-cyclopropyl-4-[4-(3-methoxy-phenyl)-piperazin-1-yl]-quinazolin-6-yl}-dimethyl-amine;
6-bromo-2-cyclopropyl-4-(4-o-tolyl-piperazin-1-yl)-quinazoline;
[2-cyclopropyl-4-(4-o-tolyl-piperazin-1-yl)-quinazolin-6-yl]-dimethyl-amine;
6-bromo-2-cyclopropyl-4-[4-(2-fluoro-phenyl)-piperazin-1-yl]-quinazoline;
6-bromo-4-[4-(2-chloro-phenyl)-piperazin-1-yl]-2-cyclopropyl-quinazoline;
{2-cyclopropyl-4-[4-(2-fluoro-phenyl)-piperazin-1-yl]-quinazolin-6-yl}-dimethyl-amine;
{4-[4-(2-chloro-phenyl)-piperazin-1-yl]-2-cyclopropyl-quinazolin-6-yl}-dimethyl-amine;
2-[4-(6-Bromo-2-cyclopropyl-quinazolin-4-yl)-piperazin-1-yl]-benzonitrile;
2-[4-(2-cyclopropyl-6-dimethylamino-quinazolin-4-yl)-piperazin-1-yl]-benzonitrile;
2-[4-(2-cyclopropyl-6-dimethylamino-quinazolin-4-yl)-piperazin-1-yl]-benzamide;
{4-[4-(2-azetidin-1-yl-phenyl)-piperazin-1-yl]-2-cyclopropyl-quinazolin-6-yl}-dimethyl-amine;
{4-[4-(2-azetidin-1-yl-phenyl)-piperazin-1-yl]-2-cyclopropyl-quinazolin-6-yl}-ethyl-methyl-amine;
{4-[4-(2-azetidin-1-yl-phenyl)-piperidin-1-yl]-2-cyclopropyl-quinazolin-6-yl}-dimethyl-amine;
2-cyclopropyl-6,7-dimethoxy-4-(4-(2-methoxyphenyl)piperazin-1-yl)quinazoline;
6,7-dimethoxy-4-(4-(2-methoxyphenyl)piperazin-1-yl)-2-methylquinazoline;

2-benzyl-6,7-dimethoxy-4-(4-(2-methoxyphenyl)piperazin-1-yl)quinazoline;
2-ethyl-6,7-dimethoxy-4-(4-(2-methoxyphenyl)piperazin-1-yl)quinazoline;
6,7-dimethoxy-4-(4-(2-methoxyphenyl)piperazin-1-yl)-2-propylquinazoline;
2-isopropyl-6,7-dimethoxy-4-(4-(2-methoxyphenyl)piperazin-1-yl)quinazoline;
2-isobutyl-6,7-dimethoxy-4-(4-(2-methoxyphenyl)piperazin-1-yl)quinazoline;
6,7-dimethoxy-4-(4-(2-methoxyphenyl)piperazin-1-yl)-2-vinylquinazoline;
6,7-dimethoxy-4-(4-(2-methoxyphenyl)piperazin-1-yl)-2-(2-(4-(2-methoxyphenyl)piperazin-1-y)ethyl)quinazoline;
2-cyclopentyl-6,7-dimethoxy-4-(4-(2-methoxyphenyl)piperazin-1-yl)quinazoline;
2-(cyclopropylmethyl)-6,7-dimethoxy-4-(4-(2-methoxyphenyl)piperazin-1-yl)quinazoline;
2-(6,7-dimethoxy-4-(4-(2-methoxyphenyl)piperazin-1-yl)quinazolin-2-yl)-N,N-dimethylethanamine;
[2-cyclobutyl-6,7-dimethoxy-4-(4-(2-methoxyphenyl)piperazin-1-yl)quinazoline;]
2-cyclobutyl-6,7-dimethoxy-4-(4-phenylpiperazin-1-yl)quinazoline;
2-cyclobutyl-6,7-dimethoxy-4-(4-(o-tolyl)piperazin-1-yl)quinazoline;
2-cyclobutyl-4-(4-(2-fluorophenyl)piperazin-1-yl)-6,7-dimethoxyquinazoline;
4-(4-(2-chlorophenyl)piperazin-1-yl)-2-cyclobutyl-6,7-dimethoxyquinazoline;
[2-cyclobutyl-6,7-dimethoxy-4-(4-(pyridin-2-yl)piperazin-1-yl)quinazoline;]
2-cyclobutyl-6,7-dimethoxy-4-(4-(2-nitrophenyl)piperazin-1-yl)quinazoline;
2-cyclobutyl-6,7-dimethoxy-4-(4-(3-methoxyphenyl)piperazin-1-yl)quinazoline;
2-cyclobutyl-6,7-dimethoxy-4-(4-(4-methoxyphenyl)piperazin-1-yl)quinazoline;
2-cyclobutyl-4-(4-(2,4-dimethoxyphenyl)piperazin-1-yl)-6,7-dimethoxyquinazoline;
2-cyclobutyl-4-(4-(2,6-dimethylphenyl)piperazin-1-yl)-6,7-dimethoxyquinazoline;
2-cyclobutyl-6-methoxy-4-(4-(2-methoxyphenyl)piperazin-1-yl)quinazoline;
2-cyclobutyl-7-methoxy-4-(4-(2-methoxyphenyl)piperazin-1-yl)quinazoline;
2-cyclobutyl-4-(4-(2-methoxyphenyl)piperazin-1-yl)quinazoline;
6-cyclobutyl-8-(4-(2-methoxyphenyl)piperazin-1-yl)-[1,3]dioxolo[4,5-g]quinazoline;
2-cyclopropyl-6-methoxy-4-(4-(2-methoxyphenyl)piperazin-1-yl)quinazoline;
2-cyclopropyl-4-(4-(2-ethoxyphenyl)piperazin-1-yl)-6,7-dimethoxyquinazoline;
4-(4-(2-chlorophenyl)piperazin-1-yl)-2-cyclopropyl-6,7-dimethoxyquinazoline;
2-cyclopropyl-6,7-dimethoxy-4-(4-(phenylsulfonyl)piperazin-1-yl)quinazoline;
2-cyclopropyl-6,7-dimethoxy-4-(4-(4-methylbenzyl)piperazin-1-yl)quinazoline;
2-cyclopropyl-6,7-dimethoxy-4-(4-(2-methoxybenzyl)piperazin-1-yl)quinazoline;
(4-(2-cyclopropyl-6,7-dimethoxyquinazolin-4-yl)piperazin-1-yl)(phenyl)methanone;
(4-(2-cyclopropyl-6,7-dimethoxyquinazolin-4-yl)piperazin-1-yl)(2-methoxyphenyl)methanone;
2-cyclopropyl-6,7-dimethoxy-4-(piperazin-1-yl)quinazoline trifluoroacetate;
2-cyclopropyl-6-methoxy-4-(4-(2-methoxyphenyl)piperazin-1-yl)-7-(trifluoromethyl)quinazoline;
or a pharmaceutically acceptable salt, solvate, or tautomer thereof.

\* \* \* \* \*